(12) United States Patent
Hatakeyama et al.

(10) Patent No.: US 12,324,667 B2
(45) Date of Patent: Jun. 10, 2025

(54) BIO-ELECTRODE COMPOSITION, BIO-ELECTRODE, METHOD FOR MANUFACTURING BIO-ELECTRODE, POLYMER COMPOUND, AND COMPOSITE

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 751 days.

(21) Appl. No.: 17/490,632

(22) Filed: Sep. 30, 2021

(65) Prior Publication Data
US 2022/0110566 A1   Apr. 14, 2022

(30) Foreign Application Priority Data

Oct. 13, 2020 (JP) .................................. 2020-172816
Jan. 4, 2021 (JP) .................................. 2021-000082

(51) Int. Cl.
*A61B 5/257* (2021.01)
*A61B 5/265* (2021.01)
(Continued)

(52) U.S. Cl.
CPC ............. *A61B 5/257* (2021.01); *A61B 5/265* (2021.01); *A61B 5/268* (2021.01); *C08F 228/02* (2013.01); *A61B 5/28* (2021.01)

(58) Field of Classification Search
CPC ............ C08F 220/1808; C08F 220/382; C08F 220/286; C08F 230/085; C08F 212/30;
(Continued)

(56) References Cited

U.S. PATENT DOCUMENTS 5,981,580 A    11/1999   Nugent et al.
5,981,680 A *  11/1999   Petroff ................. A61K 8/898
                                                    528/31
(Continued)

FOREIGN PATENT DOCUMENTS

CN    105451650 A    3/2016
JP    105-095924 A   4/1993
(Continued)

OTHER PUBLICATIONS

Yang, Q. et al., "Mesoporous silica supported water-stable perfluorobutylsulfonylimide and its catalytic applications in esterification," Microporous and Mesoporous Materials, vol. 172, pp. 51-60, 2013.

(Continued)

*Primary Examiner* — Peter A Salamon
(74) *Attorney, Agent, or Firm* — Oliff PLC

(57) ABSTRACT

A bio-electrode composition contains (A) a composite of an ionic polymer material and particles. The component (A) contains the particles bonding to the polymer containing a repeating unit having a structure selected from the group consisting of salts of ammonium, lithium, sodium, potassium, and silver formed with any of fluorosulfonic acid, fluorosulfonimide, and N-carbonyl-fluorosulfonamide. Thus, the present invention provides: a bio-electrode composition capable of forming a living body contact layer for a bio-electrode which is excellent in electric conductivity and biocompatibility, light-weight, and manufacturable at low cost, and which prevents significant reduction in the electric conductivity even when wetted with water or dried; a bio-electrode including a living body contact layer formed of the bio-electrode composition; and a method for manufacturing the bio-electrode.

27 Claims, 4 Drawing Sheets

(51) Int. Cl.
    *A61B 5/268*      (2021.01)
    *C08F 228/02*      (2006.01)
    *A61B 5/28*      (2021.01)

(58) Field of Classification Search
    CPC ............ C08F 220/1809; C08F 220/387; C08F 212/22; C08F 230/08; C08F 220/282; C08F 220/585; C08L 25/18; C08L 33/08; C08L 83/00; C08L 33/14; C08L 33/24; C08L 51/085; C09D 151/085; C09D 133/08; C09D 183/10; C09D 183/12
    See application file for complete search history.

(56) References Cited

U.S. PATENT DOCUMENTS

| | | | |
|---|---|---|---|
| 2002/0177039 A1* | 11/2002 | Lu ........................ | H01B 1/122 205/58 |
| 2002/0188069 A1 | 12/2002 | Sugo et al. | |
| 2015/0275060 A1 | 10/2015 | Kuroda et al. | |
| 2016/0155530 A1* | 6/2016 | Someya ............... | A61B 5/6846 156/60 |
| 2017/0190586 A1 | 7/2017 | Yanagita et al. | |
| 2017/0275510 A1 | 9/2017 | Quan et al. | |
| 2018/0072930 A1* | 3/2018 | Hatakeyama ......... | A61B 5/259 |
| 2018/0085019 A1* | 3/2018 | Hatakeyama ........... | C09J 11/04 |
| 2018/0086948 A1* | 3/2018 | Hatakeyama ........... | C09J 11/06 |
| 2018/0215876 A1 | 8/2018 | Hatakeyama et al. | |
| 2018/0229024 A1* | 8/2018 | Hatakeyama ......... | A61B 5/291 |
| 2018/0273811 A1 | 9/2018 | Cura et al. | |
| 2019/0106528 A1 | 4/2019 | Hatakeyama et al. | |
| 2019/0209740 A1* | 7/2019 | Hatakeyama ....... | A61B 5/0531 |
| 2019/0298891 A1* | 10/2019 | Hatakeyama ....... | A61B 5/0531 |
| 2020/0015699 A1* | 1/2020 | Hatakeyama ........... | A61B 5/25 |
| 2020/0315476 A1* | 10/2020 | Hatakeyama ......... | H01B 1/122 |

FOREIGN PATENT DOCUMENTS

| | | |
|---|---|---|
| JP | 2002-332305 A | 11/2002 |
| JP | 2003-225217 A | 8/2003 |
| JP | 2004-033468 A | 2/2004 |
| JP | 2004-527902 A | 9/2004 |
| JP | 2005-320418 A | 11/2005 |
| JP | 2011-079946 A | 4/2011 |
| JP | 2015-003839 A | 1/2015 |
| JP | 2015-019806 A | 2/2015 |
| JP | 2015-100673 A | 6/2015 |
| JP | 2015-193803 A | 11/2015 |
| JP | 2016-011338 A | 1/2016 |
| JP | 2016-065238 A | 4/2016 |
| JP | 2018-044147 A | 3/2018 |
| JP | 2018-059050 A | 4/2018 |
| JP | 2018-059052 A | 4/2018 |
| JP | 2018-070775 A | 5/2018 |
| JP | 2018-123304 A | 8/2018 |
| JP | 2018-130534 A | 8/2018 |
| JP | 2019-503406 A | 2/2019 |
| JP | 2019-070109 A | 5/2019 |
| JP | 2019-180467 A | 10/2019 |
| JP | 2020-006069 A | 1/2020 |
| JP | 2020-033224 A | 3/2020 |
| TW | 201932512 A | 8/2019 |
| WO | 2013/039151 A1 | 3/2013 |
| WO | 2015/186596 A1 | 12/2015 |

OTHER PUBLICATIONS

Mar. 16, 2022 extended Search Report issued in European Patent Application No. 21200607.6.

May 3, 2022 Search Report issued in Taiwanese Patent Application No. 110137687.

Aug. 29, 2023 Office Action issued in Korean Patent Application No. 10-2021-0134041.

Lizhen Long et al. "Polymer Electrolytes for Lithium Polymer Batteries". Journal of Materials Chemistry A, 2016, vol. 4, pp. 10038-10069.

J.F. Snyder et al. "Ion Conductivity of Comb Polysiloxane Polyelectrolytes Containing Oligoether and Perfluoroether Sidechains". Journal of the Electrochemical Society, 2003, vol. 150, No. 8, pp. A1090-A1094.

May 3, 2022 Office Action and Search Report issued in Taiwanese Patent Application No. 110137687.

Hideharu Mori, "Creation of Functional Silsesquioxane Nanoparticles", Network Polymer, Japan, (2011), vol. 32, 5, pp. 259-267.

Feb. 6, 2024 Office Action issued in Japanese Patent Application No. 2021-151665.

\* cited by examiner

[FIG. 1]
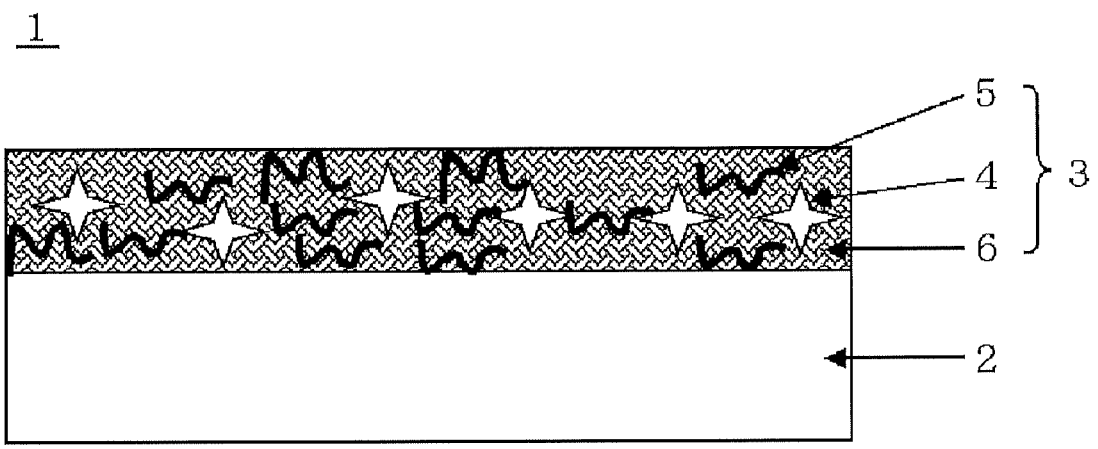
[FIG. 2]
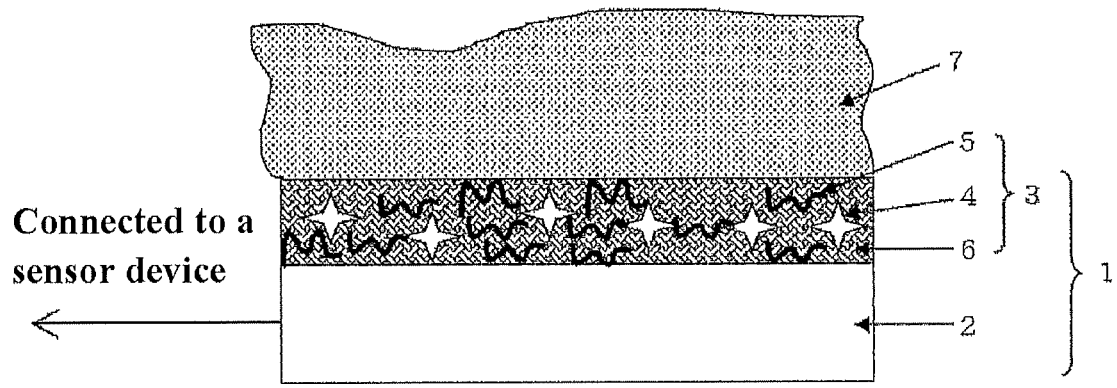

[FIG. 3]
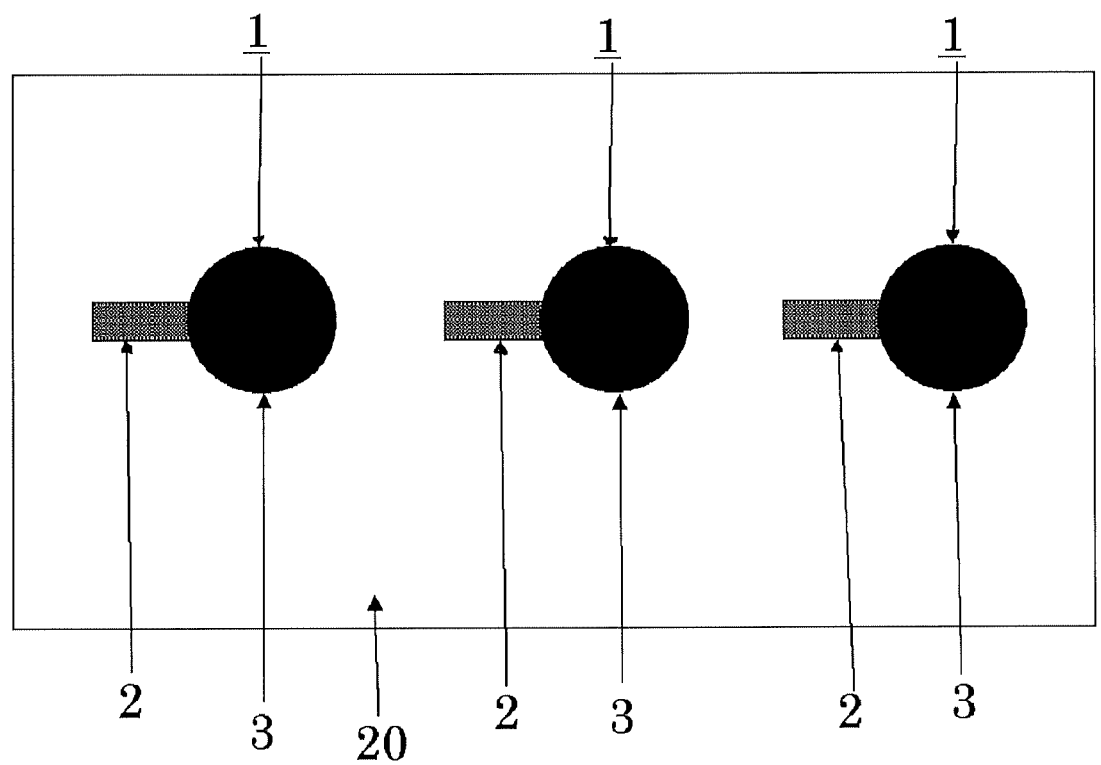

[FIG. 4]
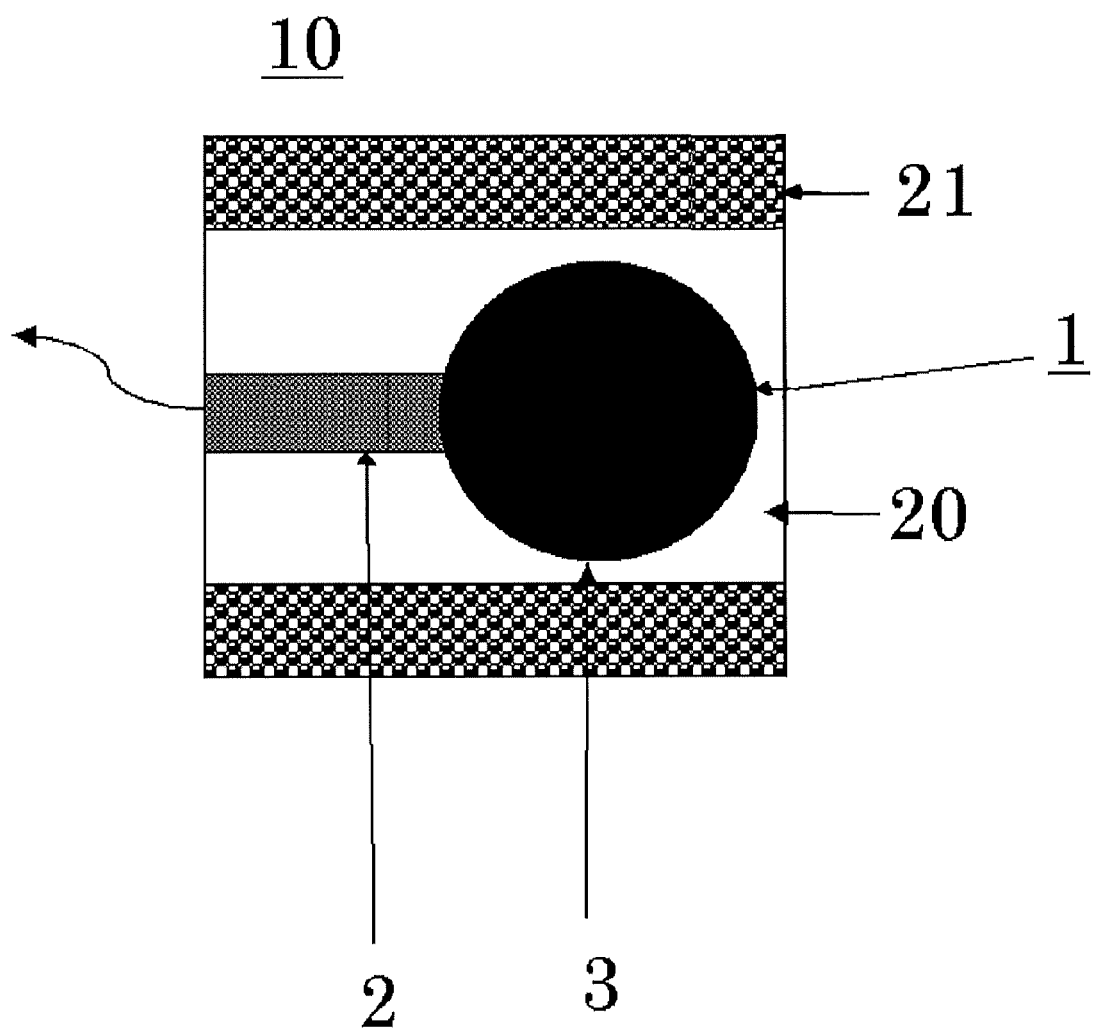

[FIG. 5]
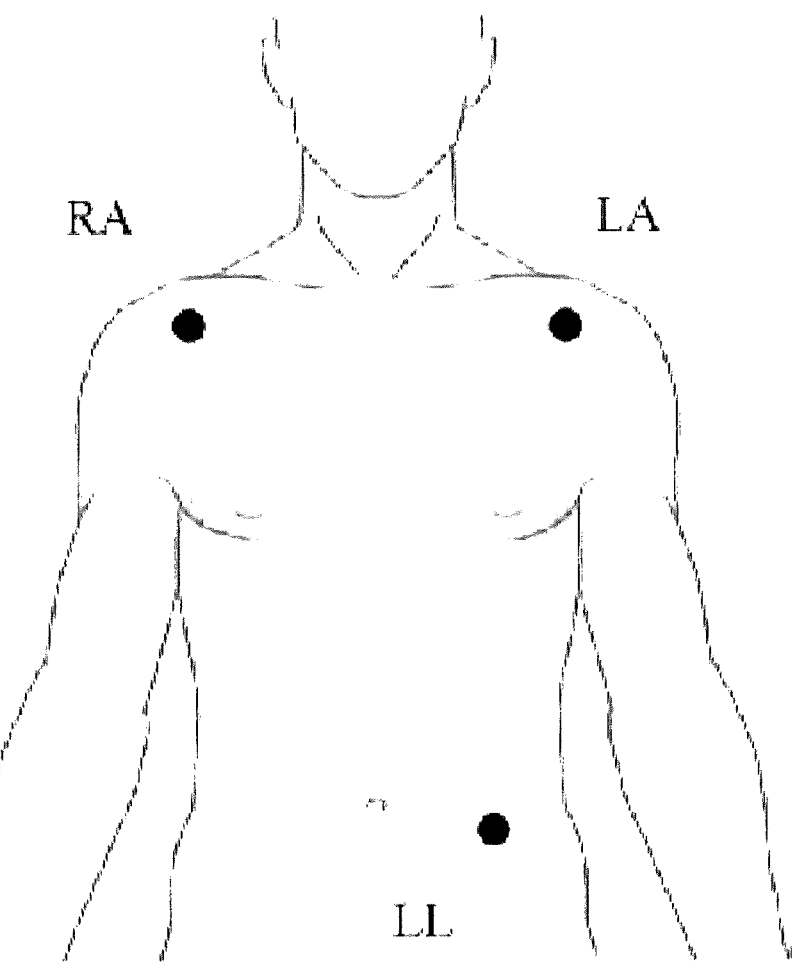
[FIG. 6]
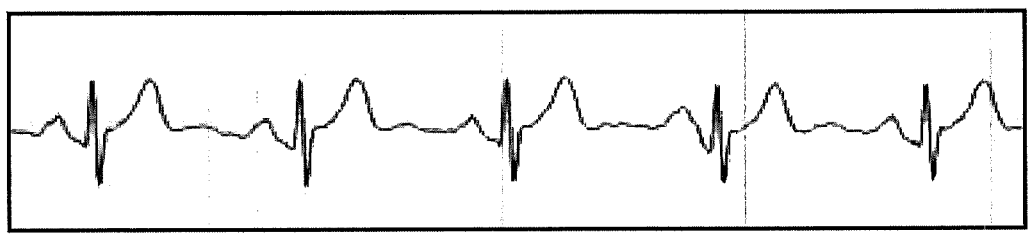

BIO-ELECTRODE COMPOSITION, BIO-ELECTRODE, METHOD FOR MANUFACTURING BIO-ELECTRODE, POLYMER COMPOUND, AND COMPOSITE

TECHNICAL FIELD

The present invention relates to: a bio-electrode that is used in contact with the skin of a living body and capable of detecting physical conditions such as heart rate by an electric signal transmitted from the skin; a method for manufacturing the bio-electrode; and a bio-electrode composition desirably used for a bio-electrode.

BACKGROUND ART

A recent growing popularity of Internet of Things (IoT) has accelerated the development of wearable devices, such as watches and eye-glasses that allow for Internet access. Even in the fields of medicine and sports, wearable devices for constantly monitoring the user's physical state are increasingly demanded, and such technological development is expected to be further encouraged.

In the field of medicine, use of wearable devices has been examined for monitoring the state of human organs by sensing extremely weak current, such as an electrocardiogram which detects an electric signal to measure the motion of the heart. The electrocardiogram measurement is conducted by attaching an electrode coated with an electro-conductive paste to a body, but this is a single (not continuous), short-time measurement. On the other hand, development of the above medical wearable device is aimed at device for continuously monitoring the health condition for a few weeks. Accordingly, a bio-electrode used in a medical wearable device is required to make no changes in electric conductivity even in long-time use and cause no skin allergy. In addition to these, it is also required that a bio-electrode is light-weight and can be produced at low cost.

Medical wearable devices are classified into two types: a type which is directly attached to body and a type which is incorporated into clothes. As the type which is attached to a body, it has been proposed a bio-electrode using water-soluble gel containing water and electrolyte, which are materials of the foregoing electro-conductive paste (Patent Document 1). The water-soluble gel contains sodium, potassium, or calcium as the electrolyte in a water-soluble polymer for retaining water, and converts changes of ion concentration from skin into electricity. On the other hand, as the type which is incorporated into clothes, it has been proposed a means to use cloth in which an electro-conductive polymer such as PEDOT-PSS (poly-3,4-ethylenedioxy-thiophene-polystyrenesulfonate) or silver paste is incorporated into the fibers for electrodes (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of the electro-conductive polymer, and further cause peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. The metal nanowire, however, can cause skin allergies since they are thin material with sharp tips. Even if these electrode materials themselves cause no allergic reaction in the manners described above, the biocompatibility may be degraded depending on the shape of a material and its inherent stimulation, thereby making it hard to satisfy both electric conductivity and biocompatibility.

Although metal films seem to function as excellent bio-electrodes thanks to extremely high electric conductivity, this is not always the case. Upon heartbeat, the human skin releases not only extremely weak current, but also sodium ion, potassium ion, and calcium ion. It is thus necessary to convert changes in ion concentration into current. Noble metals, however, are difficult to ionize and are inefficient in converting ions from skin to current. Therefore, the resulting bio-electrode using a noble metal is characterized by high impedance and high resistance to the skin during electrical conduction.

Meanwhile, the use of a battery containing an ionic liquid has been examined (Patent Document 6). Advantageously, the ionic liquid is thermally and chemically stable, and has excellent electric conductivity, providing wider battery applications. However, an ionic liquid having smaller molecular weight as shown in Patent Document 6 unfortunately dissolves into water. When a bio-electrode containing such an ionic liquid is used, the ionic liquid is extracted from the bio-electrode by sweating, which not only lowers the electric conductivity, but also causes rough dry skin as a result of the skin soaking with the liquid.

Batteries using a lithium salt of polymer type sulfonimide have also been examined (Non-Patent Document 1). Lithium has been applied to batteries because of their high ionic mobility. However, this is not a bio-compatible material. Additionally, lithium salts of fluorosulfonate have been examined in a form of a pendant on silicone (Non-Patent Document 2).

The bio-electrode fails to obtain biological information if it is apart from the skin. A change in contact area solely affects the quantity of electricity traveling through the electrode, and hence affects the baseline of an electrocardiogram (electric signal). Accordingly, in order to stably detect electric signals from the body, the bio-electrode is required to be in constant contact with the skin and make no changes in contact area. For this reason, the bio-electrode is preferably adherent. Moreover, the bio-electrode is required to have stretchability and flexibility so that the bio-electrode can follow changes in skin expansion or folding.

There has been examined a bio-electrode composed of: silver chloride at a portion which comes into contact with skin; and silver deposited at a portion through which electricity is conducted to a device. Solid silver chloride has neither adhesive strength to skin nor stretchability, so that the ability to collect biological signals is lowered particularly when the user moves. For this reason, a laminate film of silver chloride and silver is used as a bio-electrode with a water-soluble gel deposited between the bio-electrode and the skin. In this case, the aforementioned deterioration occurs when the gel is dried.

Recently, surface-modified functional silica has been developed. For example, a silicone rubber material containing silica having phosphonium salt in a pendant form on the surface has been proposed for antistatic application of a toner for printer (Patent Document 7). The silica surface is modified through reaction of the silica surface with a trialkoxysilane compound having phosphonium salt.

CITATION LIST

Patent Literature

Patent Document 1: WO 2013-039151 A1
Patent Document 2: JP 2015-100673 A
Patent Document 3: JP H05-095924 A
Patent Document 4: JP 2003-225217 A
Patent Document 5: JP 2015-019806 A
Patent Document 6: JP 2004-527902 A
Patent Document 7: JP 2020-033224 A Non Patent Literature Non Patent Document 1: J. Mater. Chem. A, 2016, 4, p 10038-10069
Non Patent Document 2: J. of the Electrochemical Society, 150(8), A1090-A1094 (2003)

SUMMARY OF INVENTION

Technical Problem

The present invention has been made to solve the above problems. An object of the present invention is to provide: a bio-electrode composition capable of forming a living body contact layer for a bio-electrode which is excellent in electric conductivity and biocompatibility, light-weight, and manufacturable at low cost, and which prevents significant reduction in the electric conductivity even when the bio-electrode is wetted with water or dried; a bio-electrode including a living body contact layer formed of the bio-electrode composition; and a method for manufacturing the bio-electrode.

Solution to Problem

To achieve the object, the present invention provides a bio-electrode composition comprising
(A) a composite comprising an ionic polymer material and particles, wherein
the component (A) comprises the particles bonded to the polymer comprising a repeating unit having a structure selected from the group consisting of salts of ammonium, lithium, sodium, potassium, and silver formed with any of fluorosulfonic acid, fluorosulfonimide, and N-carbonyl-fluorosulfonamide.

Such a bio-electrode composition makes it possible to provide a bio-electrode composition capable of forming a living body contact layer for a bio-electrode which is excellent in electric conductivity and biocompatibility, light-weight, and manufacturable at low cost, and which prevents significant reduction in the electric conductivity even when wetted with water or dried.

The particles preferably have diameters of 2 nm to 50 μm.

Moreover, the particles are preferably any of silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolium oxide particles, indium oxide particles, molybdenum oxide particles, and scandium oxide particles.

Such particles are suitably usable.

The repeating unit having a structure selected from the group consisting of salts of ammonium, lithium, sodium, potassium, and silver formed with any of fluorosulfonic acid, fluorosulfonimide, and N-carbonyl-fluorosulfonamide preferably comprises a structure shown by any of the following general formulae (1)-1 to (1)-4,

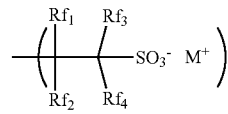

(1)-1

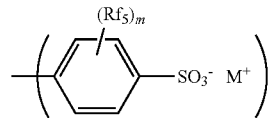

(1)-2

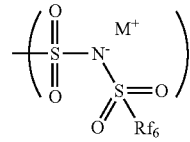

(1)-3

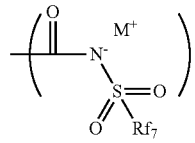

(1)-4 wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, and have at least one fluorine atom; "m" represents an integer of 1 to 4; and $M^+$ represents an ion selected from the group consisting of an ammonium ion, a lithium ion, a sodium ion, a potassium ion, and a silver ion.

Moreover, the repeating unit having a structure selected from the group consisting of salts of ammonium, lithium, sodium, potassium, and silver formed with any of fluorosulfonic acid, fluorosulfonimide, and N-carbonyl-fluorosulfonamide preferably comprises at least one repeating unit selected from the group consisting of repeating units-a1 to -a7 shown by the following general formula (2),

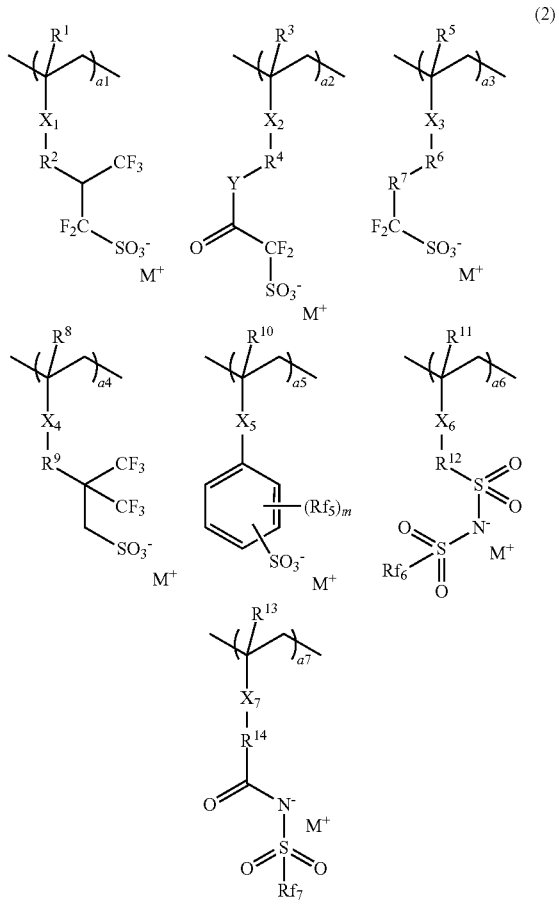

(2)

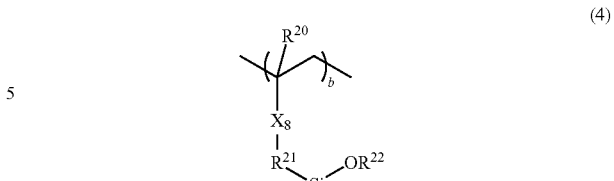

(4)

wherein $R^{20}$ represents a hydrogen atom or a methyl group; $X_8$ represents any of a single bond, a phenylene group, a naphthylene group, an ether group, an ester group, and an amide group; $R^{21}$ represents a single bond, a linear, branched, or cyclic alkylene group having 1 to 10 carbon atoms, or a phenylene group, and optionally contains an oxygen atom or a nitrogen atom; each $R^{22}$ is identical to or different from one another and represents an alkyl group having 1 to 4 carbon atoms; and "b" satisfies 0<b<1.0.

The component (A) is more preferably such that
the particles are silicon material particles, and
the component (A) is a reaction product between 100 parts by mass of the silicon material particles and 5 parts by mass or more of the polymer having an alkoxysilyl group.

Further preferably, the component (A) comprises an ammonium ion shown by the following general formula (3) as an ammonium ion for forming the ammonium salts,

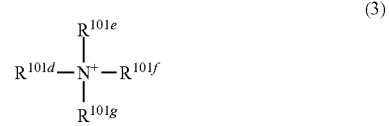

(3)

wherein $R^{101d}$, $R^{101e}$, $R^{101f}$, and $R^{101g}$ each represent a hydrogen atom, a linear, branched, or cyclic alkyl group having 1 to 14 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

Such bio-electrode compositions have a pendant of an ionic polymer on the particle surfaces, so that the permeability through the skin and the stimulus to the skin are reduced. This makes it possible to more surely prevent the composition from permeating the skin and causing allergies. Further, the ionic polymer attached on the particle surfaces forms ion conduction path on the particle surfaces, and can increase the sensitivity of the bio-electrode.

The bio-electrode composition preferably further comprises a component (B) which is an adhesive resin.

The component (B) is preferably one or more selected from the group consisting of a silicone resin, a (meth) acrylate resin, and a urethane resin.

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent any of a single bond, and a linear, branched, or cyclic hydrocarbon group having 1 to 13 carbon atoms optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom, or a linear or branched alkyl group having 1 to 4 carbon atoms and optionally bonded to $R^4$ to form a ring; "m" represents an integer of 1 to 4; a1, a2, a3, a4, a5, a6, and a7 satisfy 0≤a1≤1.0, 0≤a2≤1.0, 0≤a3≤1.0, 0≤a4≤1.0, 0≤a5≤1.0, 0≤a6≤1.0, 0≤a7≤1.0, and 0<a1+a2+a3+a4+a5+a6+a7≤1.0; $M^+$ represents an ion selected from the group consisting of an ammonium ion, a lithium ion, a sodium ion, a potassium ion, and a silver ion; and $Rf_5$, $Rf_6$, and $Rf_7$ each represent a fluorine atom, or a linear or branched alkyl group having 1 to 4 carbon atoms, and have at least one fluorine atom.

Further, the component (A) is preferably a reaction product between the particles and a polymer having the repeating unit shown by the general formula (2) and an alkoxysilyl group copolymerized with a repeating unit shown by the following general formula (4)

Such materials enable constant adhesion to skin and stable electric-signal collection for a long time.

More preferably, the component (B) comprises diorganosiloxane having an alkenyl group, and organohydrogenpolysiloxane having an SiH group.

Further preferably, the component (B) further comprises a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

Such materials can be suitably used in the bio-electrode composition.

The bio-electrode composition preferably further comprises a component (C) which is a polymer compound having an ionic repeating unit.

The ionic repeating unit of the component (C) preferably comprises a repeating unit having a structure selected from the group consisting of salts of ammonium, lithium, sodium, potassium, and silver formed with any of fluorosulfonic acid, fluorosulfonimide, and N-carbonyl-fluorosulfonamide shown by the following general formula (2),

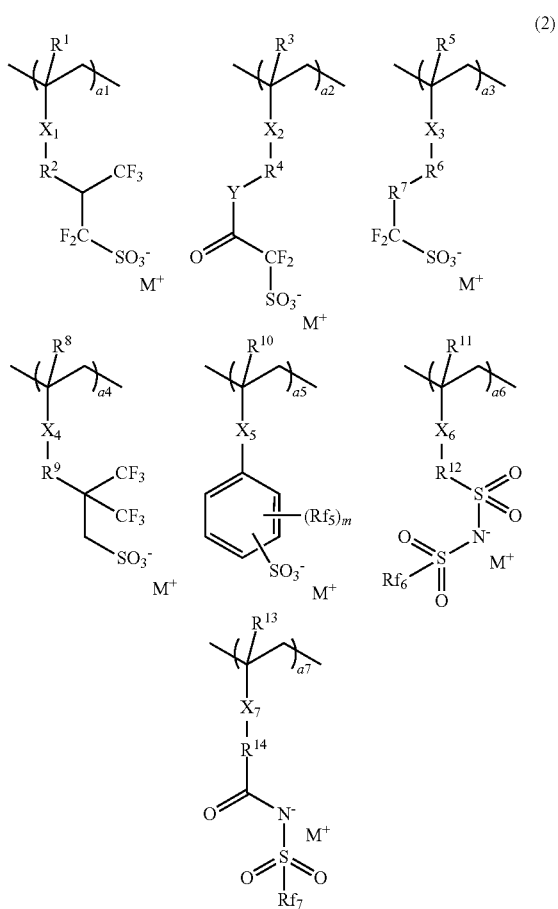

(2)

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent any of a single bond, and a linear, branched, or cyclic hydrocarbon group having 1 to 13 carbon atoms optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom, or a linear or branched alkyl group having 1 to 4 carbon atoms and optionally bonded to $R^4$ to form a ring; "m" represents an integer of 1 to 4; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$; $M^+$ represents an ion selected from the group consisting of an ammonium ion, a lithium ion, a sodium ion, a potassium ion, and a silver ion; and $Rf_5$, $Rf_6$, and $Rf_7$ each represent a fluorine atom, or a linear or branched alkyl group having 1 to 4 carbon atoms, and have at least one fluorine atom.

When the bio-electrode composition contains a polymer compound having such repeating units, the effects of the present invention can be further enhanced.

The bio-electrode composition preferably further comprises a component (D) which is a carbon powder and/or a metal powder.

The carbon powder is preferably one or both of carbon black and carbon nanotube.

The metal powder is preferably a powder of a metal selected from the group consisting of gold, silver, platinum, copper, tin, titanium, nickel, aluminum, tungsten, molybdenum, ruthenium, chromium, and indium.

More preferably, the metal powder is a silver powder.

Such materials further improve the electric conductivity.

The bio-electrode composition preferably further comprises a component (E) which is an organic solvent.

Such a material makes the coating property of the bio-electrode composition further favorable.

Furthermore, the present invention provides a bio-electrode comprising an electro-conductive base material and a living body contact layer formed on the electro-conductive base material, wherein the living body contact layer is a cured product of the above-described bio-electrode composition.

The inventive bio-electrode is excellent in electric conductivity and biocompatibility, light-weight, and manufacturable at low cost. Even when wetted with water or dried, the bio-electrode prevents significant reduction in the electric conductivity.

The electro-conductive base material preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the inventive bio-electrode, such electro-conductive base materials are particularly suitably usable.

Furthermore, the present invention provides a method for manufacturing a bio-electrode having an electro-conductive base material and a living body contact layer formed on the electro-conductive base material, comprising:

applying the above-described bio-electrode composition onto the electro-conductive base material; and curing the bio-electrode composition to form the living body contact layer.

According to the inventive method for manufacturing a bio-electrode, it is possible to easily manufacture a bio-electrode which is excellent in electric conductivity and biocompatibility, light-weight, and manufacturable at low cost, and which prevents significant reduction in the electric conductivity even when the bio-electrode is wetted with water or dried.

The electro-conductive base material used in the method for manufacturing a bio-electrode preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the inventive method for manufacturing a bio-electrode, such electro-conductive base materials are particularly suitably usable.

In addition, the present invention provides a polymer compound comprising:
a repeating unit having a structure selected from the group consisting of salts of ammonium, lithium, sodium, potassium, and silver formed with N-carbonyl-fluorosulfonamide; and
a repeating unit having an alkoxysilyl group, wherein
the polymer compound has a weight-average molecular weight in a range of 1,000 to 1,000,000.

Preferably, the repeating unit having a structure selected from the group consisting of salts of ammonium, lithium, sodium, potassium, and silver formed with N-carbonyl-fluorosulfonamide is a repeating unit-a7 shown by the following general formula (5), and
the repeating unit having an alkoxysilyl group is a repeating unit-b shown by the following general formula (5),

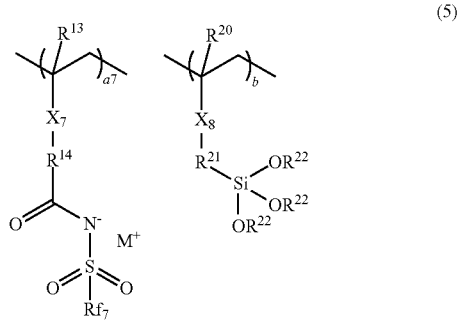

(5)

wherein each $R^{13}$ independently represents a hydrogen atom or a methyl group; each $R^{14}$ independently represents any of a single bond, and a linear, branched, or cyclic hydrocarbon group having 1 to 13 carbon atoms optionally having either or both of an ester group and an ether group; each $X_7$ independently represents any of a single bond, a phenylene group, a naphthylene group, an ether group, an ester group, and an amide group; $M^+$ represents an ion selected from the group consisting of an ammonium ion, a lithium ion, a sodium ion, a potassium ion, and a silver ion; $Rf_7$ represents a fluorine atom, or a linear or branched alkyl group having 1 to 4 carbon atoms, and has at least one fluorine atom; $R^{20}$ represents a hydrogen atom or a methyl group; $X^8$ represents any of a single bond, a phenylene group, a naphthylene group, an ether group, an ester group, and an amide group; $R^{21}$ represents a single bond, a linear, branched, or cyclic alkylene group having 1 to 10 carbon atoms, or a phenylene group, and optionally contains an oxygen atom or a nitrogen atom; each $R^{22}$ is identical to or different from one another and represents an alkyl group having 1 to 4 carbon atoms; a7 satisfies 0<a7<1.0; and "b" satisfies 0<b<1.0.

Such ionic polymer compounds can be suitably used as polymer compounds to be bonded to particles used in bio-electrode compositions.

Moreover, the present invention provides a composite comprising an ionic polymer material and particles bonded thereto, wherein
the composite comprises the particles bonded to the polymer comprising a repeating unit having a structure selected from the group consisting of salts of ammonium, lithium, sodium, potassium, and silver formed with any of fluorosulfonic acid, fluorosulfonimide, and N-carbonyl-fluorosulfonamide.

The composite preferably comprises the particles bonded to the polymer comprising a repeating unit having a structure selected from the group consisting of salts of ammonium, lithium, sodium, potassium, and silver formed with N-carbonyl-fluorosulfonamide.

The particles preferably have diameters of 2 nm to 50 μm.

Further, the particles are preferably any of silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolinium oxide particles, indium oxide particles, molybdenum oxide particles, and scandium oxide particles.

Through modification of the particles with such ionic polymers, the resulting particles become a particularly useful component of a bio-electrode composition capable of forming a living body contact layer for a bio-electrode which enables high-sensitive and efficient conduction of ions released from skin and electric signals to a device (i.e., excellent in electric conductivity), which causes no allergy even when the bio-electrode is attached to skin for a long period (i.e., excellent in biocompatibility), and which prevents significant reduction in the electric conductivity even when the bio-electrode is wetted with water or dried.

Advantageous Effects of Invention

As described above, the inventive bio-electrode composition containing particles having an ionic polymer bonded thereto (composite of the ionic polymer material and the particles) makes it possible to form a living body contact layer for a bio-electrode that is capable of efficiently conducting electric signals from skin to a device (i.e., excellent in electric conductivity), free from the risk of causing allergies even when the bio-electrode is worn on skin for a long period (i.e., excellent in biocompatibility), lightweight, manufacturable at low cost, and free from significant reduction of the electric conductivity even when the bio-electrode is wetted with water or dried. The electric conductivity can be further enhanced by additionally adding an ionic polymer compound and/or an electro-conductive powder (carbon powder, metal powder). A bio-electrode having particularly high adhesive strength and high stretchability can be produced by the combination with a resin that has adhesion and stretchability. Moreover, the stretchability and the adhesion to skin can be enhanced using additives, etc. The stretchability and the adhesion can also be adjusted by appropriately controlling the composition of the resin or the thickness of the living body contact layer.

With the above-described particles having an ionic polymer bonding thereto, the inventive bio-electrode is allowed to achieve both of electric conductivity and biocompatibility, and is also allowed to have adhesion. Thus, it is possible to keep the contact area with skin constant and to stably obtain electric signals from skin with high sensitivity.

Additionally, the inventive method for manufacturing a bio-electrode enables simple and low-cost manufacturing of the inventive bio-electrode, which is excellent in electric conductivity and biocompatibility, light-weight, and free from significant reduction of the electric conductivity even when it is wetted with water or dried.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3 is a schematic view of printed bio-electrodes prepared in Examples of the present invention;

FIG. 4 is a schematic view of one of the bio-electrodes prepared in Examples of the present invention, the bio-electrode being cut out and provided with an adhesive layer thereon;

FIG. 5 is a view showing locations where electrodes and earth are attached on a human body in measuring biological signals in Examples of the present invention; and FIG. 6 shows one of electrocardiogram waveforms obtained using the bio-electrodes in Examples of the present invention.

DESCRIPTION OF EMBODIMENTS

As noted above, it has been desired to develop: a bio-electrode composition that can form a living body contact layer for a bio-electrode which is excellent in electric conductivity and biocompatibility, light-weight, and manufacturable at low cost, and which prevents significant reduction in the electric conductivity even when wetted with water or dried and prevents residue from remaining on skin after peeling from the skin; a bio-electrode including a living body contact layer formed of the bio-electrode composition; and a method for manufacturing the bio-electrode.

The surface of skin releases ions of sodium, potassium, and calcium in accordance with heartbeat. A bio-electrode has to convert the increase and decrease of these ions released from skin to electric signals. Accordingly, the bio-electrode requires a material that is excellent in ionic conductivity to transmit the increase and decrease of ions.

To stably obtain biological signals after attachment to skin, a bio-electrode film needs to have adhesion. Meanwhile, if a residue remains on skin when a bio-electrode is peeled after long-time attachment, the residue may cause rash or rough skin. The present invention has been devised, considering that the bio-electrode needs to incorporate an ionic polymer bonded to particles, such as silica, to prevent such residue.

The present inventors herein propose: a bio-electrode composition which contains an ionic polymer material bonded to particles (hereinafter, such ionic polymer material is also referred to as ionic polymer); and a bio-electrode including the cured bio-electrode composition.

In neutralized salts formed from highly acidic acids, the ions are strongly polarized to improve the ionic conductivity. This is why lithium salts of bis(trifluoromethanesulfonyl) imidic acid and tris(trifluoromethanesulfonyl)methide acid show high ionic conductivity as a lithium ion battery. On the other hand, the higher acidity of the acid before the neutral salt formation results in a problem that the salt has stronger irritation to a body. That is, ionic conductivity and irritation to a body are in relation of trade-off. However, a salt applied to a bio-electrode has to achieve both higher ionic conductivity and lower irritation to a body.

An ion compound decreases its permeability through skin and irritation to the skin as the molecular weight is larger. Accordingly, an ion compound is preferably a polymer type with higher molecular weight. Thus, the present inventors have conceived that such an ion compound is prepared into a form having a polymerizable double bond and polymerized to form a polymer, and also that adding a composite of the polymerized ionic polymer bonded to particles prevents residue by the peeling after long-time attachment on the skin.

Further, the present inventors have found that when this salt is mixed with, for example, a silicone-based, acrylic-based, or urethane-based adhesive (resin) the use of this mixture enables constant adhesion to skin and stable electric-signal collection for a long term.

High ionic conductivity alone is insufficient to form a bio-electrode with high sensitivity, and high electron conductivity is also necessary. To increase the electron conductivity, adding a metal powder and/or a carbon powder is effective.

Specifically, the present invention is a bio-electrode composition comprising (A) a composite comprising an ionic polymer material and particles, wherein
  the component (A) comprises the particles bonded to the polymer comprising a repeating unit having a structure selected from the group consisting of salts of ammonium, lithium, sodium, potassium, and silver formed with any of fluorosulfonic acid, fluorosulfonimide, and N-carbonyl-fluorosulfonamide.

Hereinafter, the present invention will be described in detail, but the present invention is not limited thereto.
<Bio-Electrode Composition>

The inventive bio-electrode composition contains (A) a composite of an ionic polymer material and particles, and preferably contains (B) an adhesive resin. Hereinbelow, each component will be described in more details. Note that, in the following description, the composite of an ionic polymer material and particles is also referred to as "component (A)", the adhesive resin as "component (B)", a blend ionic polymer as "component (C)", an electro-conductive powder as "component (D)", an organic solvent as "component (E)", and other additive(s) as "component (F)".

[(A) Composite (Salt) of Ionic Polymer Material and Particles]

In the inventive bio-electrode composition, the composite salt (A) of an ionic polymer material and particles is in a particulate form bonded to the polymer (the ionic polymer) containing a repeating unit having a structure selected from the group consisting of salts of ammonium, lithium, sodium, potassium, and silver formed with any of fluorosulfonic acid, fluorosulfonimide, and N-carbonyl-fluorosulfonamide. Among these salts, salts of N-carbonyl-fluorosulfonamide are particularly preferable in view of high ionic conductivity as disclosed in JP 2018-70775 A. As a preferable material, the polymer further contains a repeating unit having an alkoxysilyl group, and the polymer is bonded to particles by reaction.

The structures of the salts of ammonium, lithium, sodium, potassium, and silver formed with any of fluorosulfonic acid, fluorosulfonimide, and N-carbonyl-fluorosulfonamide are preferably shown by the following general formulae (1)-1 to (1)-4.

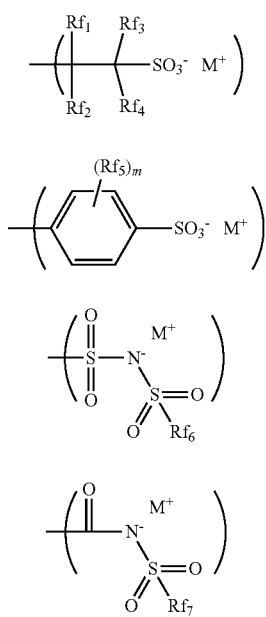

(1)-1

(1)-2

(1)-3

(1)-4

In the formulae, $Rf_1$ and $Rf_2$ each represent a hydrogen atom, a fluorine atom, an oxygen atom, a methyl group, or a trifluoromethyl group. When $Rf_1$ and $Rf_2$ represent an oxygen atom, the single oxygen atom represented by $Rf_1$ and $Rf_2$ bonds to a single carbon atom to form a carbonyl group. $Rf_3$ and $Rf_4$ each represent a hydrogen atom, a fluorine atom, or a trifluoromethyl group. At least one of $Rf_1$ to $Rf_4$ is a fluorine atom or a trifluoromethyl group. $Rf_5$, $Rf_6$, and $Rf_7$ each represent a fluorine atom, or a linear or branched alkyl group having 1 to 4 carbon atoms, and have at least one fluorine atom. "m" represents an integer of 1 to 4. $M^+$ represents an ion selected from the group consisting of an ammonium ion, a lithium ion, a sodium ion, a potassium ion, and a silver ion.

The repeating unit having a structure selected from the group consisting of salts of ammonium, lithium, sodium, potassium, and silver formed with fluorosulfonic acid as shown by the general formula (1)-1 or (1)-2, sulfonimide as shown by (1)-3, or N-carbonyl-fluorosulfonamide as shown by (1)-4 is preferably at least one repeating unit selected from the group consisting of repeating units-a1 to -a7 shown by the following general formula (2)

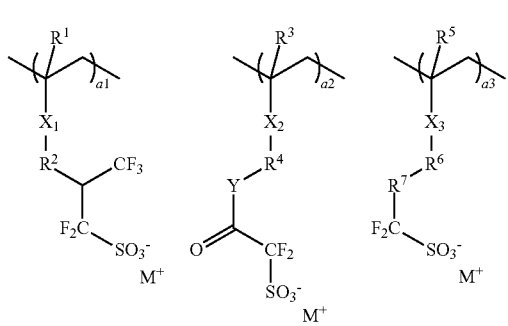

(2)

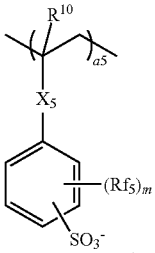 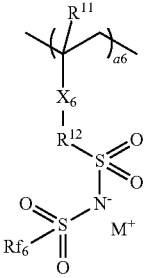

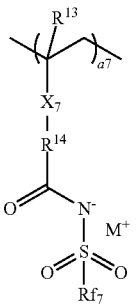

In the formula, $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, $R^{12}$, and $R^{14}$ each independently represent any of a single bond, and a linear, branched, or cyclic hydrocarbon group having 1 to 13 carbon atoms optionally having either or both of an ester group and an ether group. $R^7$ represents a linear or branched alkylene group having 1 to 4 carbon atoms, and one or two hydrogen atoms in $R^7$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. $X_5$ represents any of a single bond, an ether group, and an ester group. Y represents an oxygen atom or a —$NR^{19}$— group. $R^{19}$ represents a hydrogen atom, or a linear or branched alkyl group having 1 to 4 carbon atoms and optionally bonded to $R^4$ to form a ring. "m" represents an integer of 1 to 4. a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$. $M^+$ represents an ion selected from the group consisting of an ammonium ion, a lithium ion, a sodium ion, a potassium ion, and a silver ion. $Rf_5$, $Rf_6$, and $Rf_7$ each represent a fluorine atom, or a linear or branched alkyl group having 1 to 4 carbon atoms, and have at least one fluorine atom.

Among the repeating units-a1 to -a7 shown by the general formula (2), the repeating units-a1 to -a5 can be obtained from fluorosulfonic acid salt monomers specifically exemplified below.

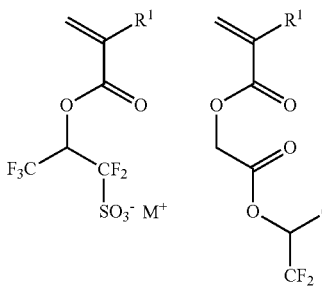

-continued
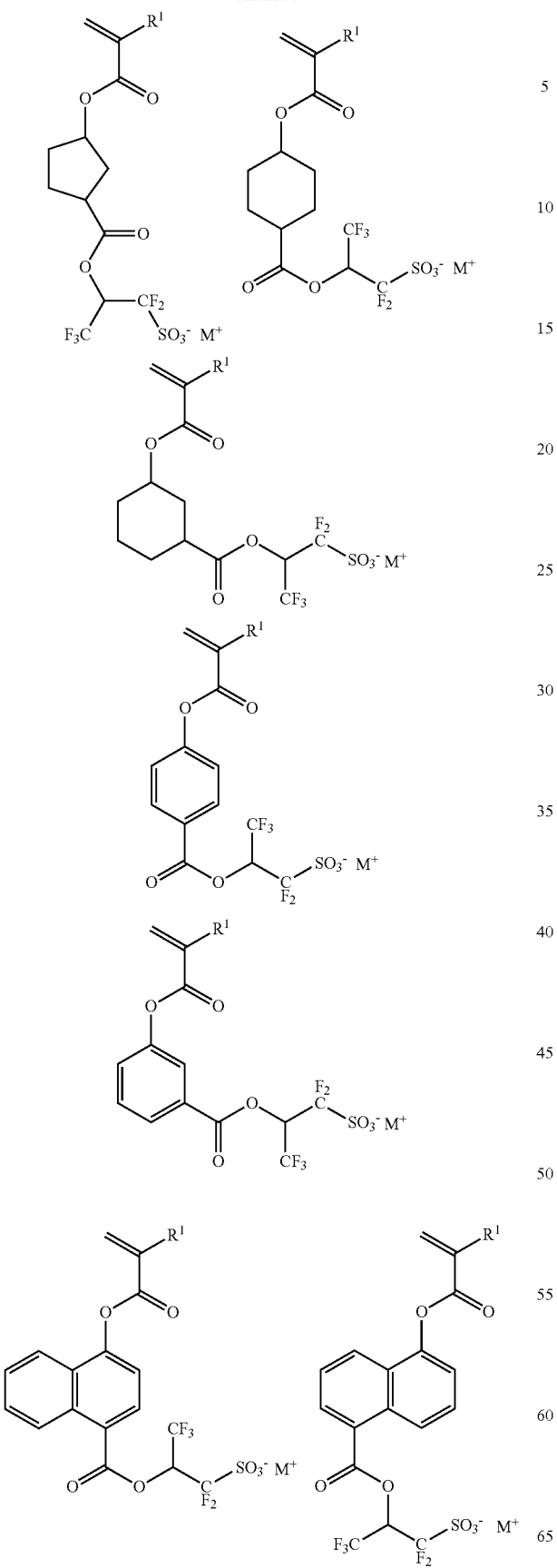
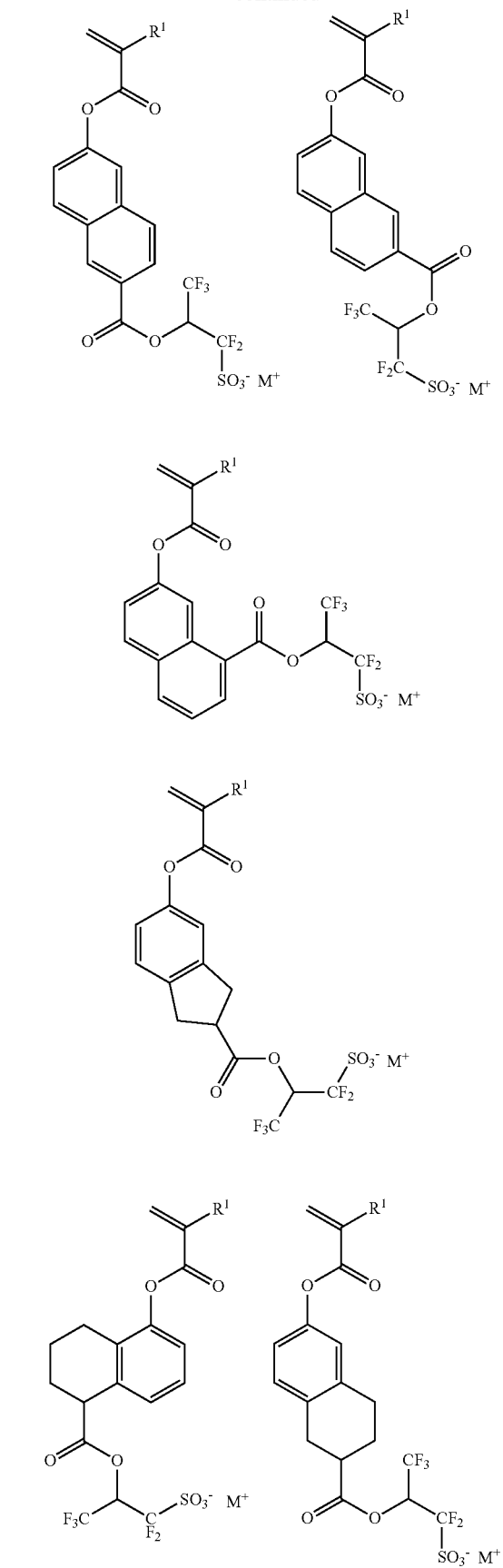

-continued
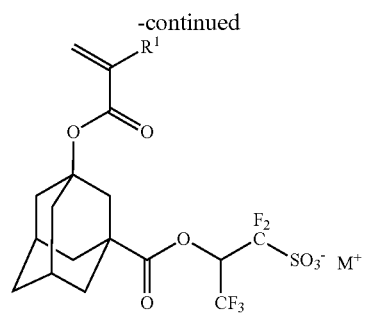
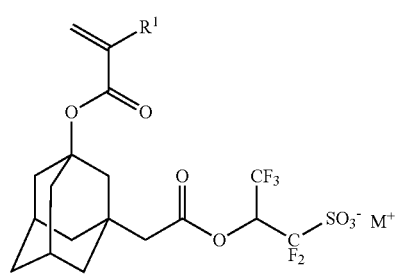
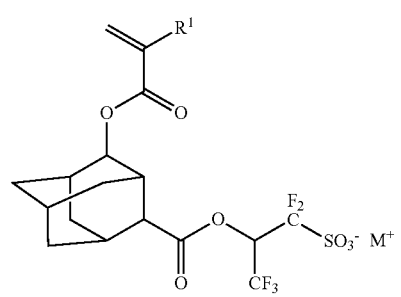
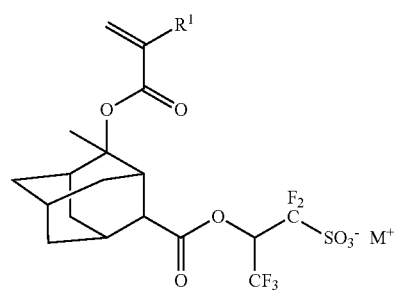
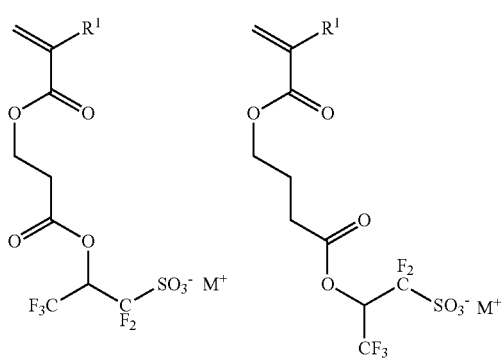
-continued
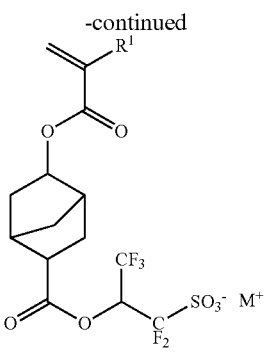
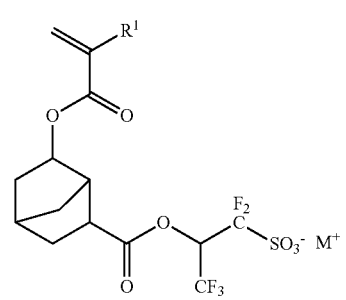
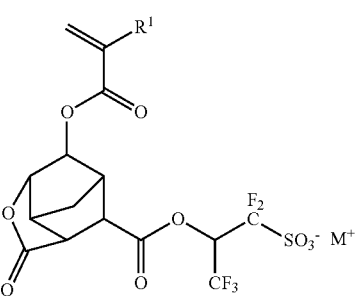
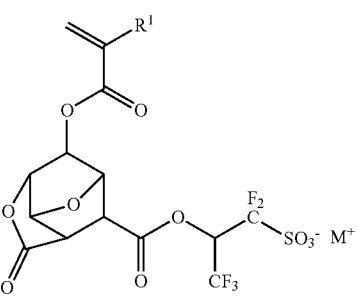
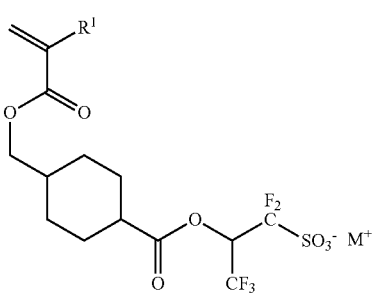

-continued
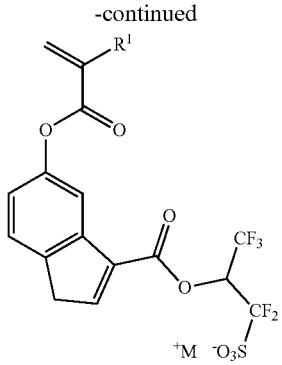
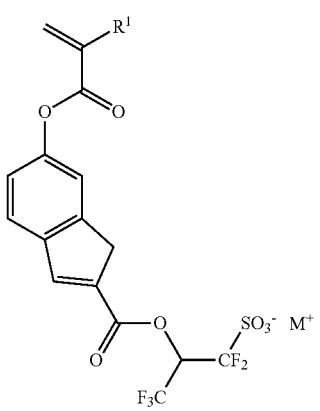
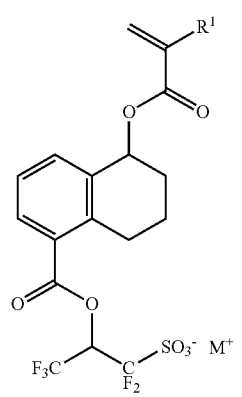
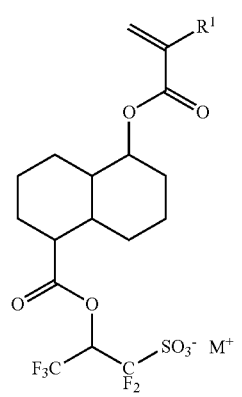
-continued
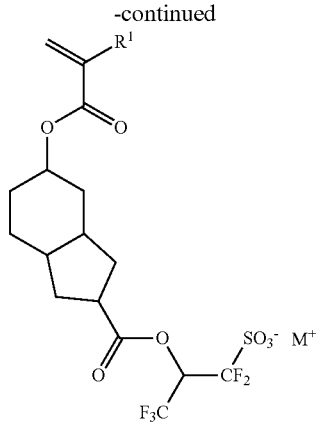
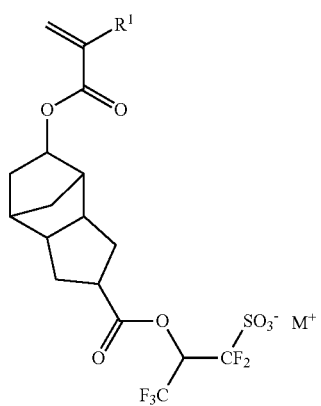
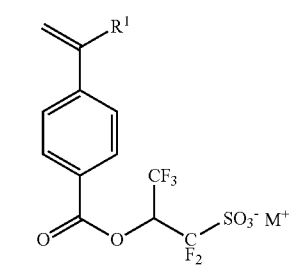
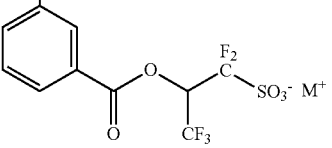
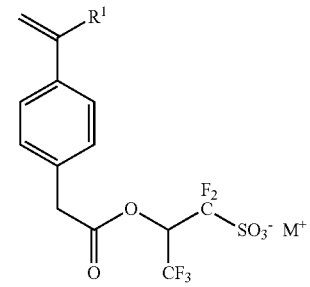

21
-continued
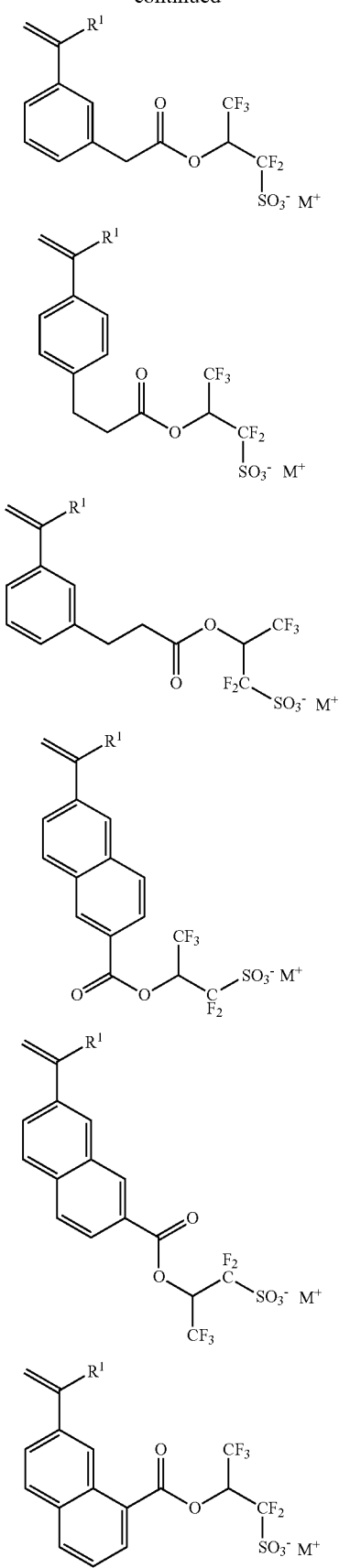
22
-continued
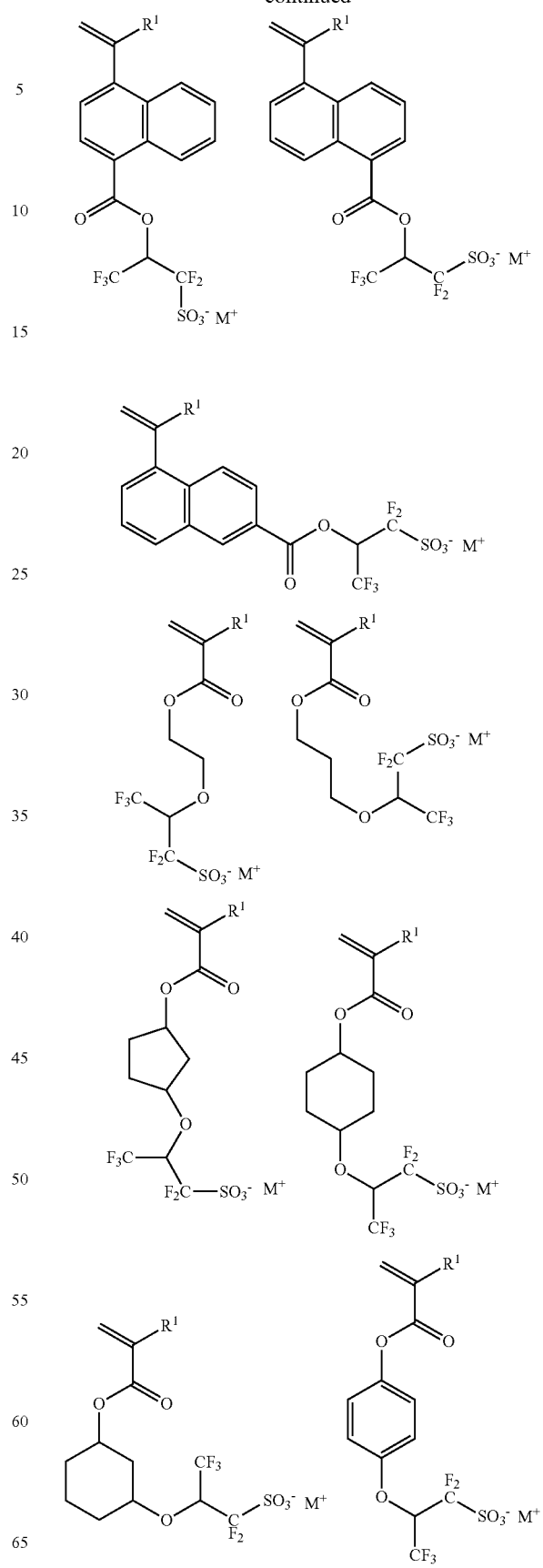

-continued
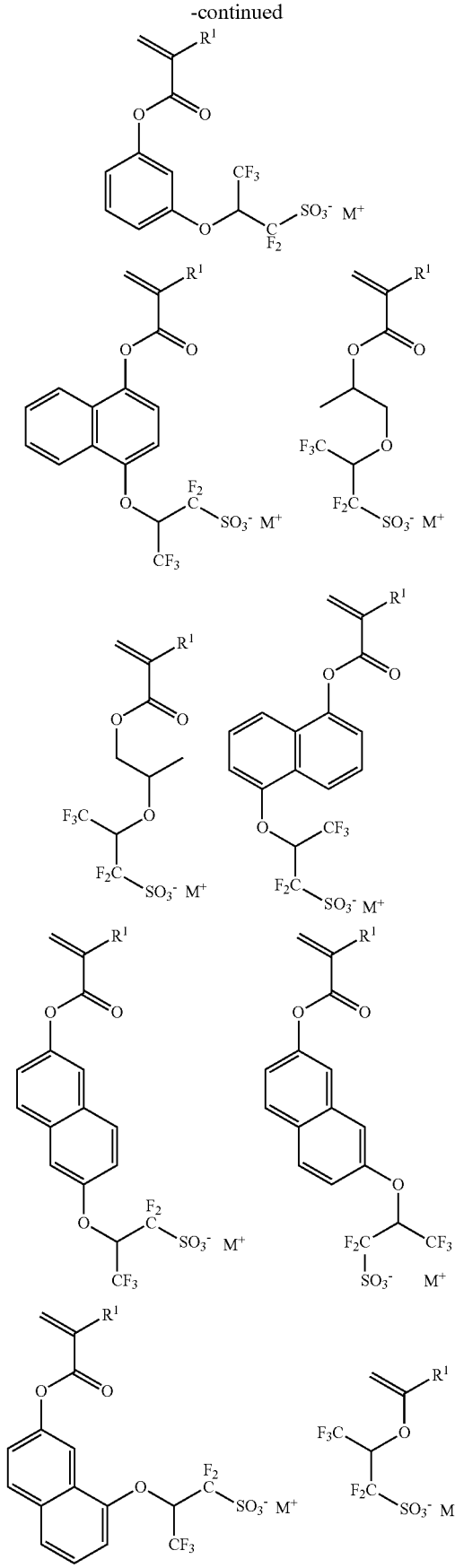
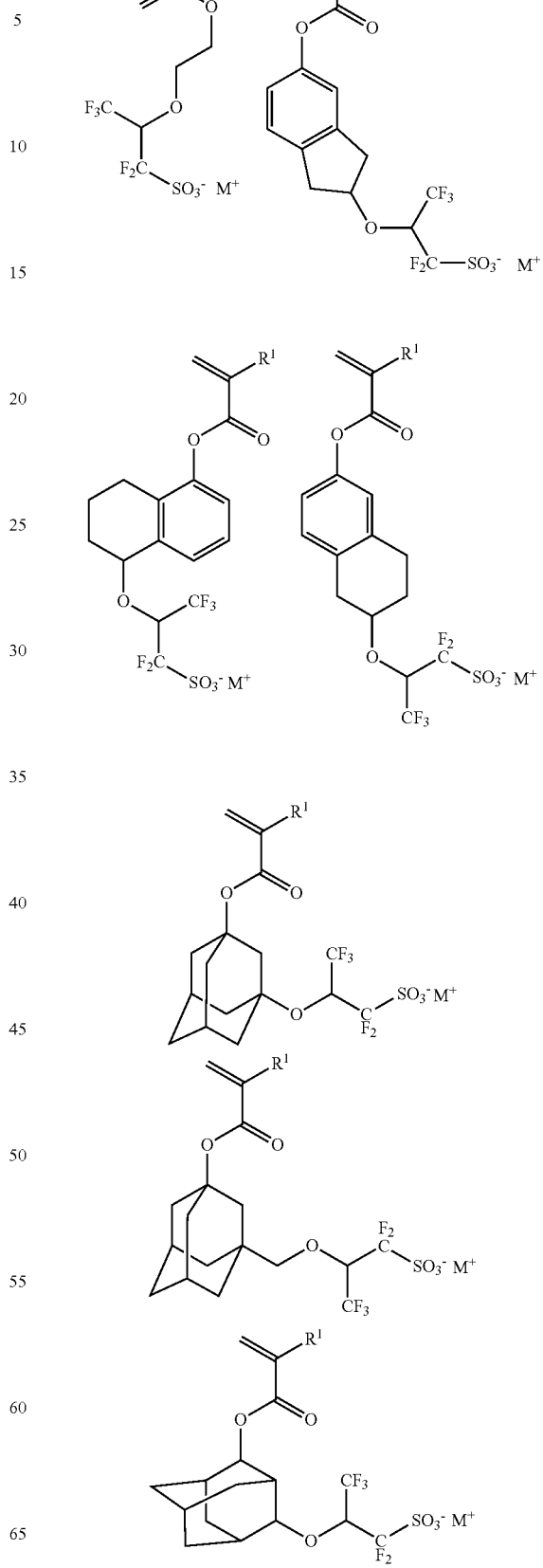

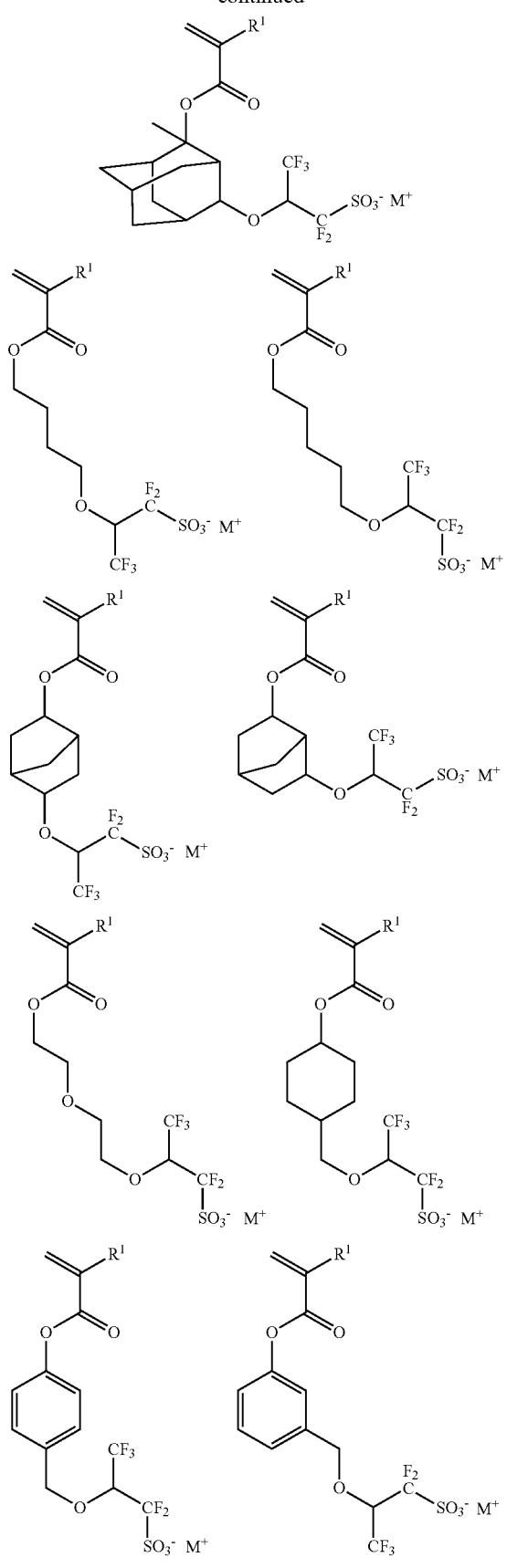
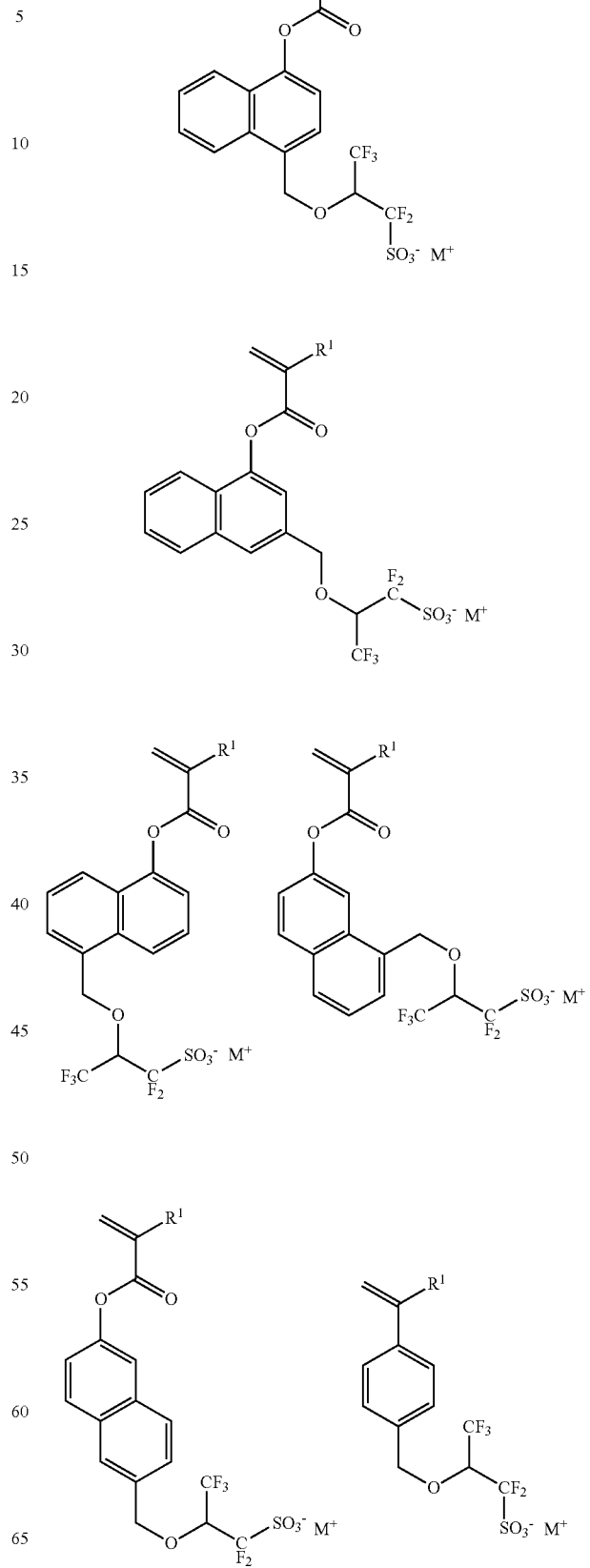

27
-continued
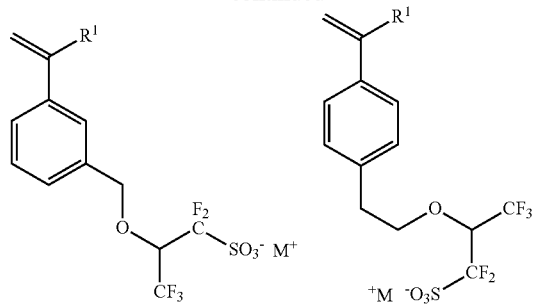
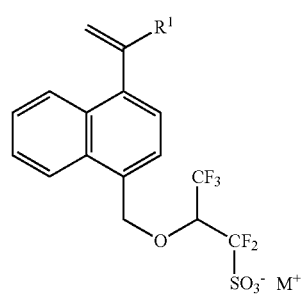
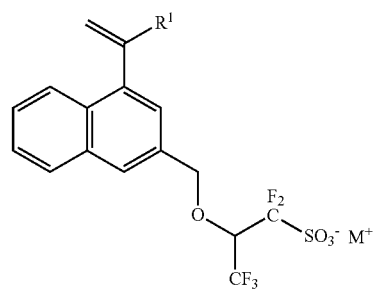
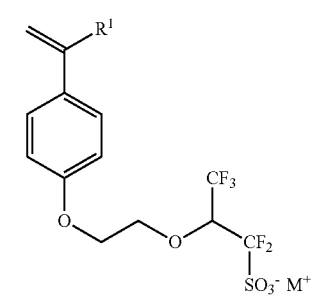
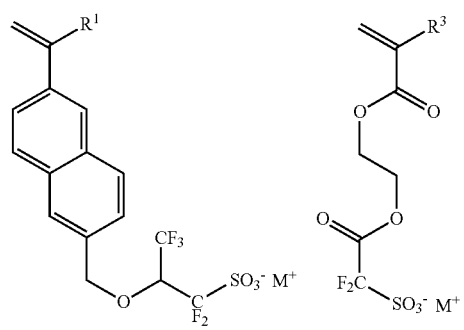
28
-continued
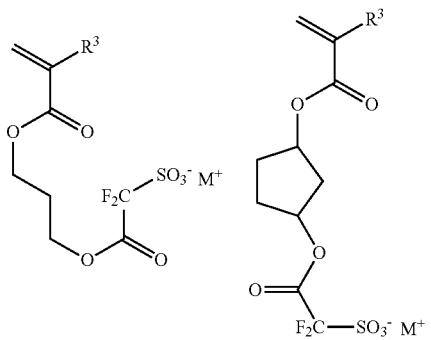
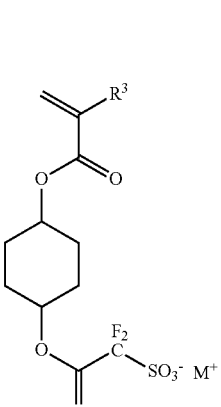 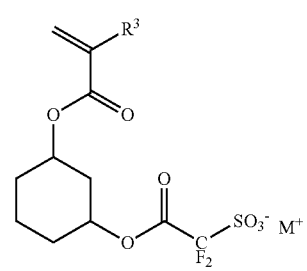
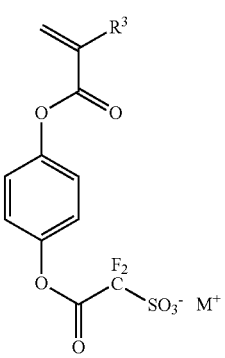 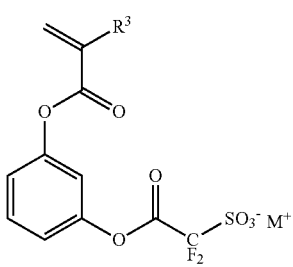
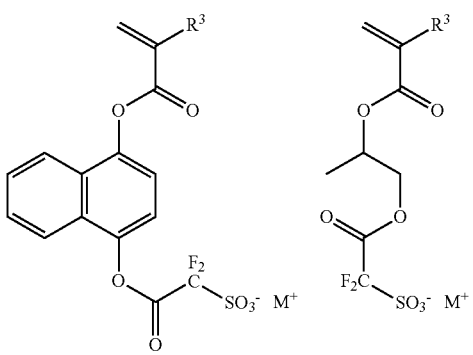

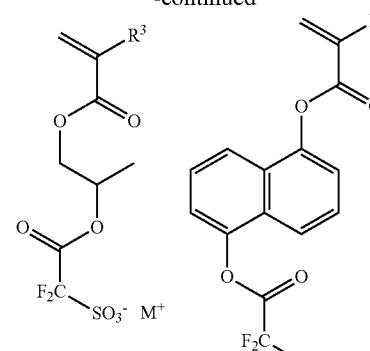
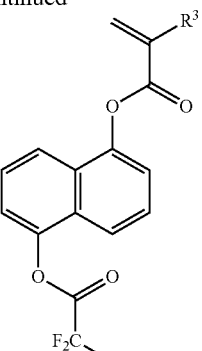
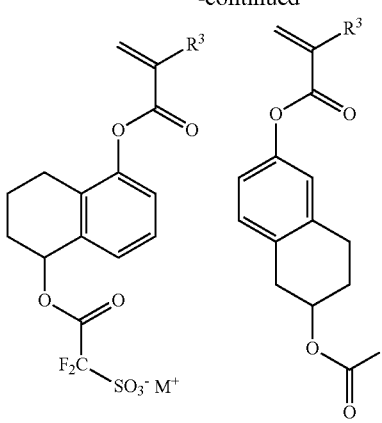
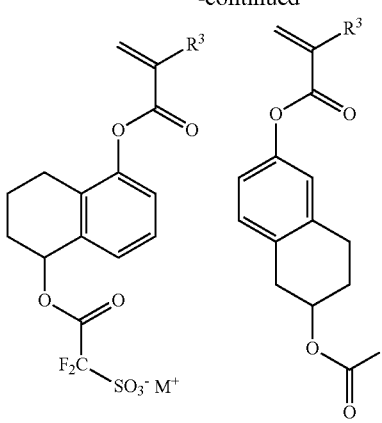
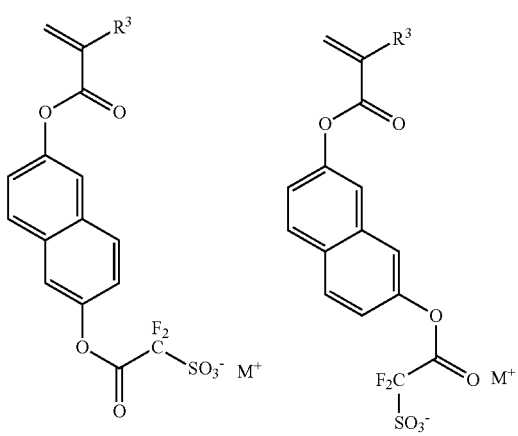
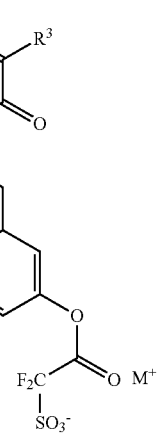
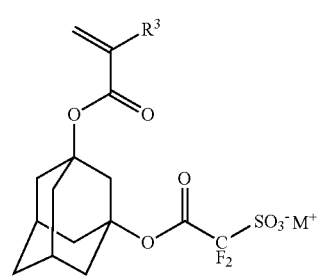
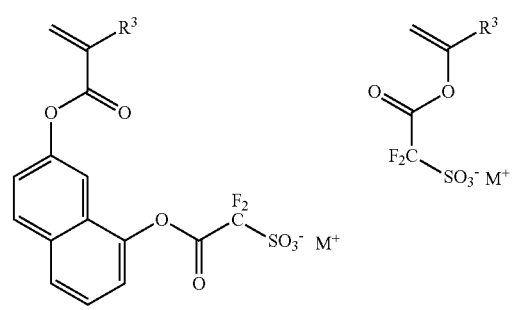
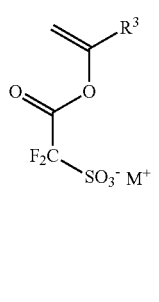
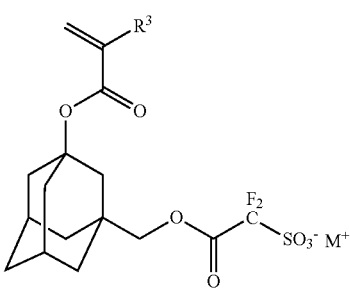
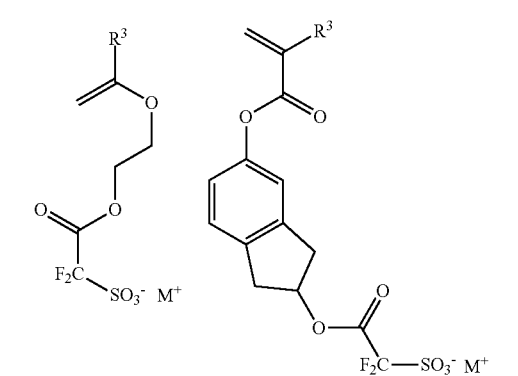
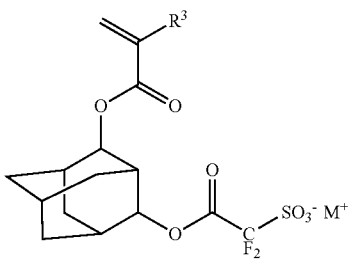
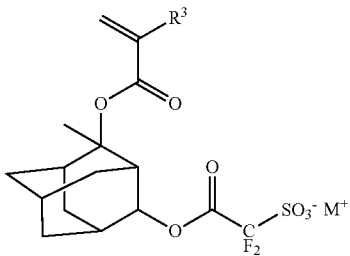

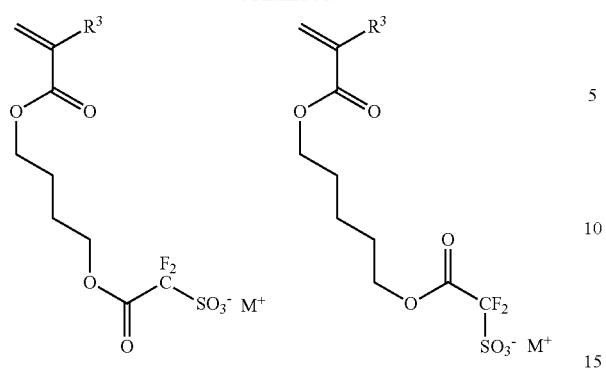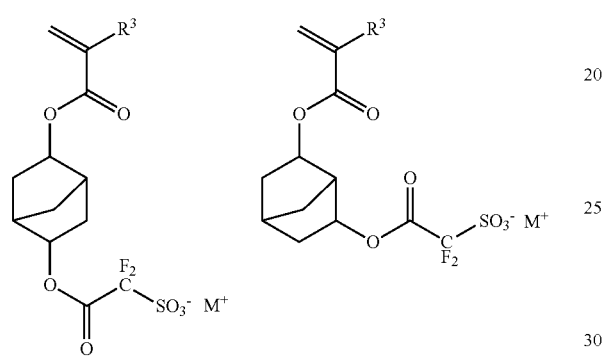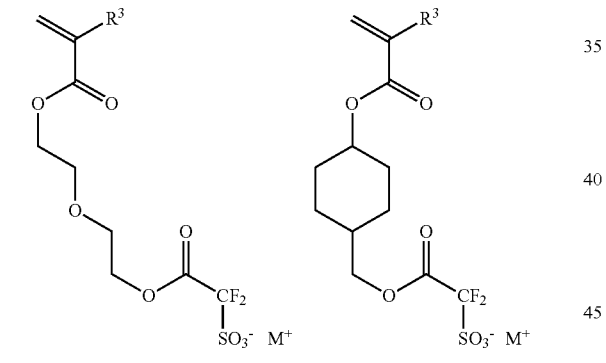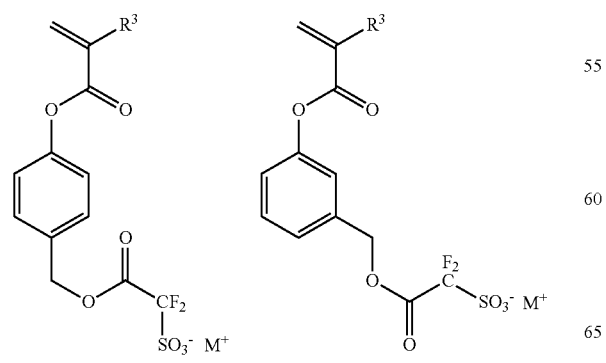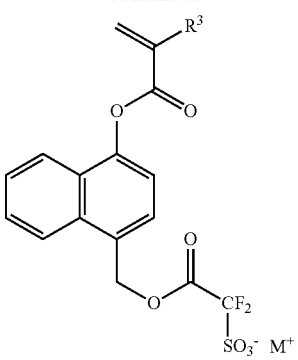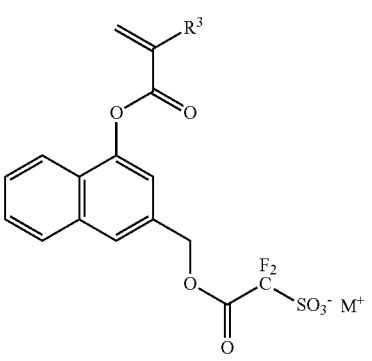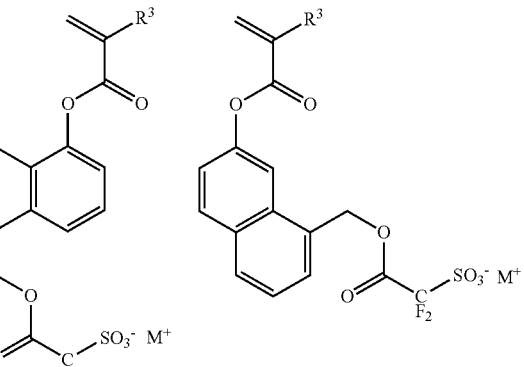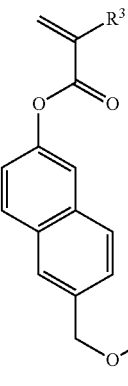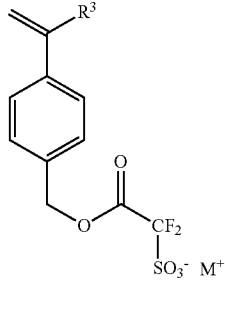

-continued
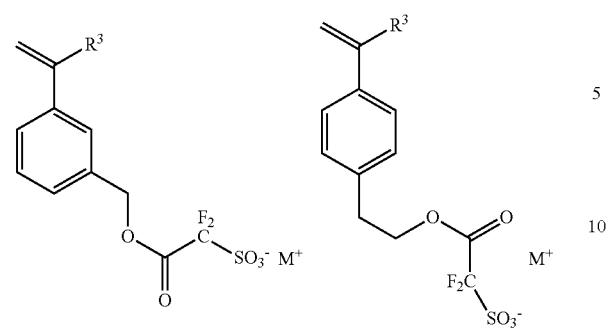
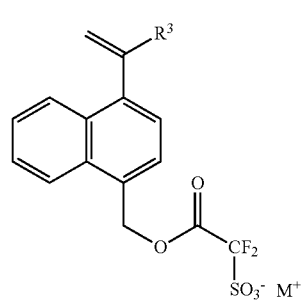
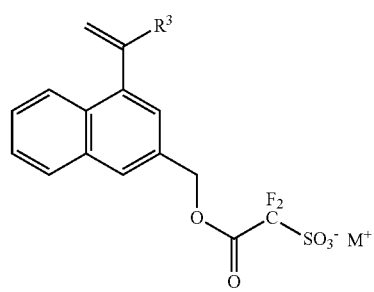
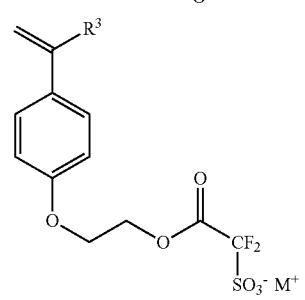
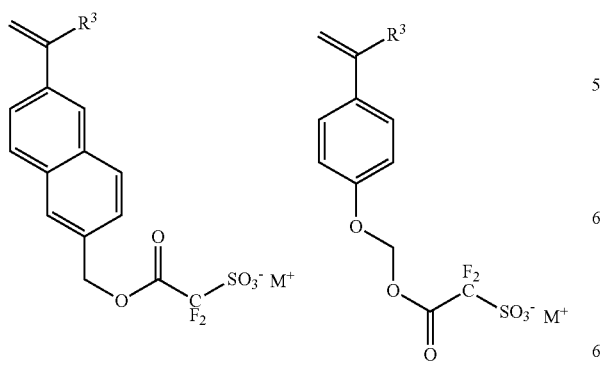
-continued
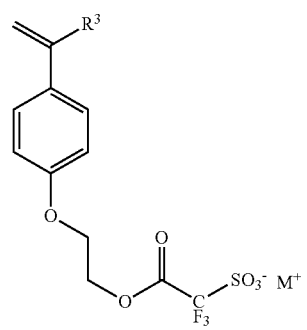
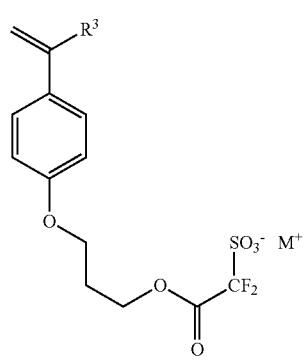
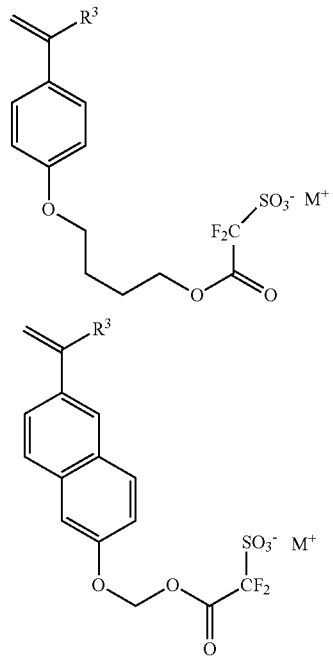
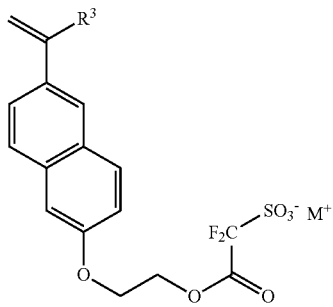

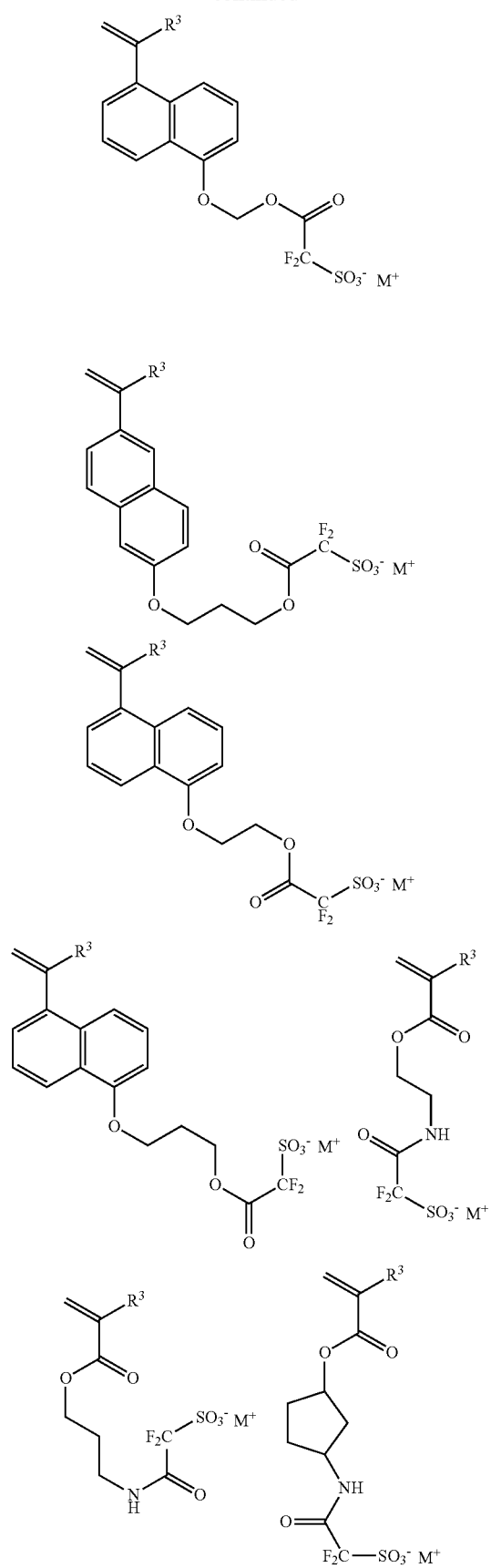

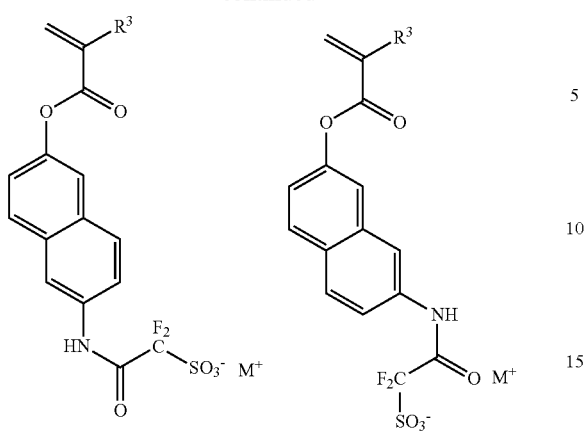
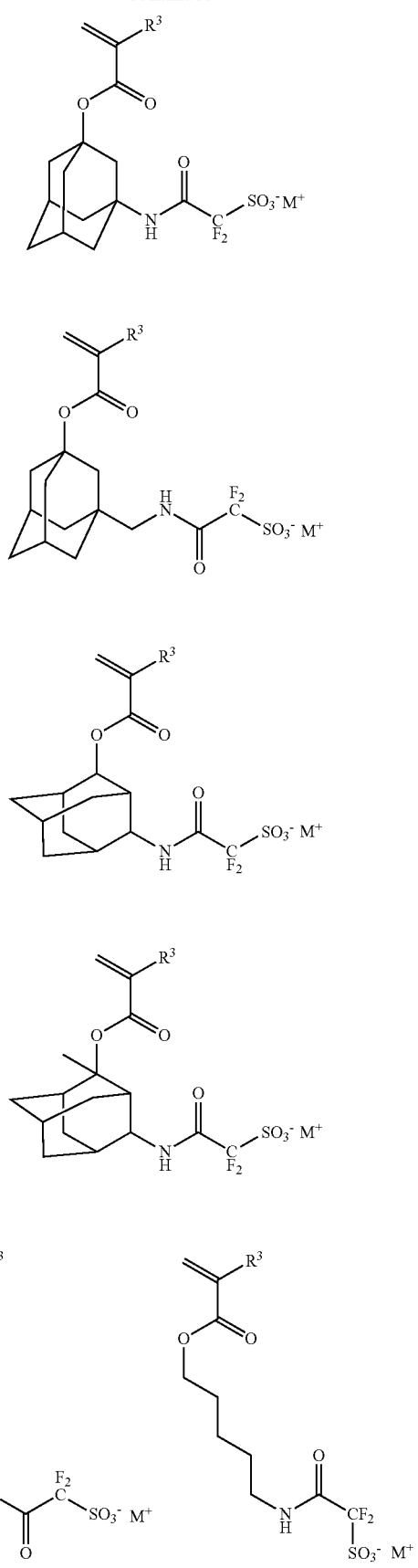

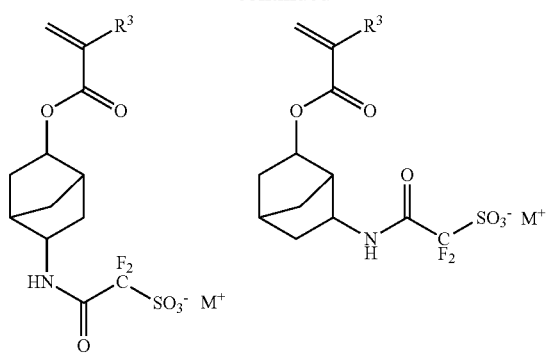
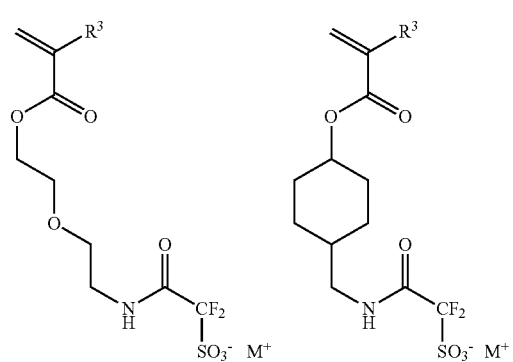
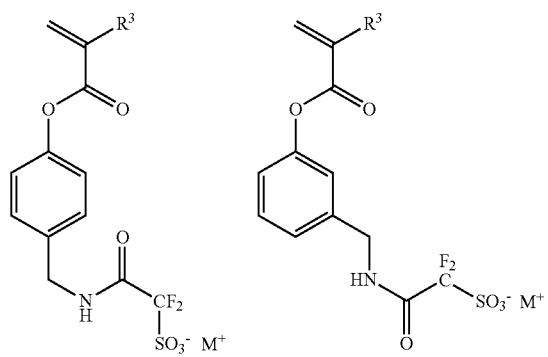
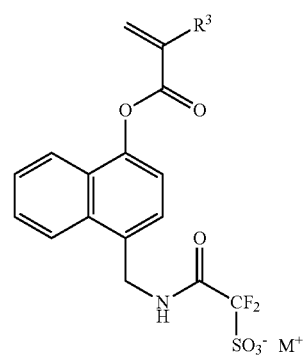
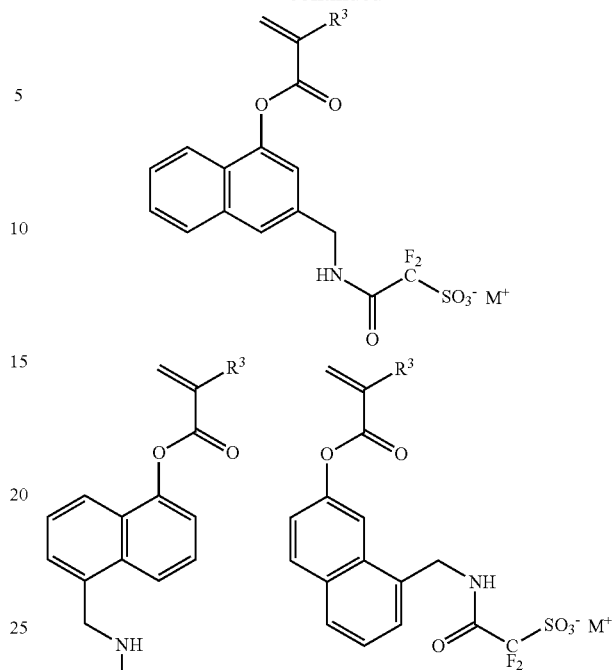
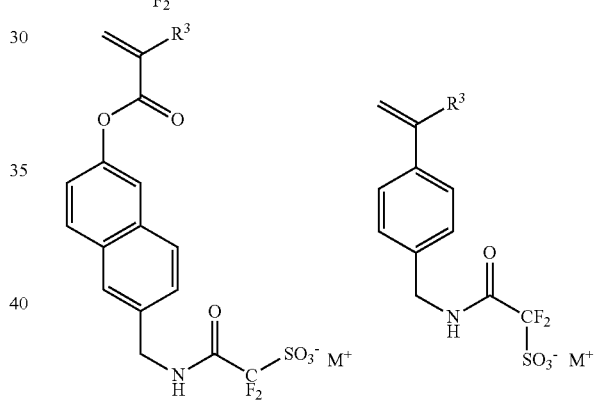
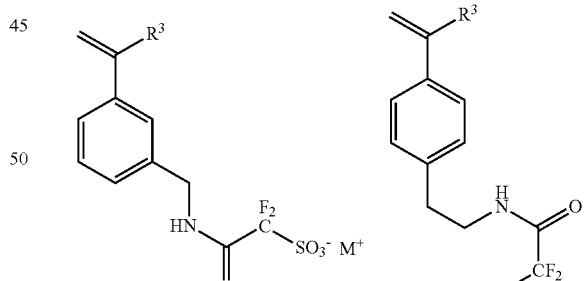
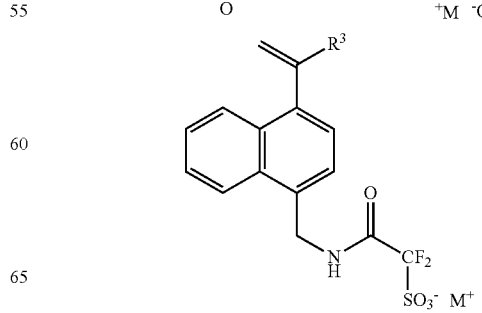

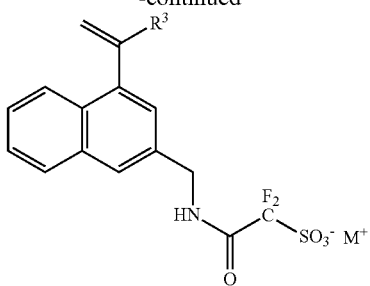
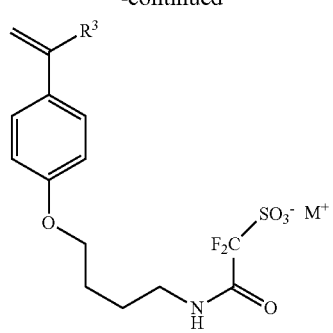

-continued
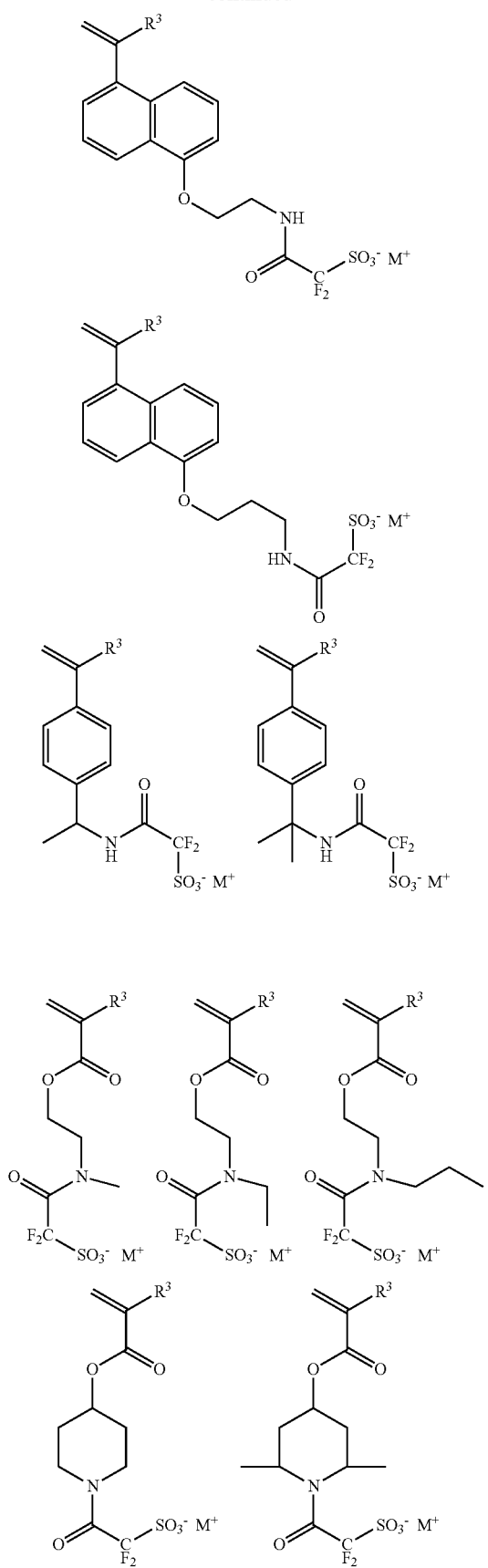
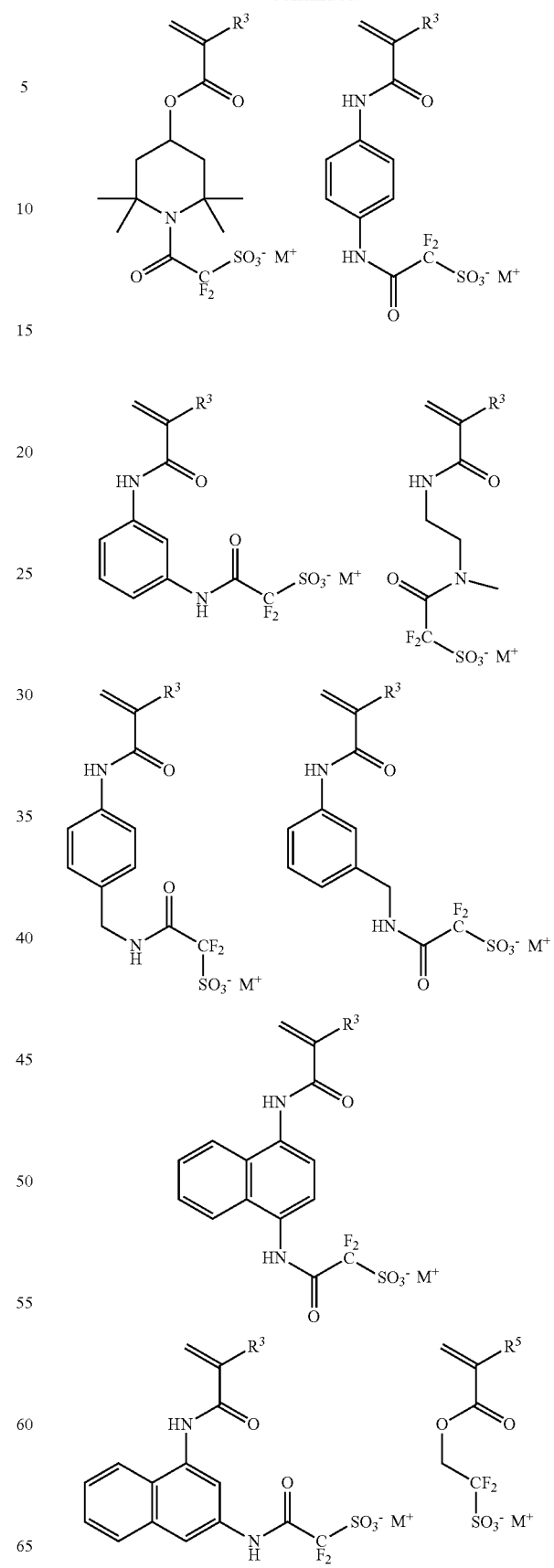

-continued
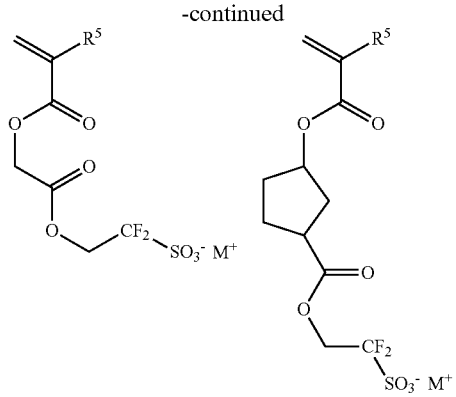
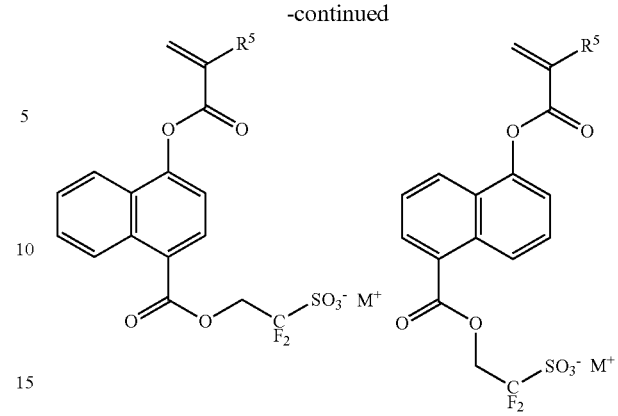
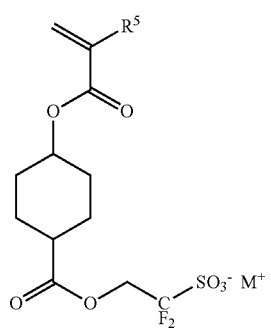
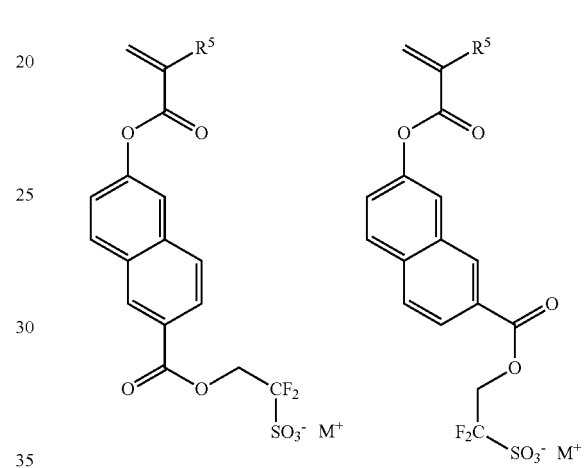
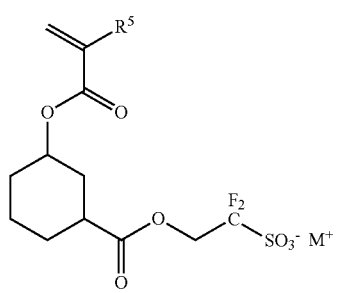
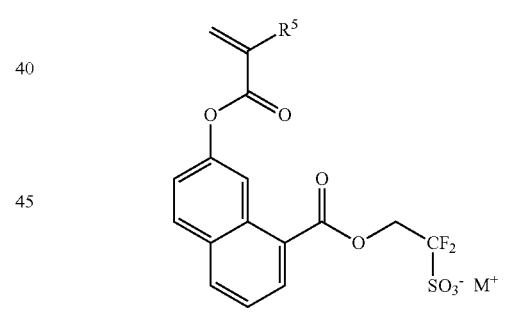
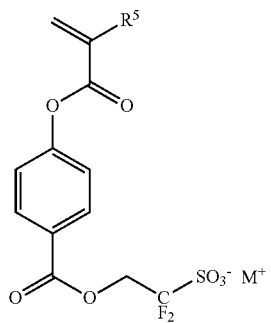
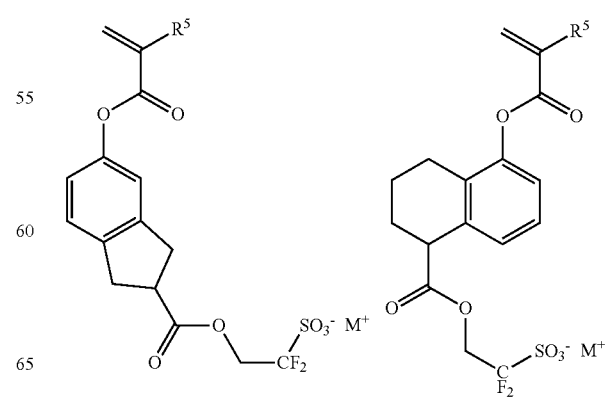
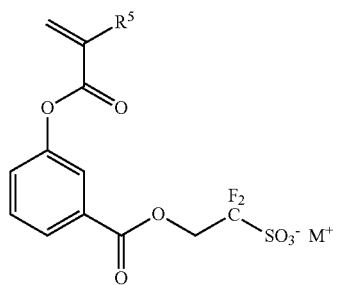

-continued
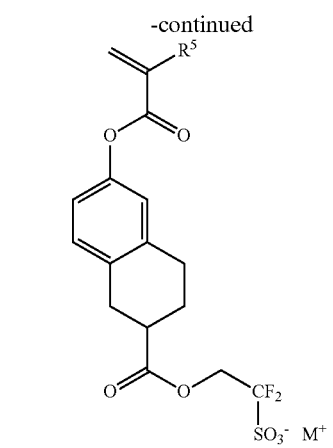
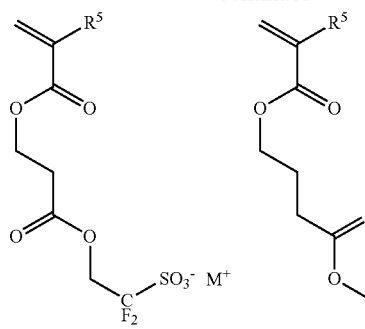
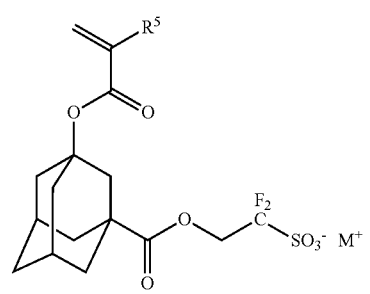
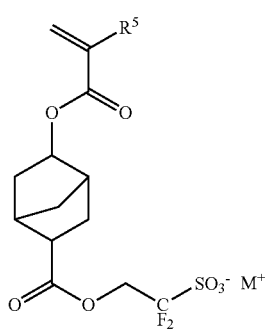
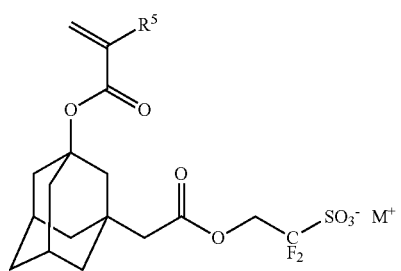
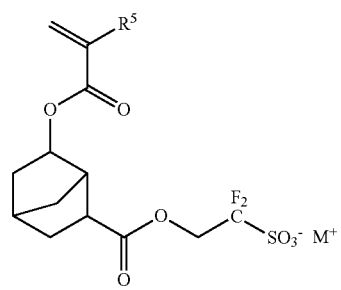
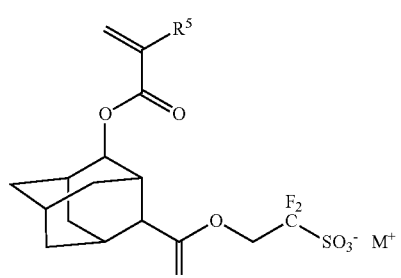
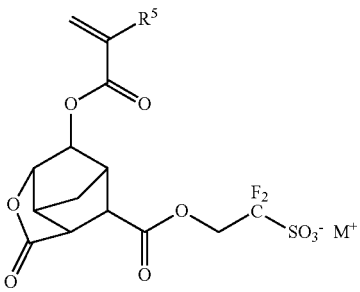
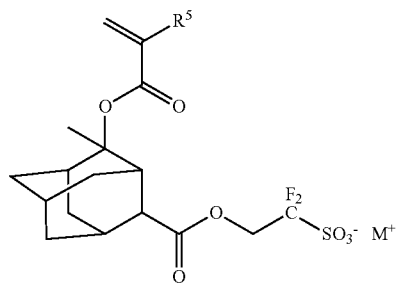
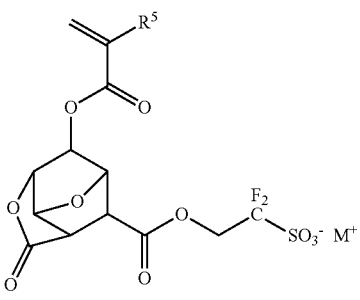

-continued
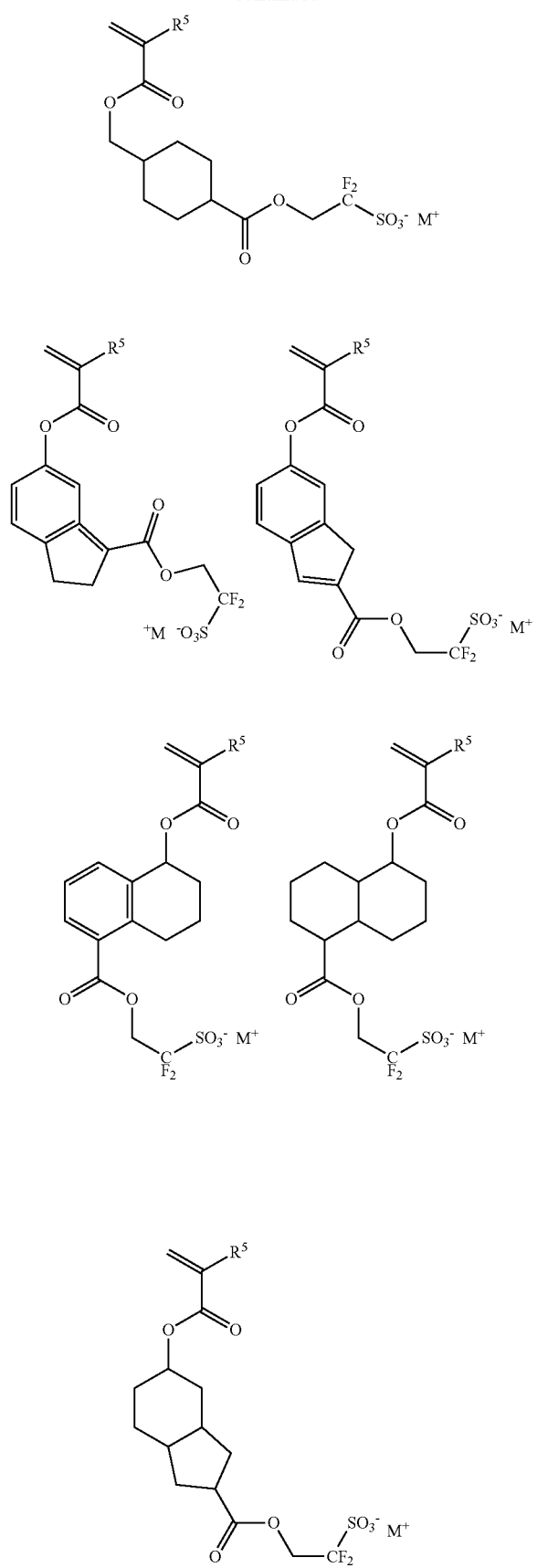
-continued
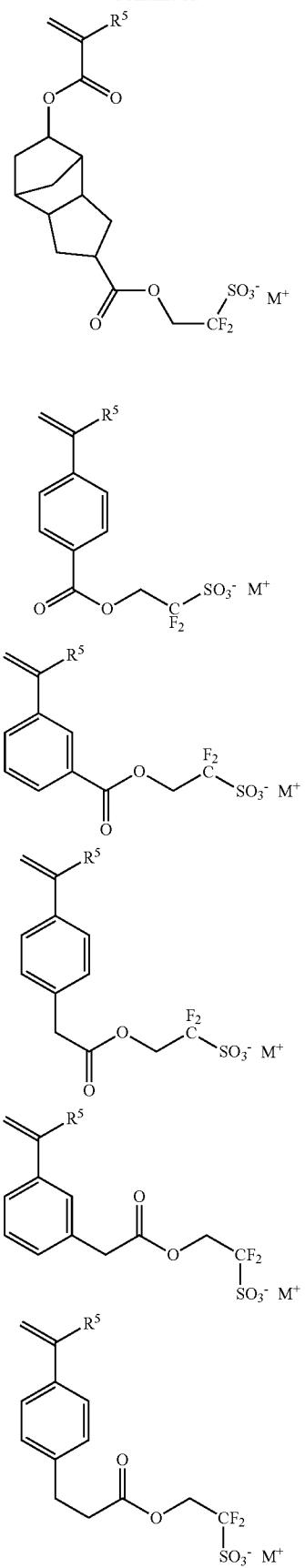

51
-continued
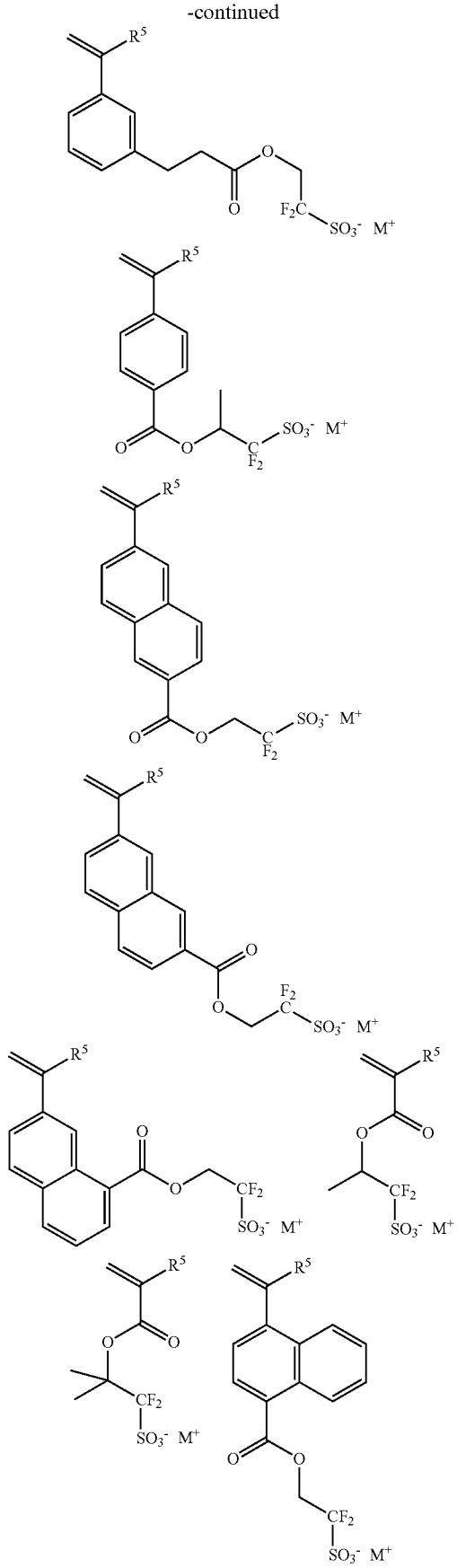
52
-continued
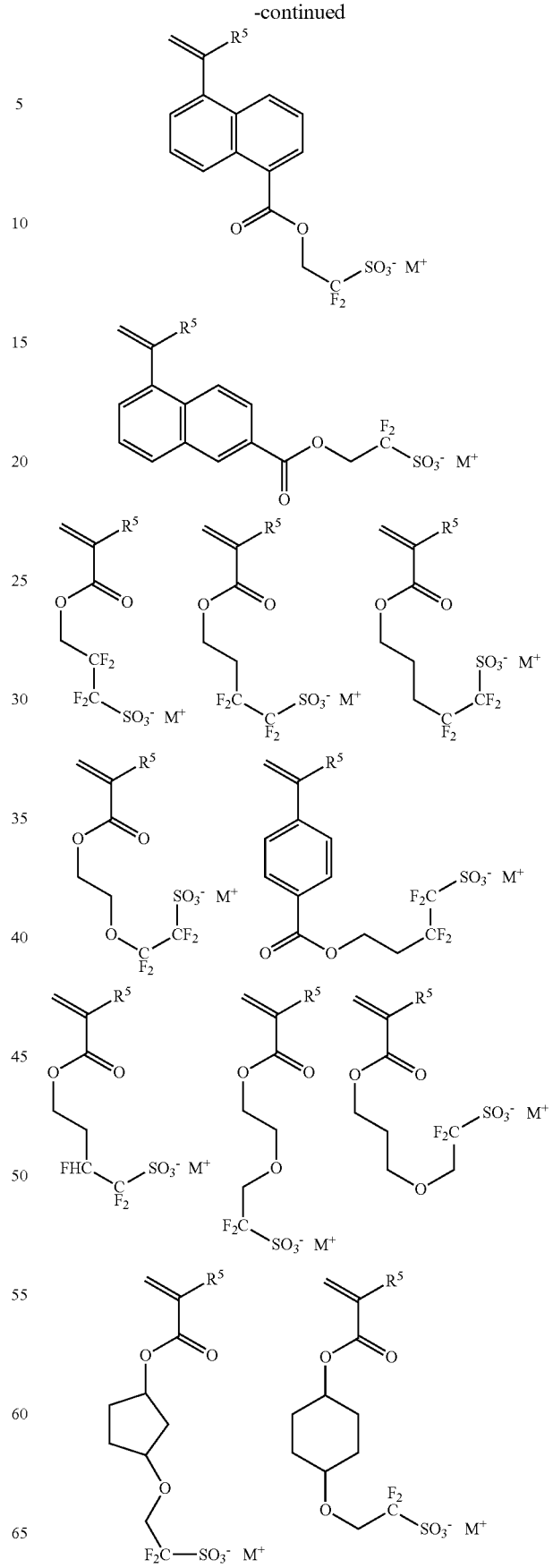

-continued
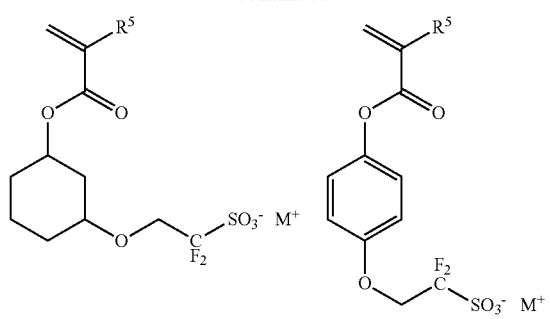
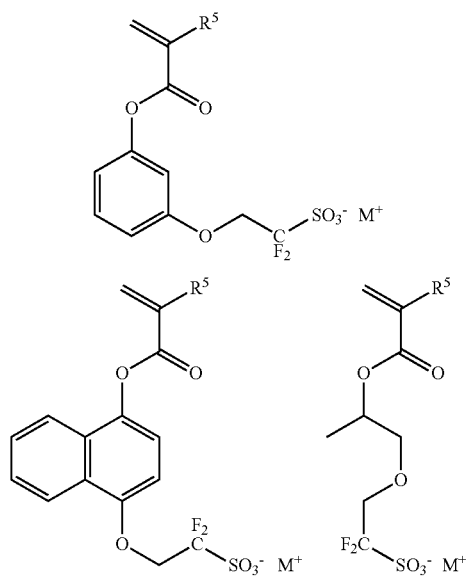
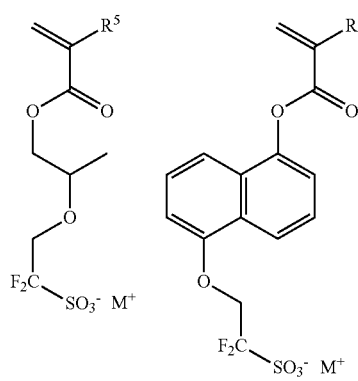
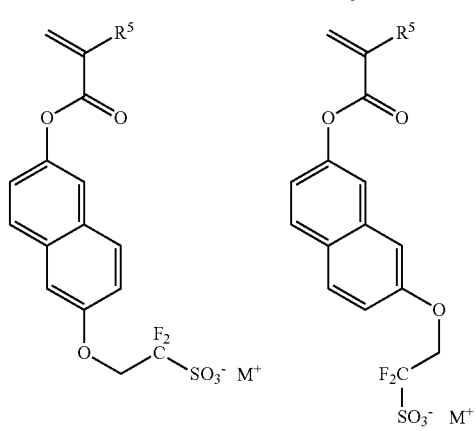
-continued
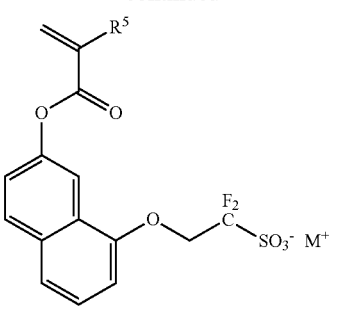
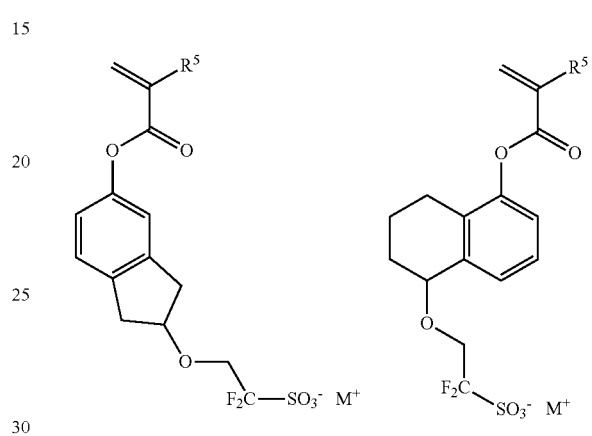
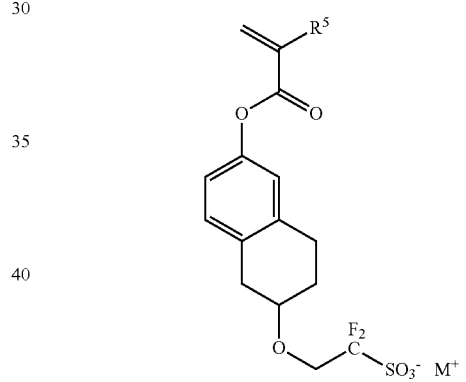
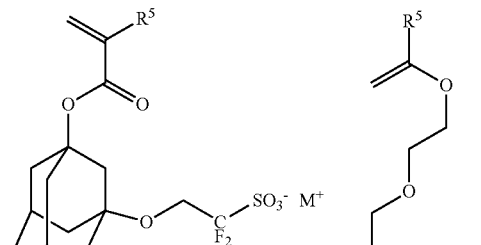
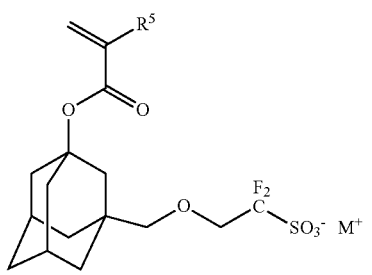

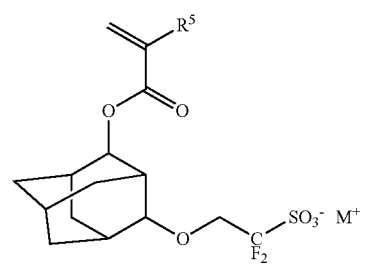
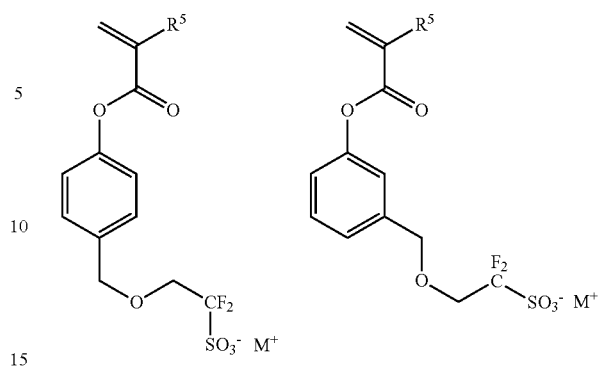
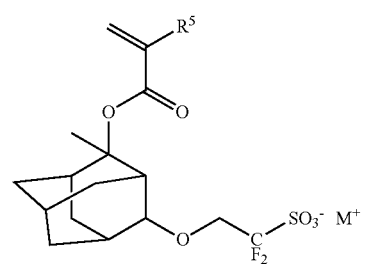
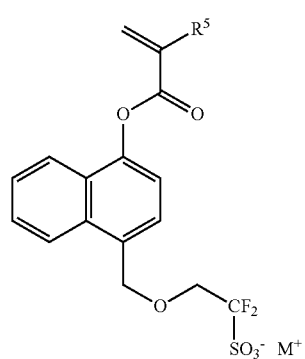
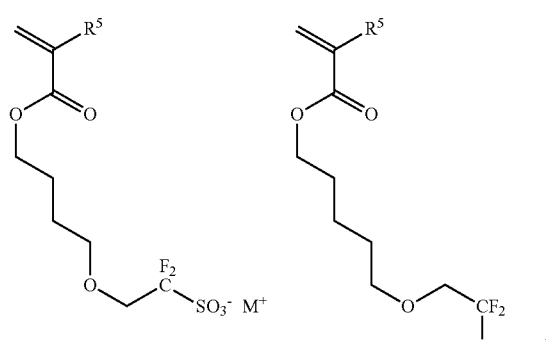
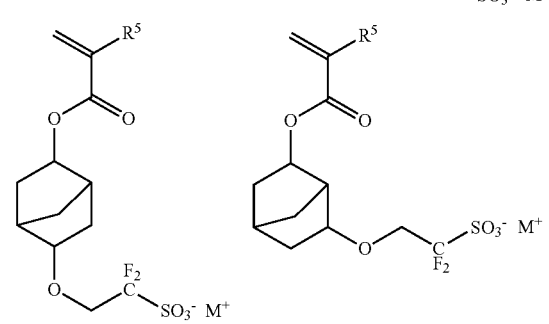
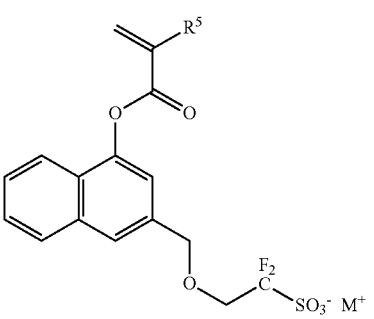
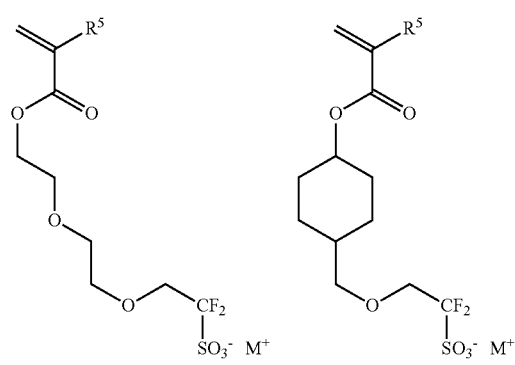
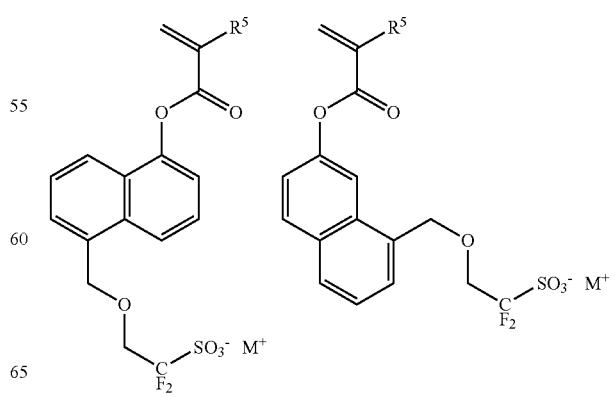

57
-continued
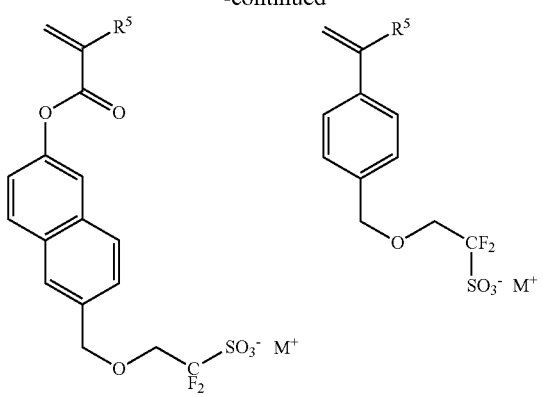
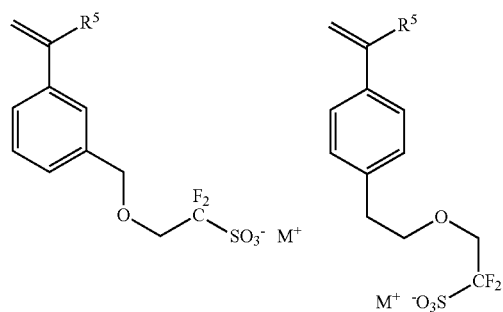
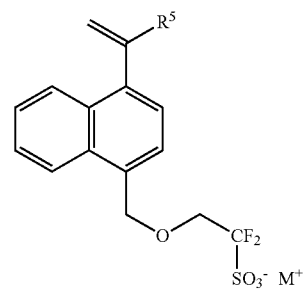
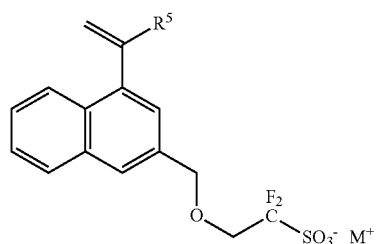
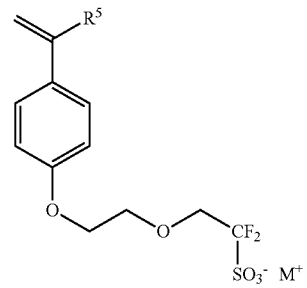
58
-continued
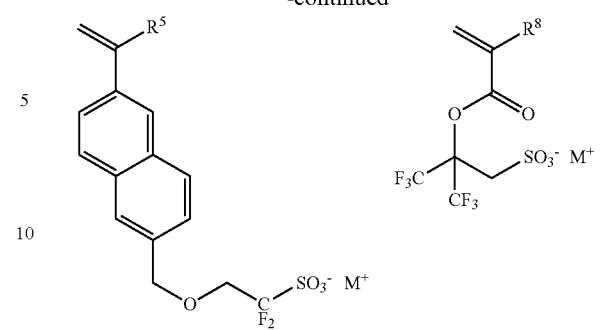
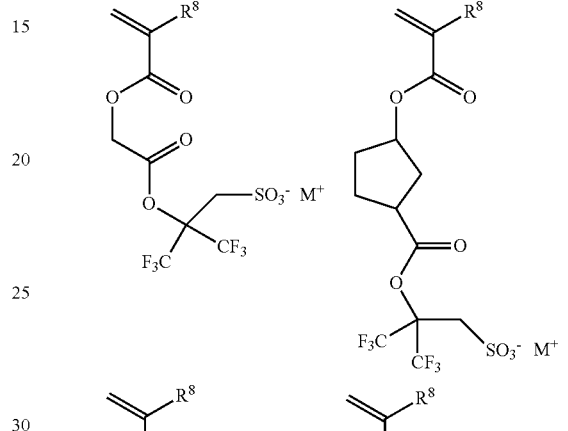
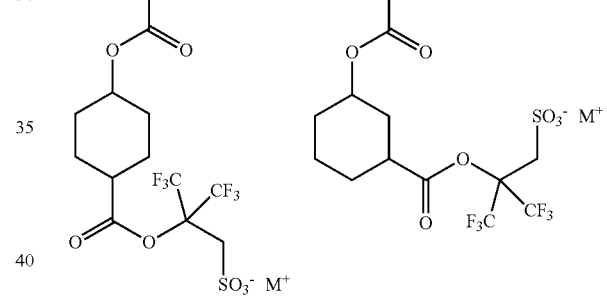
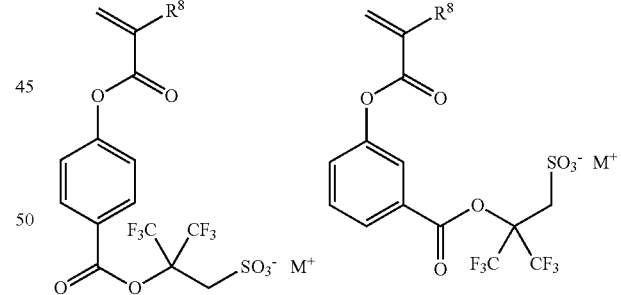
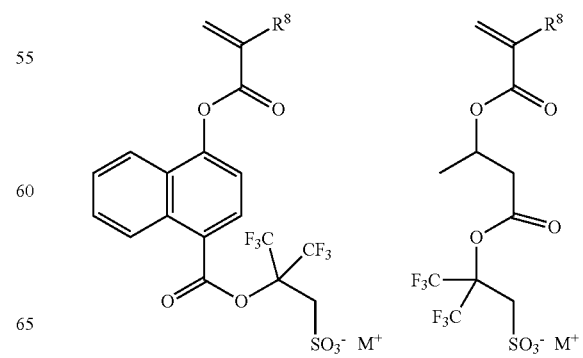

-continued
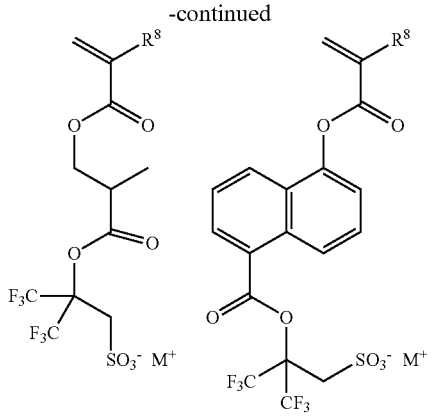 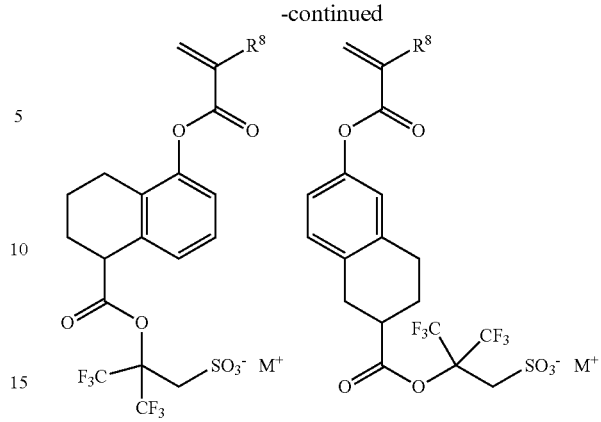
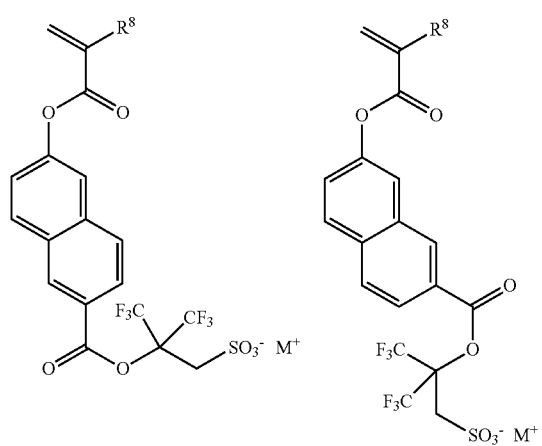 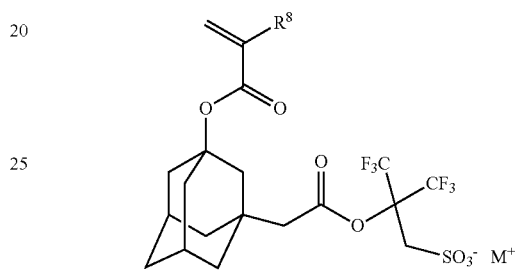
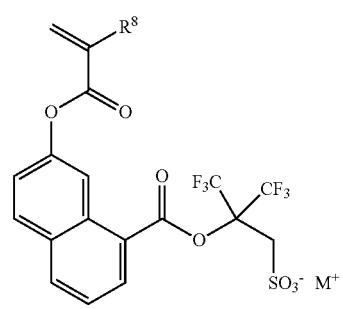 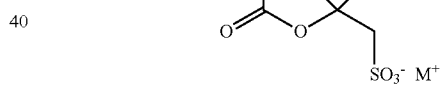
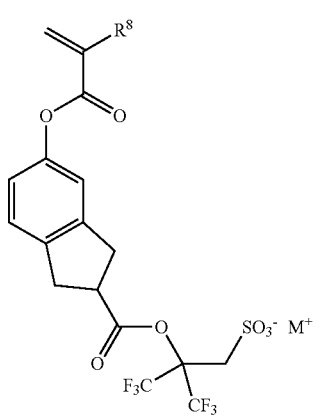 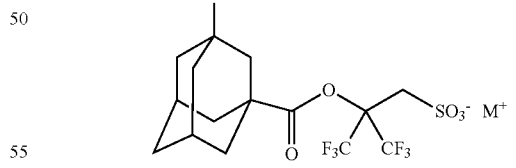
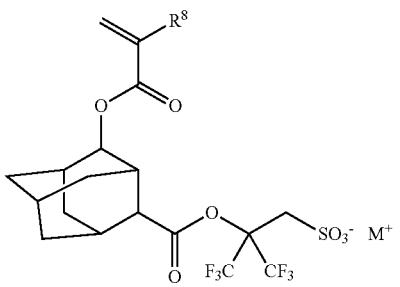

-continued
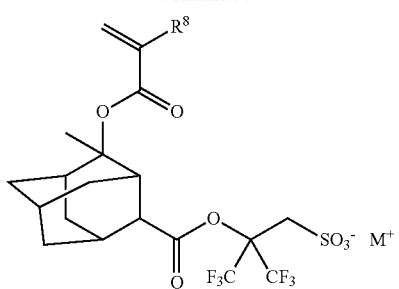
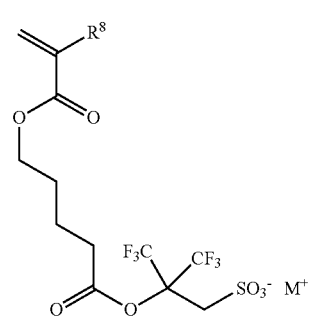
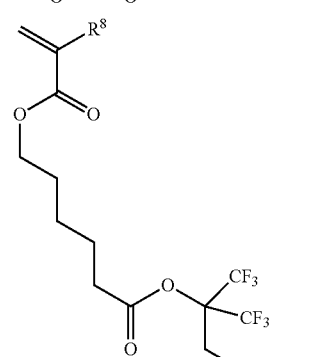
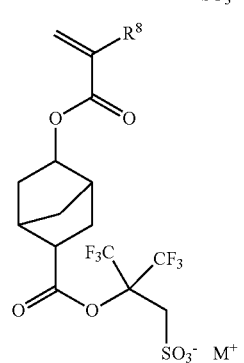
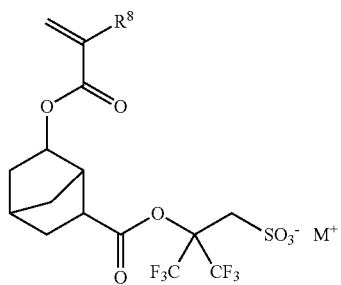
-continued
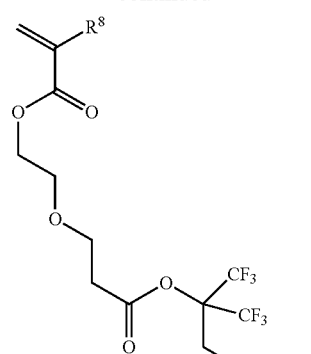
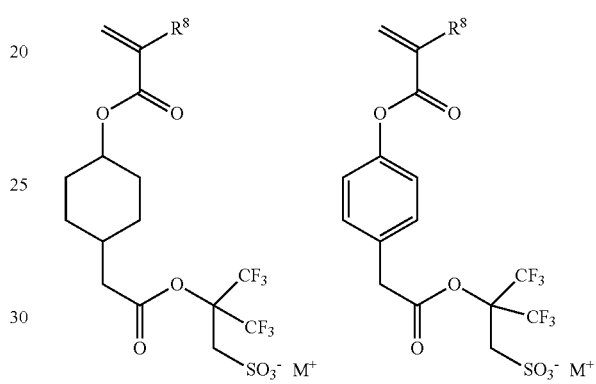
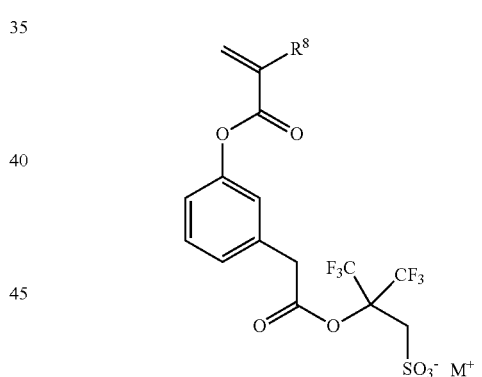
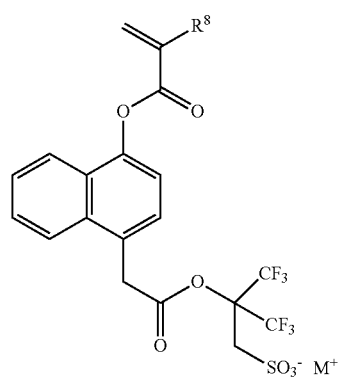

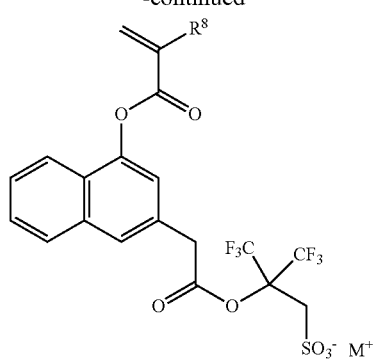
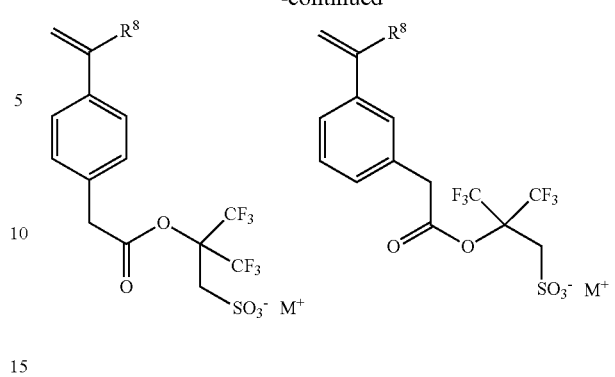
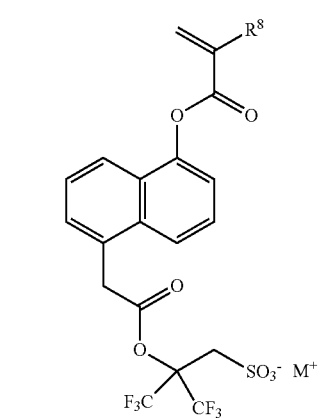
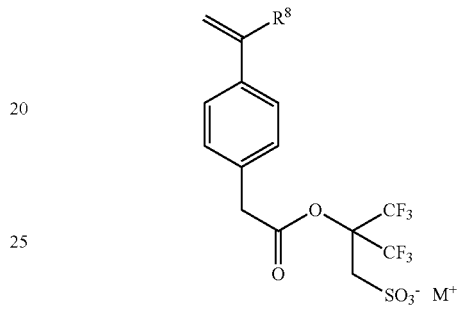
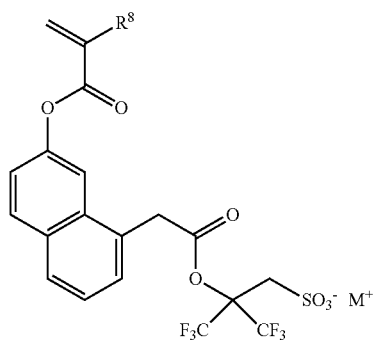
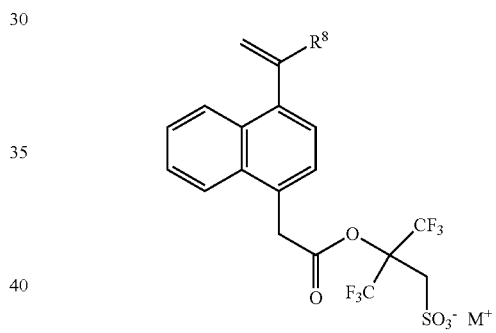
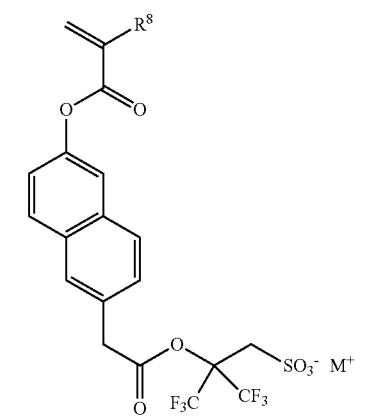
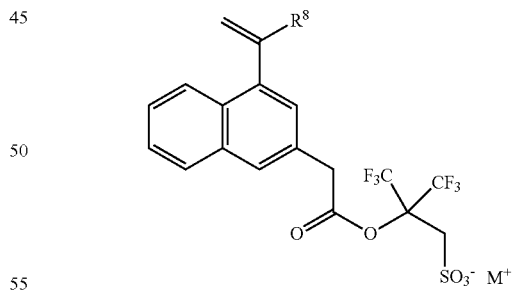
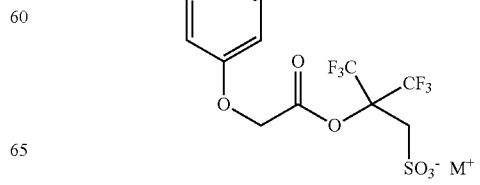

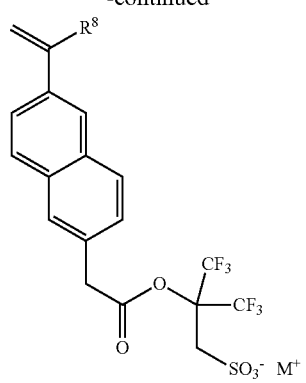
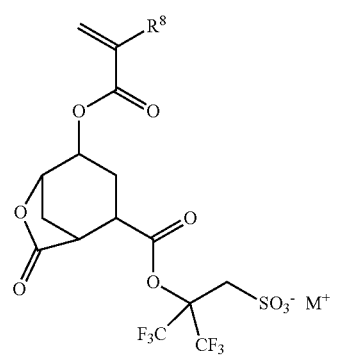
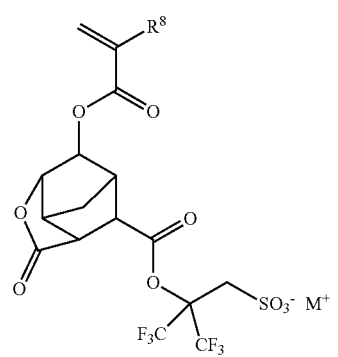
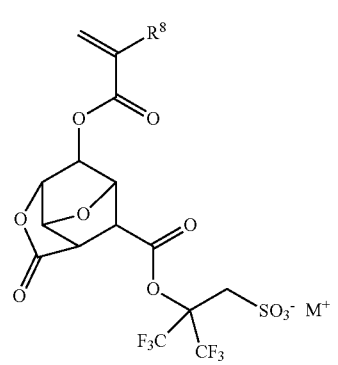
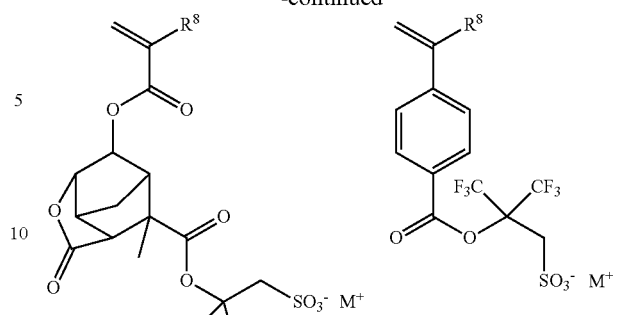
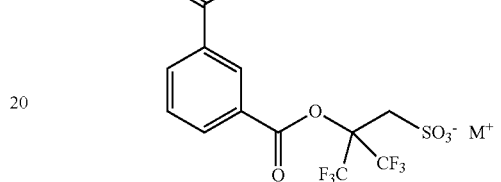
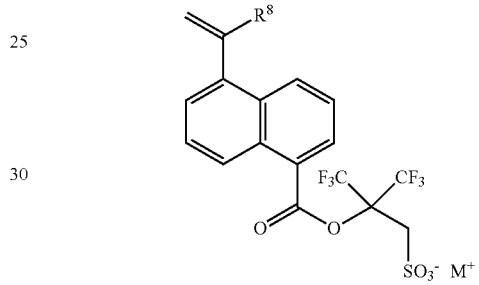
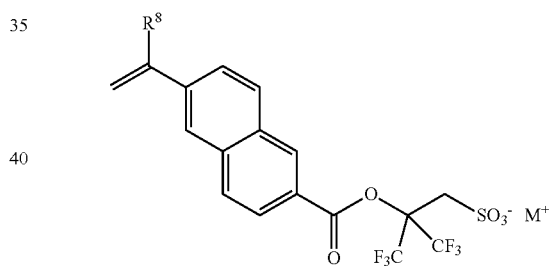
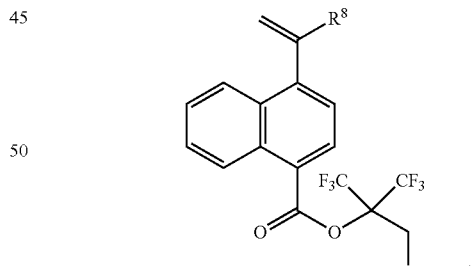
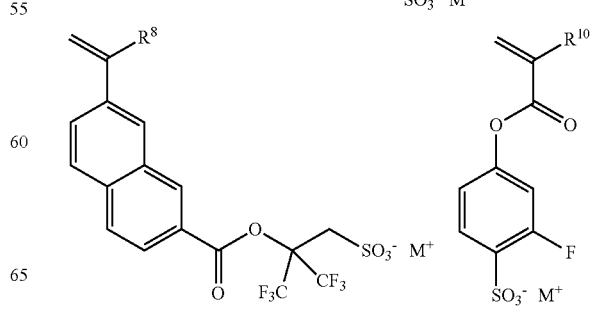

-continued
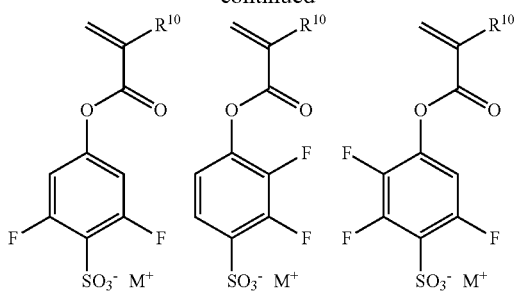
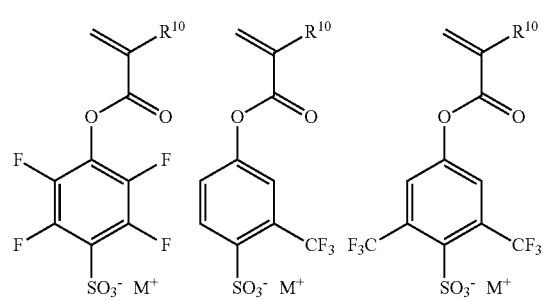
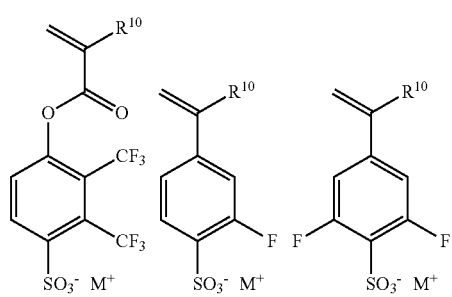
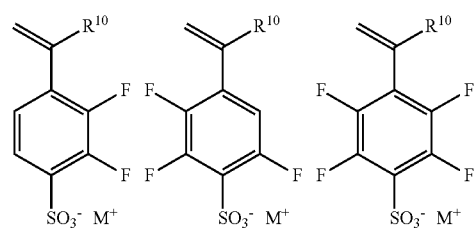
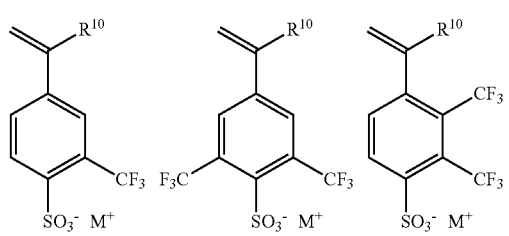
Specific examples of sulfonimide salt monomer to give the repeating unit-a6 in the above can include the following.
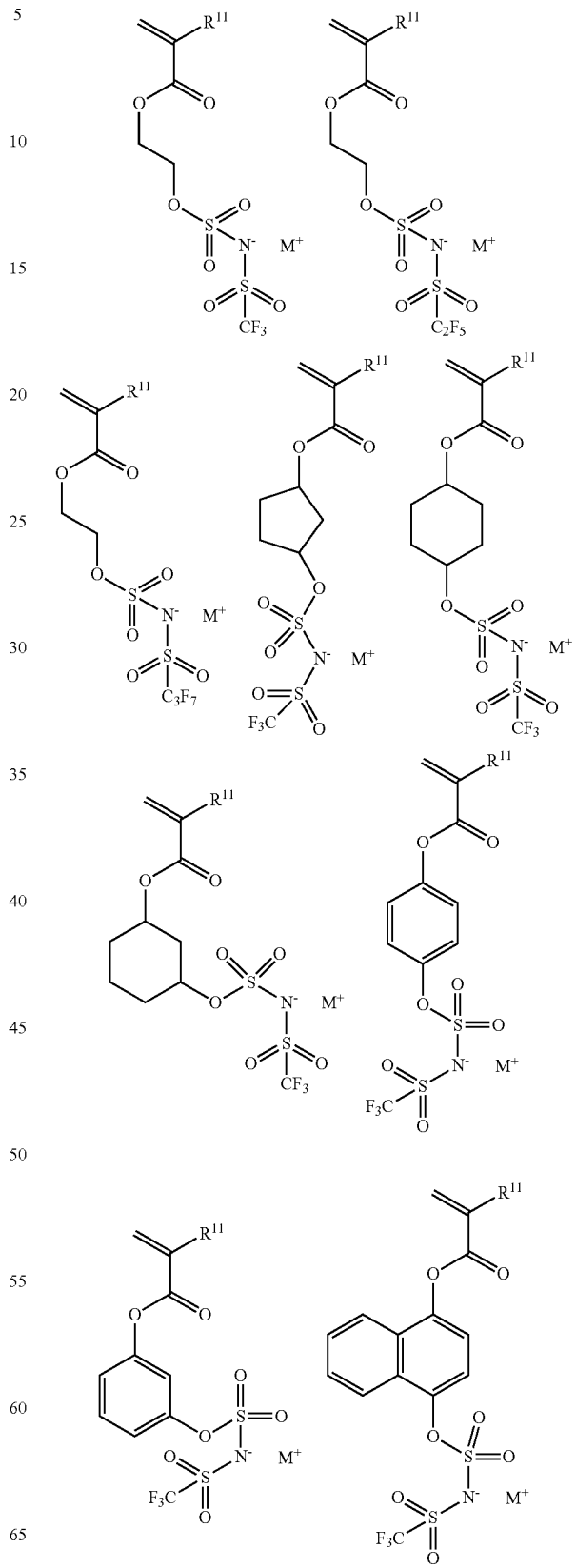

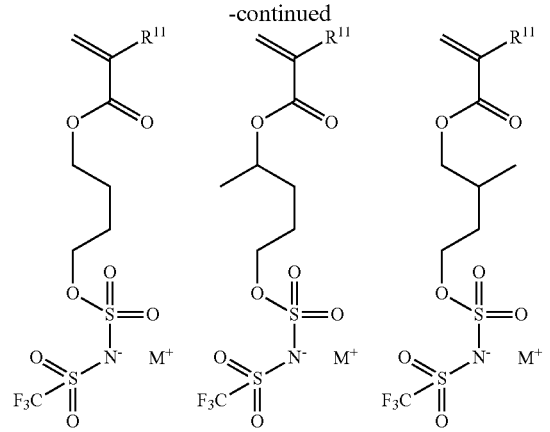
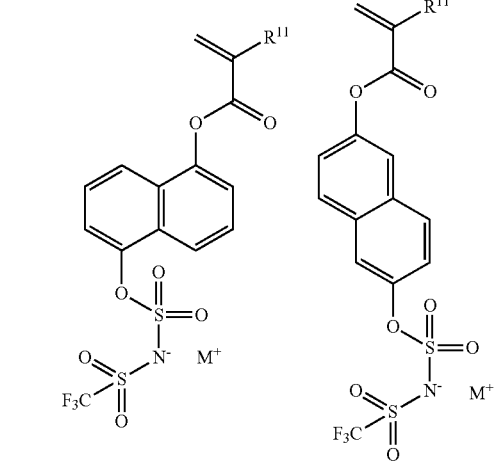
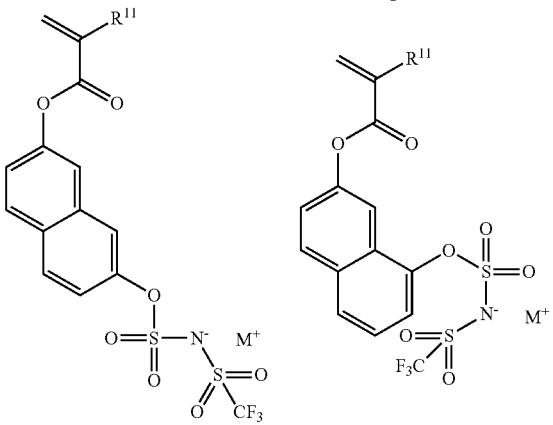
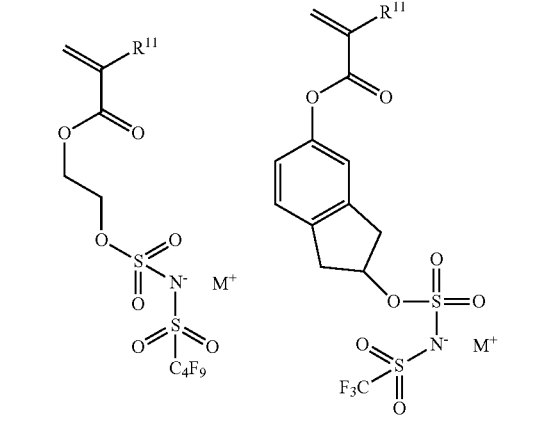
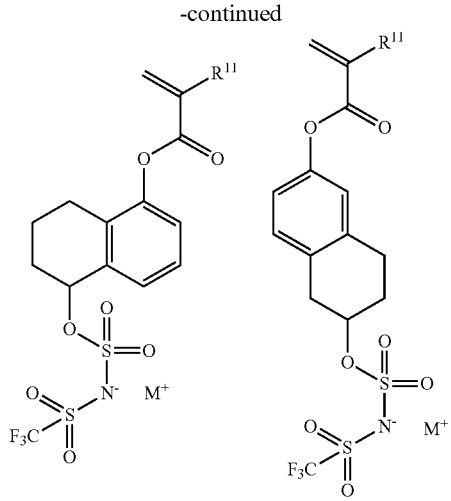
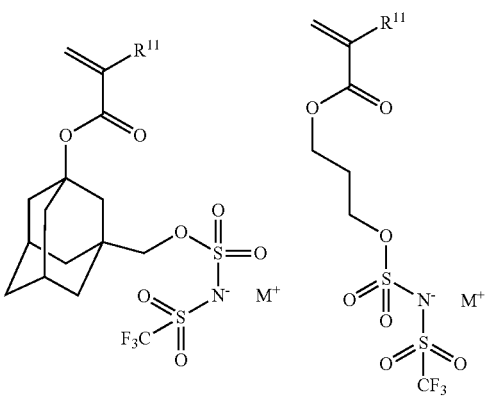
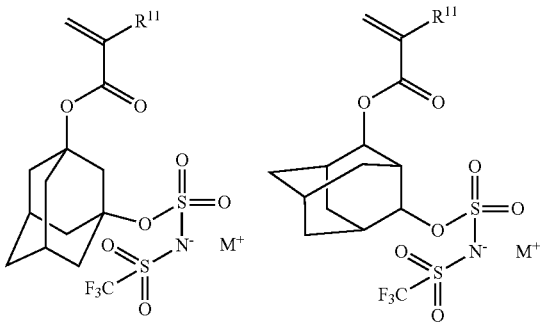
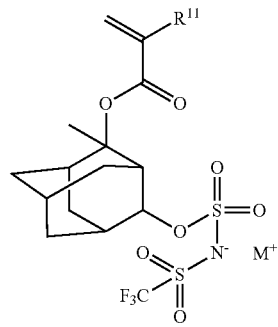

71
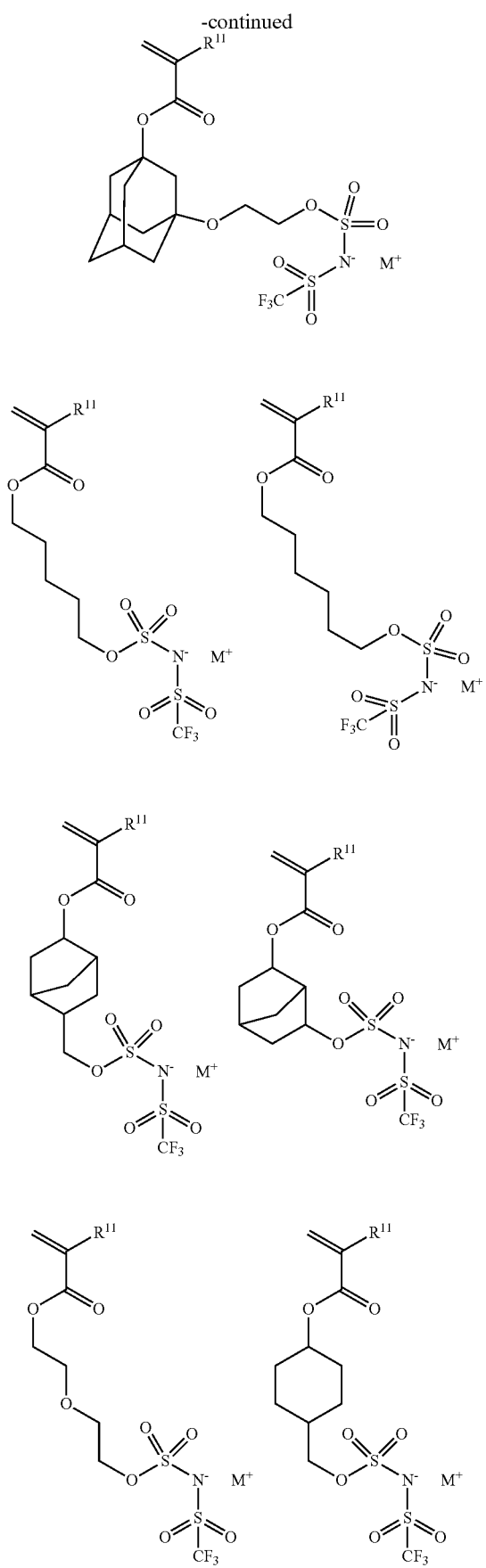
72
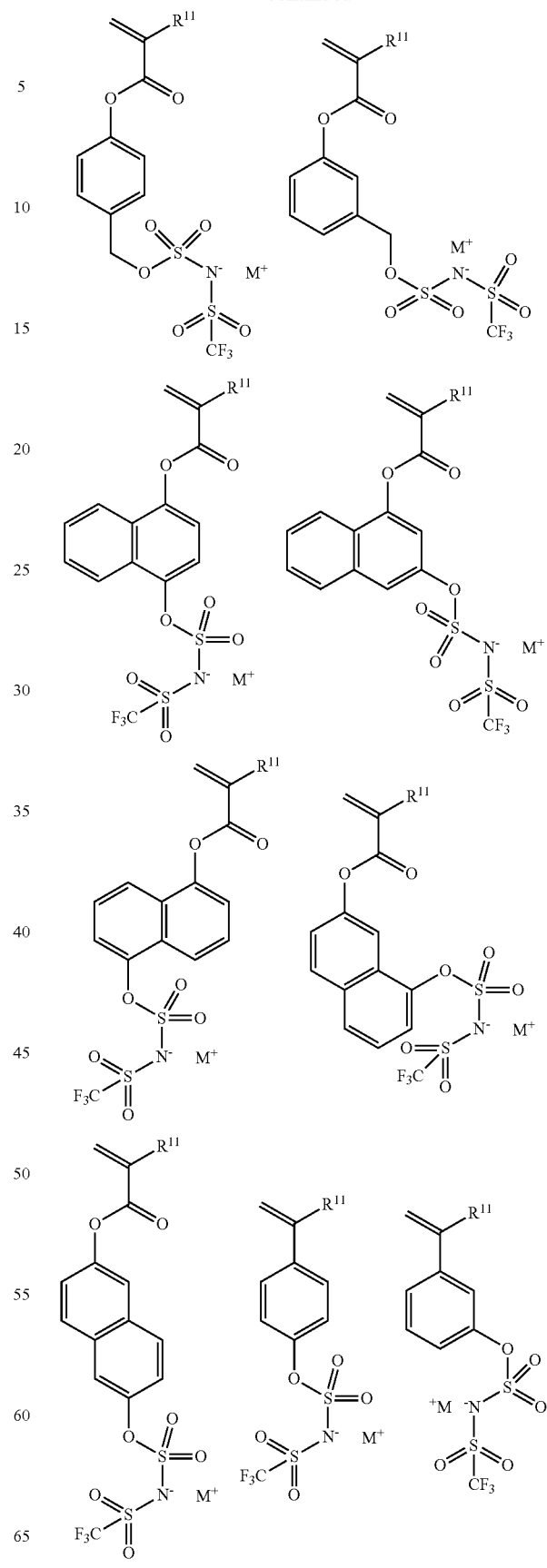

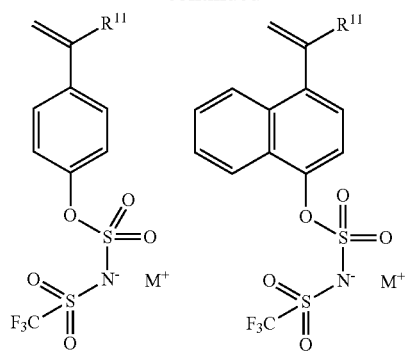
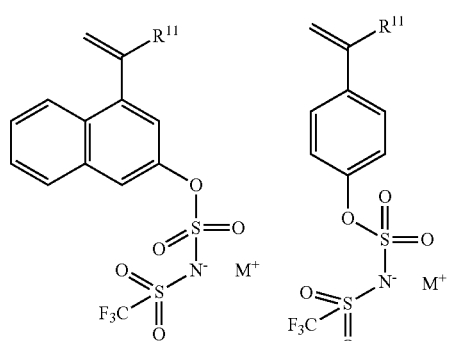
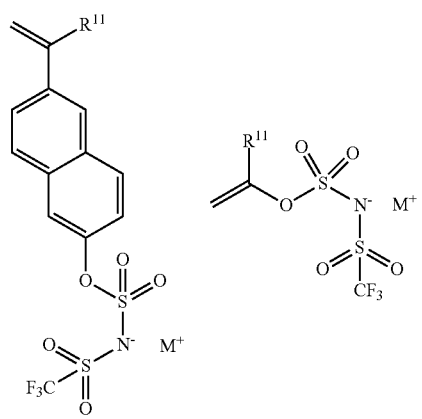
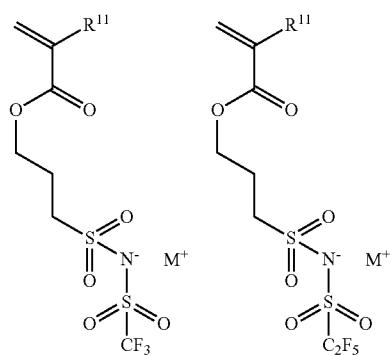
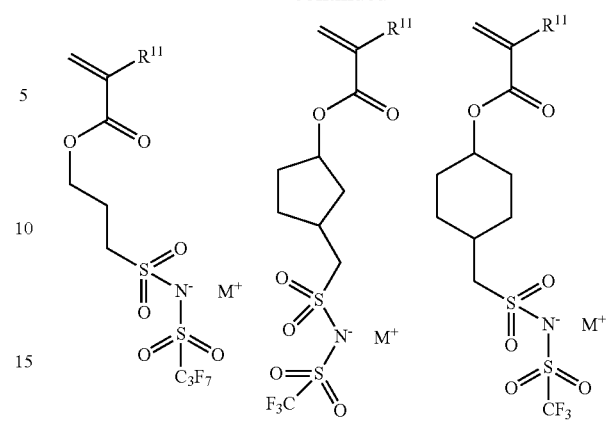
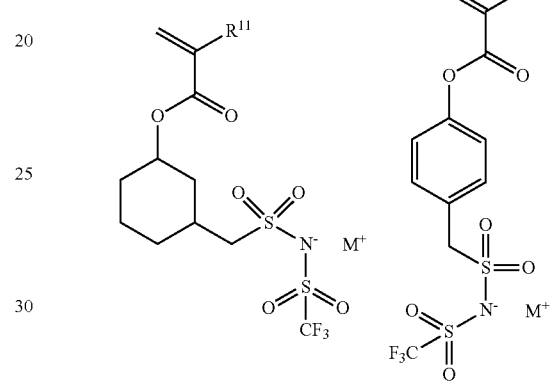
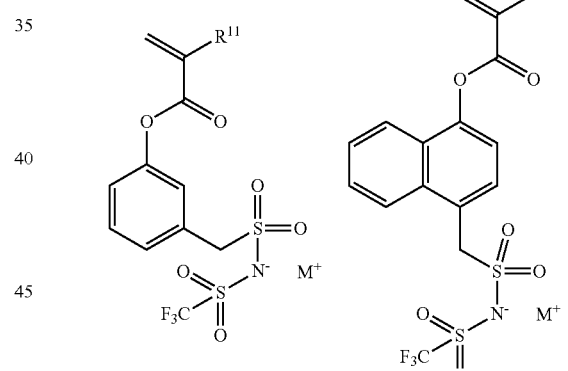
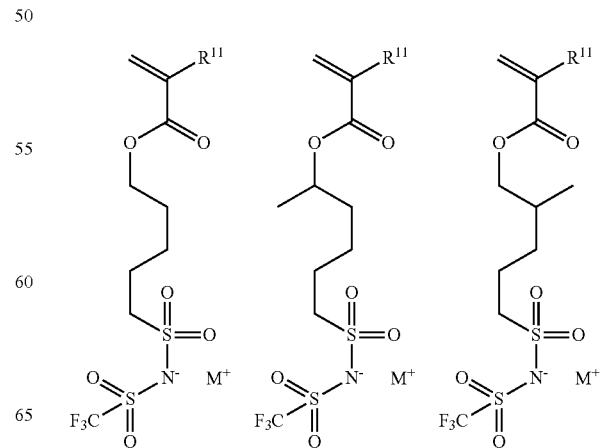

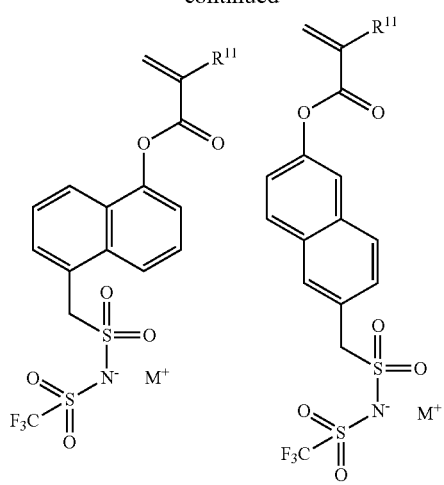
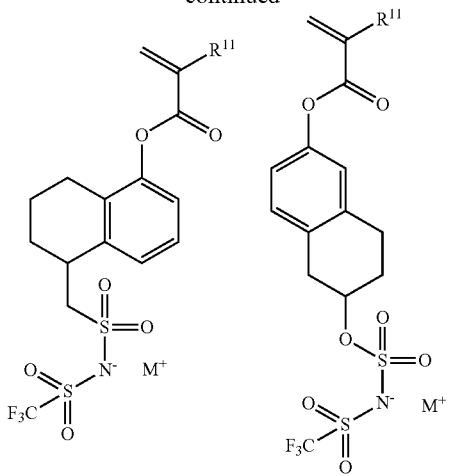
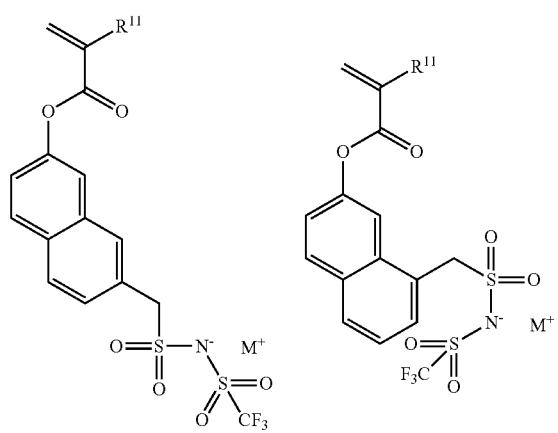
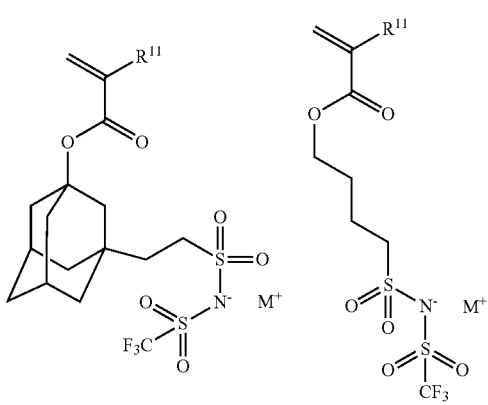
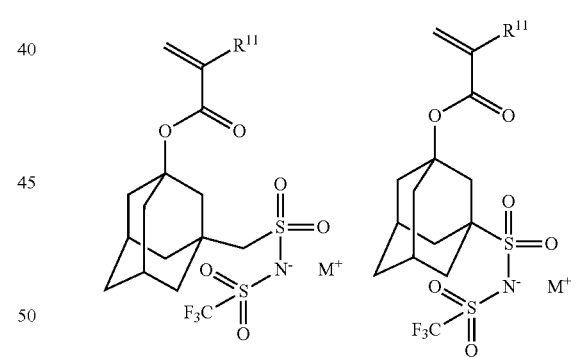
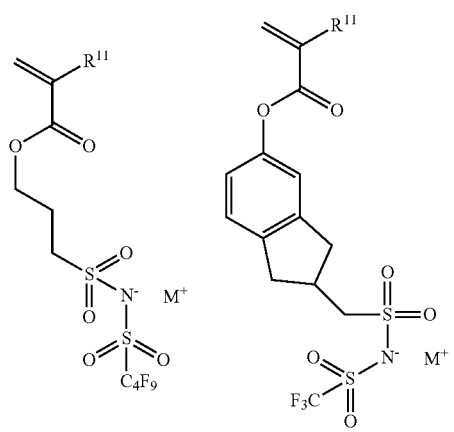
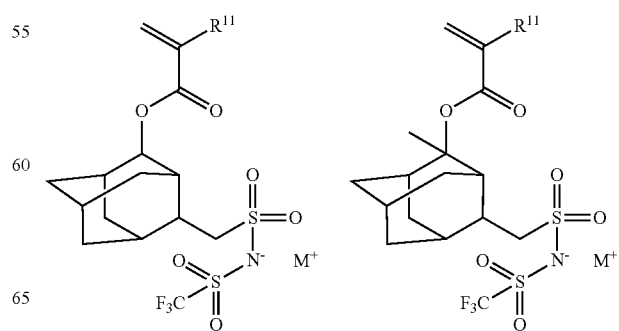

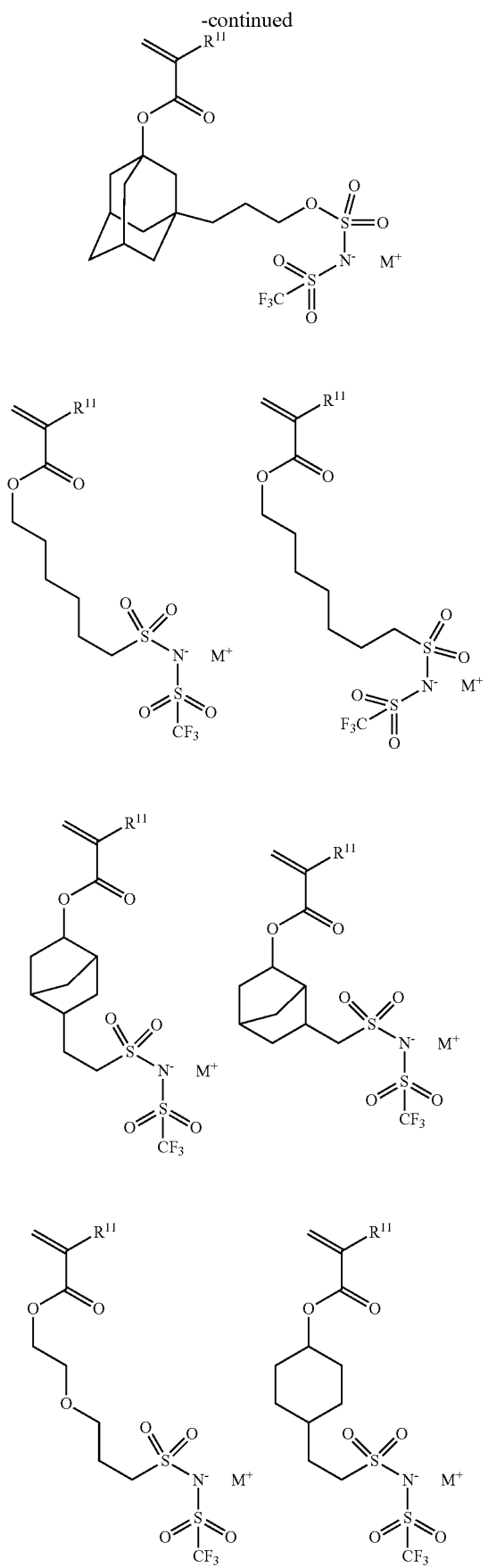
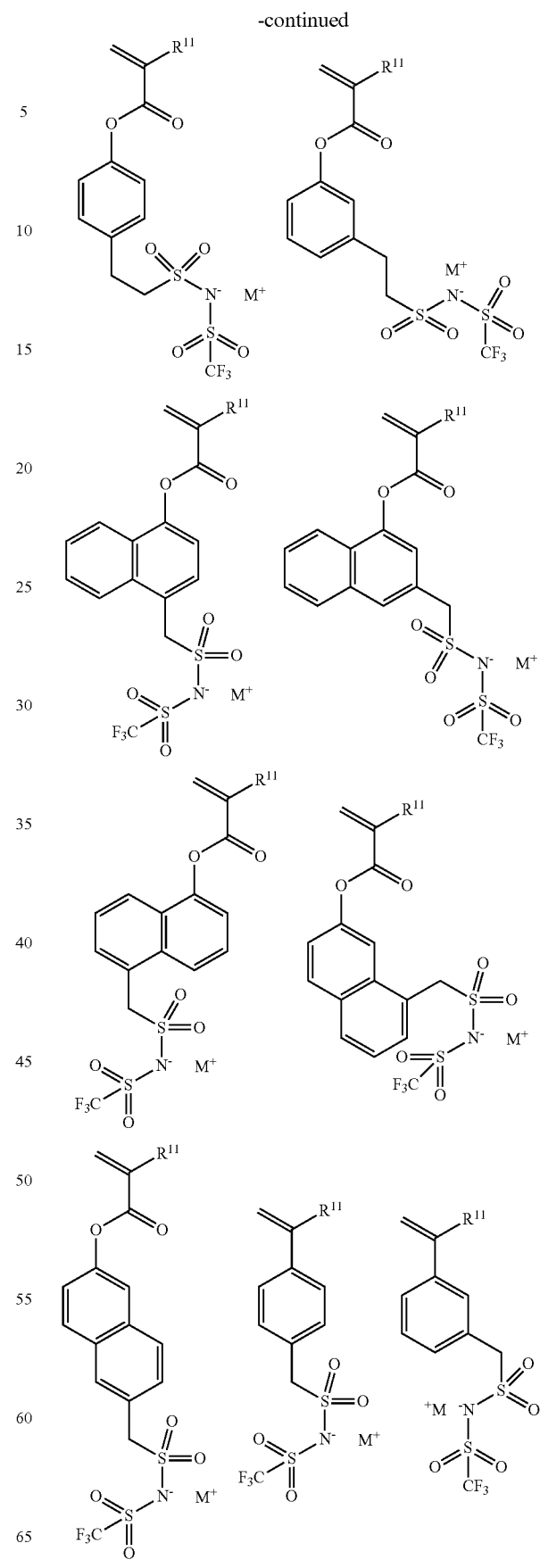

-continued
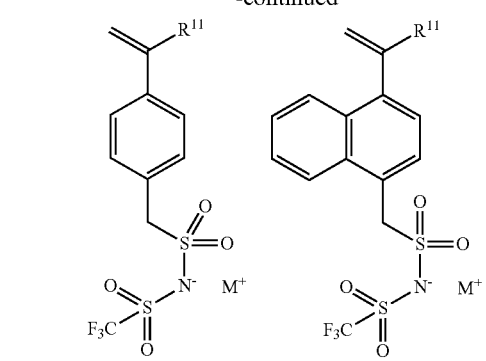
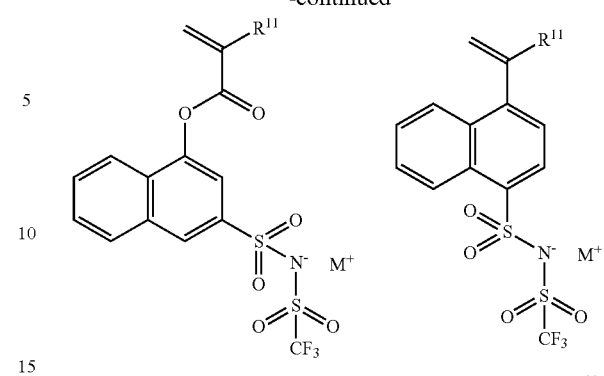
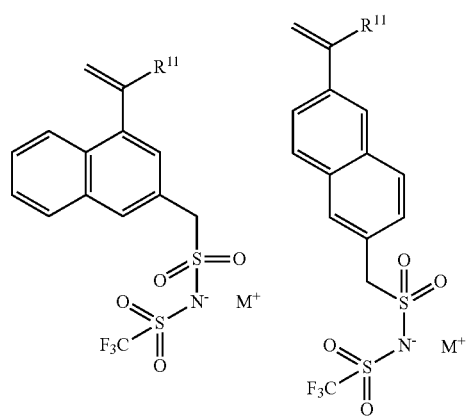
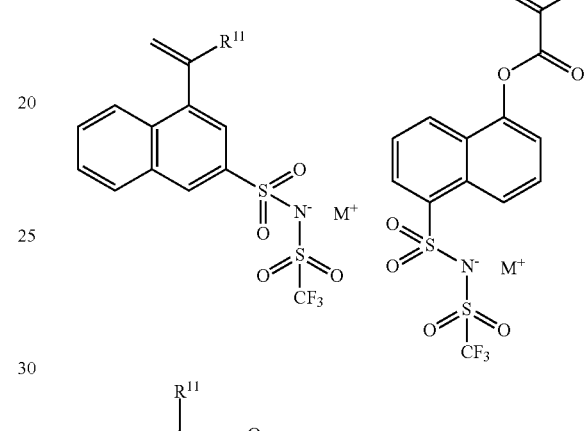
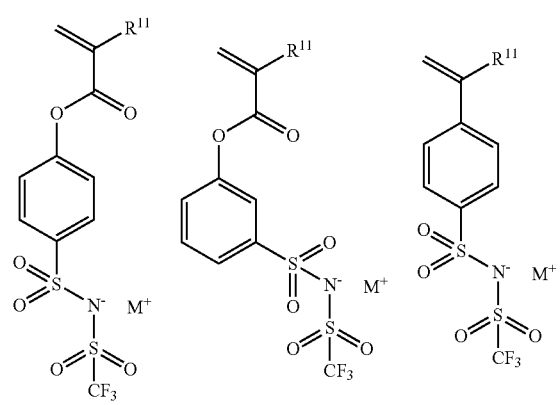
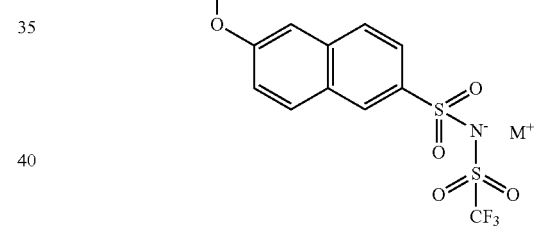
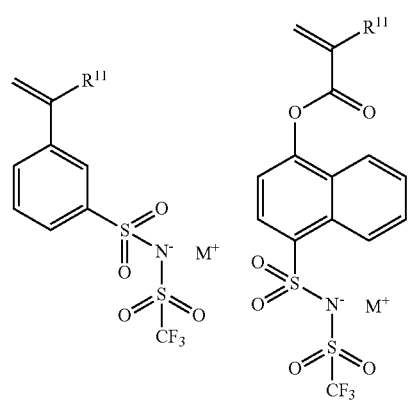
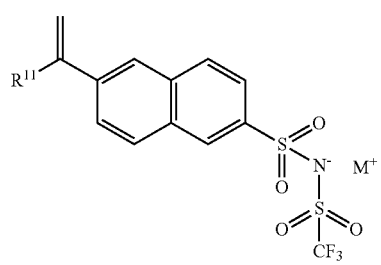

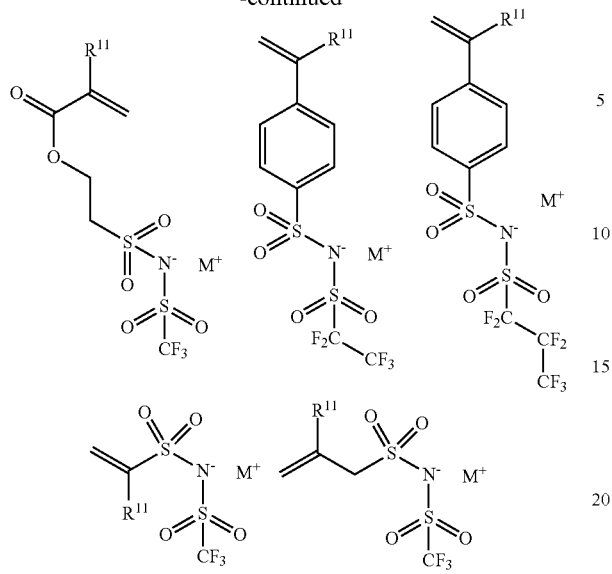
Specific examples of N-carbonyl-fluorosulfonamide salt monomer to give the repeating unit-a7 in the above can include the following.
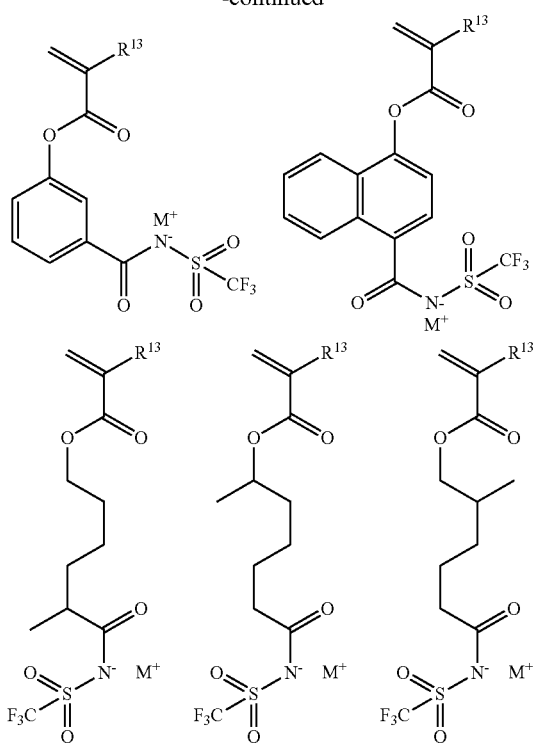
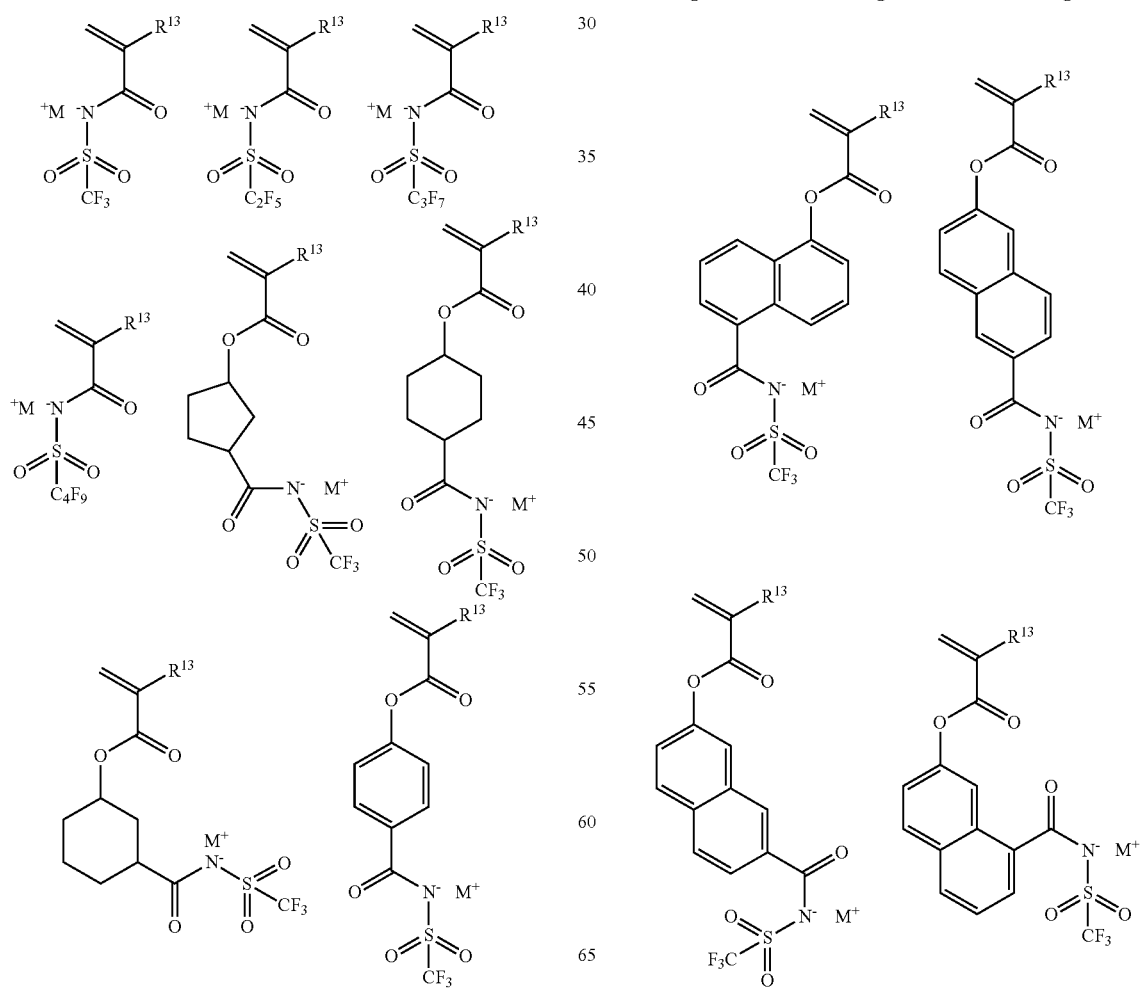

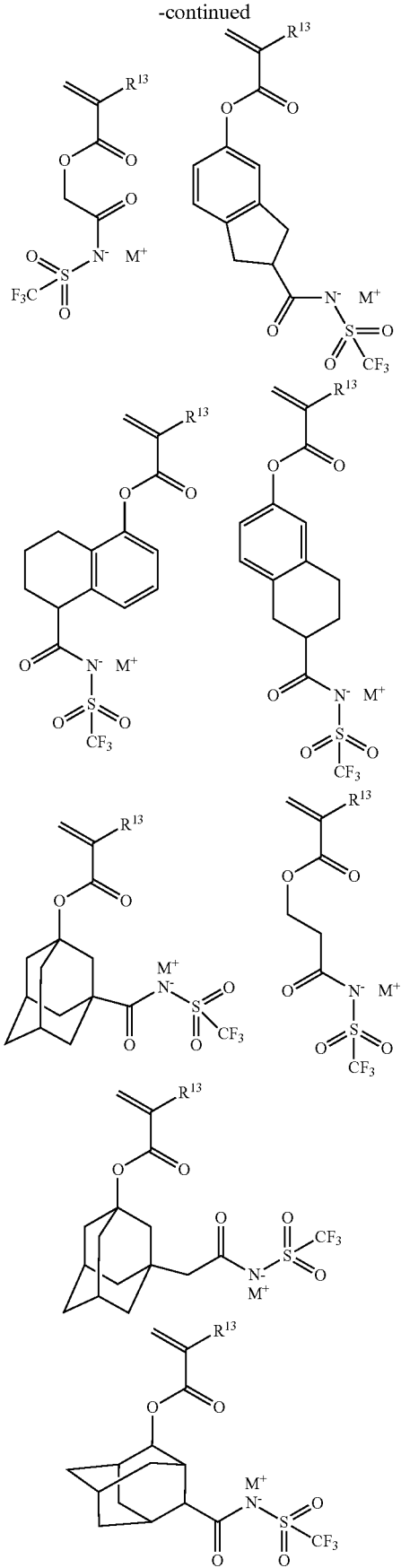
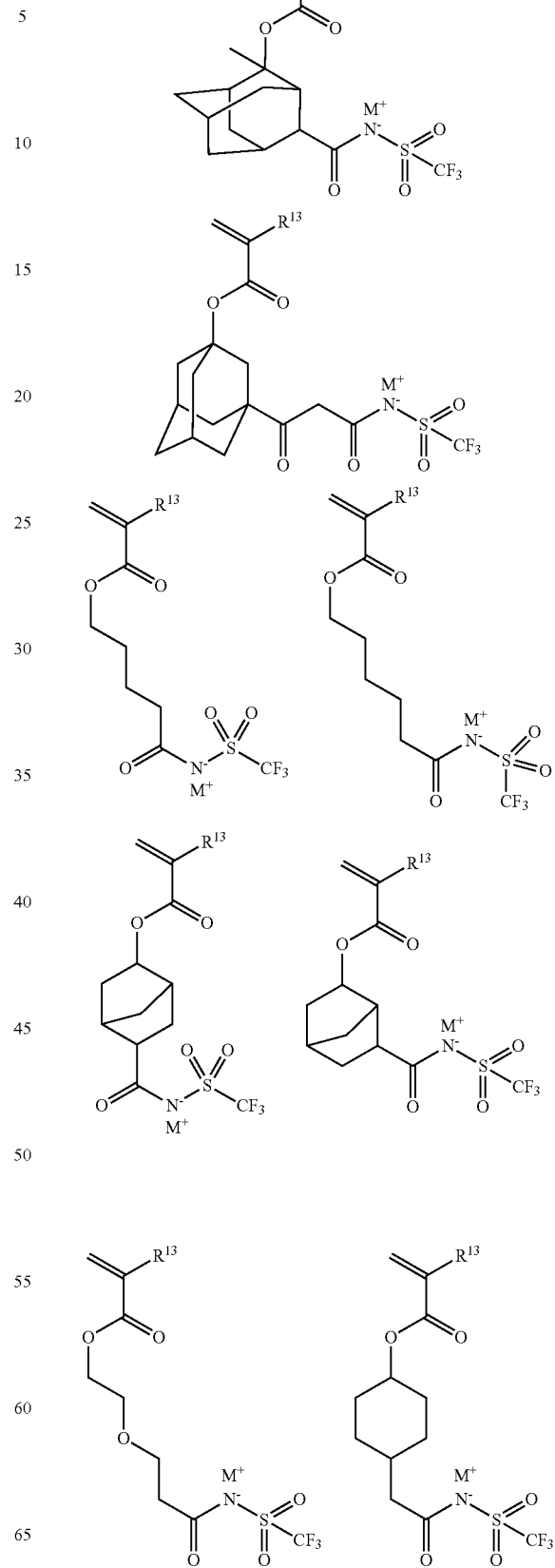

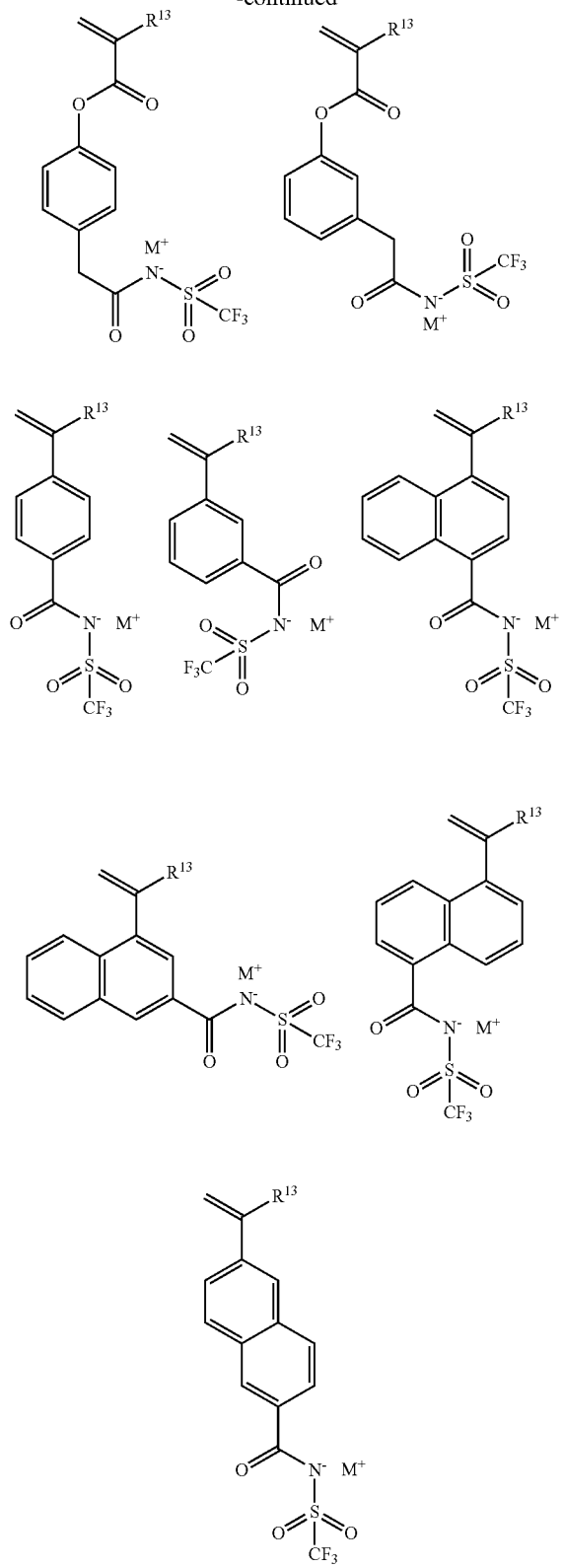

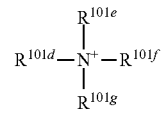

In the formula, $R^{101d}$, $R^{101e}$, $R^{101f}$, and $R^{101g}$ each represent a hydrogen atom, a linear, branched, or cyclic alkyl group having 1 to 14 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

Specific examples of the ammonium ion shown by the general formula (3) can include the following.

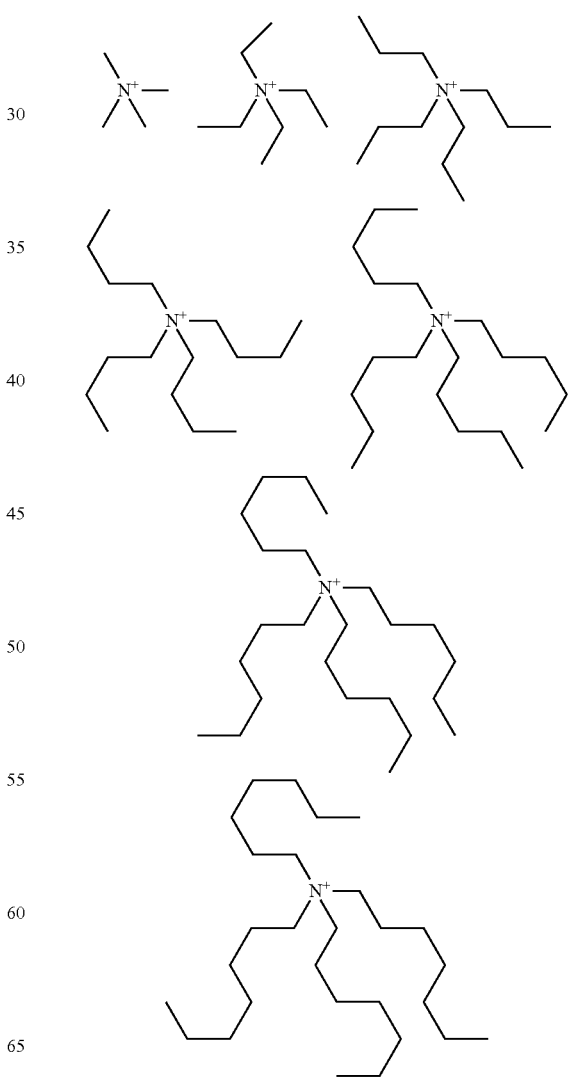

The component (A) preferably contains an ammonium ion (ammonium cation) shown by the following general formula (3) as an ammonium ion for forming the ammonium salts, particularly as $M^+$ in repeating units-a (e.g., the repeating units-a1 to -a7).

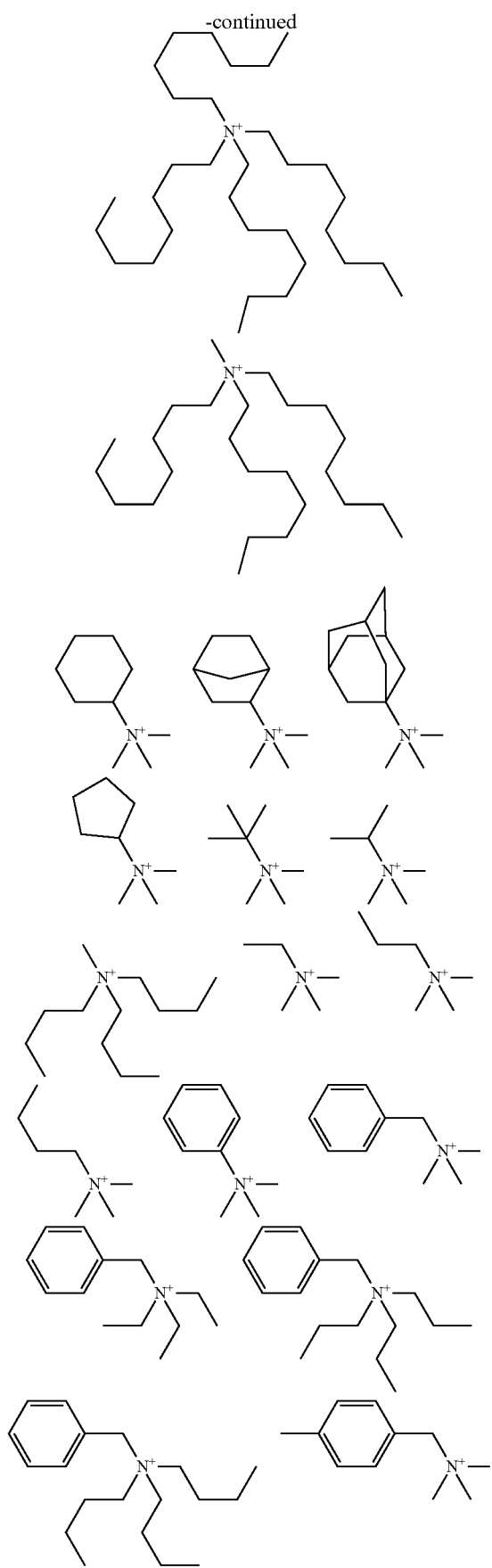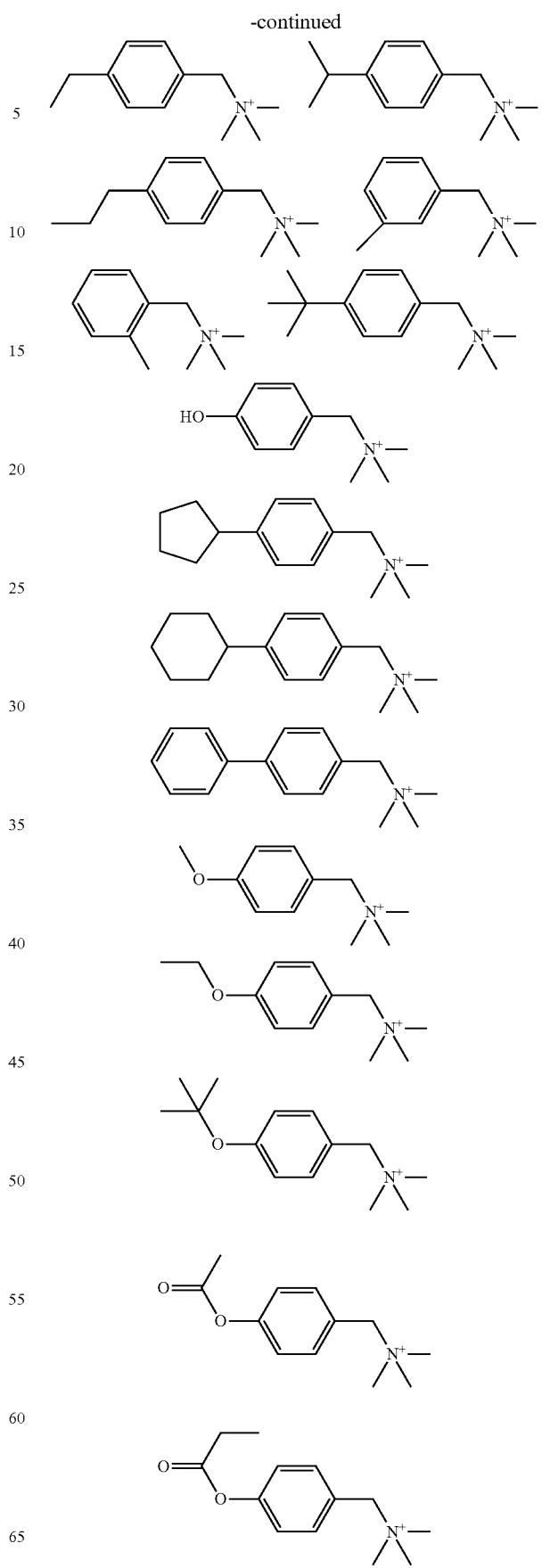

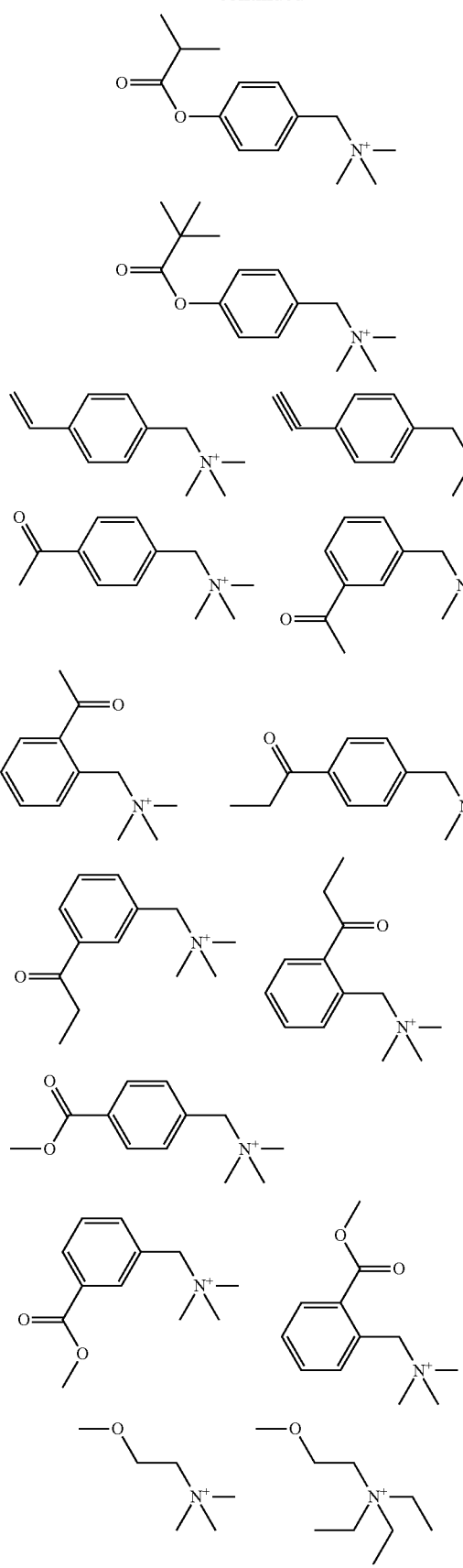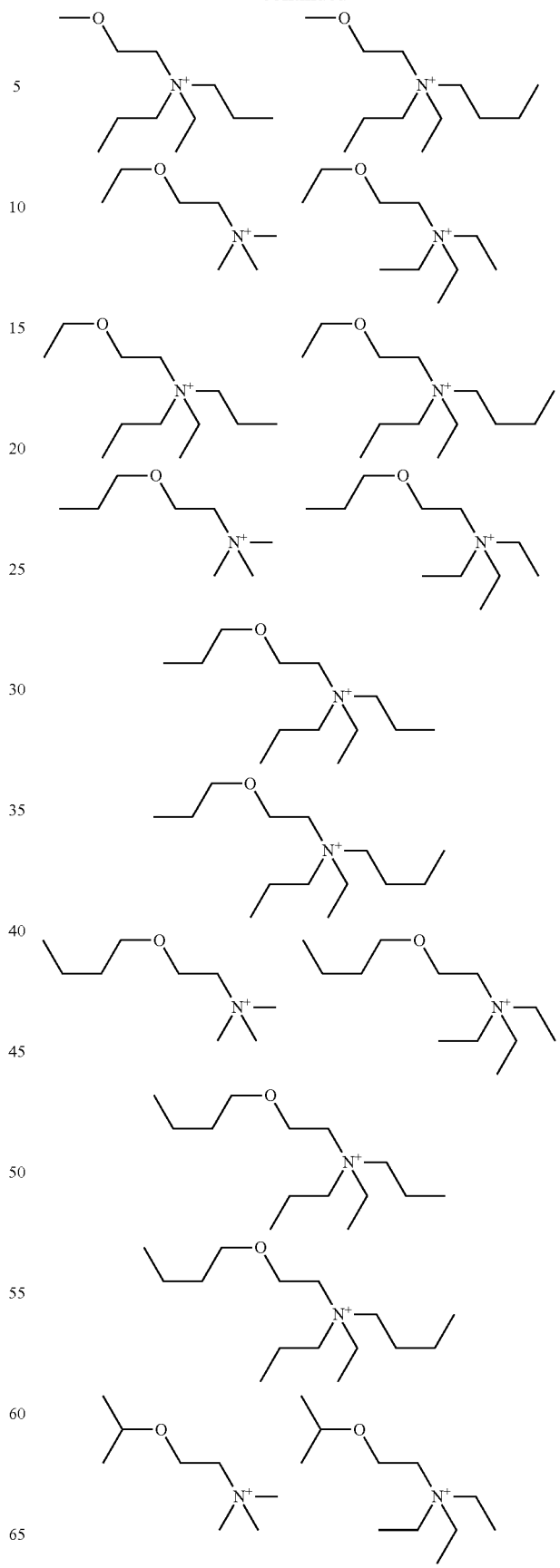

-continued
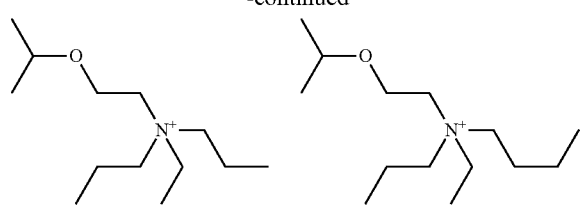
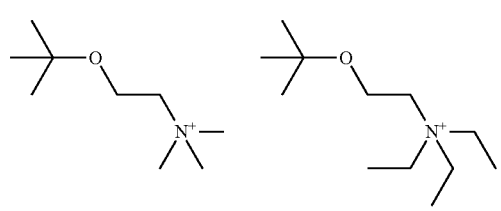
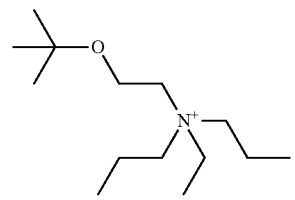
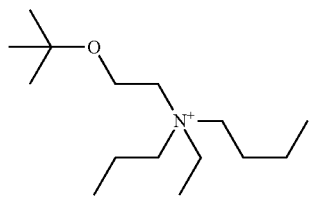
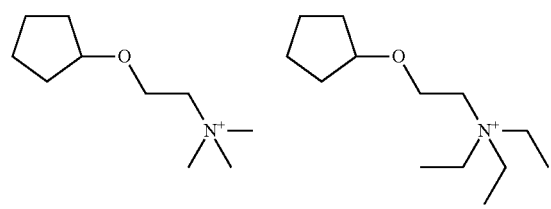
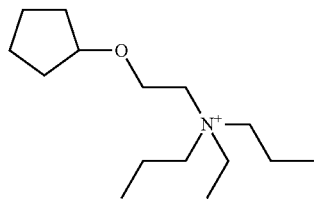
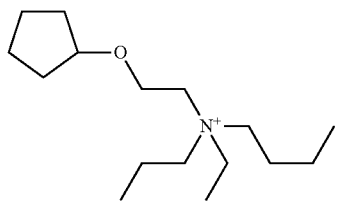
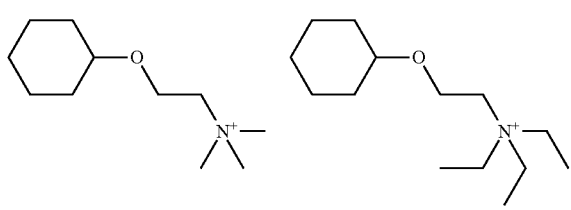
-continued
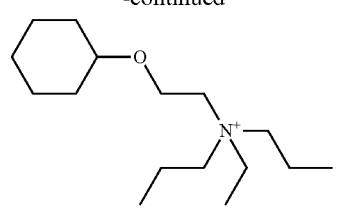
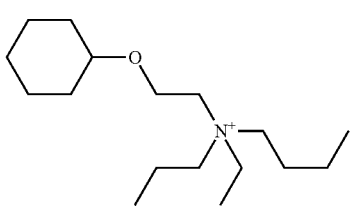
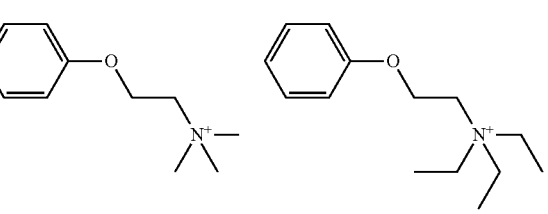
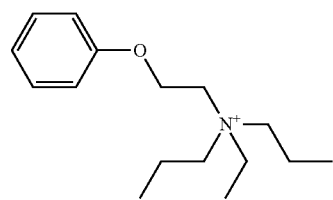
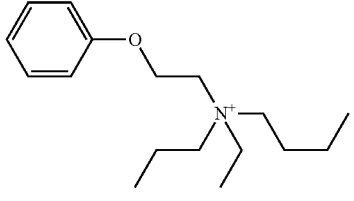
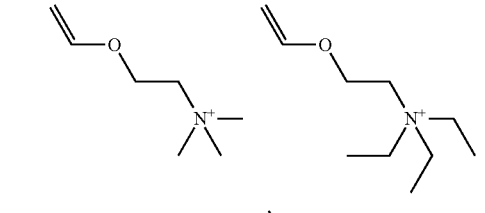
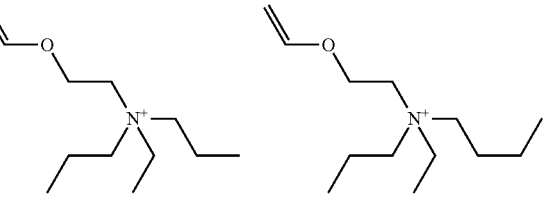
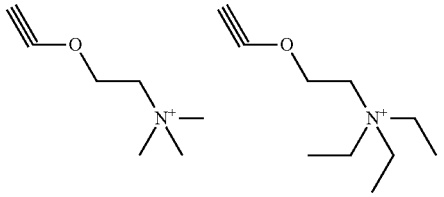

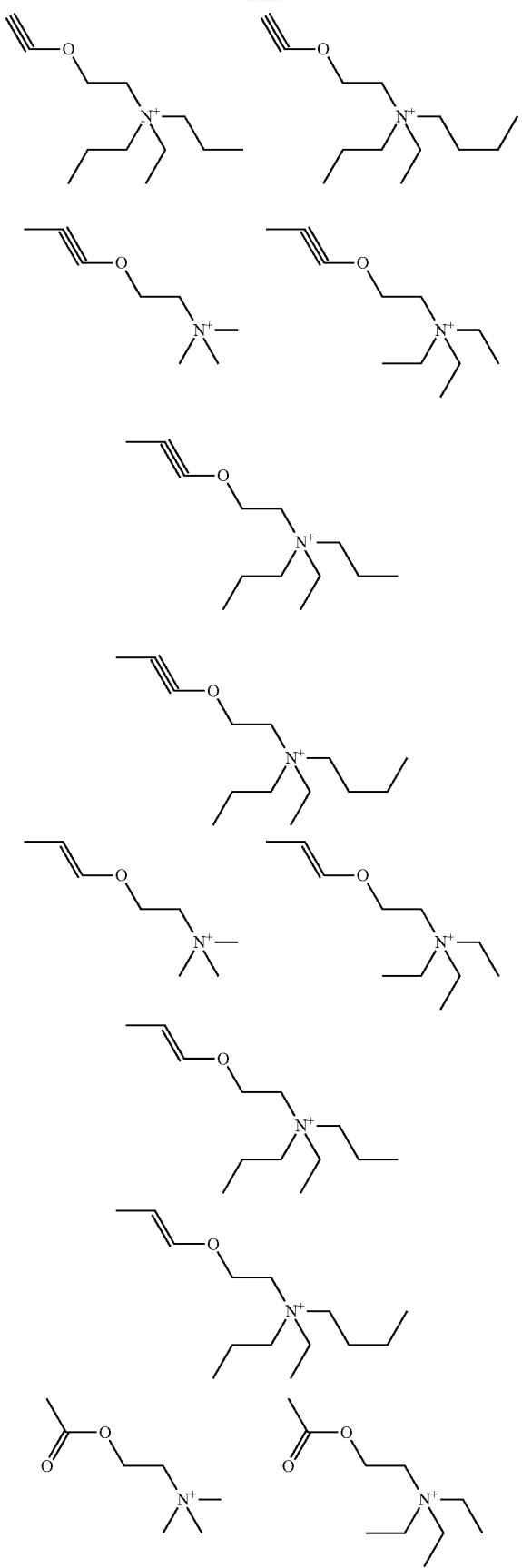
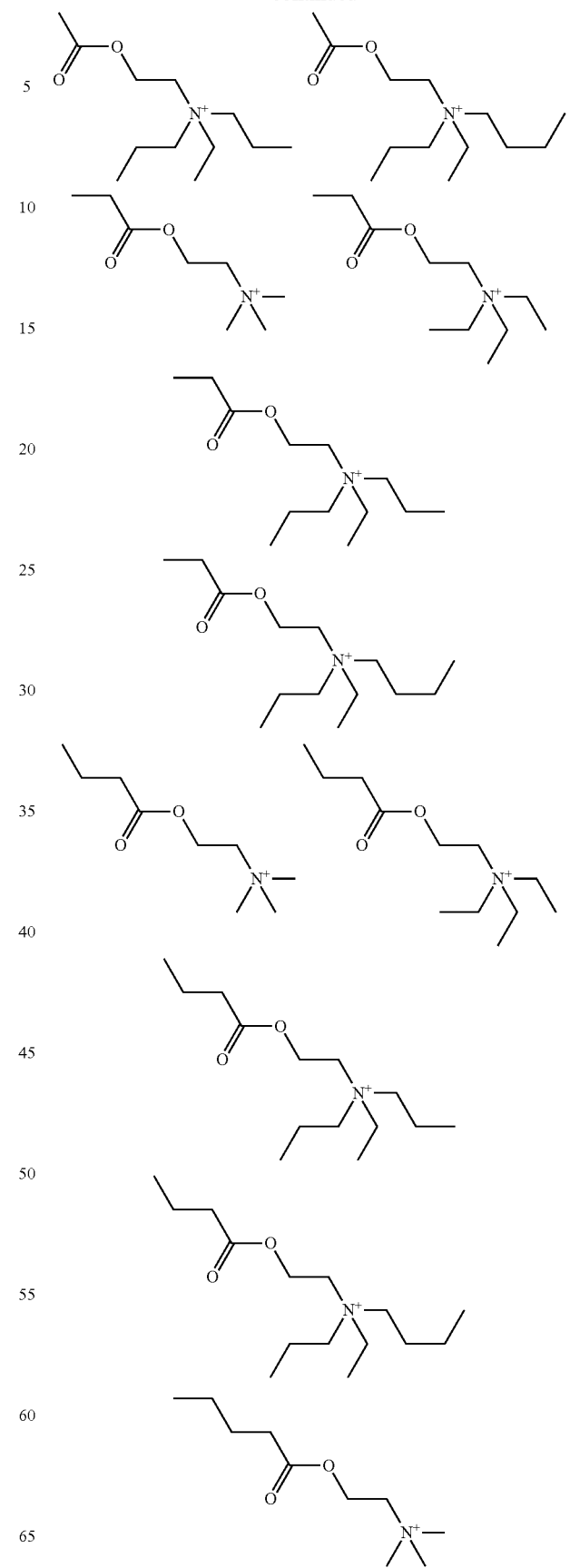

95
-continued
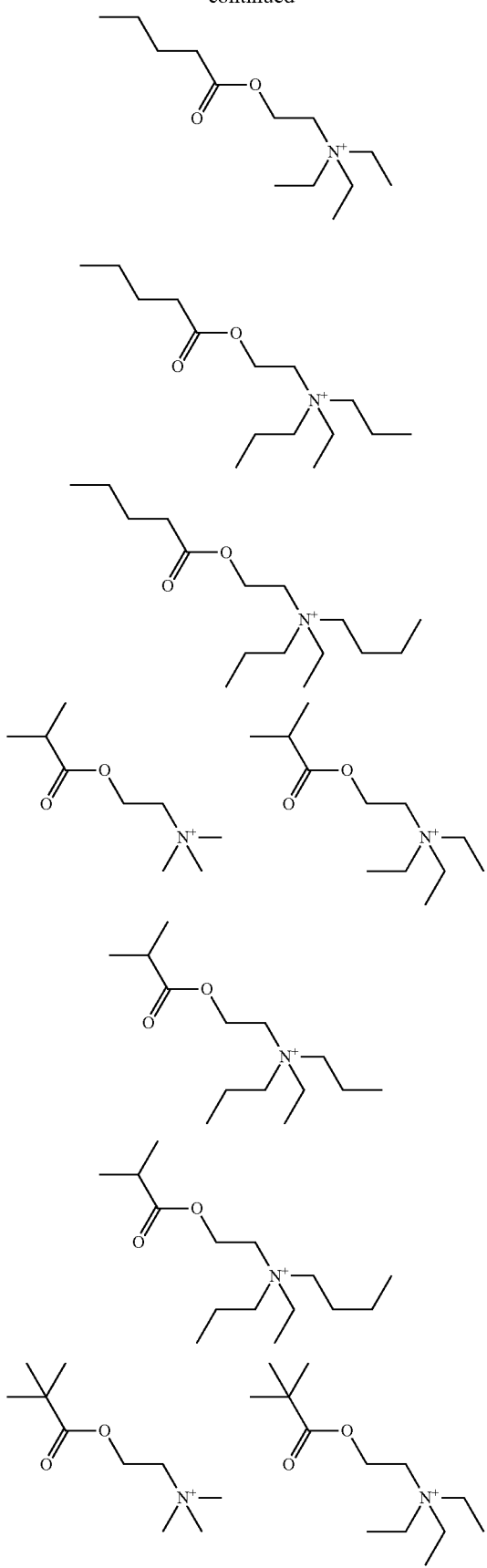
96
-continued
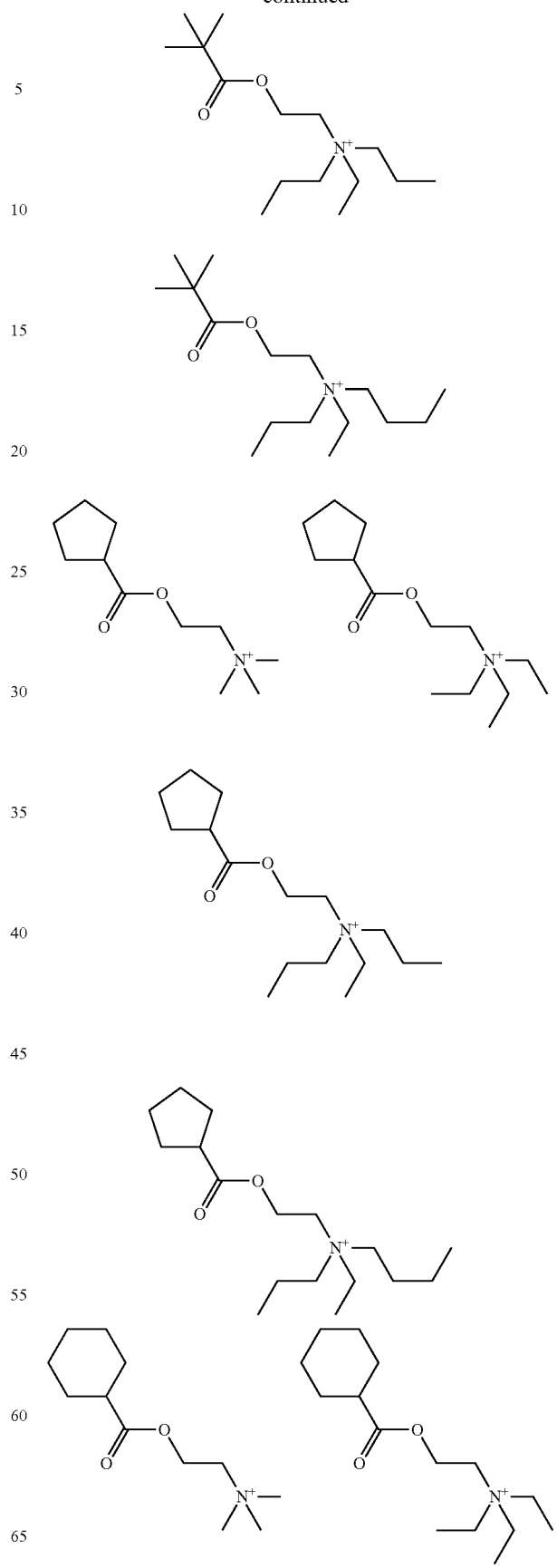

97
-continued
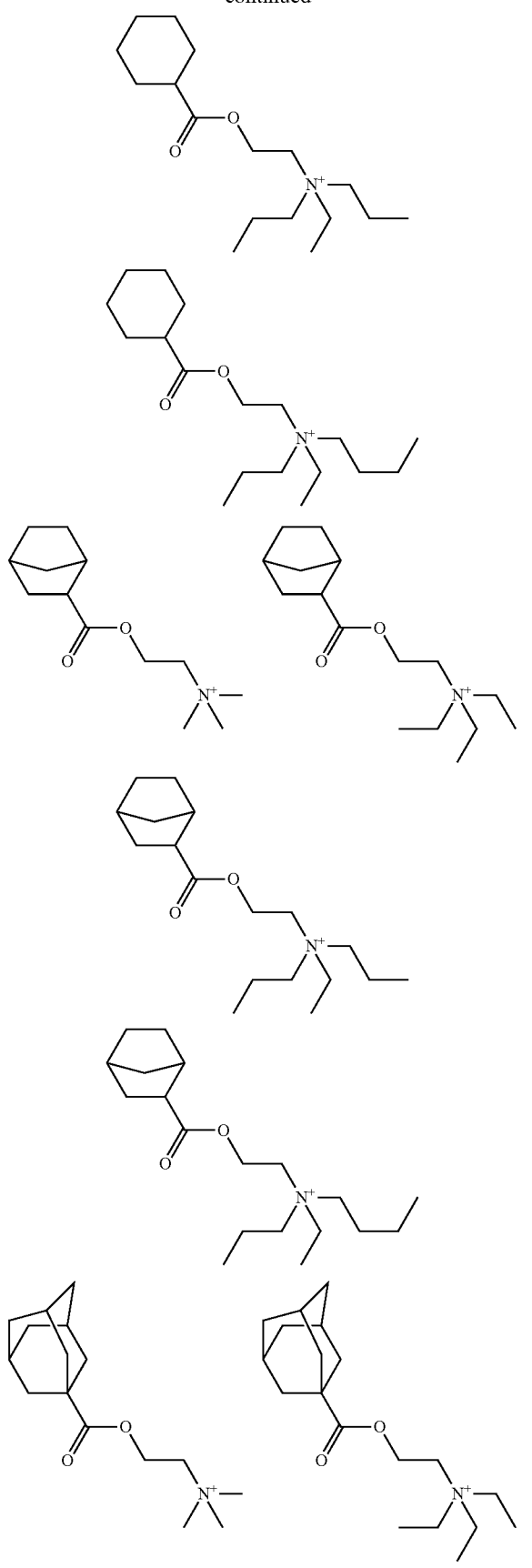
98
-continued
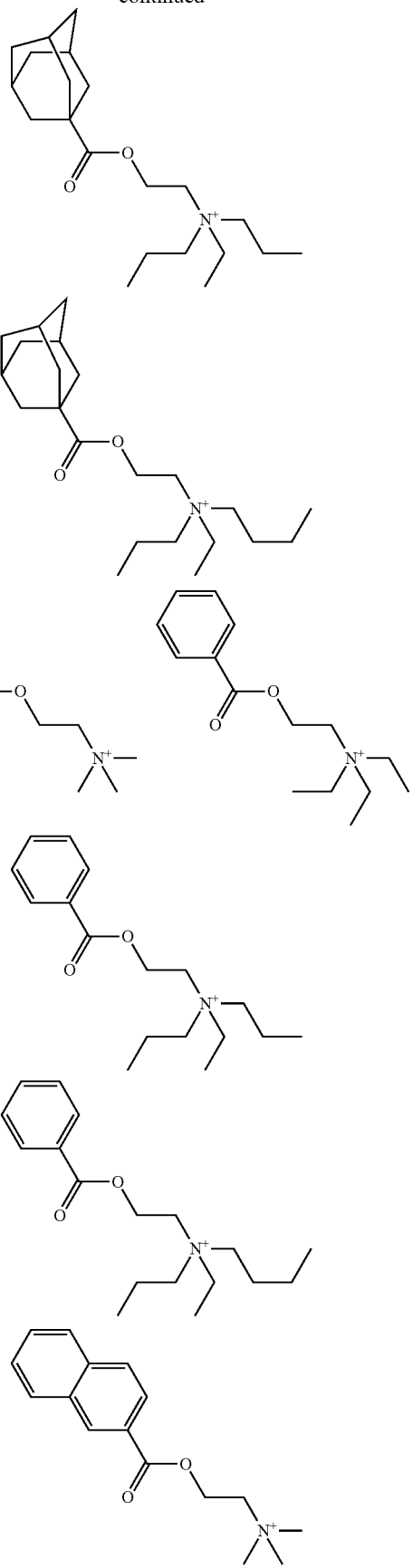

99
-continued
100
-continued
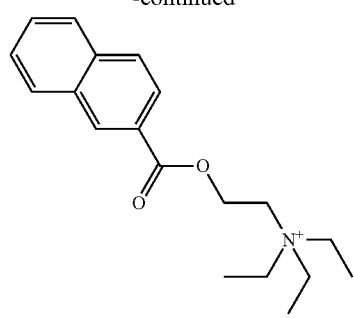
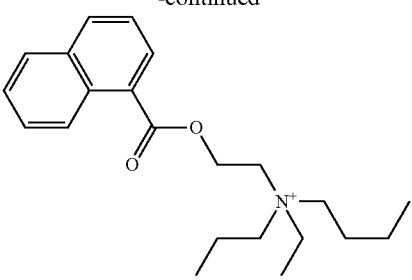
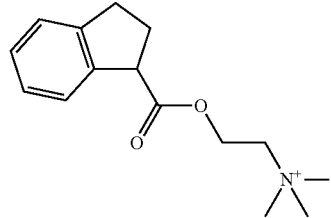
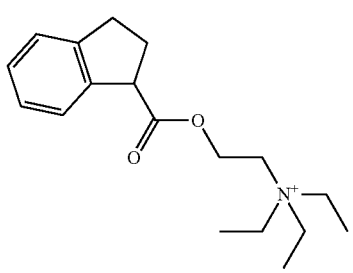
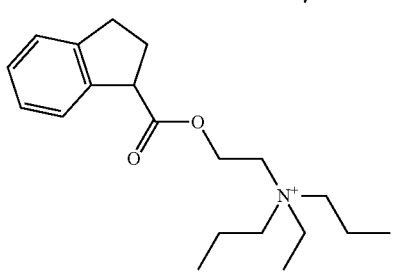
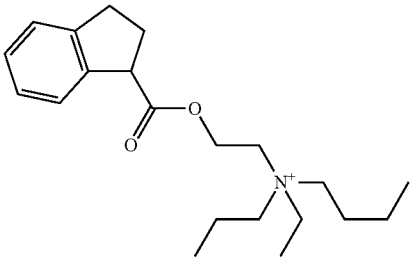

101
-continued
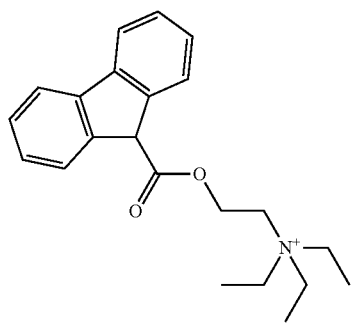
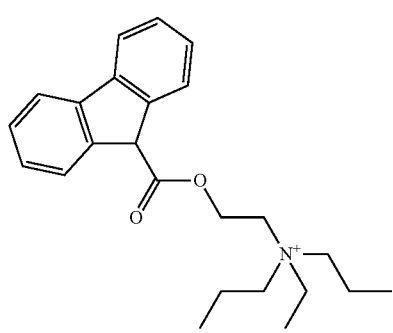
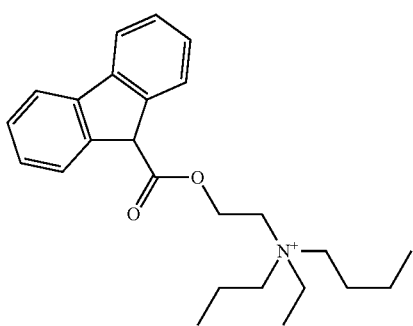
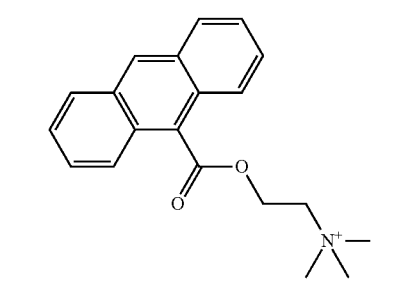
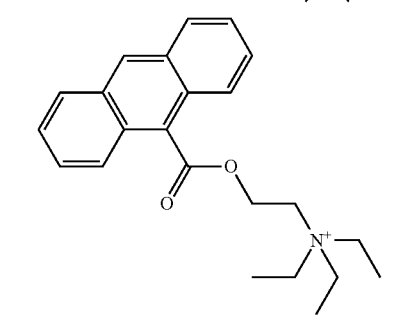
102
-continued
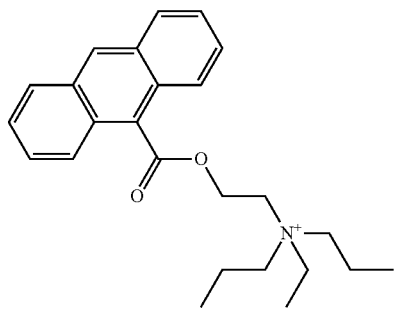
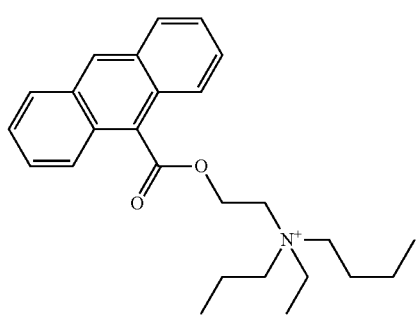
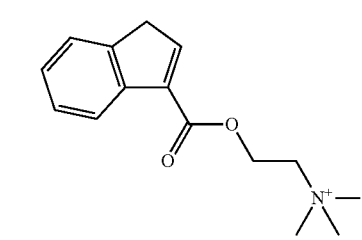
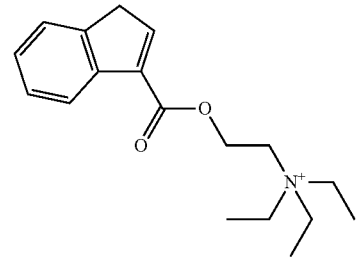
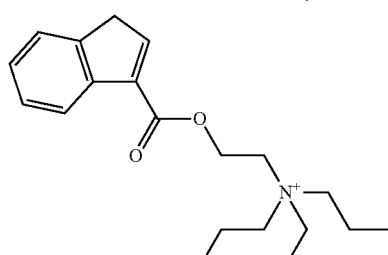
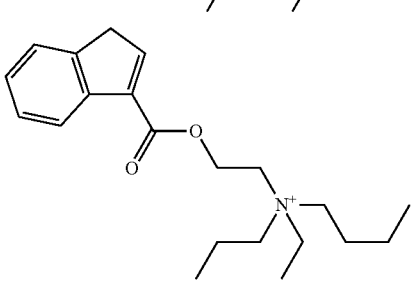

103
-continued
104
-continued
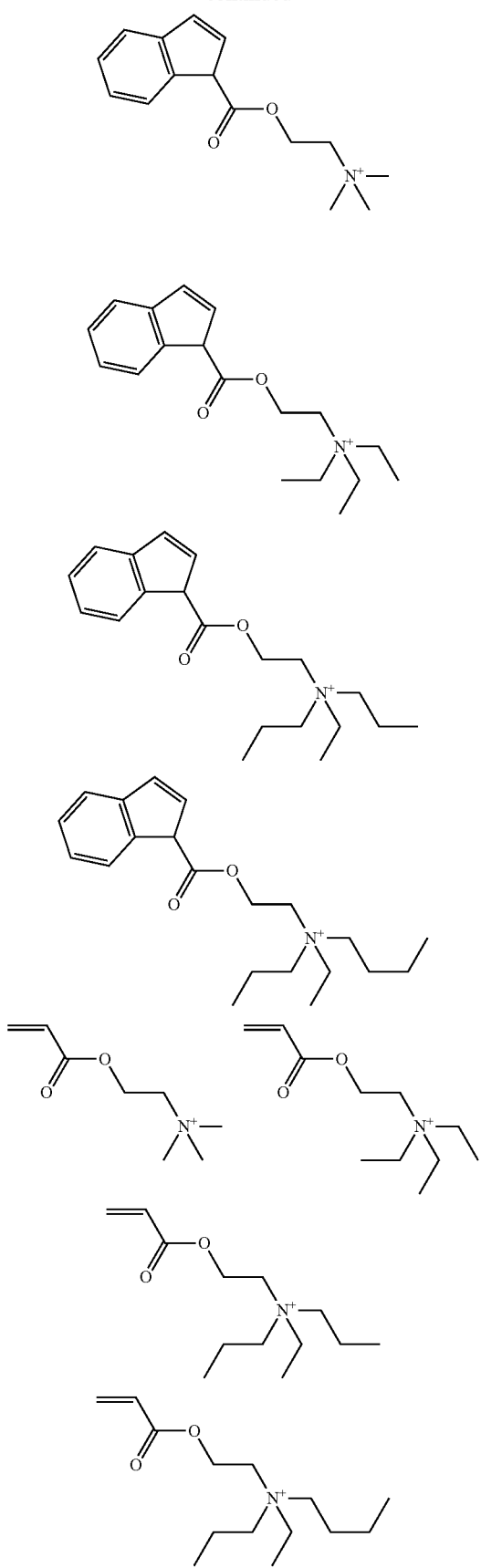

-continued
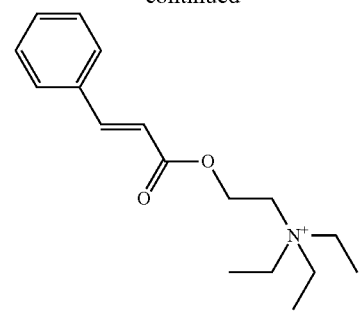
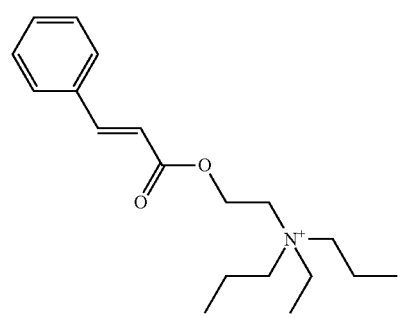
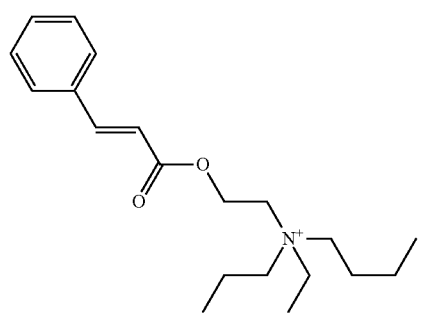
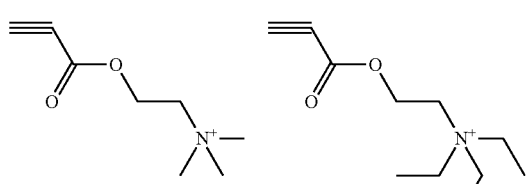
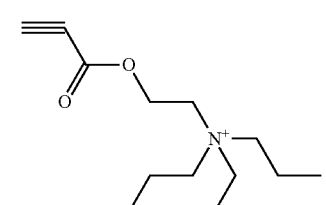
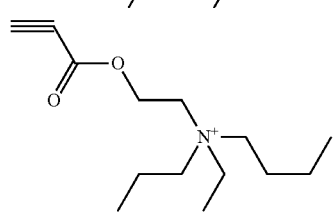
-continued
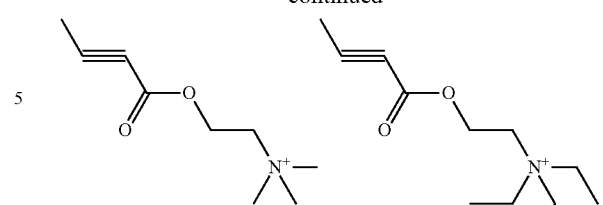
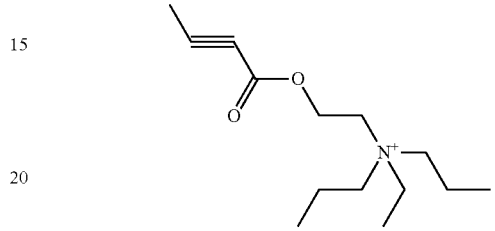
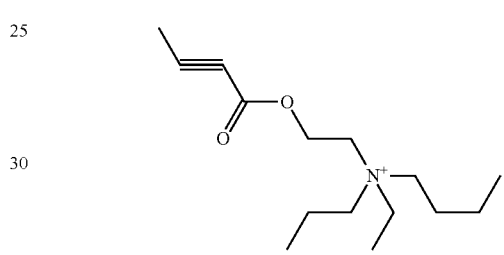
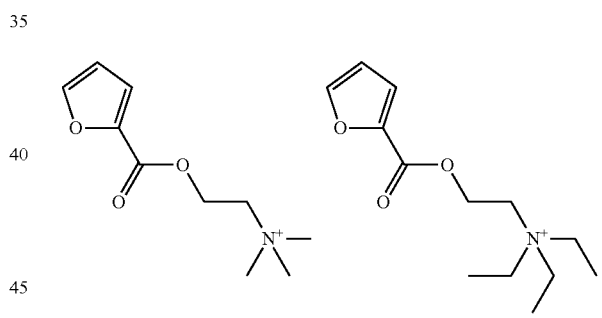
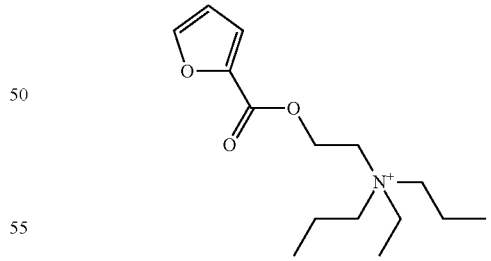
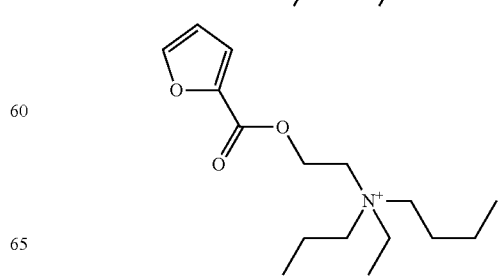

107
-continued
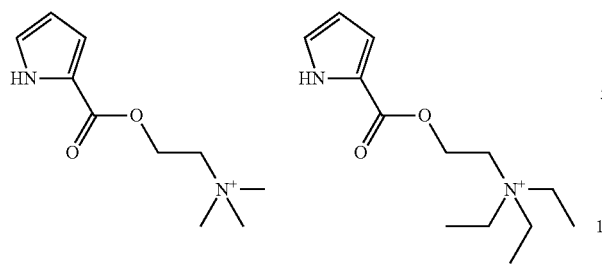
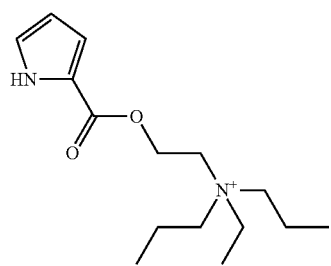
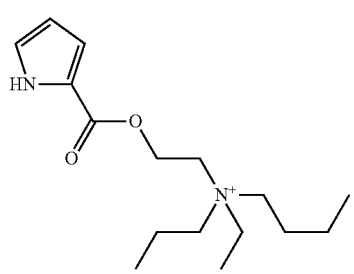
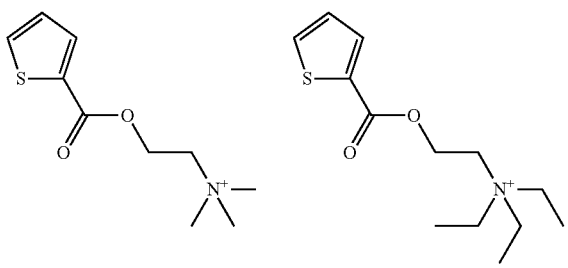
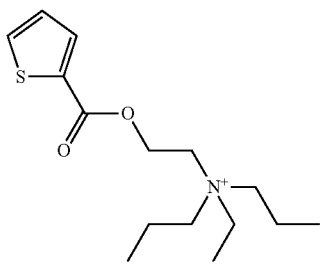
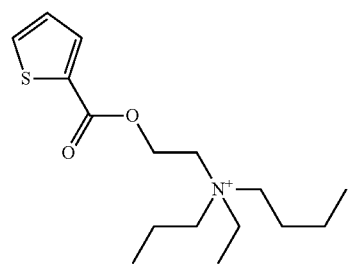
108
-continued
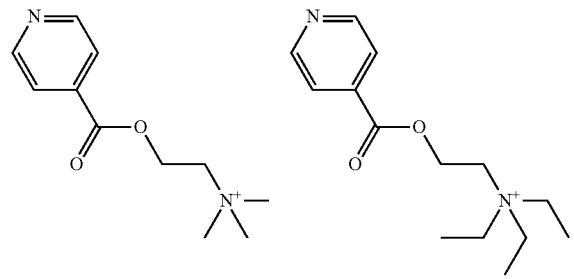
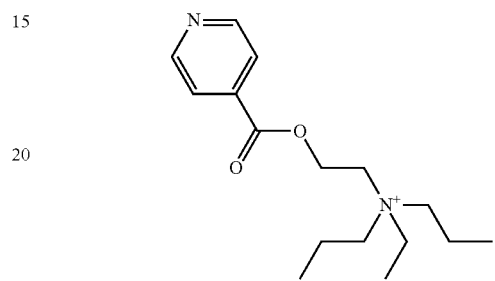
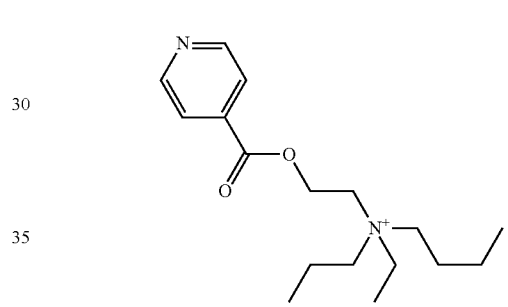
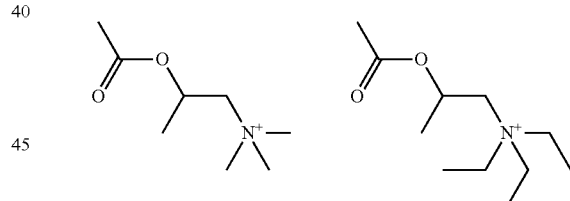
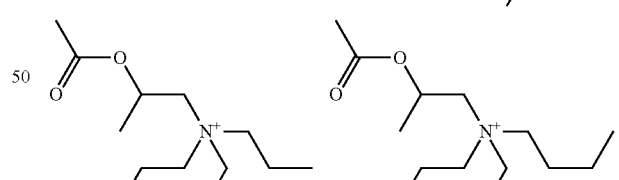
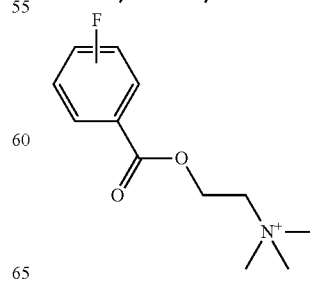

-continued
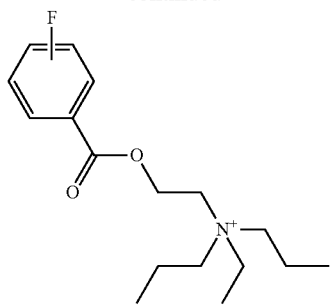
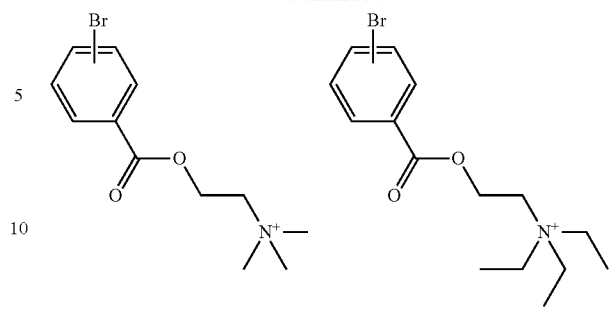
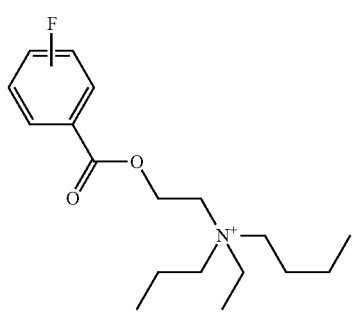
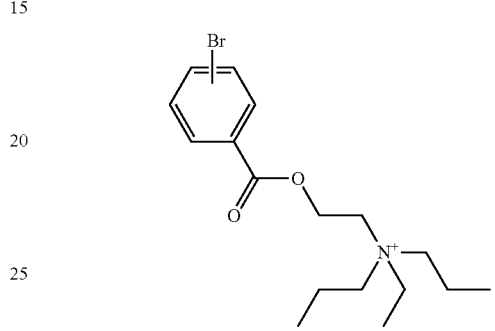
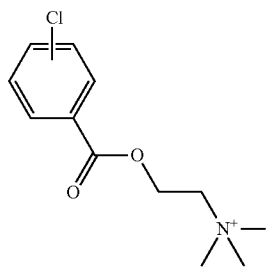
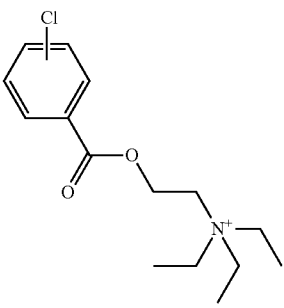
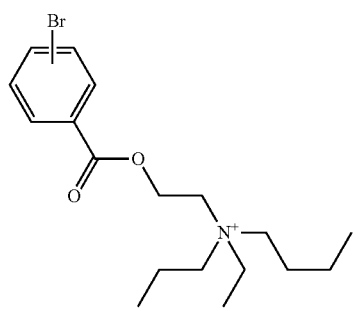
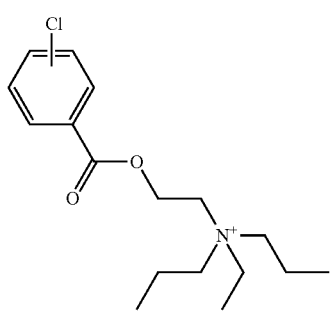
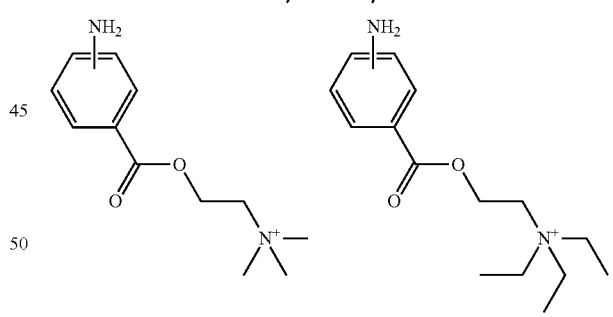
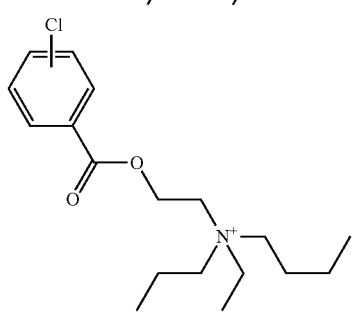
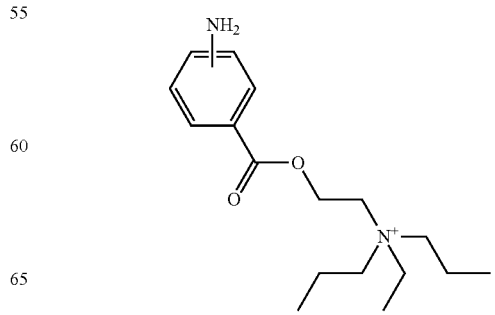

111
-continued
112
-continued
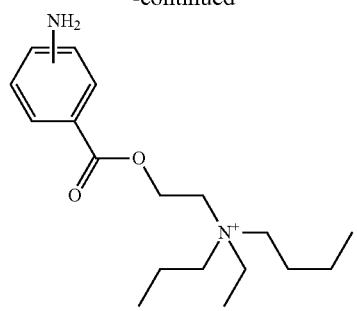
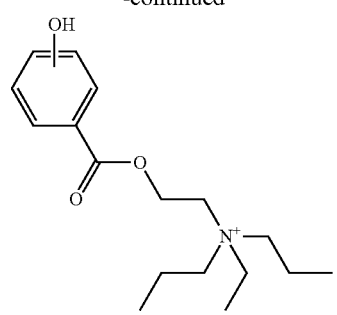
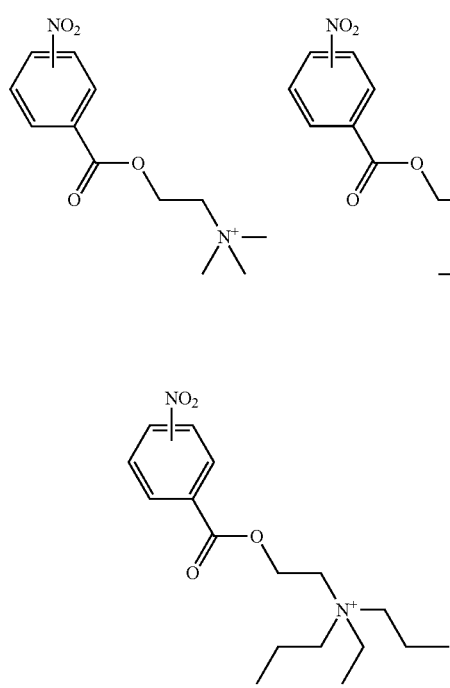
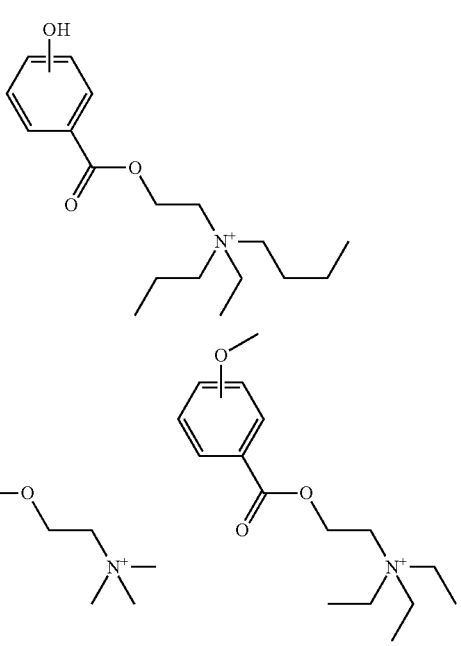
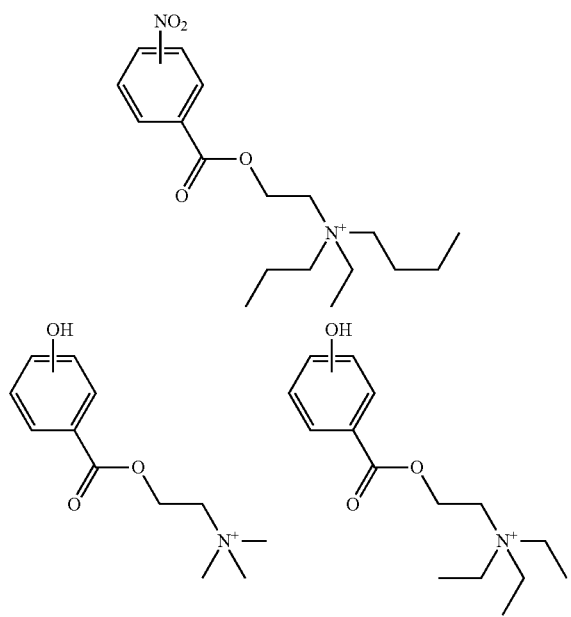
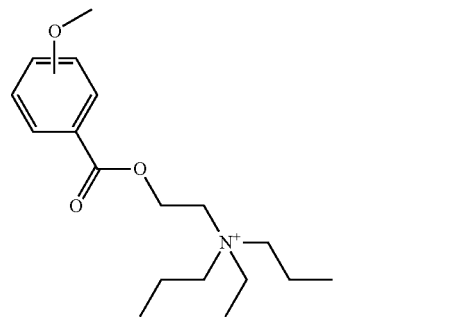

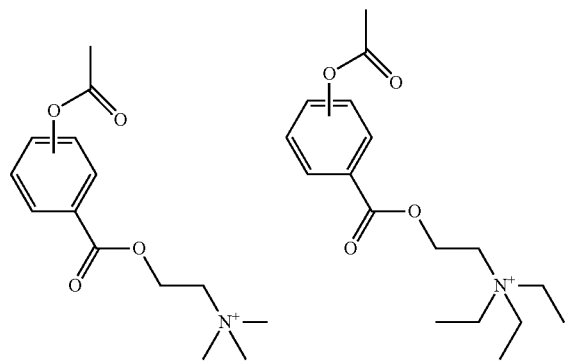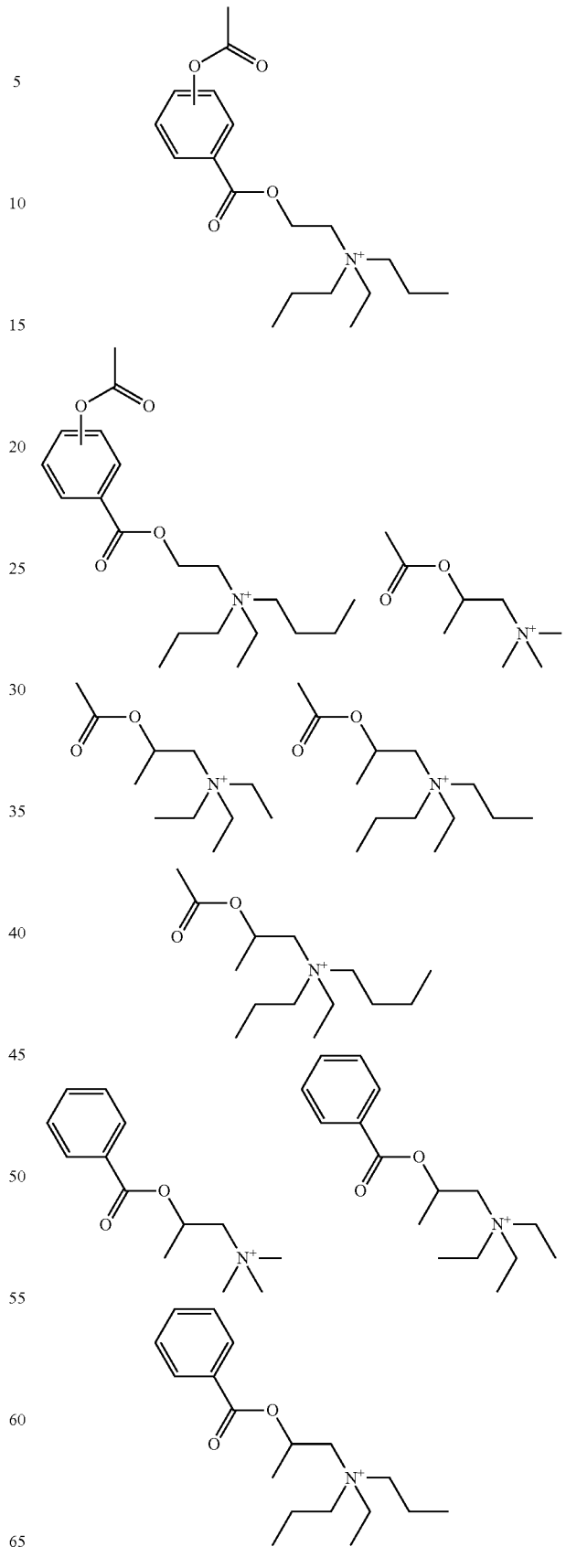

115
-continued
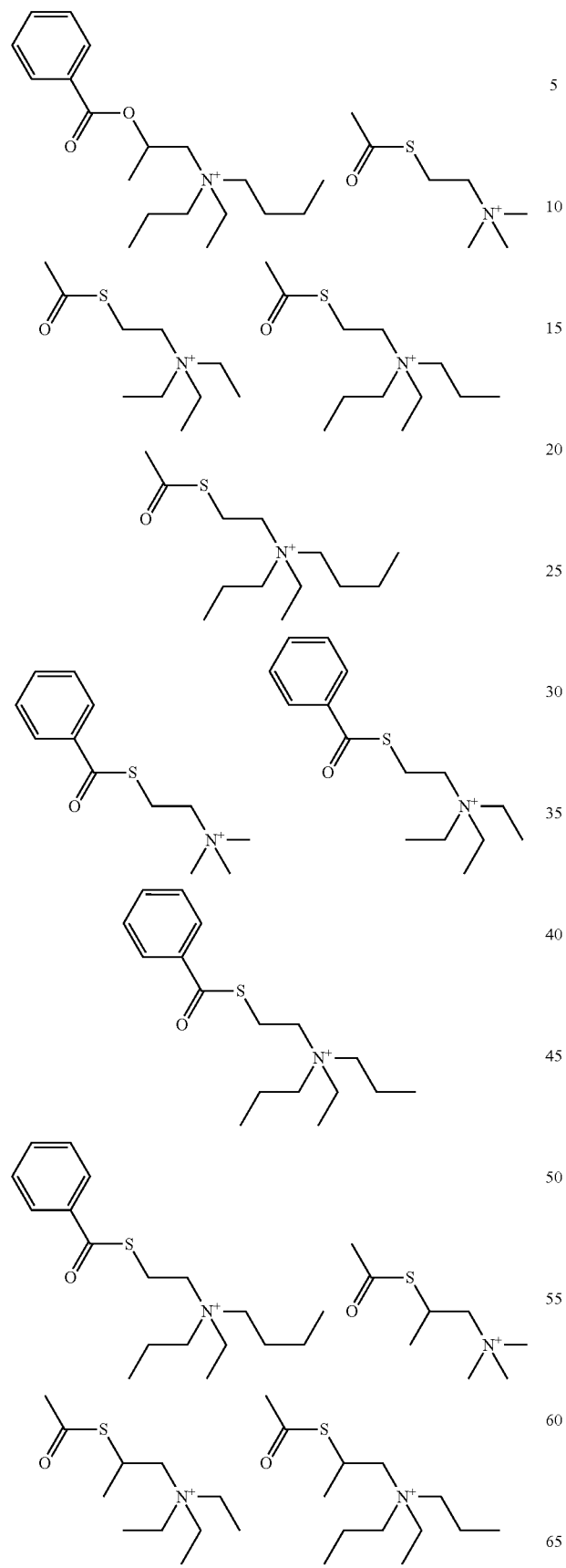
116
-continued
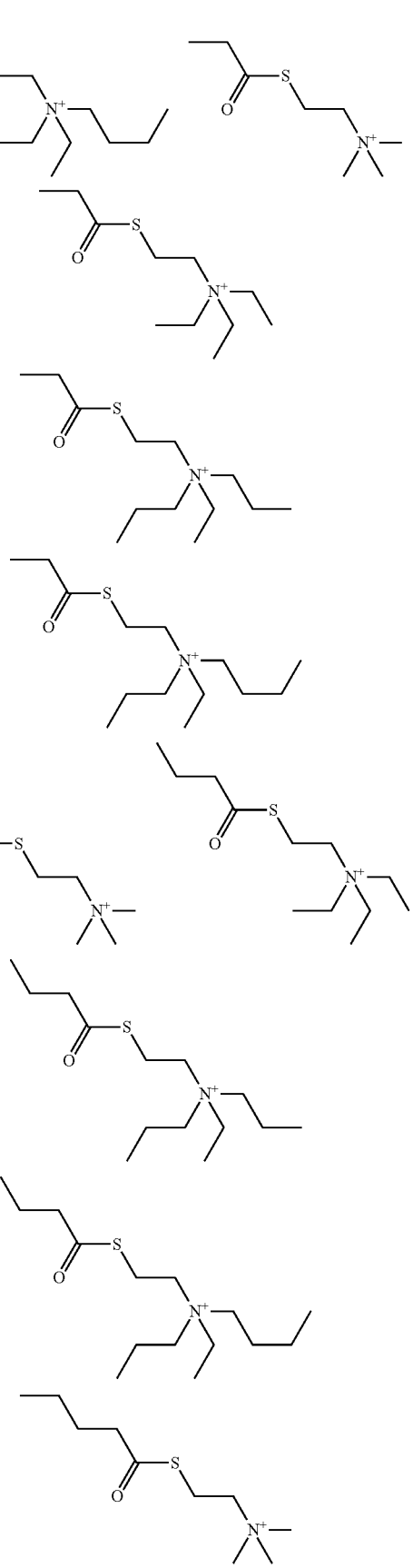

117
-continued
118
-continued
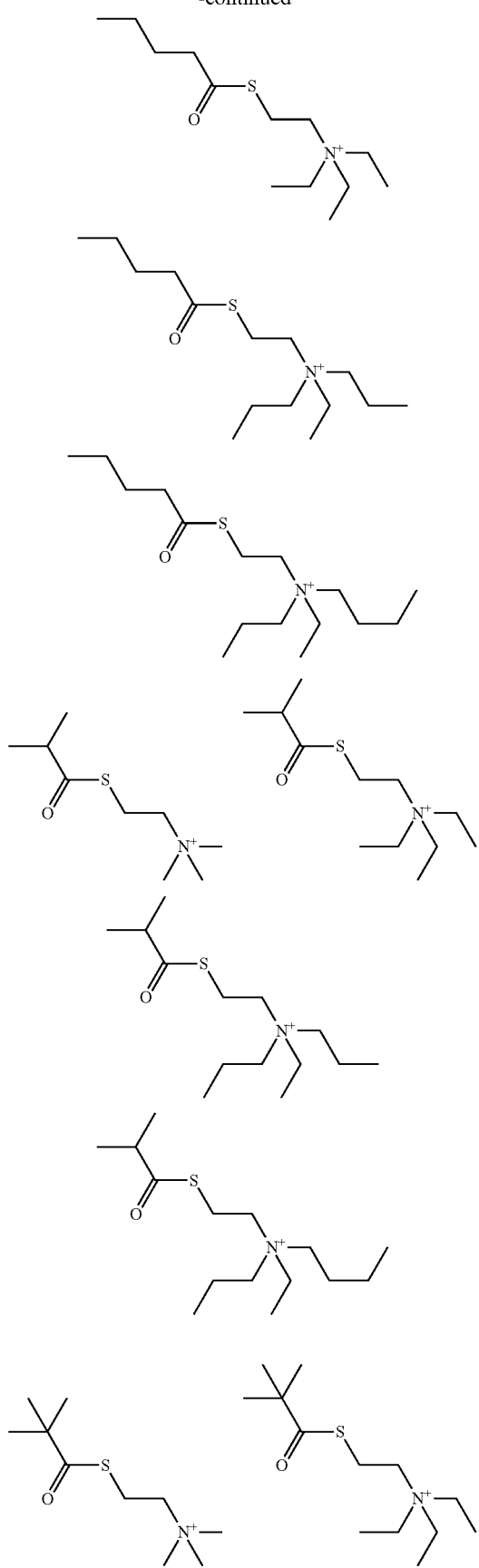
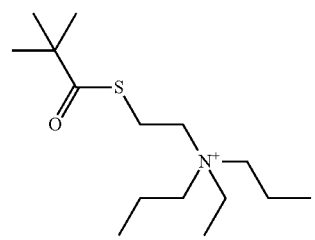
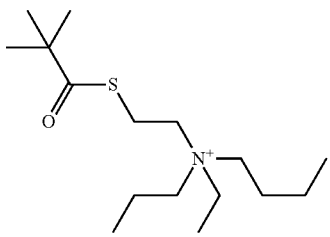
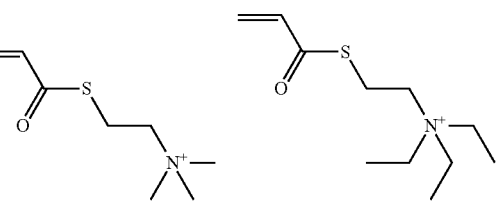
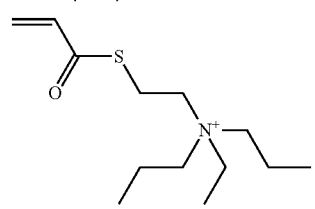
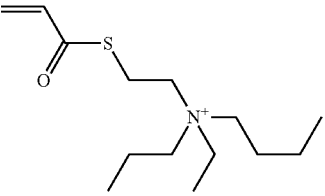
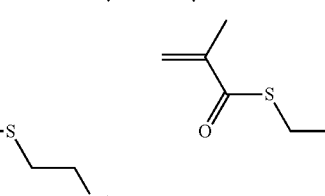
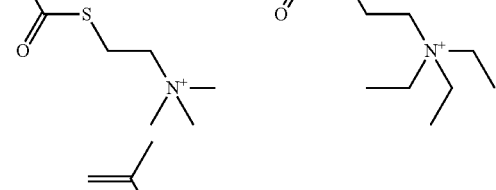
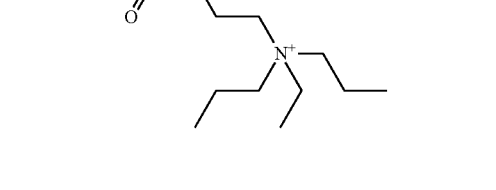

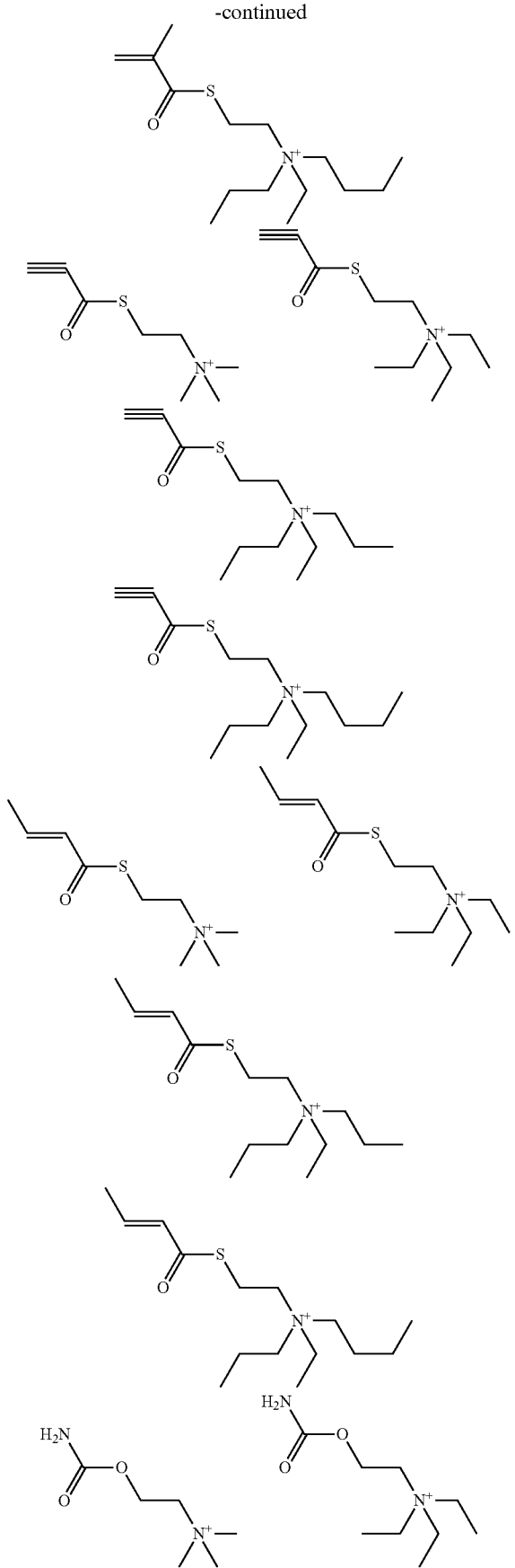
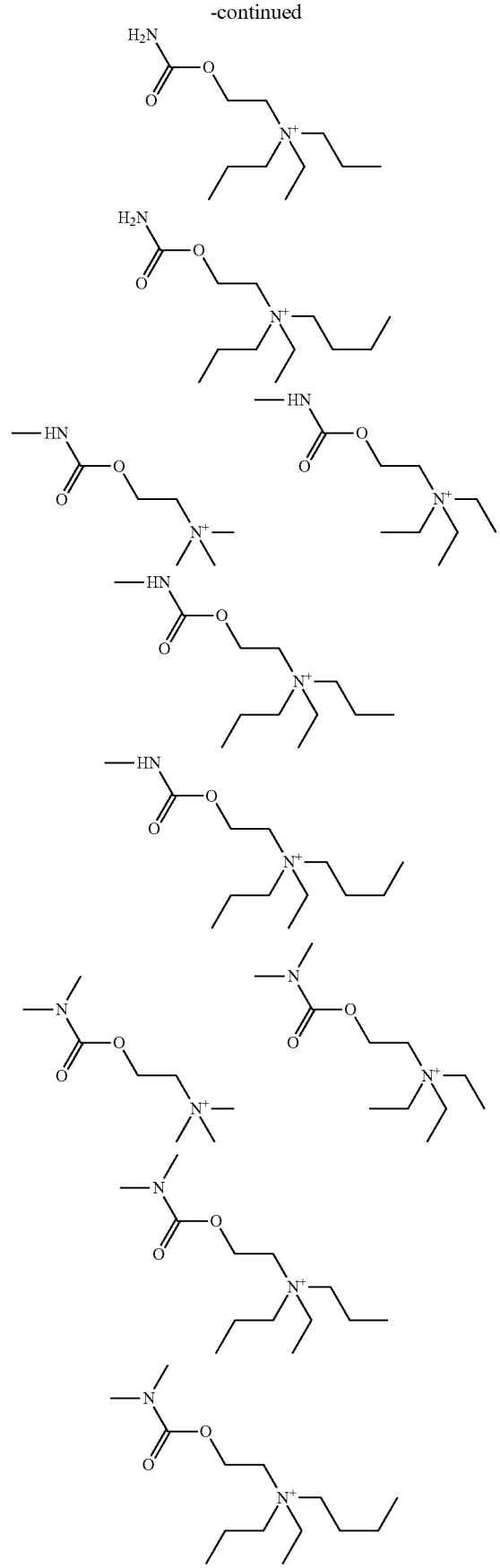

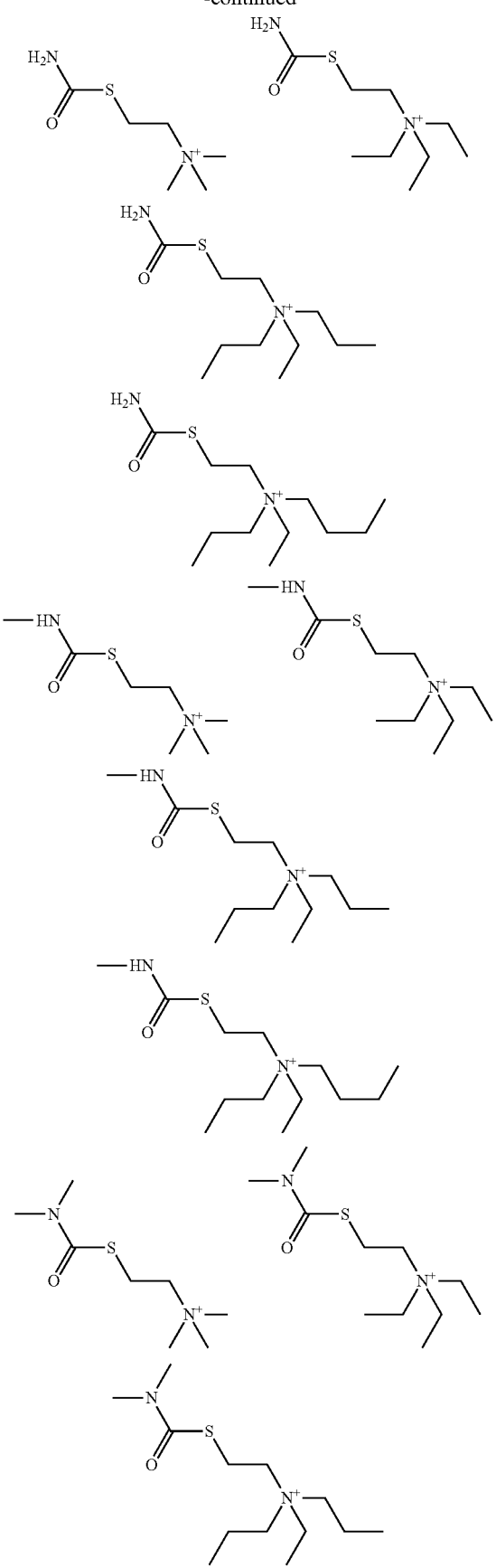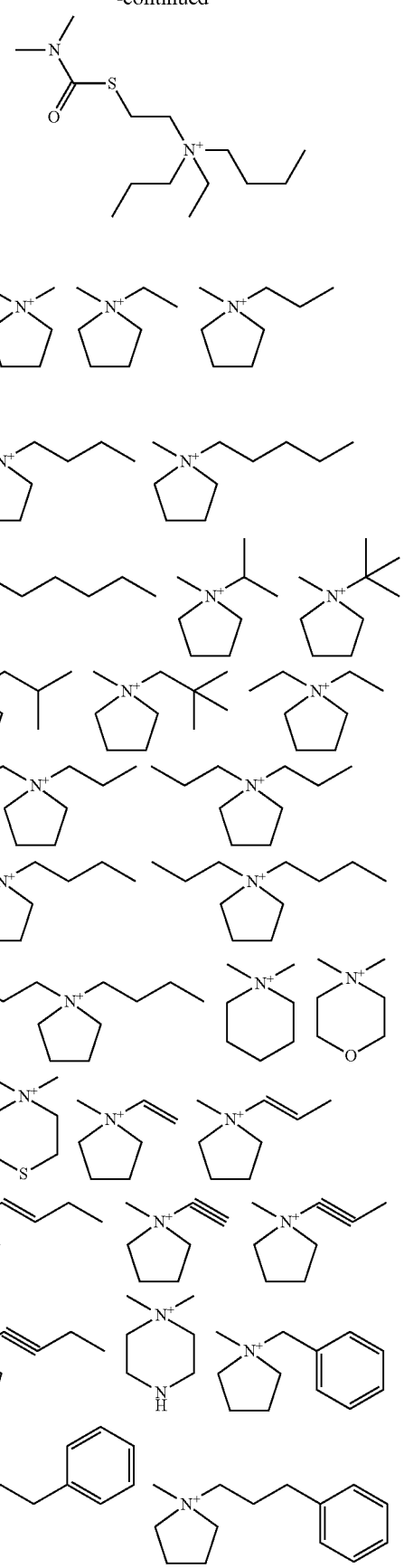

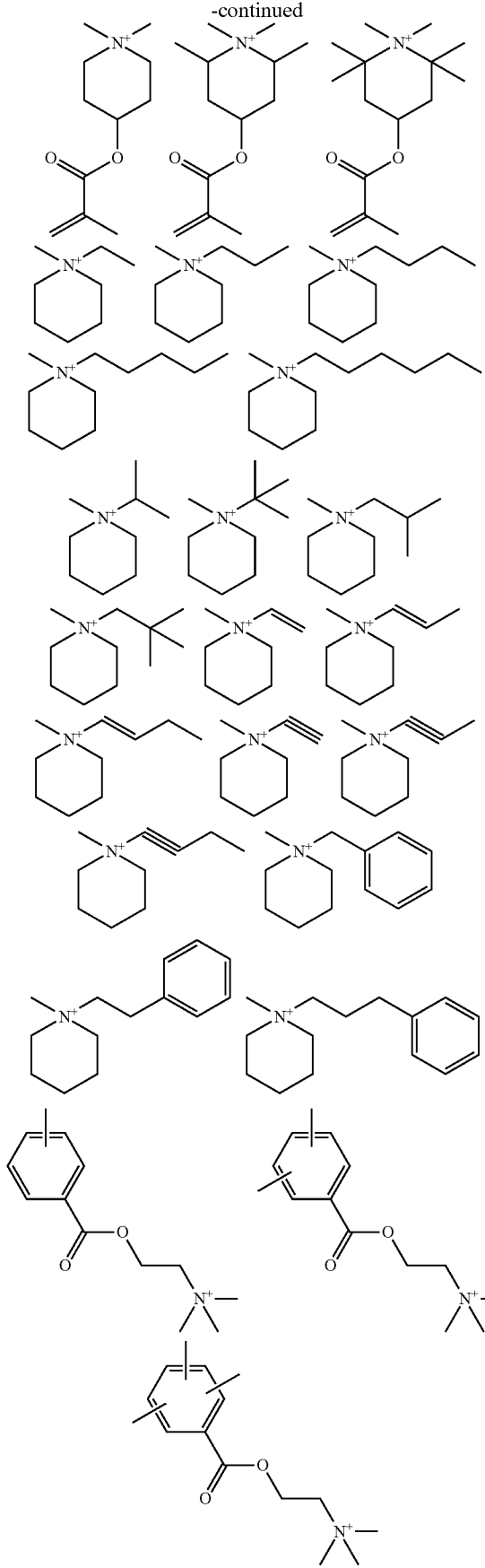
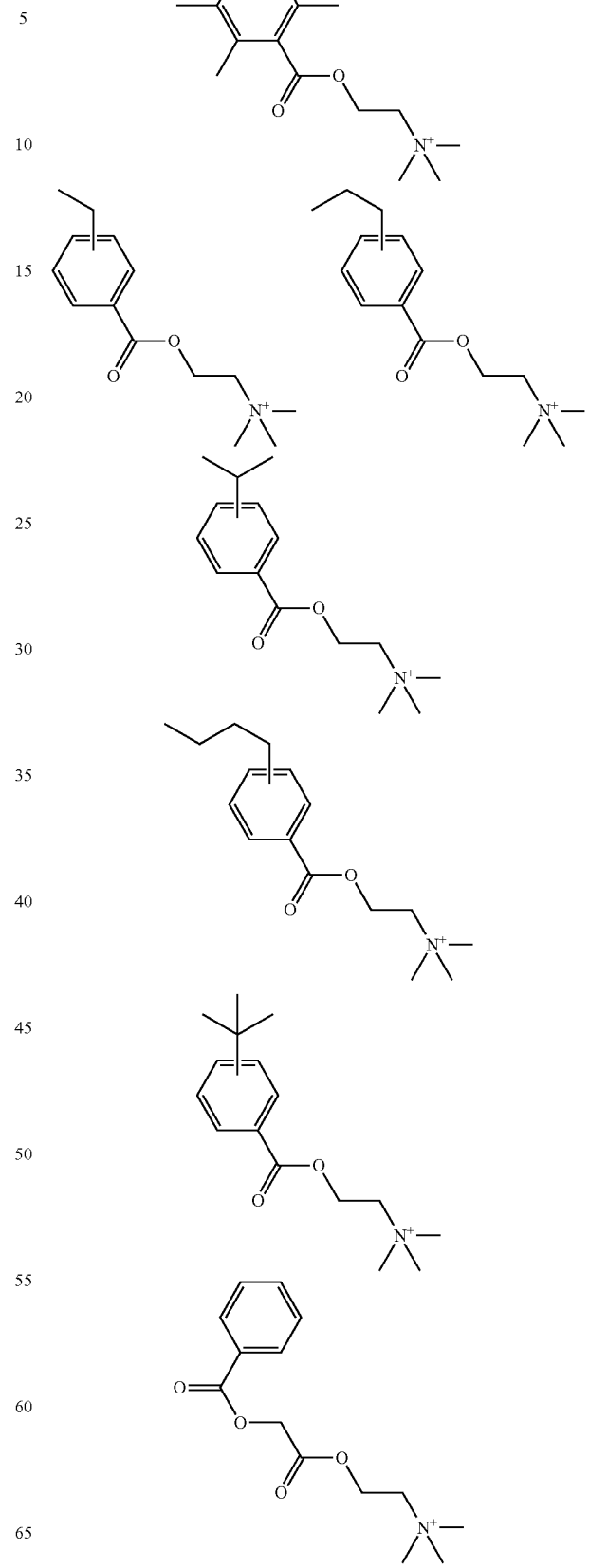

125
-continued
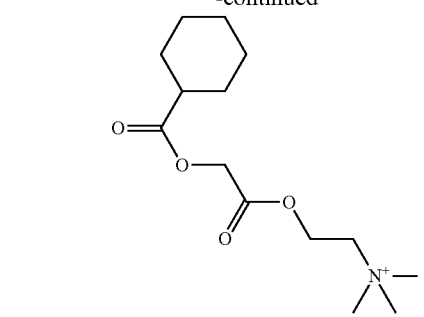
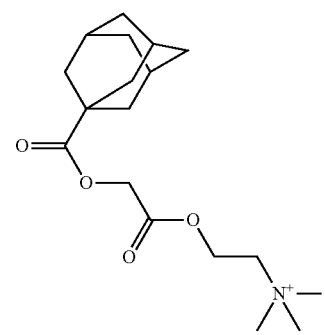
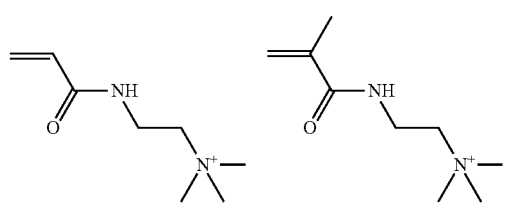
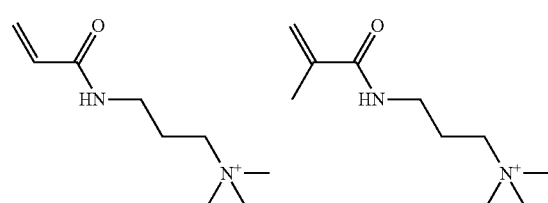
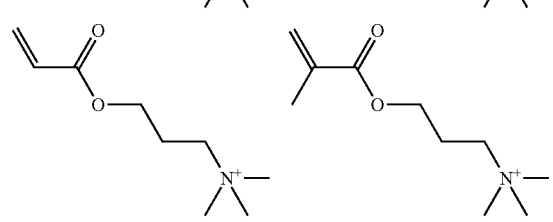
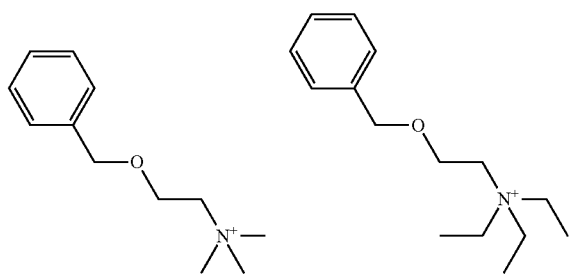
126
-continued
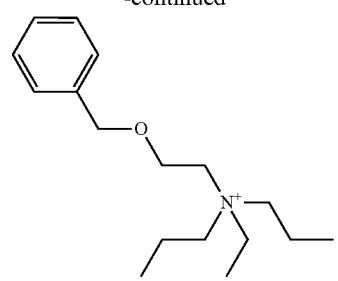
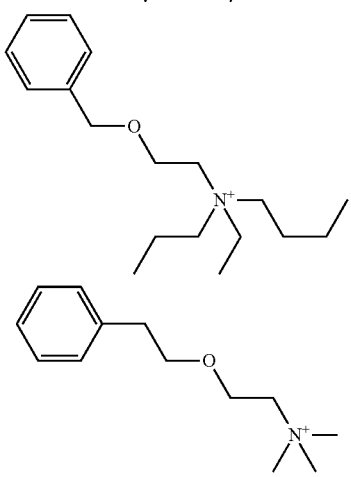
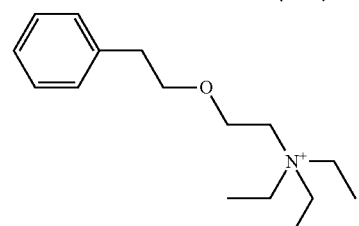
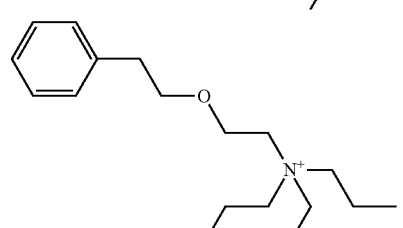
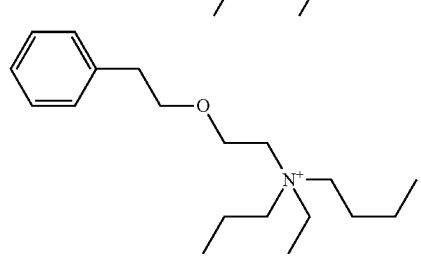
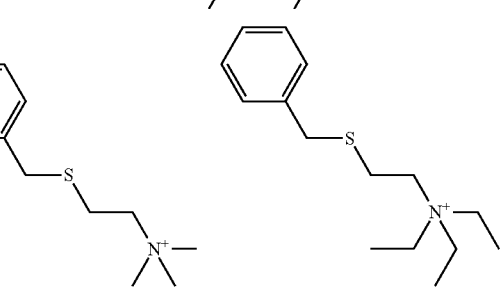

127
-continued
128
-continued
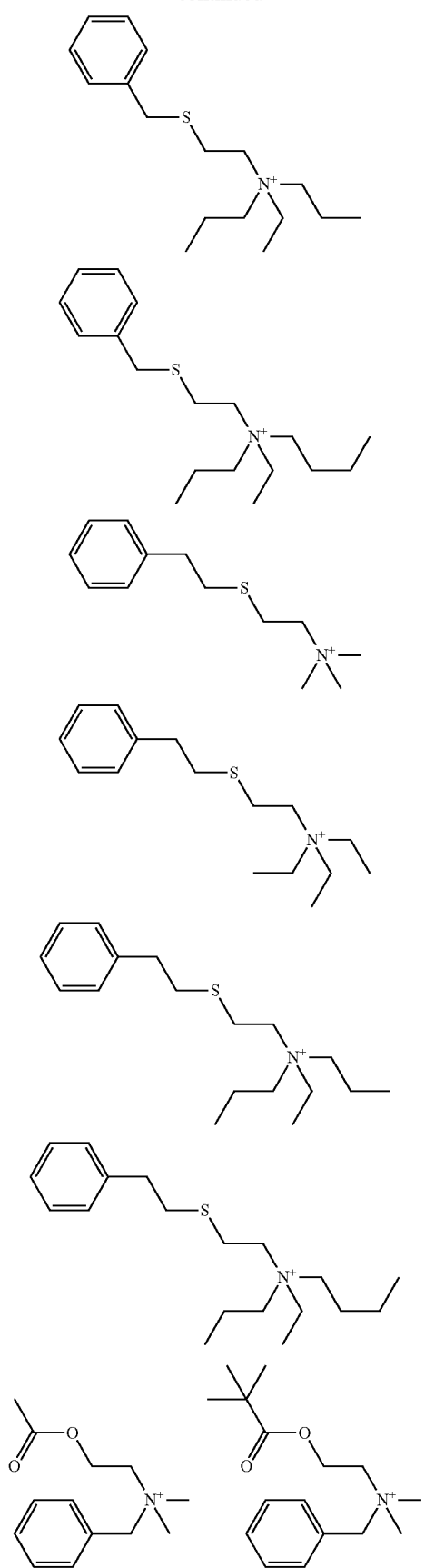
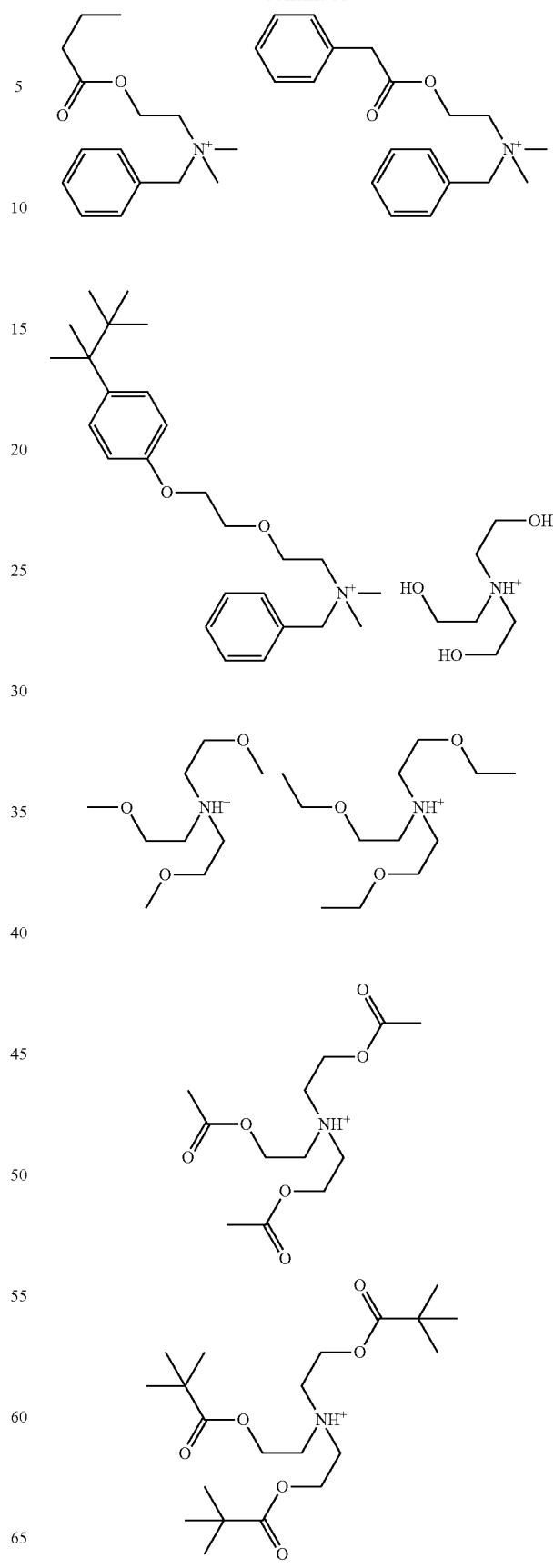

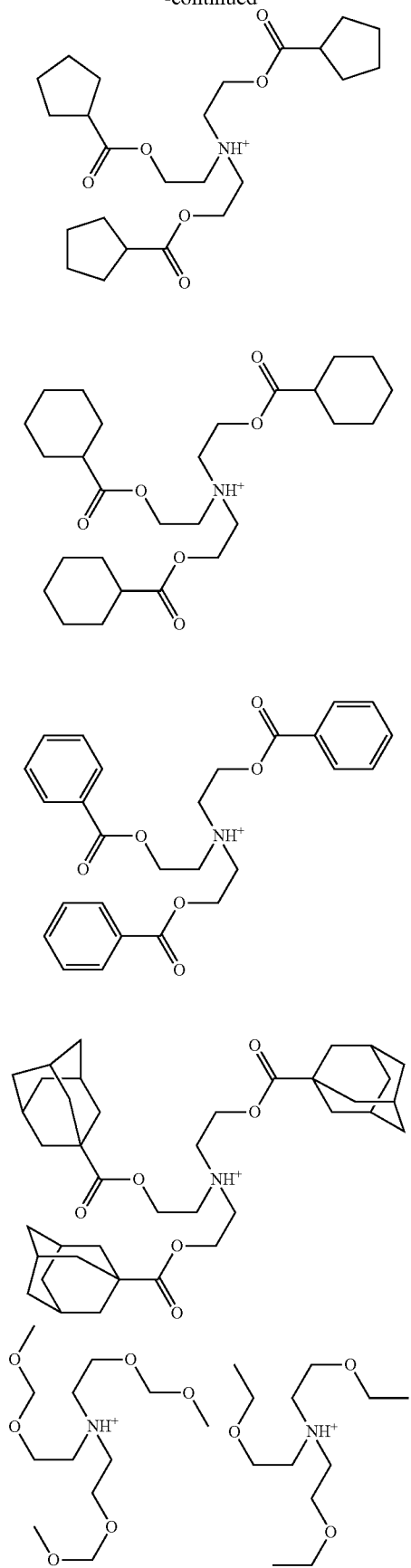
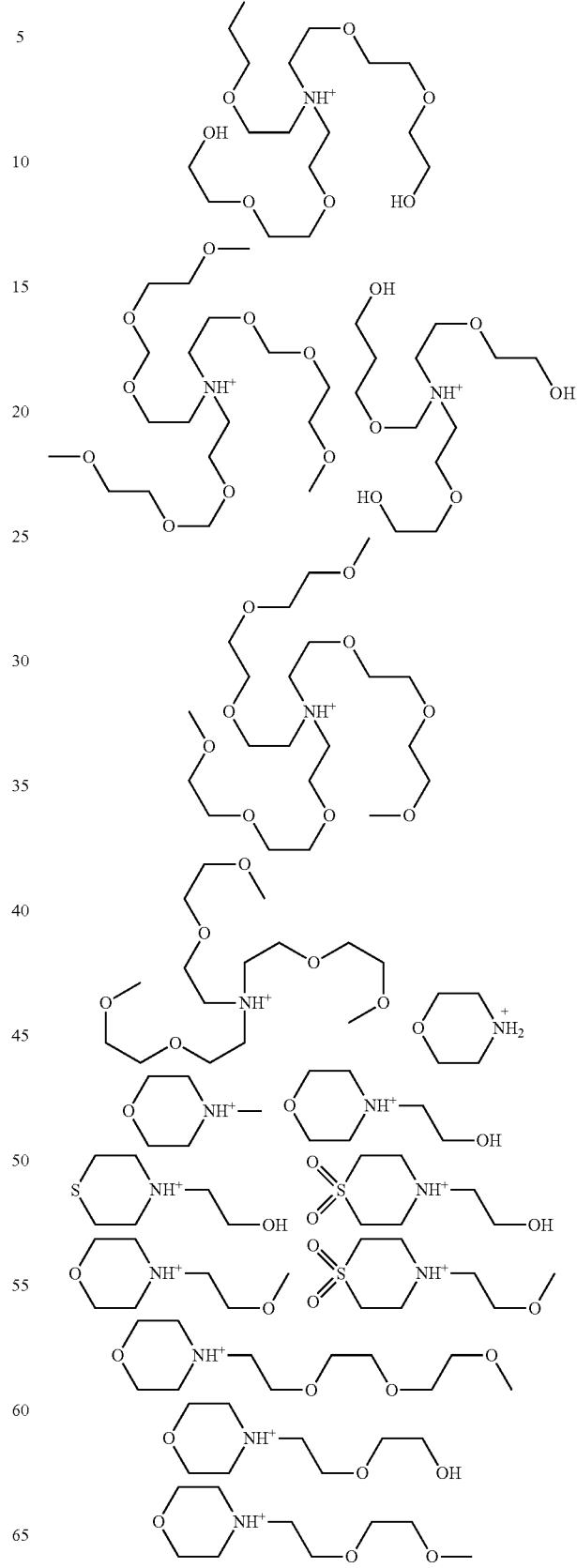

-continued

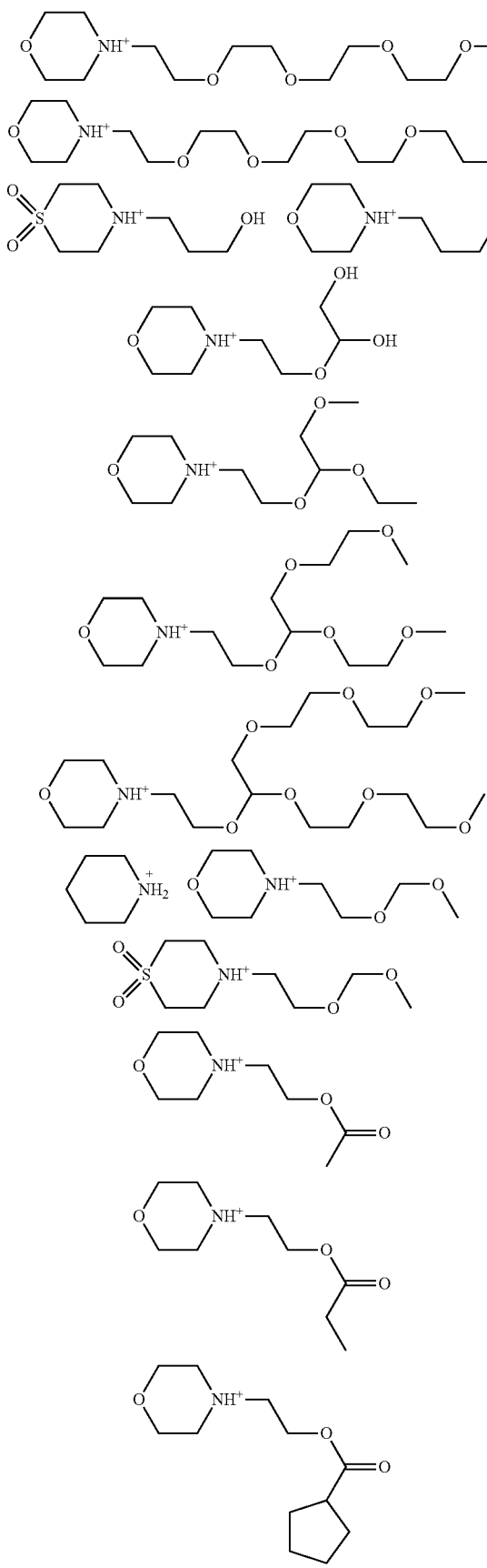

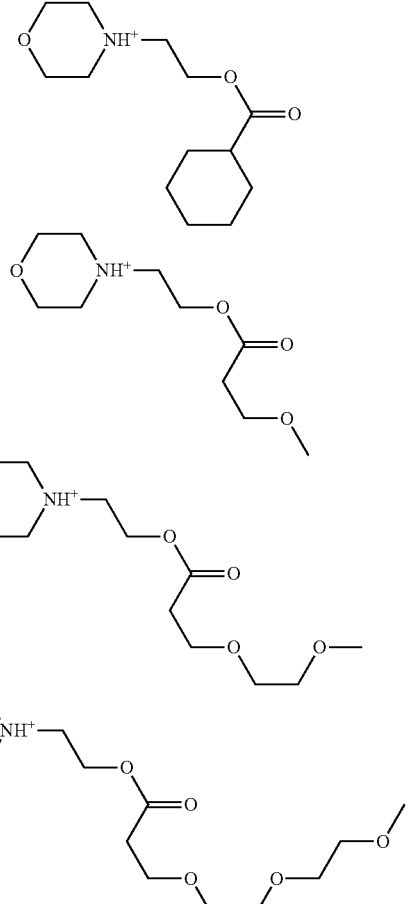

The ammonium ion shown by the general formula (3) is particularly preferably a tertiary or quaternary ammonium ion.

(Repeating Unit-b)

In addition to the repeating units-a1 to -a7, the inventive ionic polymer preferably contains a repeating unit-b having an alkoxysilyl group shown by the following general formula (4).

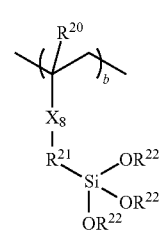

(4)

In the formula, $R^{20}$ represents a hydrogen atom or a methyl group. $X_8$ represents any of a single bond, a phenylene group, a naphthylene group, an ether group, an ester group, and an amide group. $R^{21}$ represents a single bond, a linear, branched, or cyclic alkylene group having 1 to 10 carbon atoms, or a phenylene group, and optionally contains an oxygen atom or a nitrogen atom. Each $R^{22}$ is identical to or different from one another and represents an alkyl group having 1 to 4 carbon atoms. "b" satisfies 0<b<1.0.

Specific examples of a monomer to give the repeating unit-b shown by the general formula (4) can include the following.

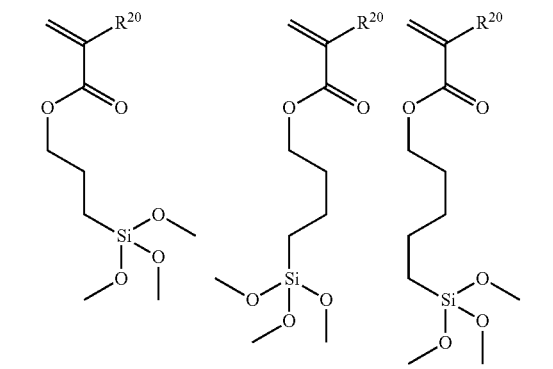

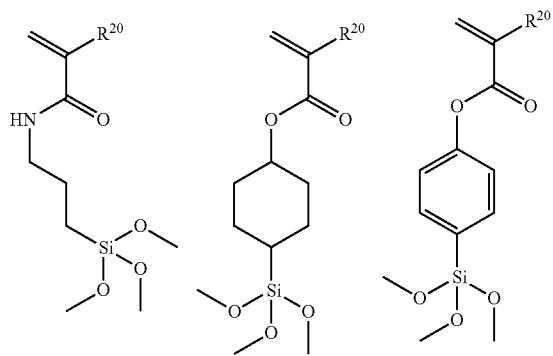

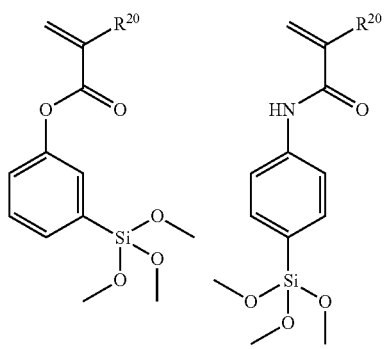

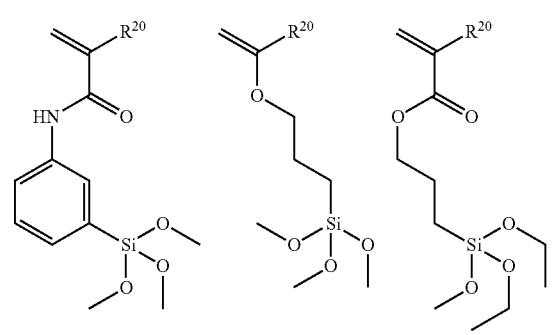

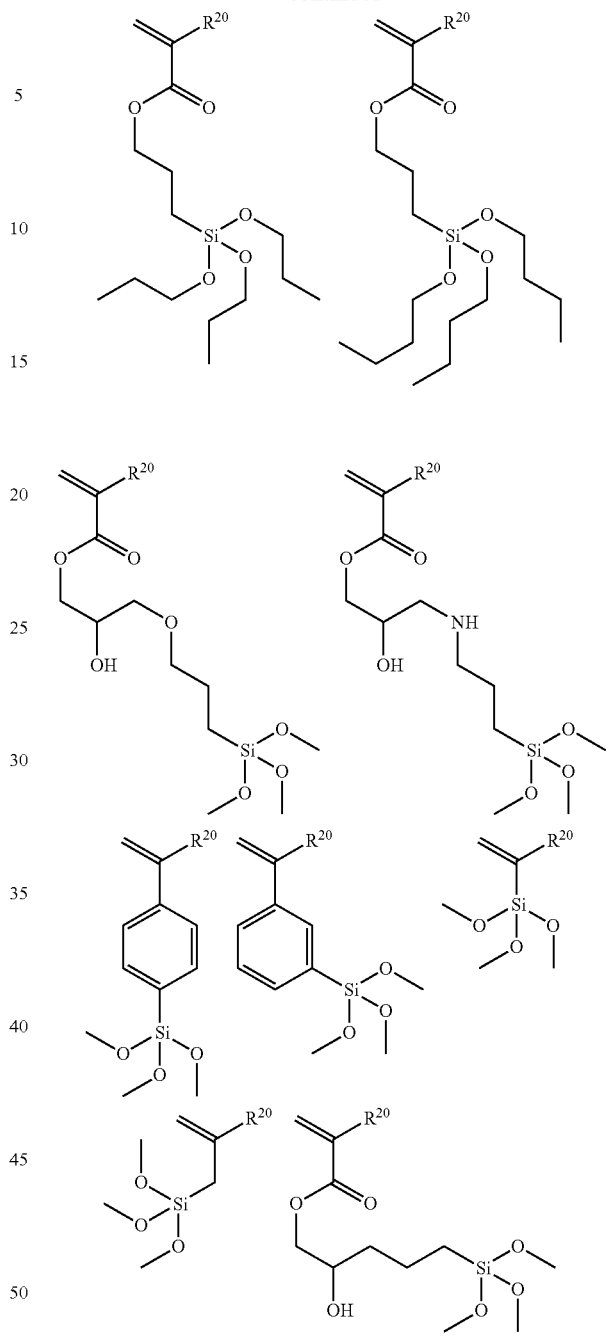

(Repeating Unit-c)

Besides the repeating units-a1 to -a7 and -b, a repeating unit-c having a glyme chain can also be copolymerized in the ionic polymer in the component (A) of the inventive bio-electrode composition in order to enhance the electric conductivity. Specific examples of a monomer to give the repeating unit-c having a glyme chain can include the following. In a case where a bio-electrode according to the present invention is a dry electrode, the copolymerization with a repeating unit having a glyme chain facilitates the movement of ions released from skin in the dry electrode film, and thus can increase the sensitivity of the dry electrode.

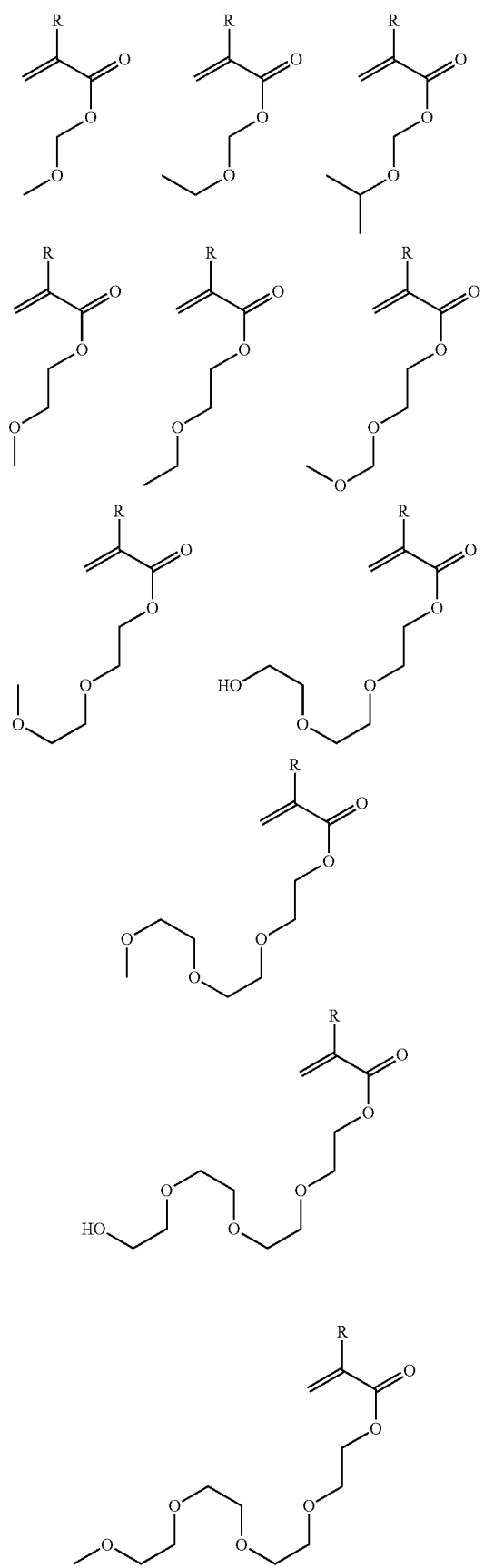
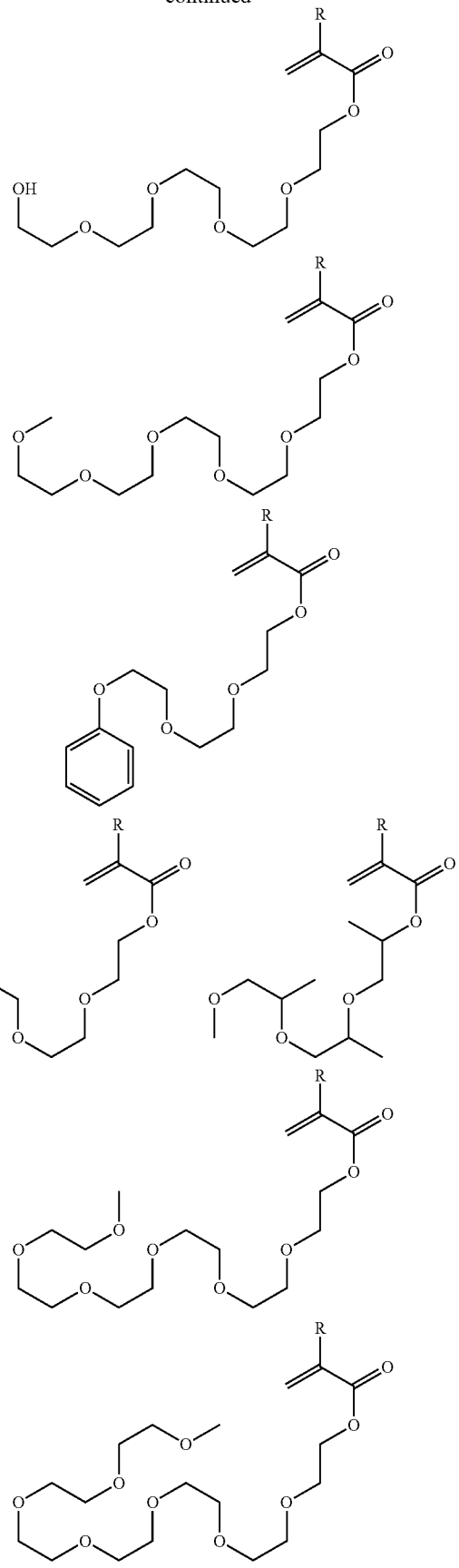

137
-continued
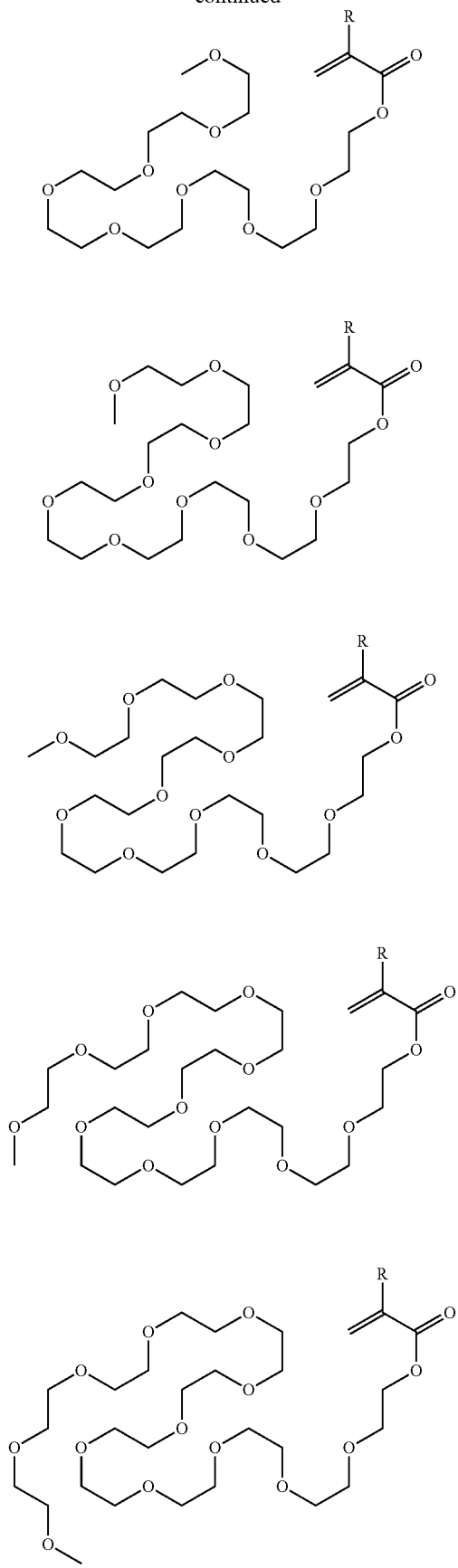
138
-continued
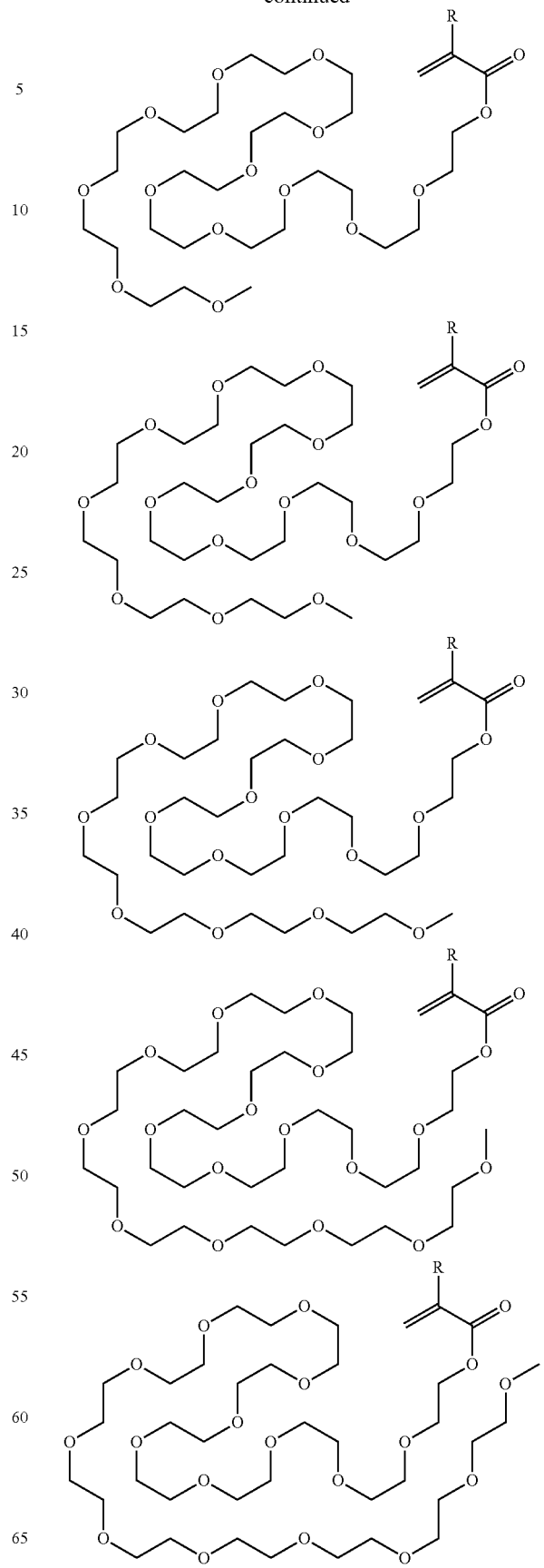

139
-continued
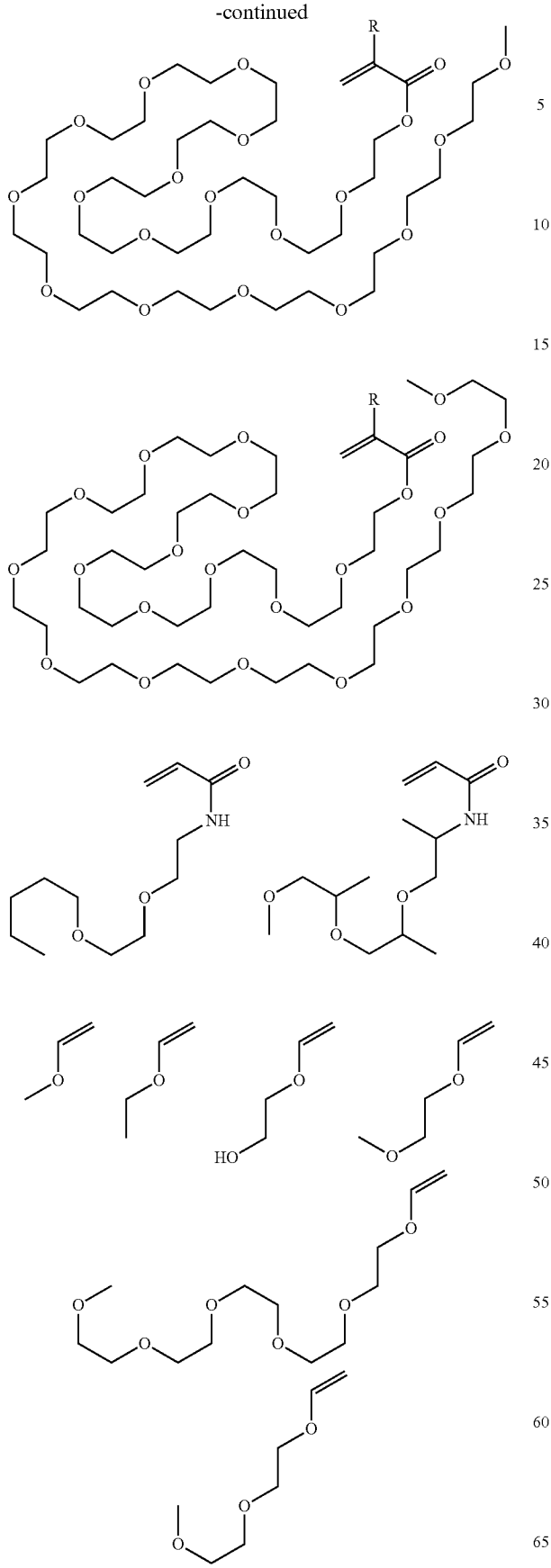
140
-continued
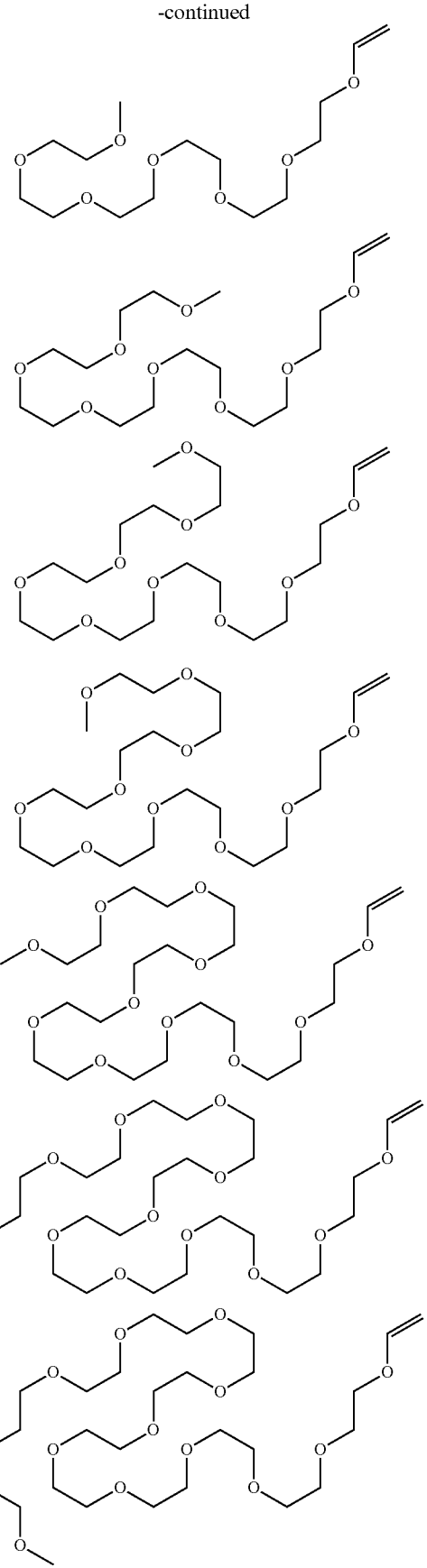

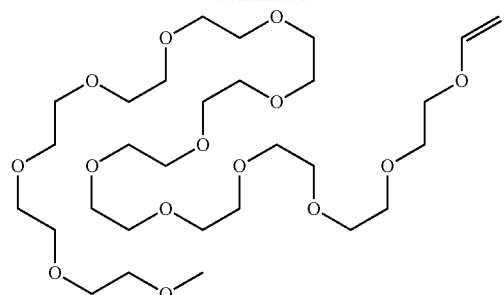
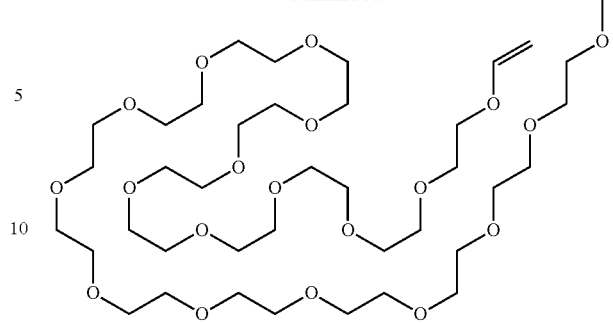
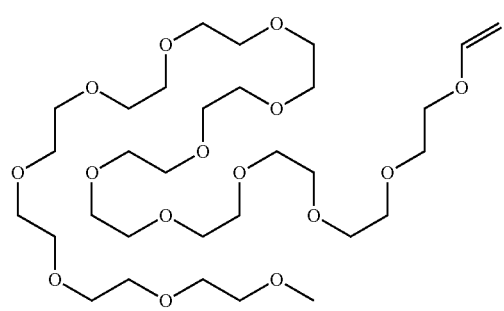
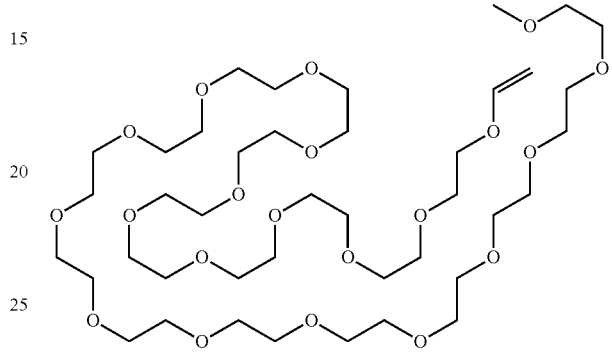
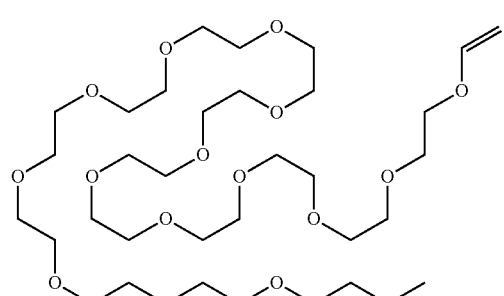
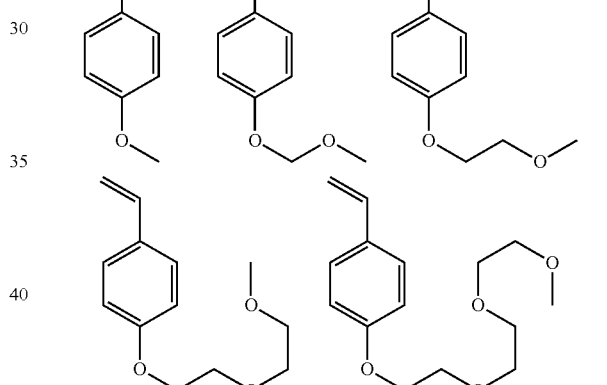
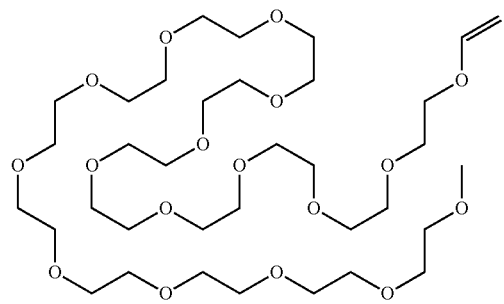
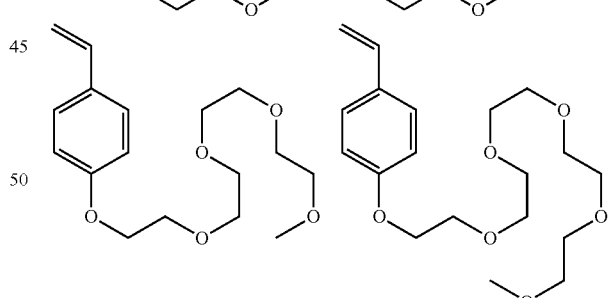
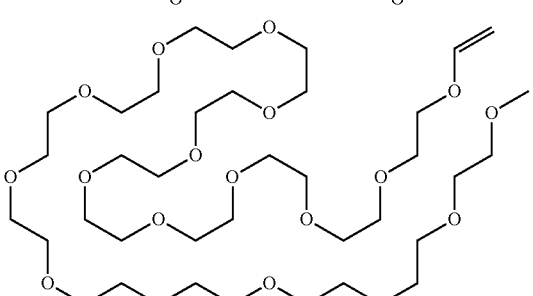
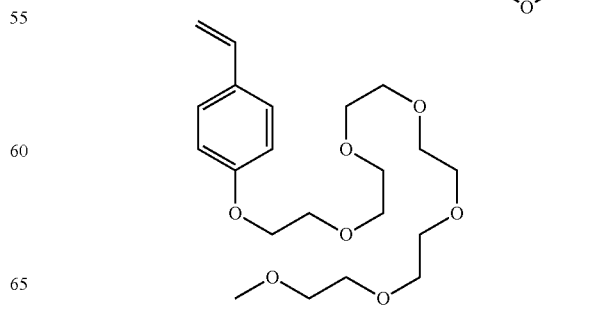

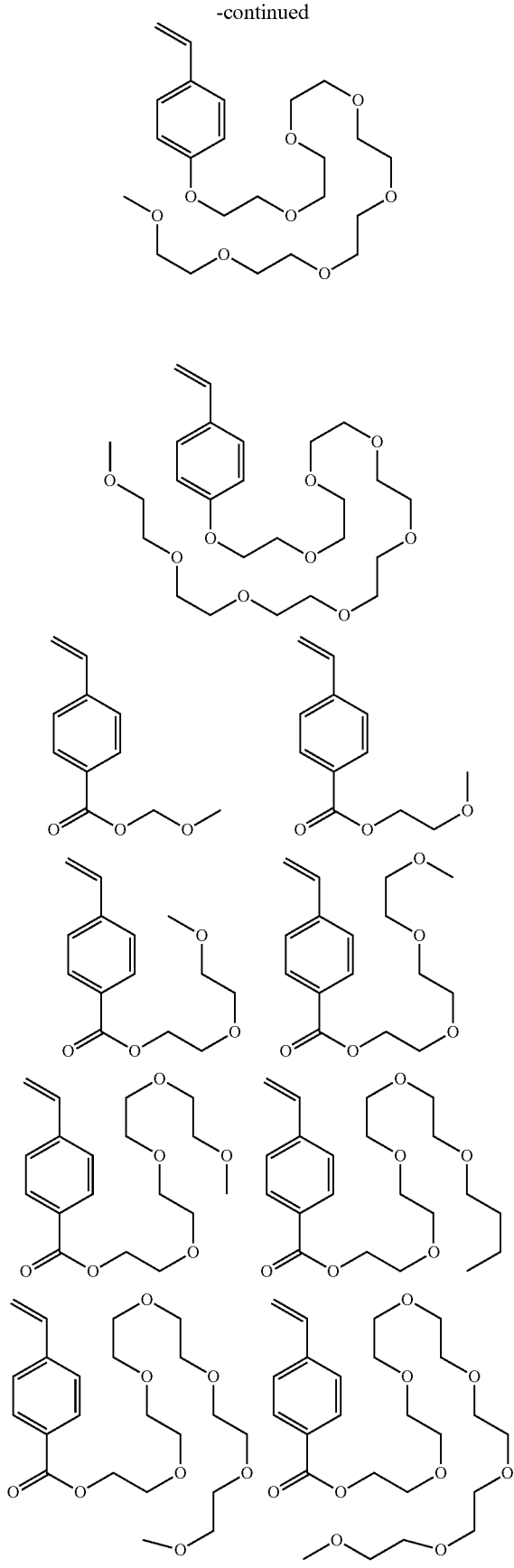

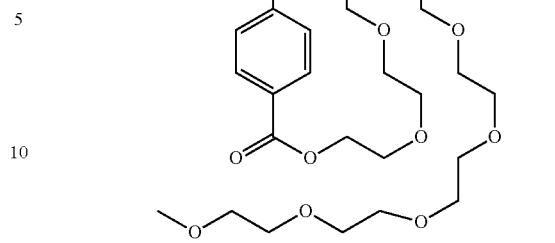

R represents a hydrogen atom or a methyl group.

(Repeating Unit-d)

Besides the repeating units-a1 to -a7, -b, and -c, a hydrophilic repeating unit-d having a hydroxy group, a carboxyl group, an ammonium salt, a betaine, an amide group, pyrrolidone, a lactone ring, a lactam ring, a sultone ring, a sodium salt of sulfonic acid, or a potassium salt of sulfonic acid can also be copolymerized in the ionic polymer in the component (A) of the inventive bio-electrode composition in order to enhance the electric conductivity. Specific examples of a monomer to give the hydrophilic repeating unit-d can include the following. The copolymerization with repeating units containing such hydrophilic groups can increase the sensitivity of the dry electrode by increasing the sensitivity to ions released from skin.

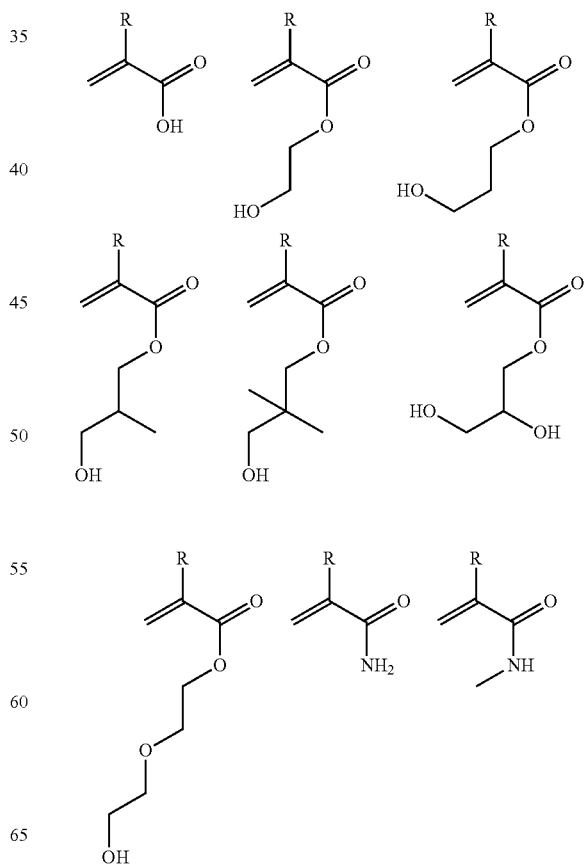

-continued
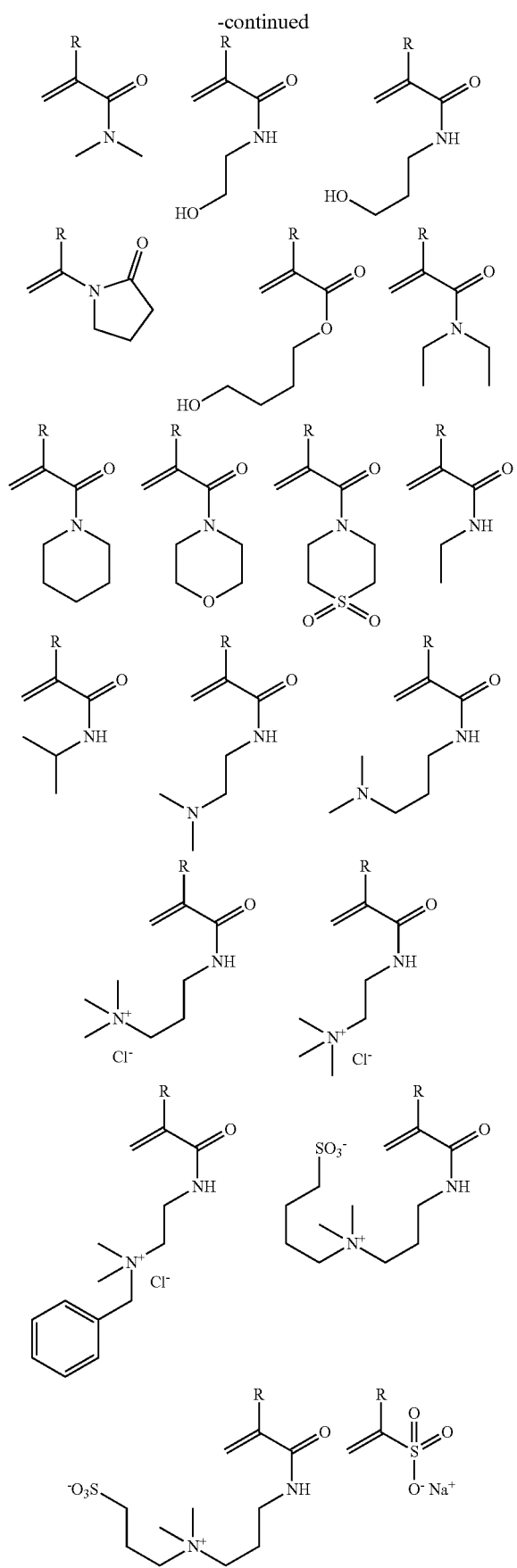
-continued
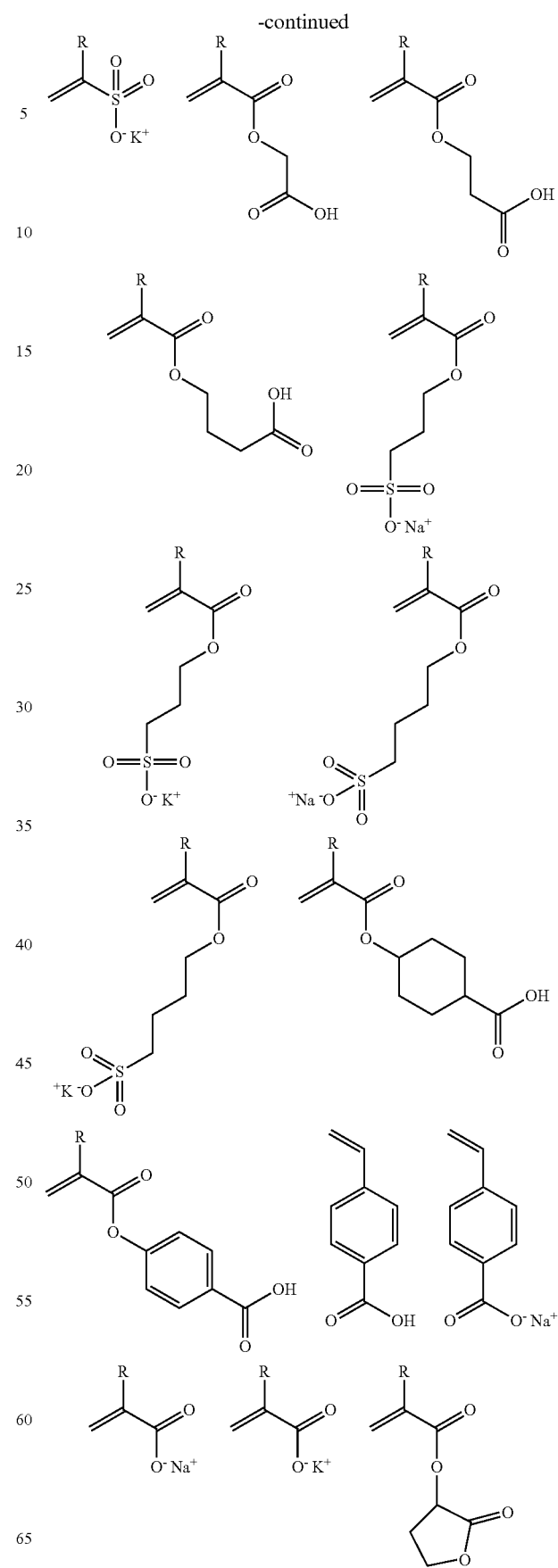

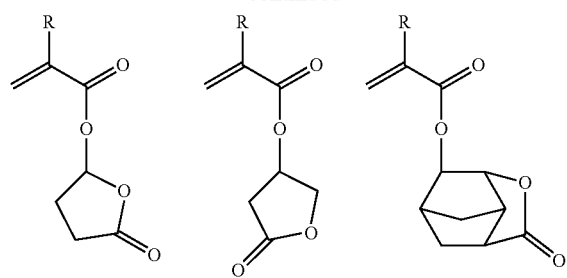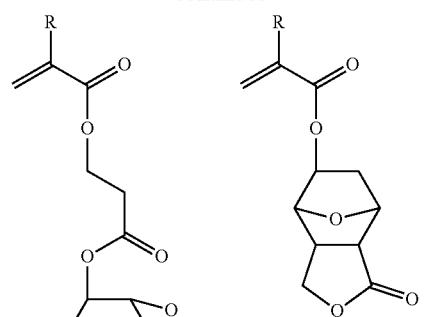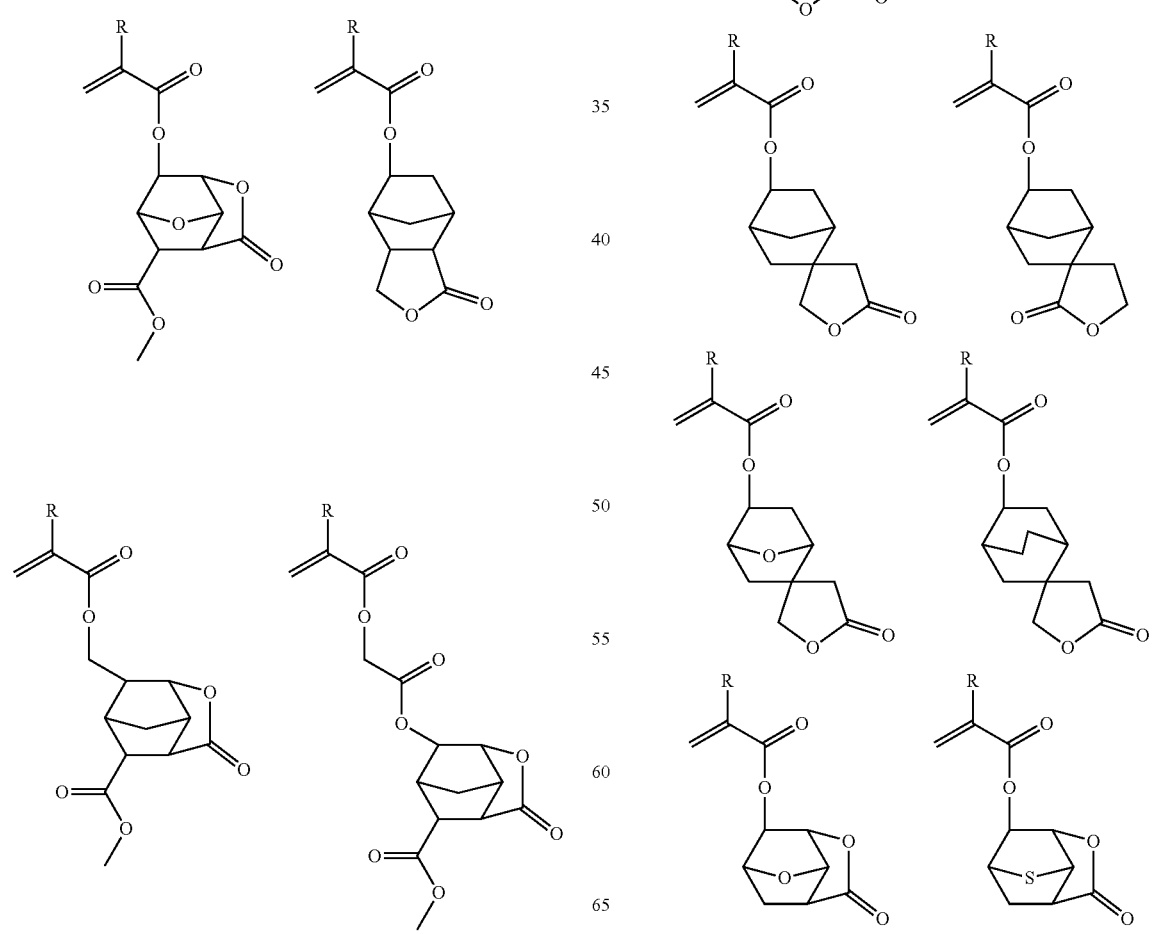

-continued
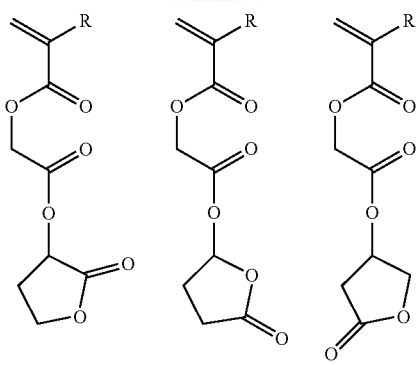
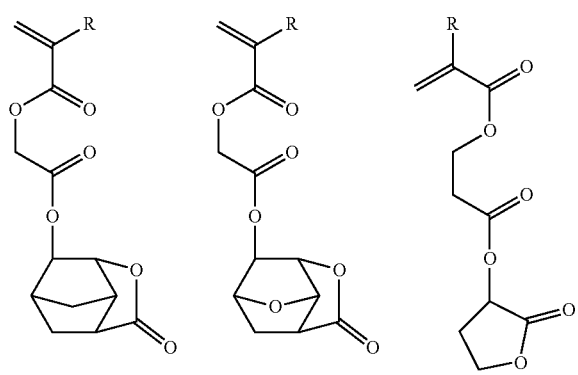
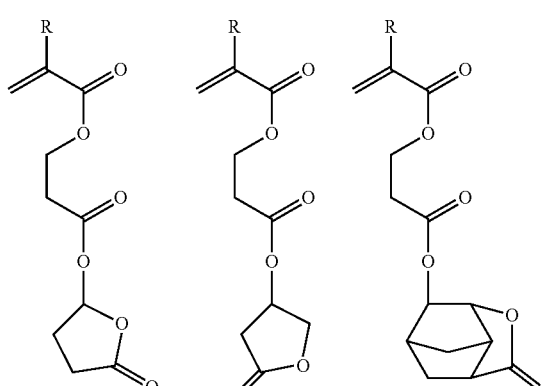
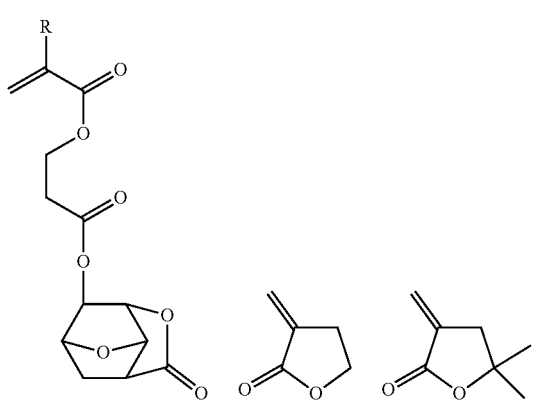
-continued
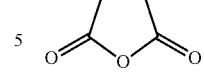
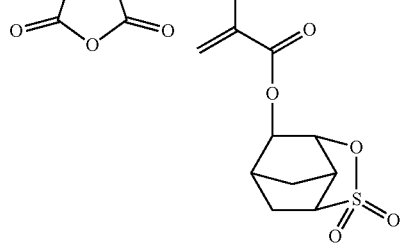
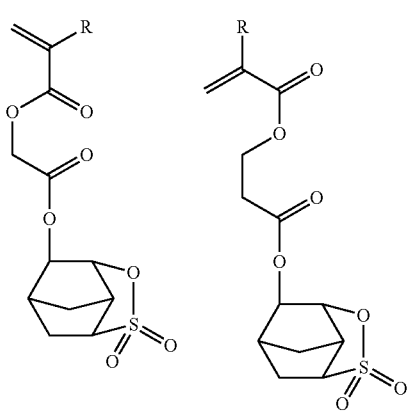
R represents a hydrogen atom or a methyl group.
The ionic polymer in the component (A) of the inventive bio-electrode composition can have a repeating unit-e to impart adhesion properties. Specific examples of a monomer to give the repeating unit-e can include the following.
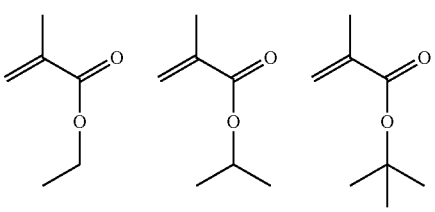
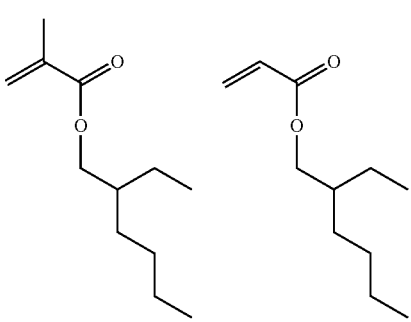

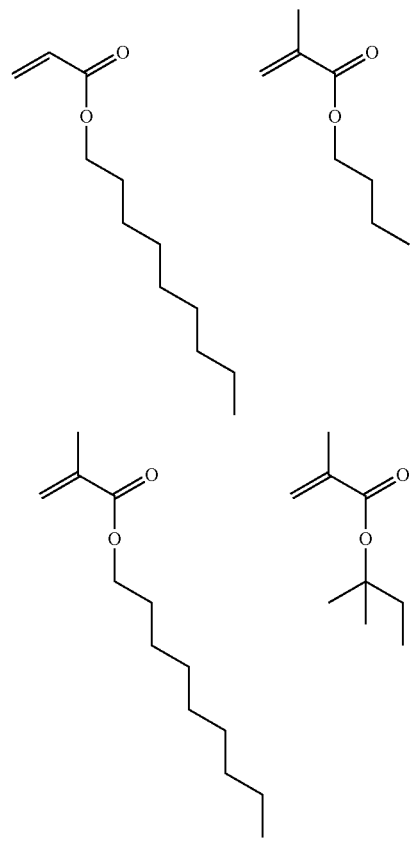
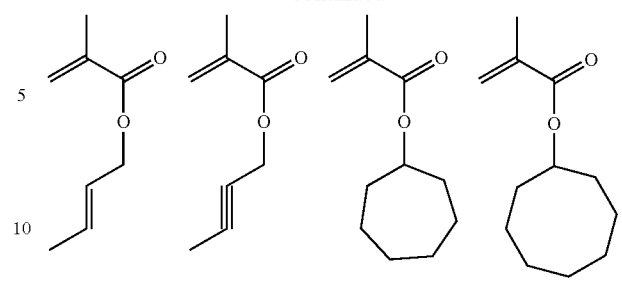

153
-continued
154
-continued
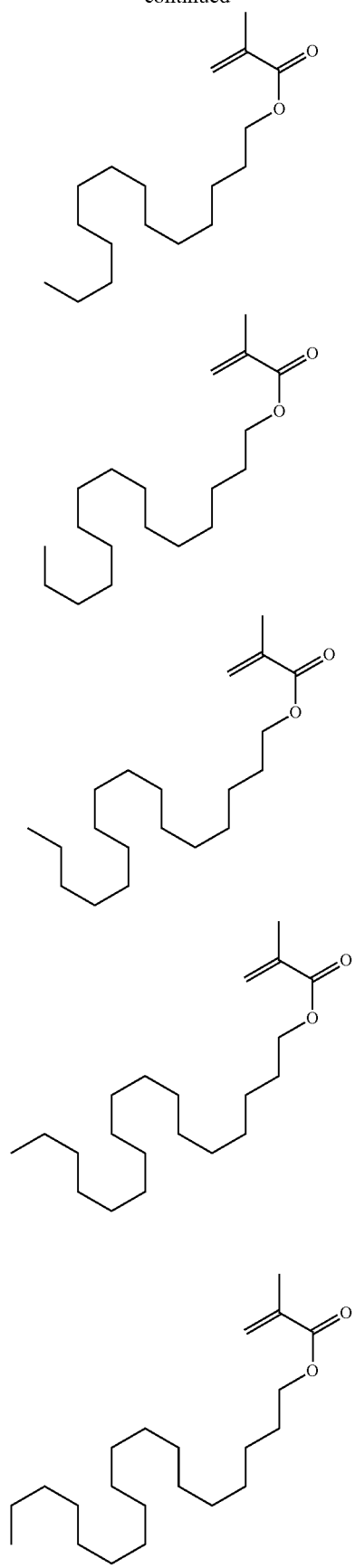
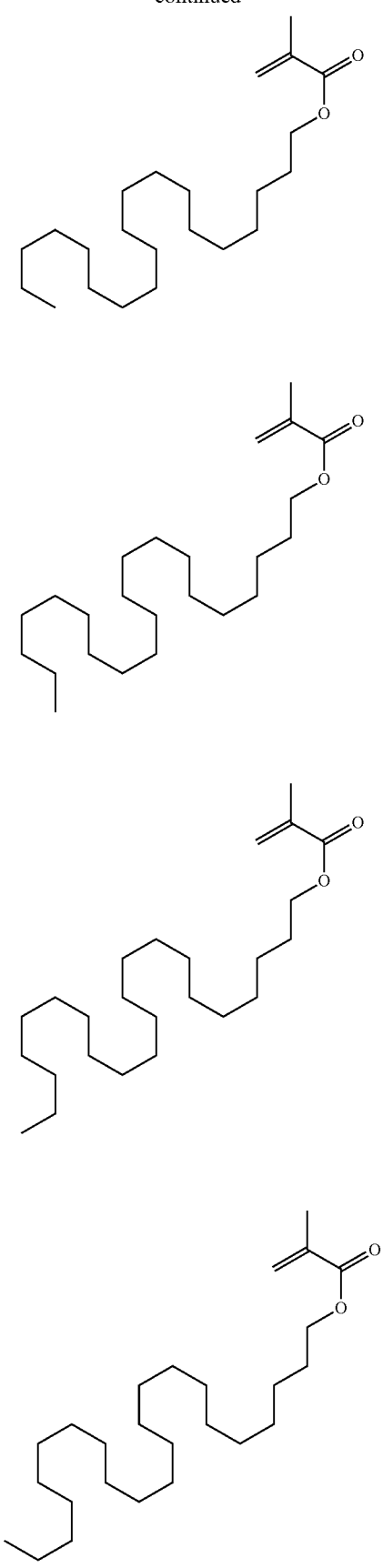

155
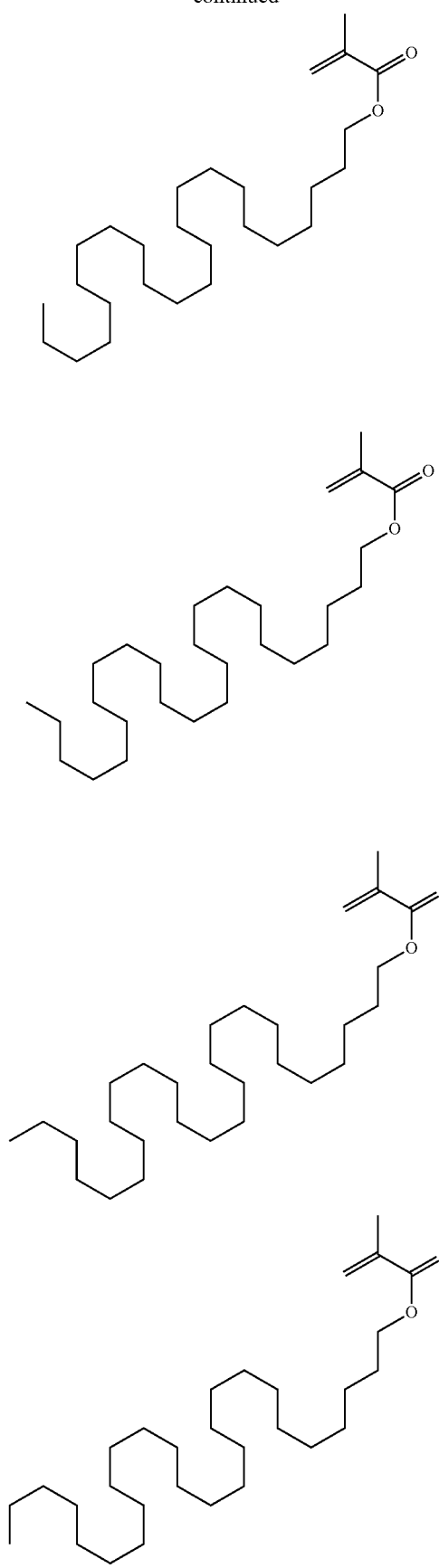
156
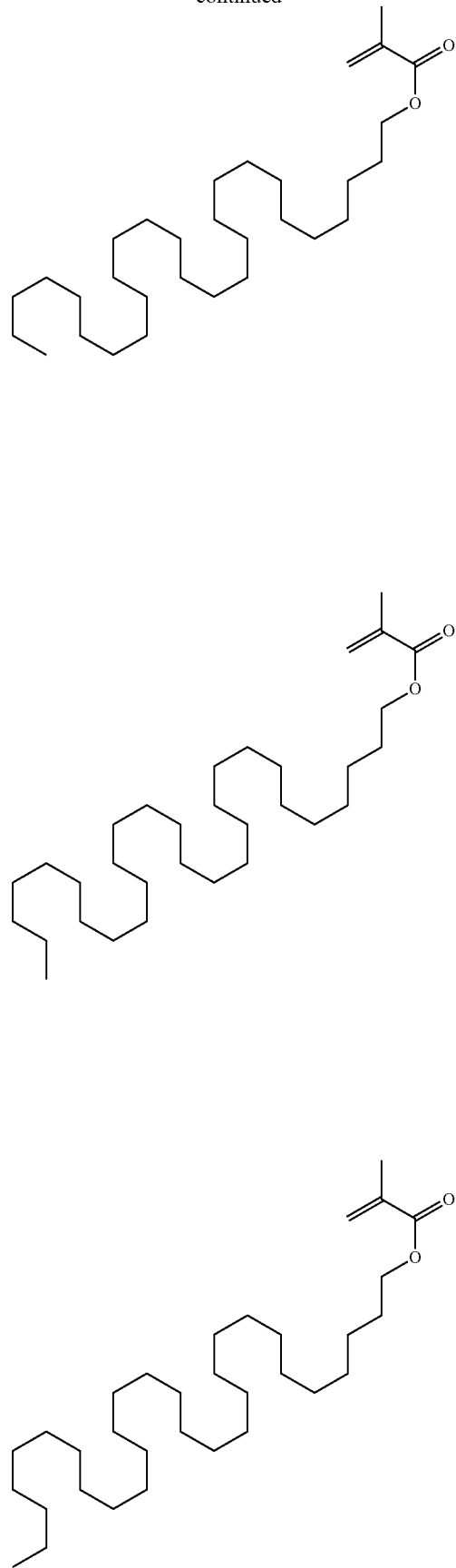

157
-continued
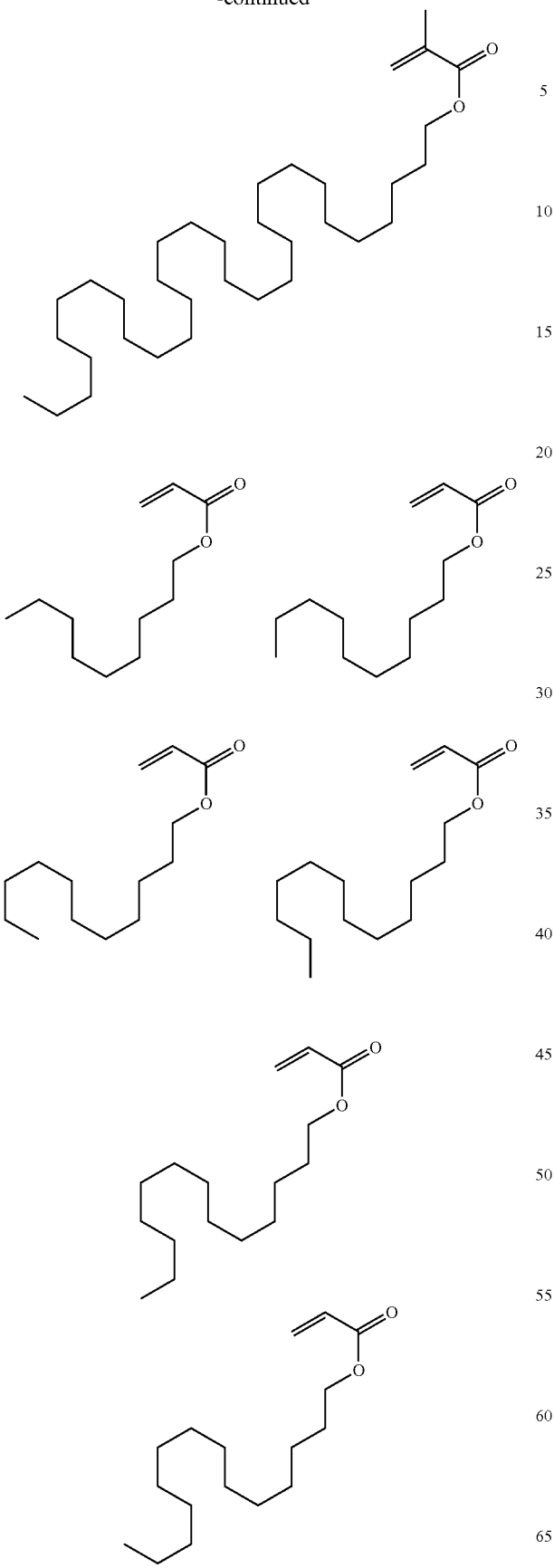
158
-continued
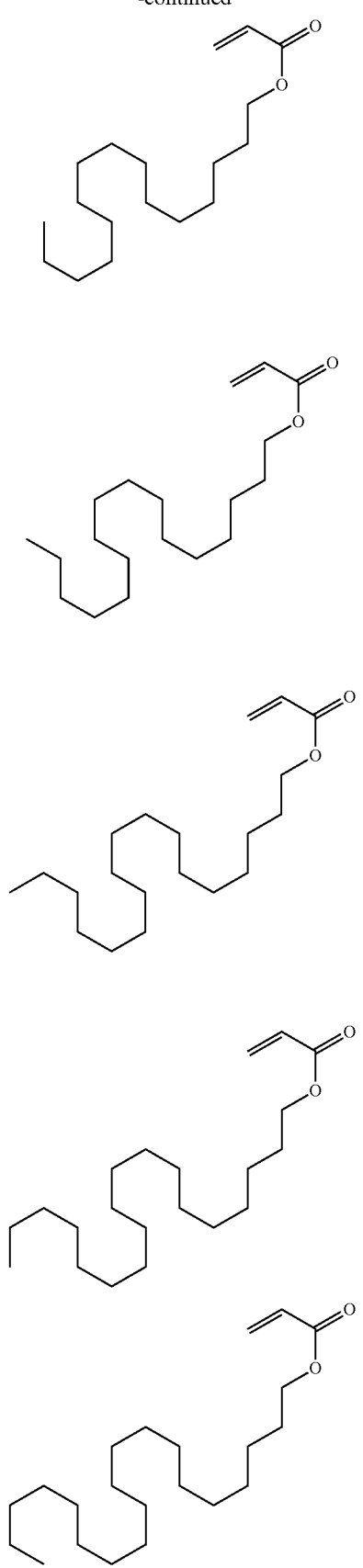

159
-continued
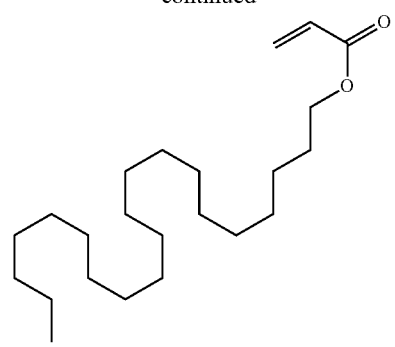
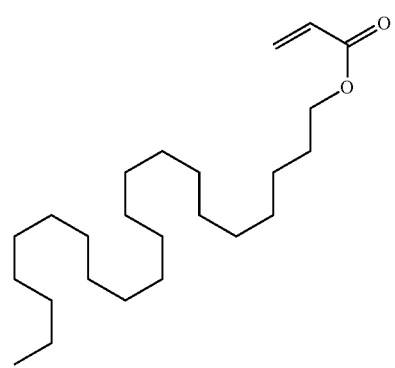
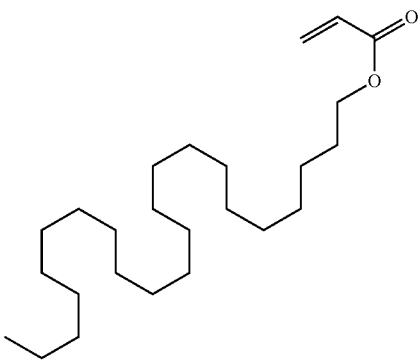
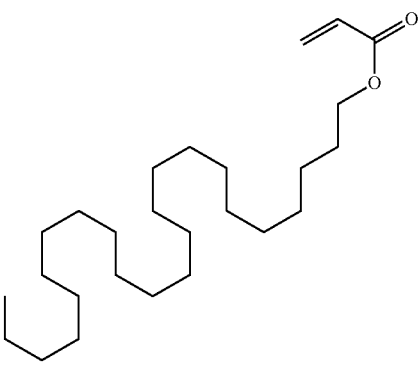
160
-continued
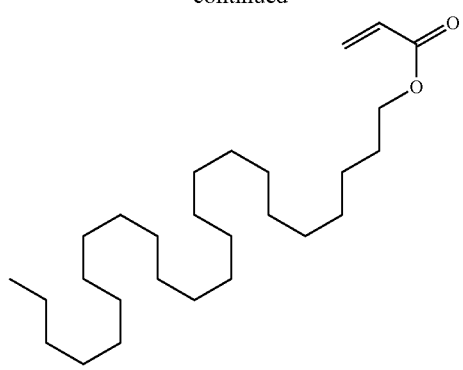
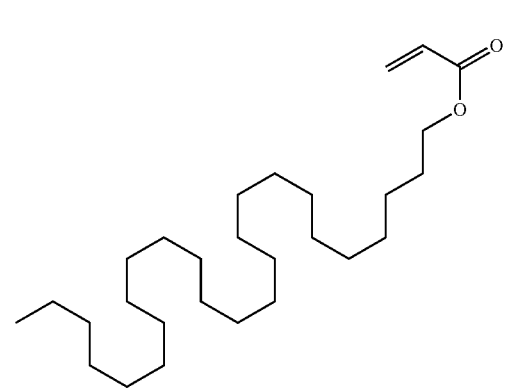
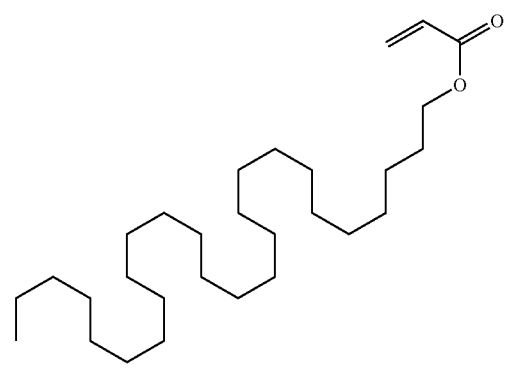
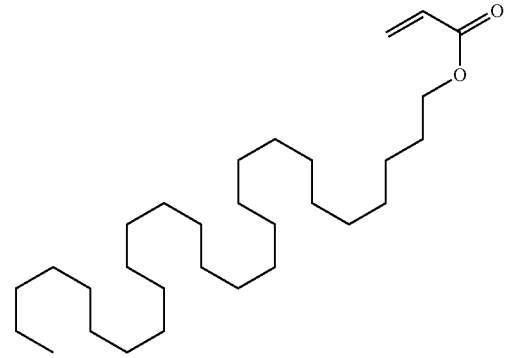

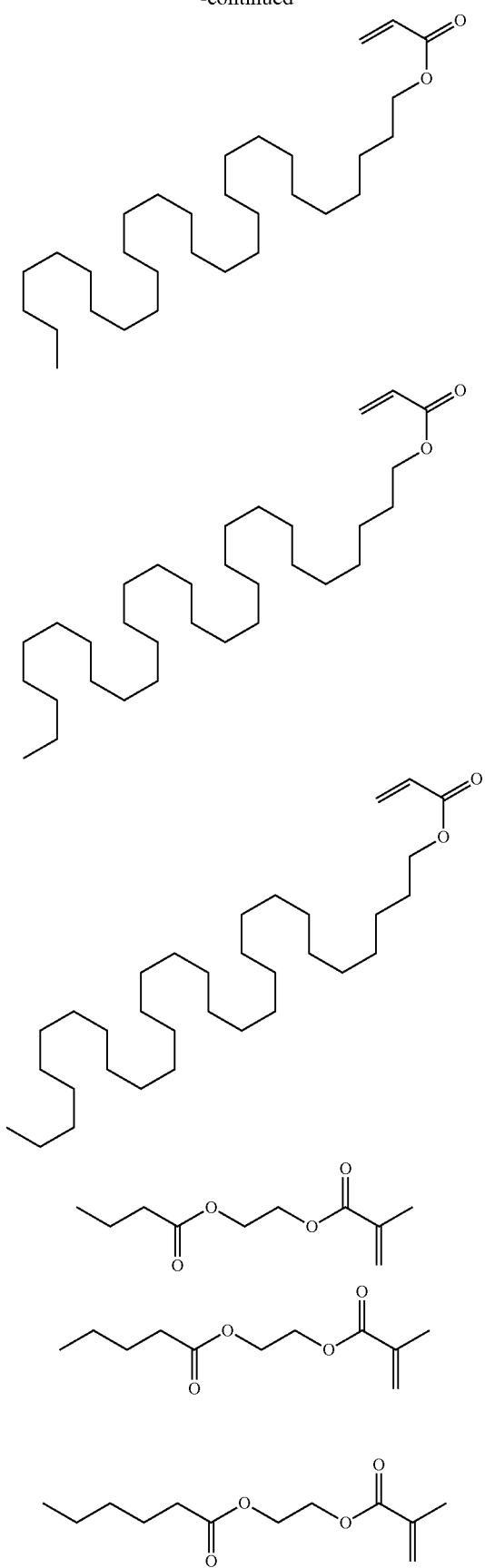
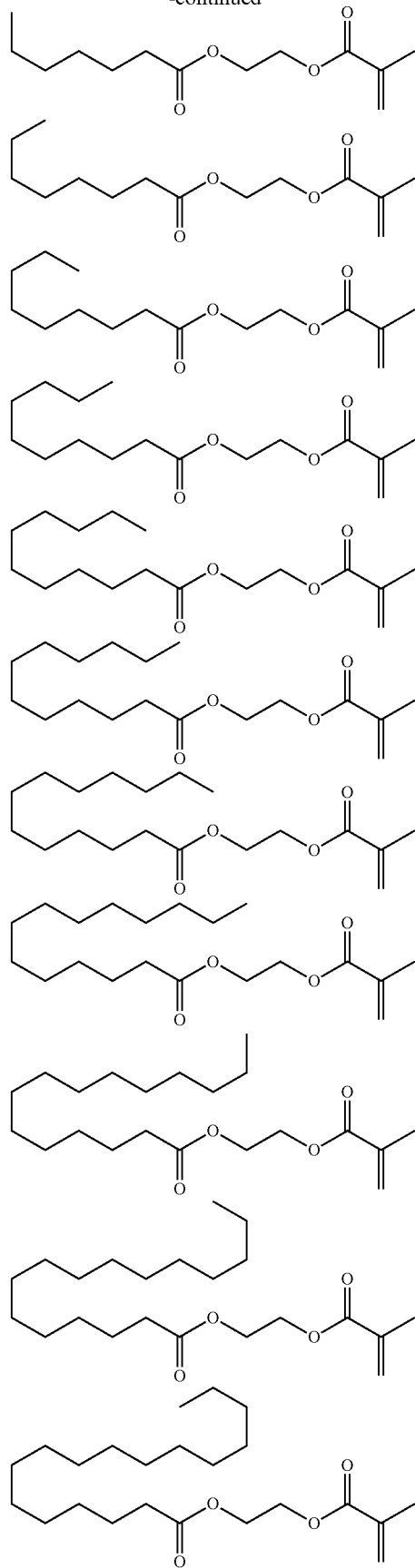

163
-continued
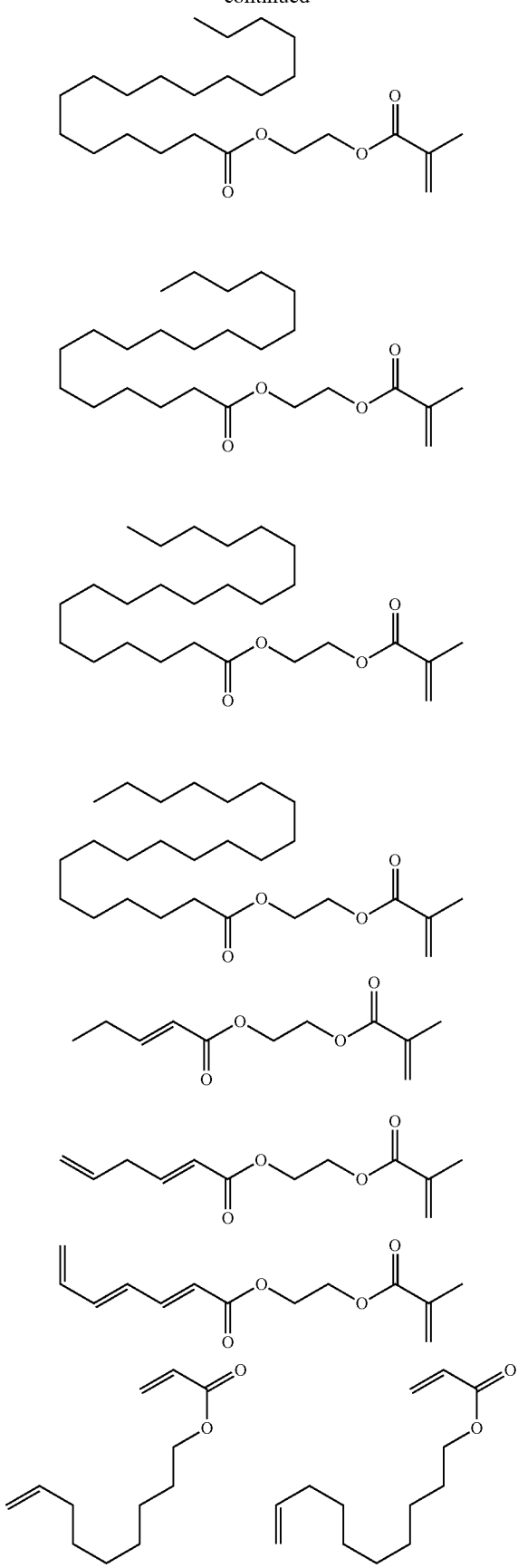
164
-continued
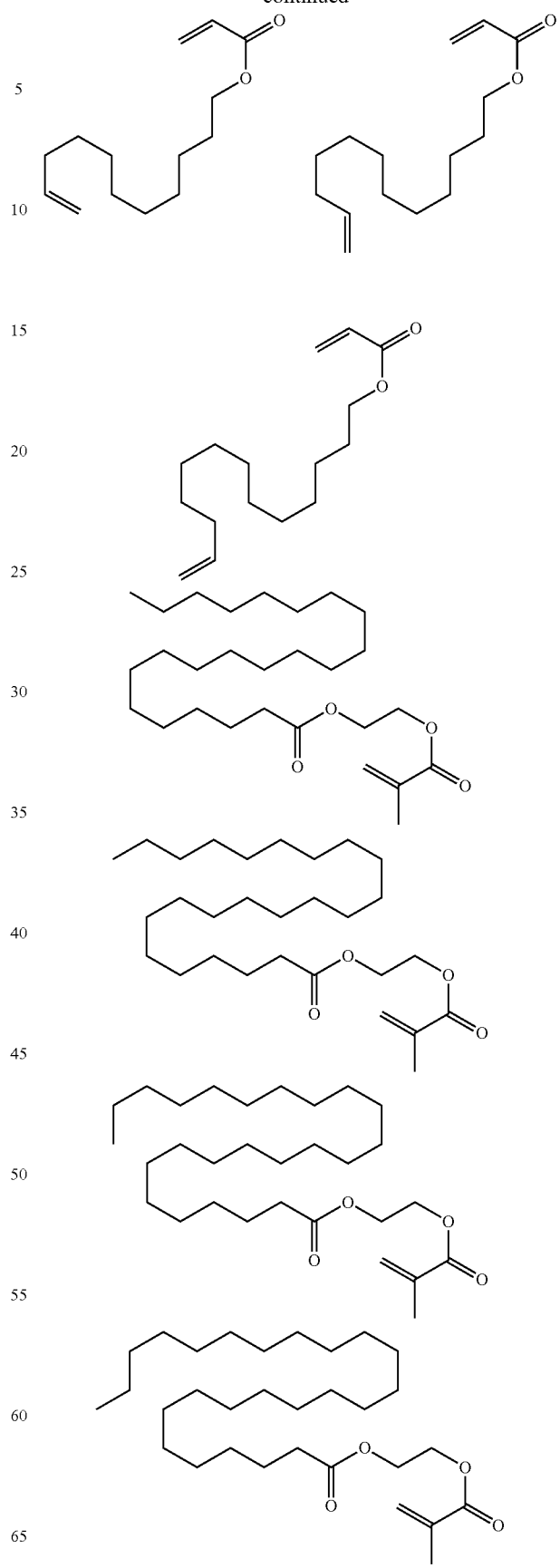

-continued
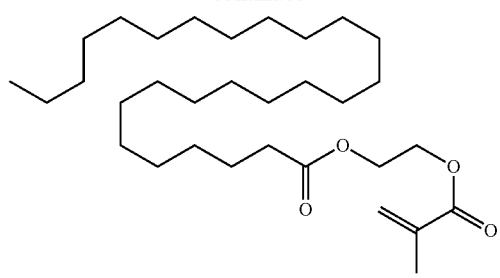
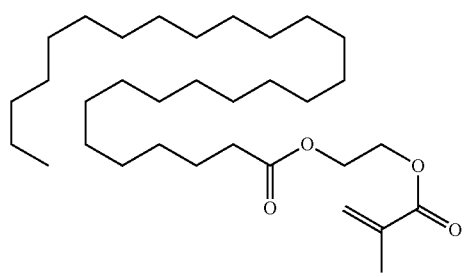
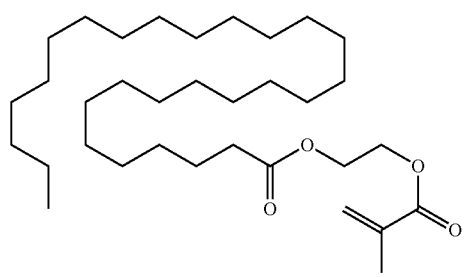
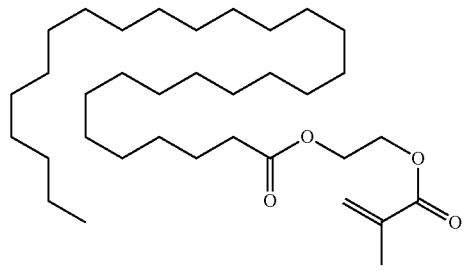
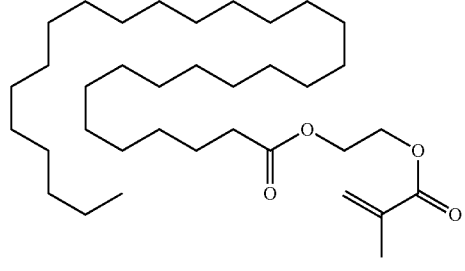
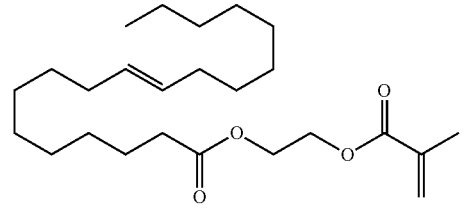
-continued
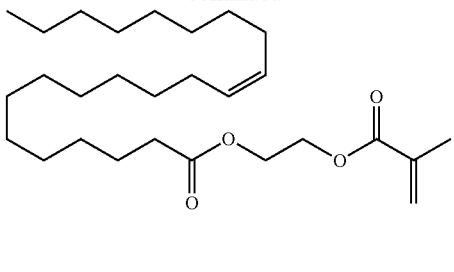
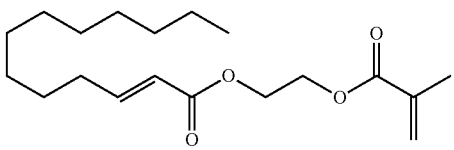
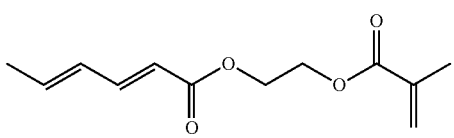
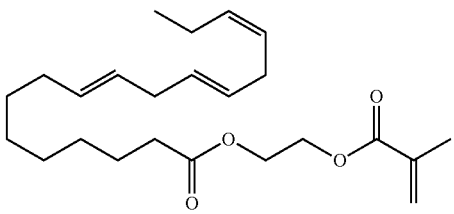
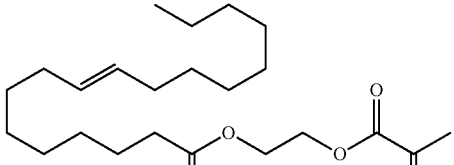
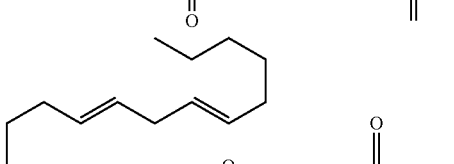
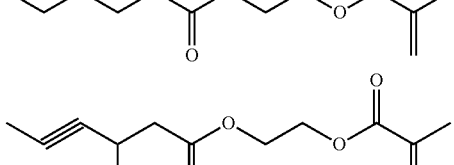
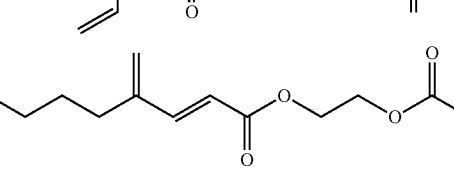
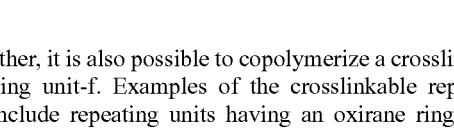
Further, it is also possible to copolymerize a crosslinkable repeating unit-f. Examples of the crosslinkable repeating unit include repeating units having an oxirane ring or an oxetane ring.

Specific examples of monomers to give the repeating unit-f having an oxirane ring or an oxetane ring can include the following.
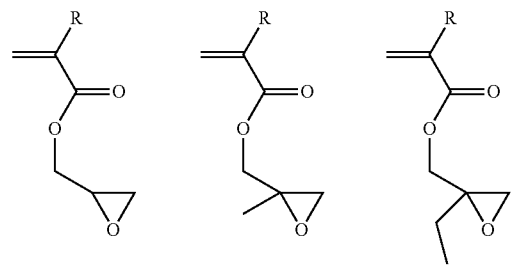
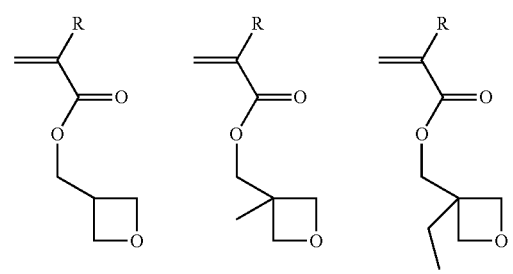
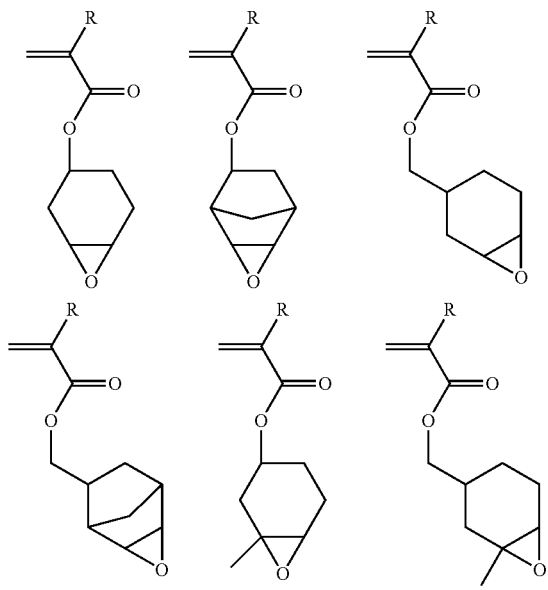
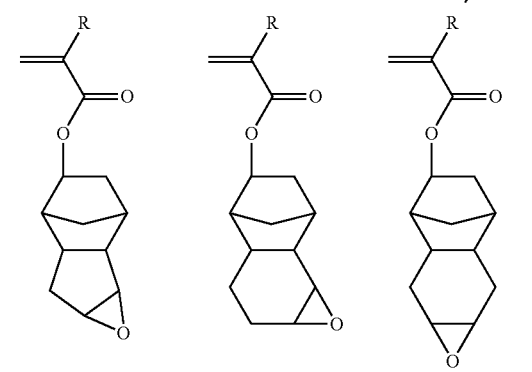
-continued
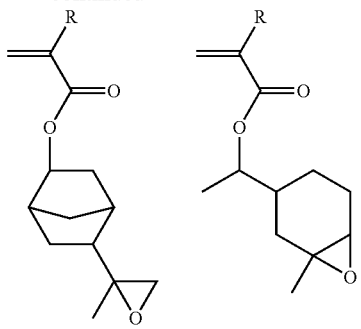
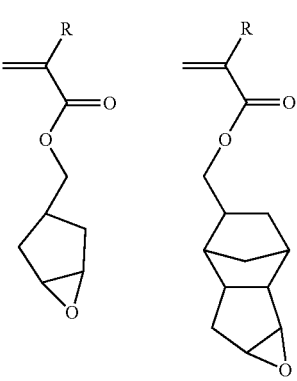
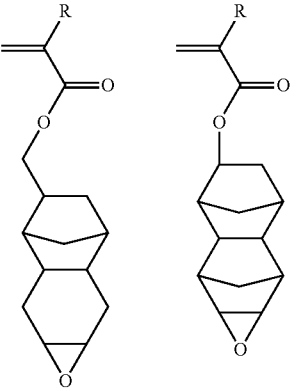
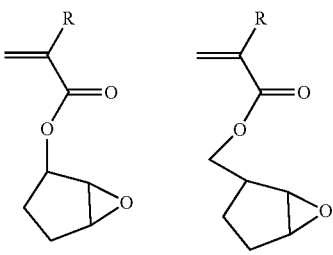

169
-continued
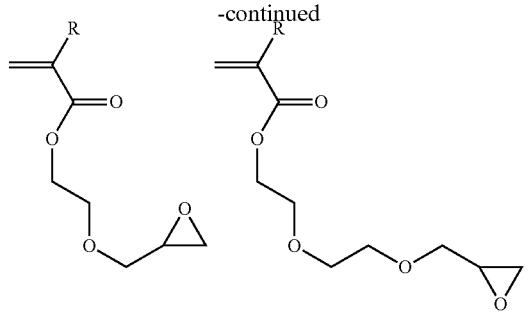
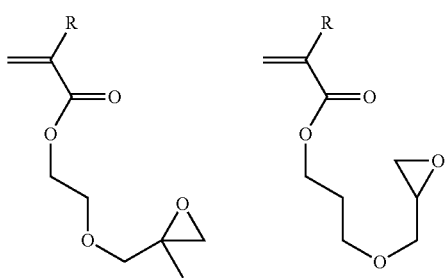
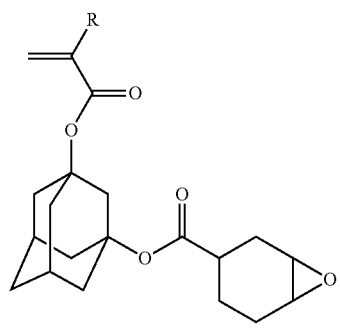
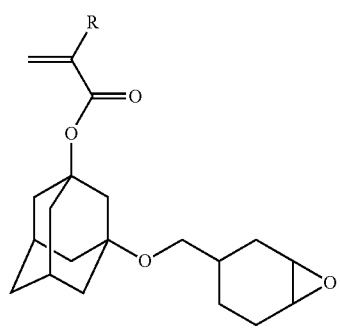
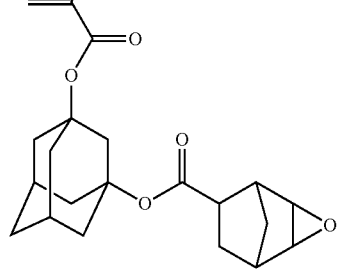
170
-continued
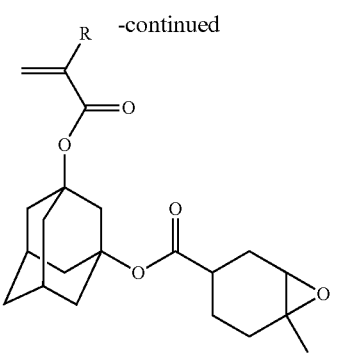
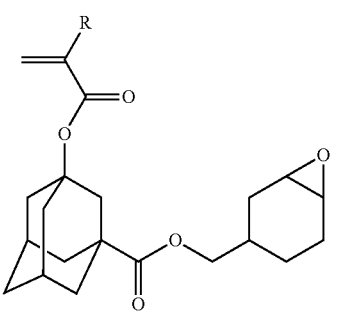
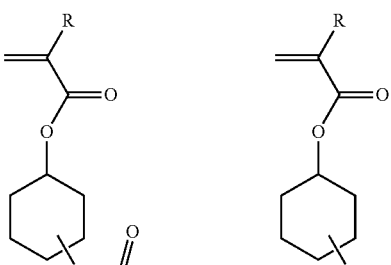
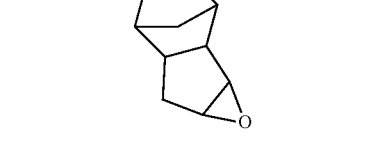
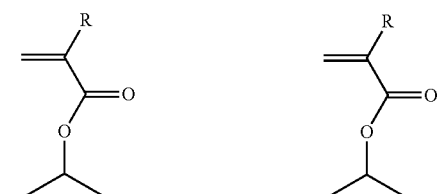
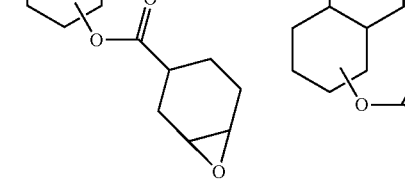

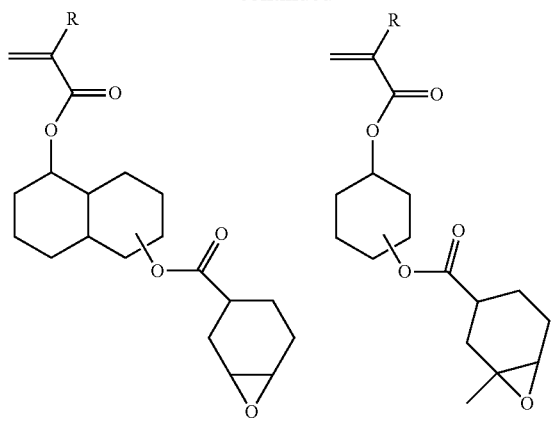
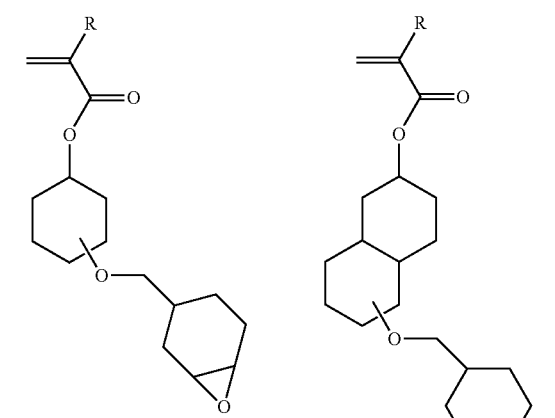
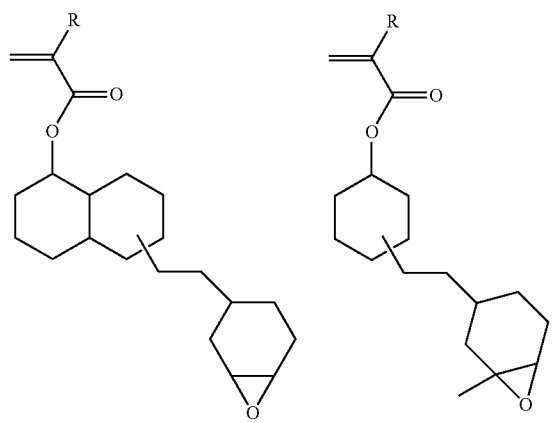
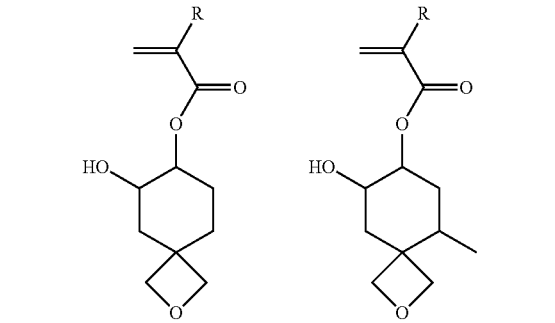
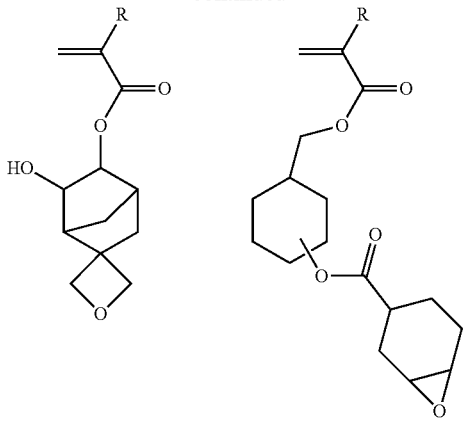
In these formulae, R represents a methyl group or a hydrogen atom.
The ionic polymer in the component (A) of the inventive bio-electrode composition can have a repeating unit-g having silicon, besides the repeating unit(s) selected from -a1 to -a7, -b, and -c to -f. Specific examples of a monomer to give the repeating unit-g can include the following.
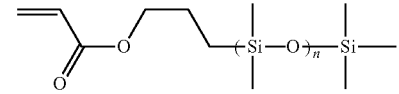
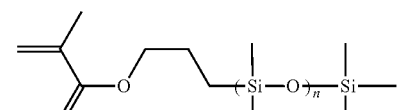
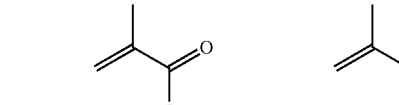
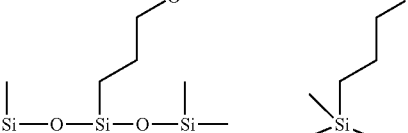
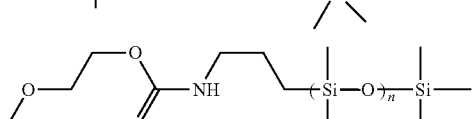
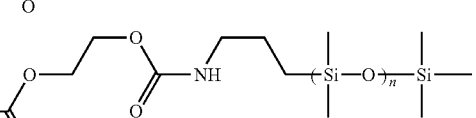

173
-continued
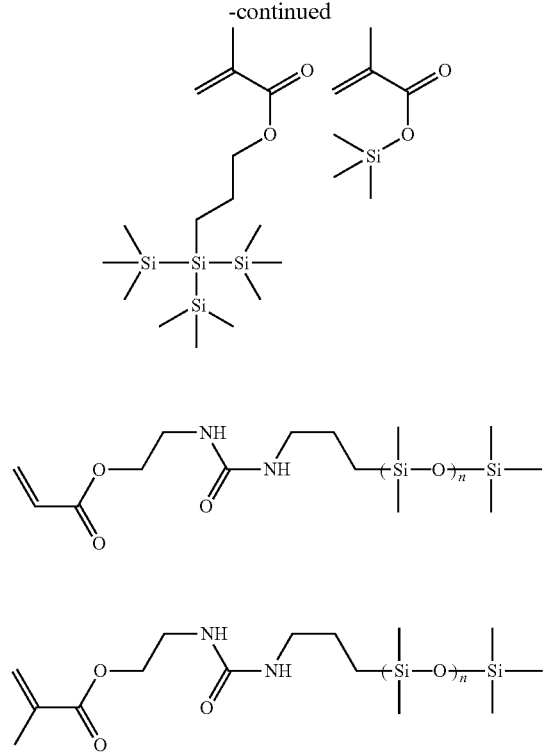
174
-continued
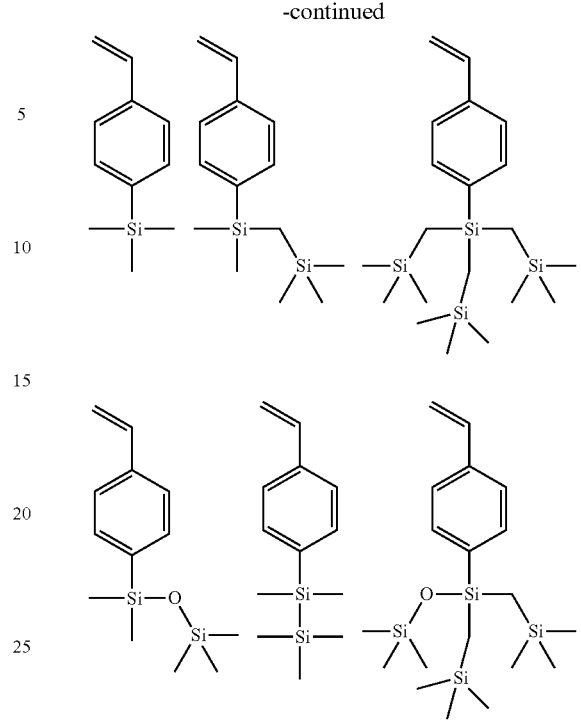
"n" represents the number from 0 to 100.
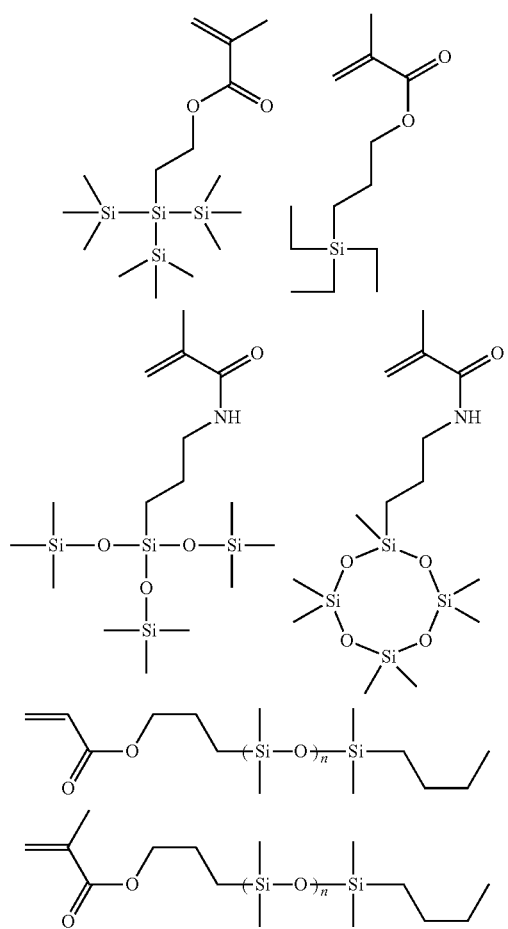
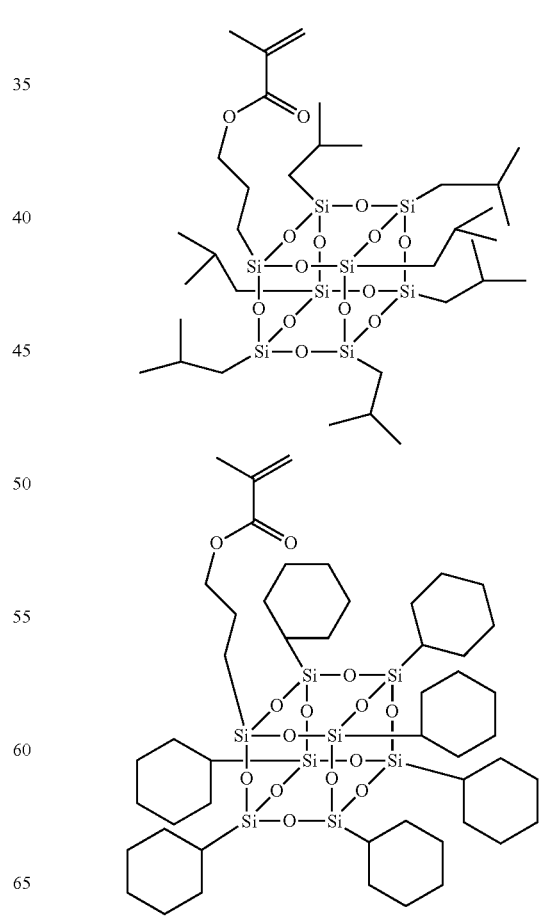

-continued
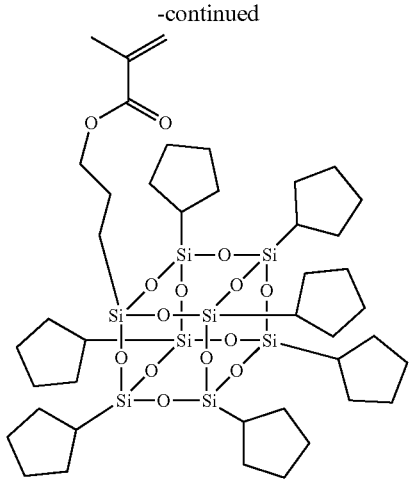
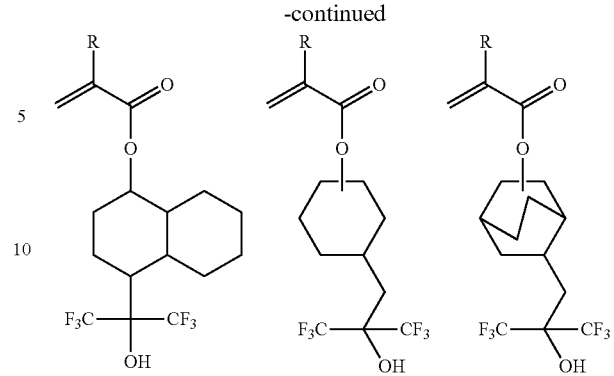
The ionic polymer in the component (A) of the inventive bio-electrode composition can have a repeating unit-h having fluorine, besides the repeating unit(s) selected from -a1 to -a7 and -b to -g.
Specific examples of a monomer to give the repeating unit-h having fluorine can include the following.
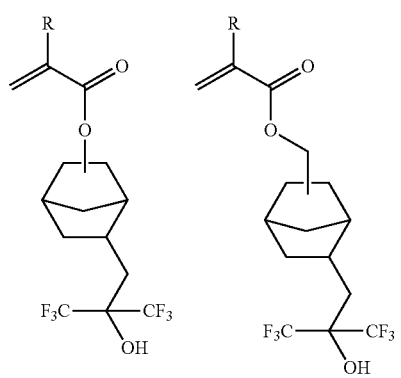
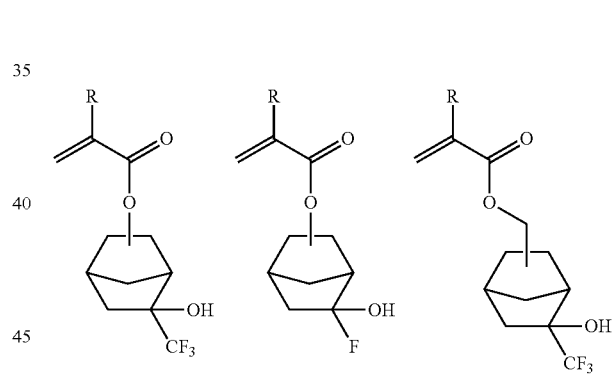
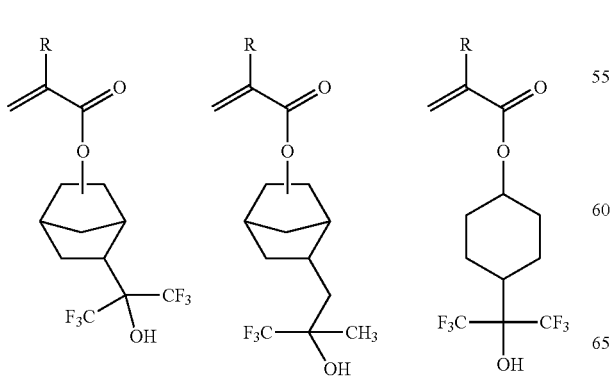

177
-continued
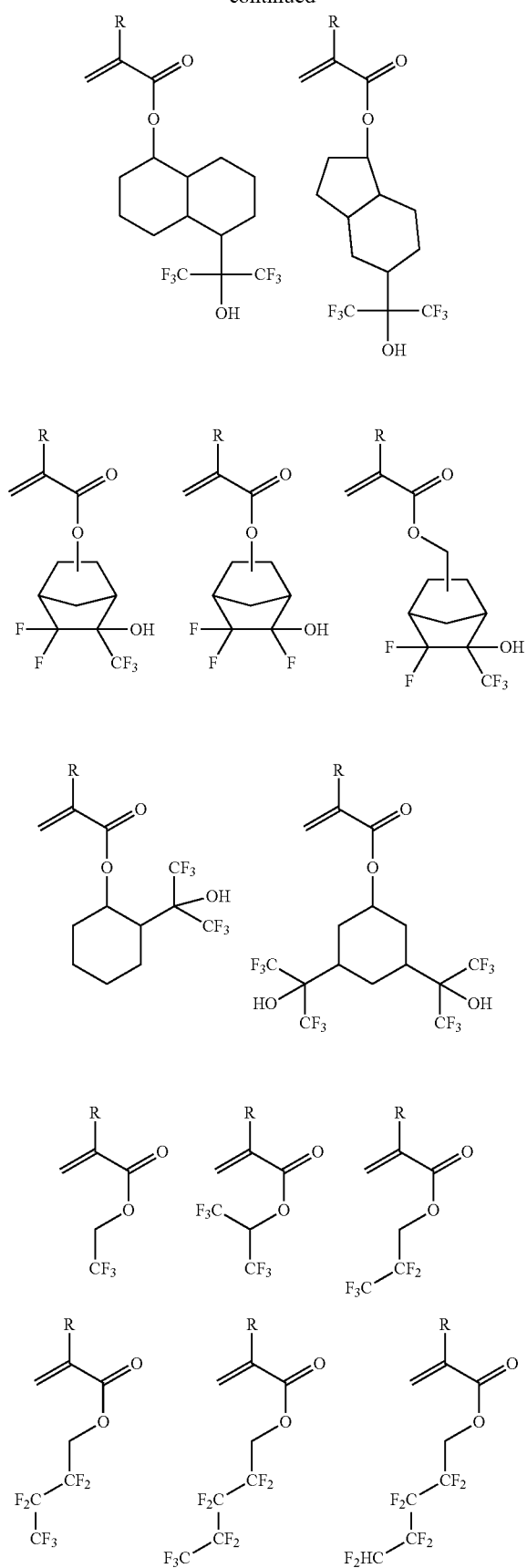
178
-continued
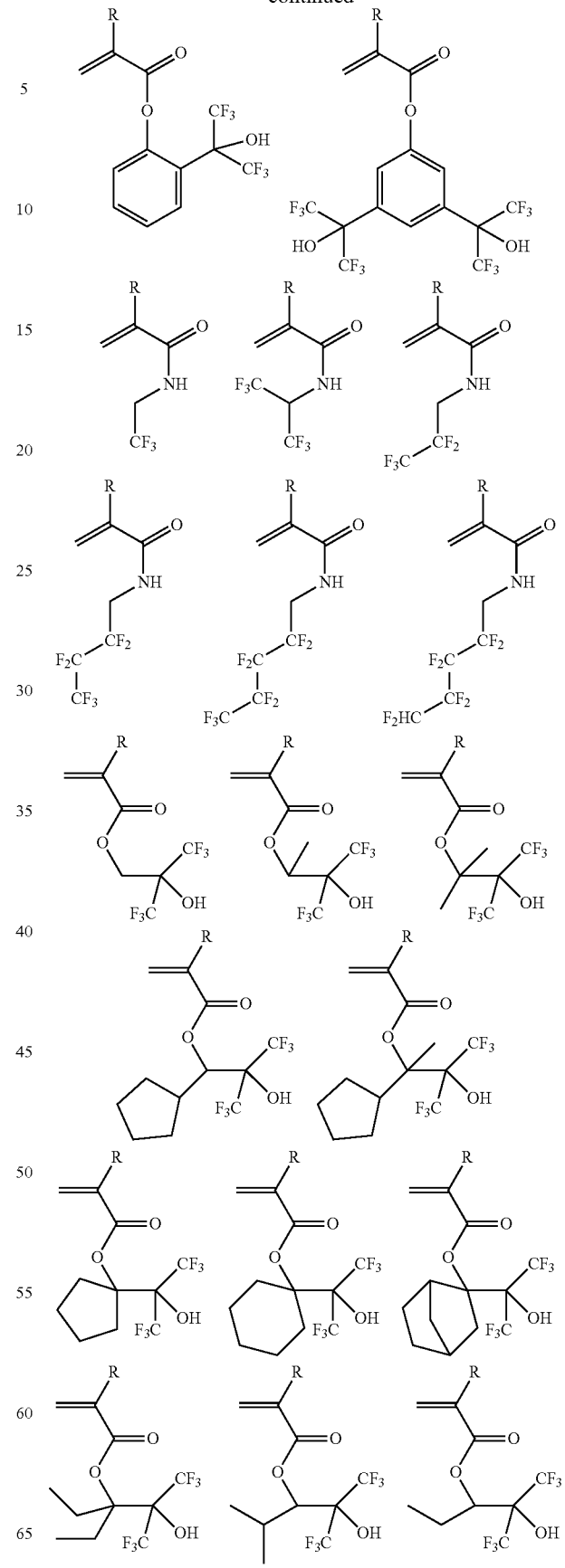

179
-continued
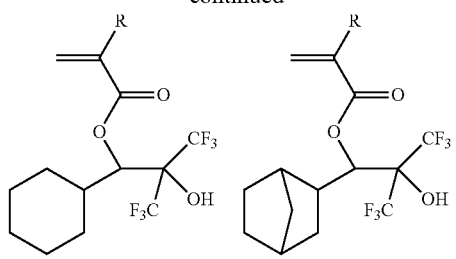
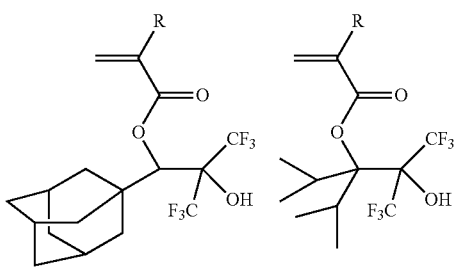
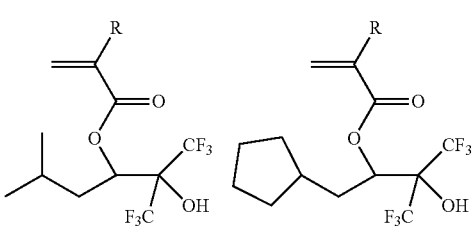
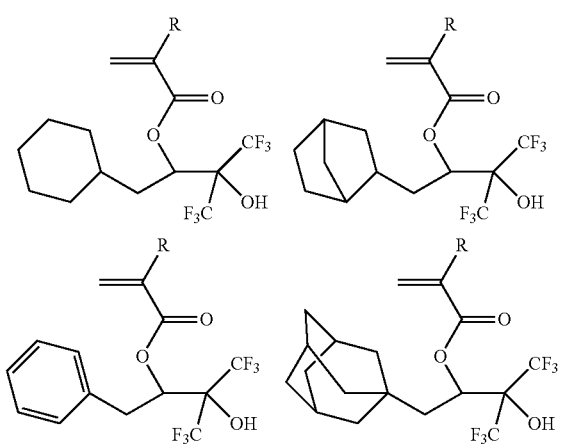
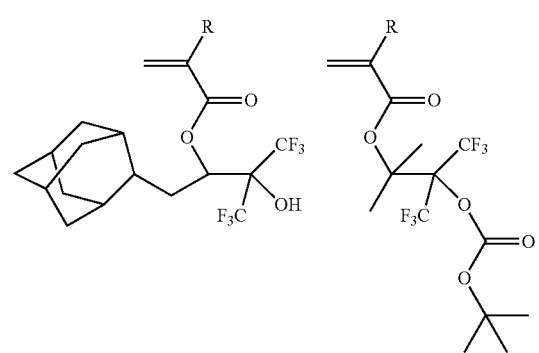
180
-continued
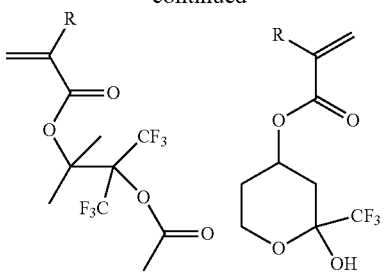
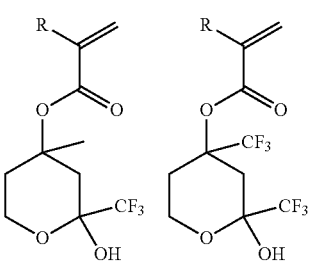
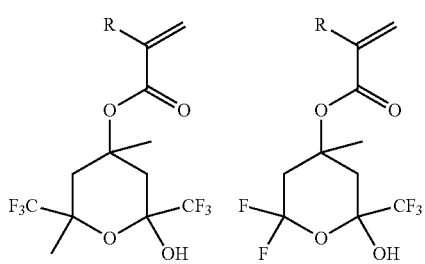
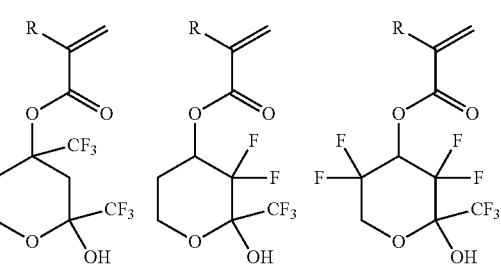
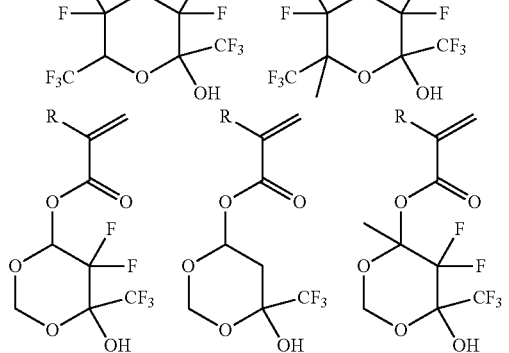

-continued
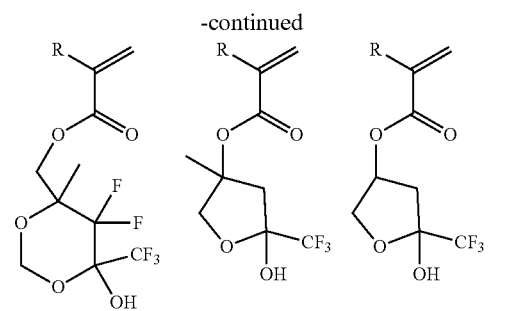
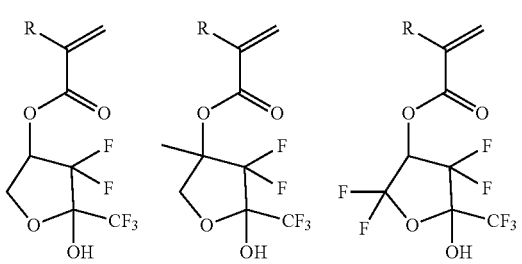
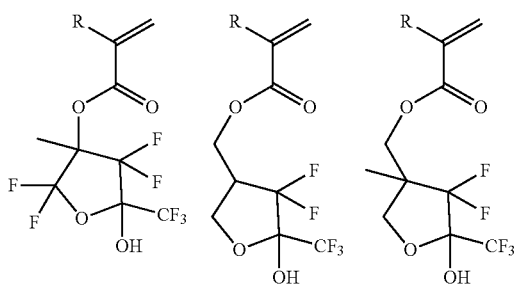
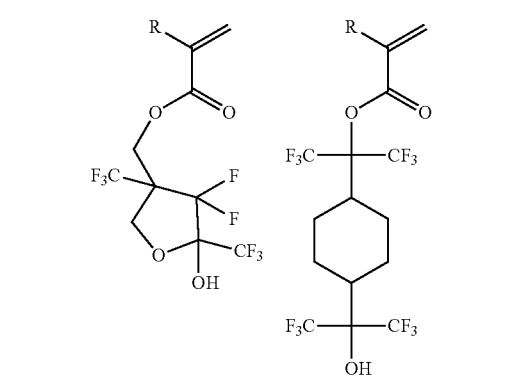
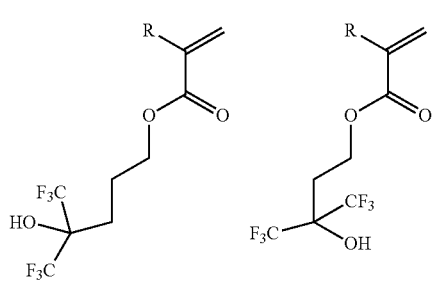
-continued
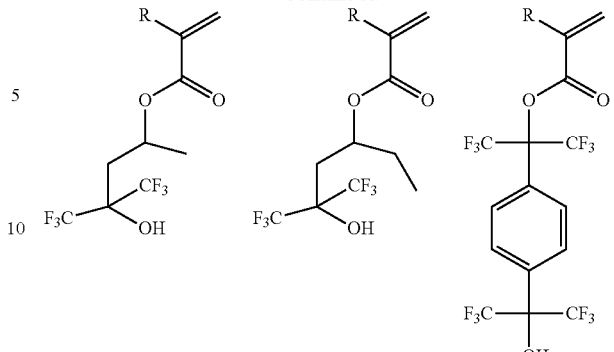
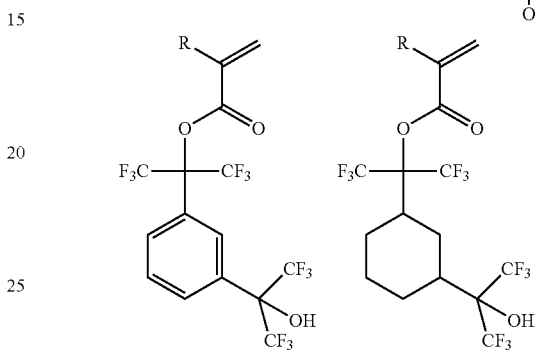
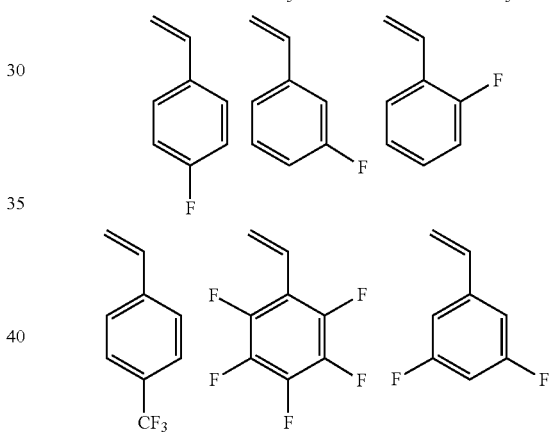
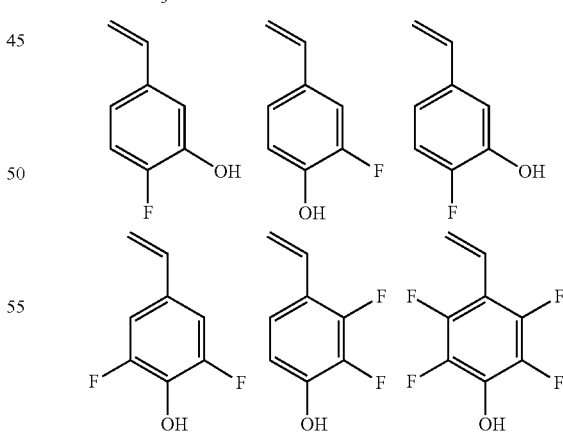
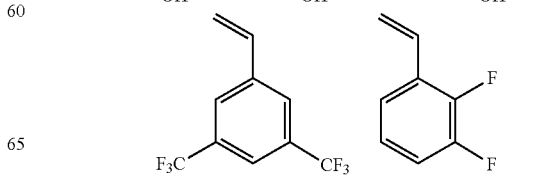

-continued
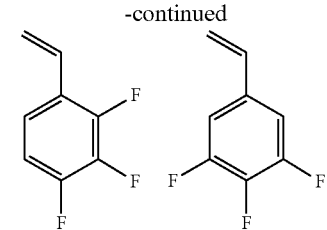
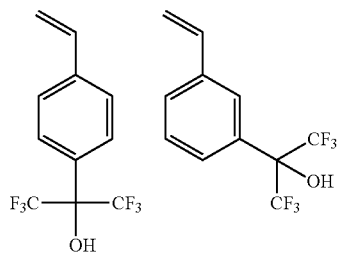
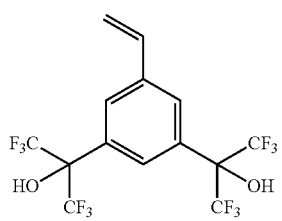
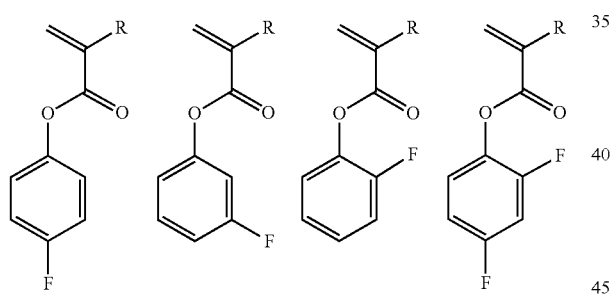
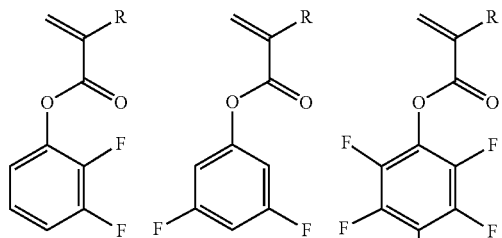
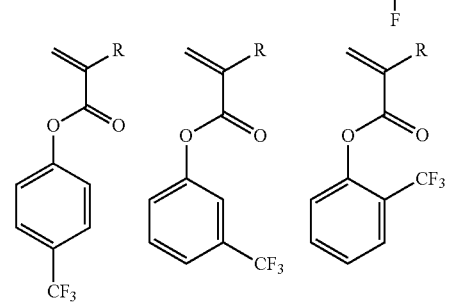
-continued
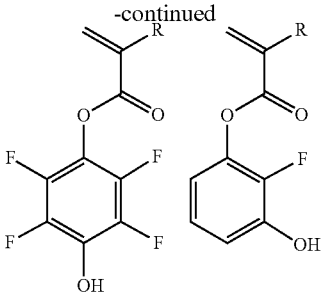
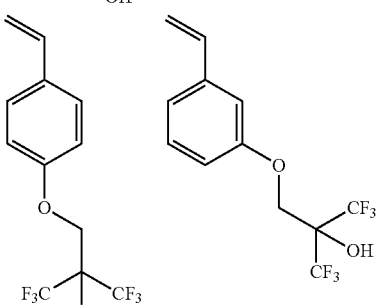
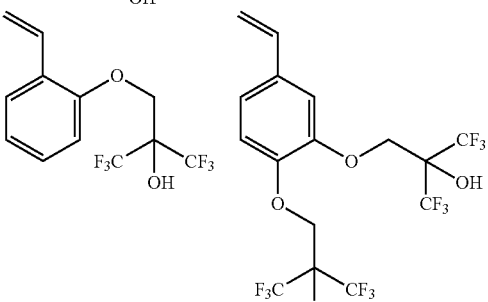
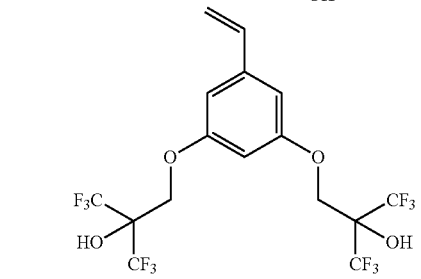
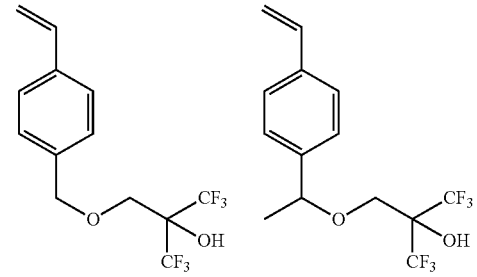
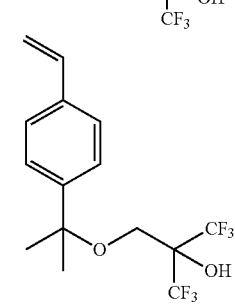

-continued

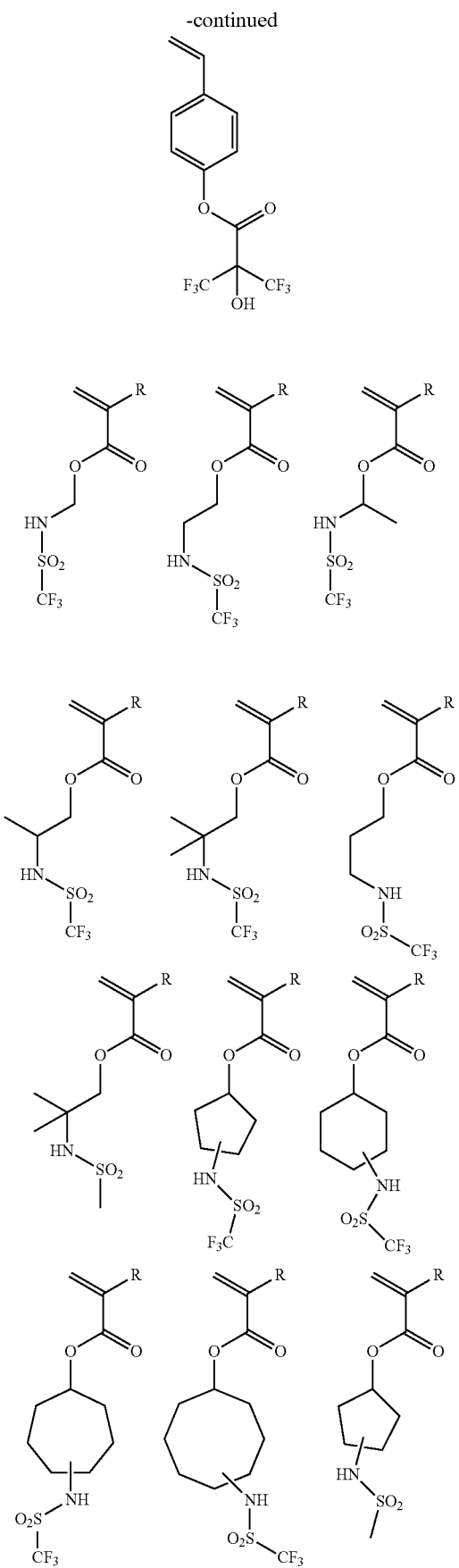

-continued

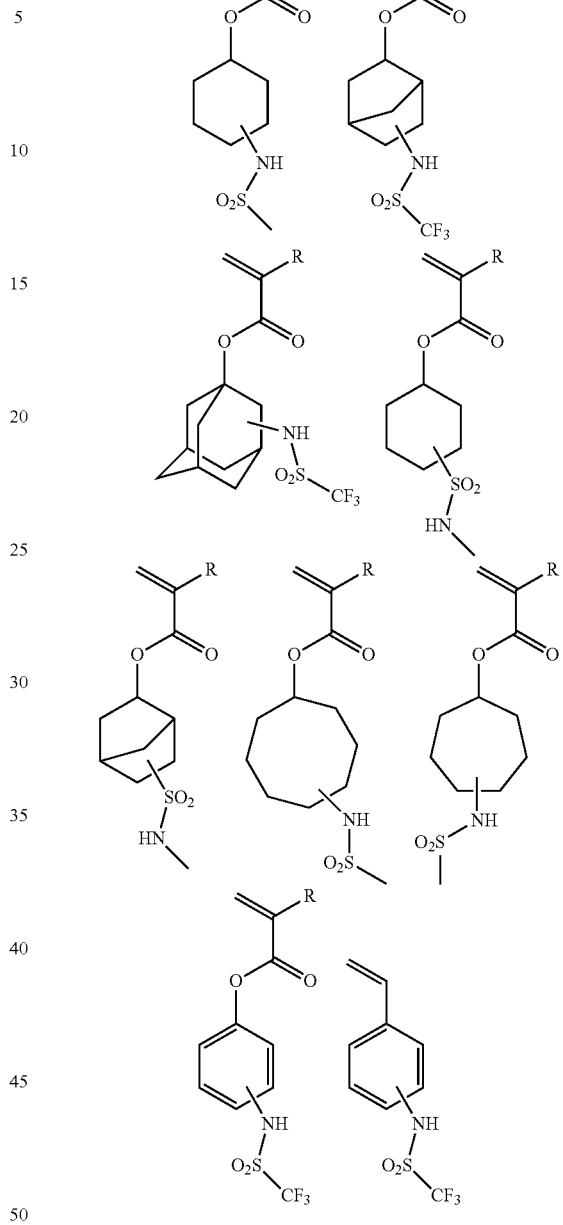

In these formulae, R represents a hydrogen atom or a methyl group.

As one method for synthesizing the ionic polymer in the component (A) (this polymer compound is one before reaction with the fine particles), a copolymer compound can be obtained, for example, by a method in which desired monomer (s) among the monomers to give the repeating units-a1 to -a7, -b, -c, -d, -e, -f, -g, and -h undergo heat polymerization in an organic solvent to which a radical polymerization initiator is added.

Examples of the organic solvent used in the polymerization include toluene, benzene, tetrahydrofuran, diethyl ether, dioxane, etc. Examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, etc. The heating temperature is preferably 50 to 80° C., and the reaction time is preferably 2 to 100 hours, more preferably 5 to 20 hours.

Here, the ratios of the repeating units-a1 to -a7, -b, -c, -d, -e, -f, -g, and -h in the ionic polymer in the component (A) can be $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, $0 < a1+a2+a3+a4+a5+a6+a7 \leq 1.0$, $0 \leq b < 1.0$, $0 \leq c < 1.0$, $0 \leq d < 1.0$, $0 \leq e < 0.9$, $0 \leq f < 0.9$, $0 \leq g < 0.9$, and $0 \leq h < 0.9$; preferably $0 \leq a1 \leq 0.9$, $0 \leq a2 \leq 0.9$, $0 \leq a3 \leq 0.9$, $0 \leq a4 \leq 0.9$, $0 \leq a5 \leq 0.9$, $0 \leq a6 \leq 0.9$, $0 \leq a7 \leq 0.9$, $0.01 \leq a1+a2+a3+a4+a5+a6+a7 \leq 0.99$, $0.001 \leq b \leq 0.8$, $0 \leq c \leq 0.8$, $0 \leq d \leq 0.8$, $0 \leq e < 0.8$, $0 \leq f < 0.8$, $0 \leq g < 0.8$, and $0 \leq h < 0.8$; more preferably $0 \leq a1 \leq 0.8$, $0 \leq a2 \leq 0.8$, $0 \leq a3 \leq 0.8$, $0 \leq a4 \leq 0.8$, $0 \leq a5 \leq 0.8$, $0 \leq a6 \leq 0.8$, $0 \leq a7 \leq 0.8$, $0.02 \leq a1+a2+a3+a4+a5+a6+a7 \leq 0.95$, $0.01 \leq b \leq 0.7$, $0 \leq c \leq 0.7$, $0 \leq d \leq 0.5$, $0 \leq e < 0.3$, $0 \leq f < 0.7$, $0 \leq g < 0.7$, and $0 \leq h < 0.7$.

Incidentally, for example, $a1+a2+a3+a4+a5+a6+a7+b+c+d+e+f+g+h=1$ means that the total amount of the repeating units-a1, -a2, -a3, -a4, -a5, -a6, -a7, -b, -c, -d, -e, -f, -g, and -h is 100 mol % on the basis of the total amount of the whole repeating units in the polymer compound containing the repeating units-a1, -a2, -a3, -a4, -a5, -a6, -a7, -b, -c, -d, -e, -f, -g, and -h; and $a1+a2+a3+a4+a5+a6+a7+b+c+d+e+f+g+h<1$ means that the total amount of the repeating units-a1, -a2, -a3, -a4, -a5, -a6, -a7, -b, -c, -d, -e, -f, -g, and -h is less than 100 mol % on the basis of the total amount of the whole repeating units, which indicates that the polymer compound contains another repeating unit(s) besides the repeating units-a1, -a2, -a3, -a4, -a5, -a6, -a7, -b, -c, -d, -e, -f, -g, and -h.

Regarding the molecular weight of the ionic polymer in the component (A), the weight-average molecular weight is preferably 500 or more, more preferably 1,000 or more and 1,000,000 or less, further preferably 2,000 or more and 500,000 or less. Regarding the ionic monomer (residual monomer) that is not incorporated into the ionic polymer after the polymerization, if the amount is small, the residual monomer can be prevented from permeating to skin in a biocompatibility test to cause allergy. Accordingly, it is preferable to decrease the amount of residual monomer(s). The amount of residual monomer(s) is preferably 10 parts by mass or less on the basis of 100 parts by mass of the whole ionic polymer in the component (A). One kind of the ionic polymer may be used singly, or there can be used a mixture of two or more kinds which differ in molecular weight, dispersity, and constitutive polymerizable monomer.

The ionic polymer particularly preferably contains:
a repeating unit having a structure selected from the group consisting of salts of ammonium, lithium, sodium, potassium, and silver formed with N-carbonyl-fluorosulfonamide; and
a repeating unit having an alkoxysilyl group. The weight-average molecular weight of this ionic polymer is in a range of 1,000 to 1,000,000.

Further preferably, the repeating unit having a structure selected from the group consisting of salts of ammonium, lithium, sodium, potassium, and silver formed with N-carbonyl-fluorosulfonamide is a repeating unit-a7 shown by the following general formula (5), while the repeating unit having an alkoxysilyl group is a repeating unit-b shown by the following general formula (5).

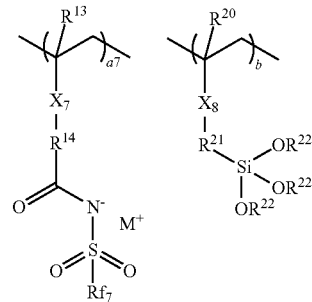

(5)

In the formula, each $R^{13}$ independently represents a hydrogen atom or a methyl group. Each $R^{14}$ independently represents any of a single bond, and a linear, branched, or cyclic hydrocarbon group having 1 to 13 carbon atoms optionally having either or both of an ester group and an ether group. Each $X_7$ independently represents any of a single bond, a phenylene group, a naphthylene group, an ether group, an ester group, and an amide group. $M^+$ represents an ion selected from the group consisting of an ammonium ion, a lithium ion, a sodium ion, a potassium ion, and a silver ion. $Rf_7$ represents a fluorine atom, or a linear or branched alkyl group having 1 to 4 carbon atoms, and has at least one fluorine atom. $R^{20}$ represents a hydrogen atom or a methyl group. $X^8$ represents any of a single bond, a phenylene group, a naphthylene group, an ether group, an ester group, and an amide group. $R^{21}$ represents a single bond, a linear, branched, or cyclic alkylene group having 1 to 10 carbon atoms, or a phenylene group, and optionally contains an oxygen atom or a nitrogen atom. Each $R^{22}$ is identical to or different from one another and represents an alkyl group having 1 to 4 carbon atoms. a7 satisfies $0 < a7 < 1.0$. "b" satisfies $0 < b < 1.0$.

The particles are preferably silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolium oxide particles, indium oxide particles, molybdenum oxide particles, or scandium oxide particles. Among these, silicon material particles are particularly preferably used. Hereinafter, description will be given of silicon material particles as an example.

When the ionic polymer in the component (A) has an alkoxysilyl group, this reacts with and bonds to the fine particle surfaces. As the reaction method between the repeating unit having an alkoxysilyl group and silica particles, it is possible to employ, for example, the methods disclosed in paragraphs 0065 to 0073 of JP 2020-33224 A and in WO 2015-186596 A1.

Preferably, the particles in the component (A) are silicon material particles, and the component (A) is a reaction product between 100 parts by mass of the silicon material particles and 5 parts by mass or more of the polymer having an alkoxysilyl group.

Having a pendant of an ionic polymer on the surfaces of the silicon material particles reduces the permeability through the skin and the irritation to the skin. Thus, the composition can be more surely prevented from permeating the skin and causing allergies.

Further, attaching the ion component to the silicon material particle surfaces forms ion conduction path on the silicon material particle surfaces, and can increase the sensitivity as a bio-electrode.

The silicon material particles in the state of primary particles have a median diameter (D50) within a range of preferably 2 nm to 50 µm, more preferably 3 nm to 30 µm, further preferably 4 nm to 20 µm. Note that, in the present invention, particle diameters can be determined by a laser diffraction method.

The synthesis method of the silicon material particles is not particularly limited, and may be either dry or wet synthesis method. Alternatively, the silicon material particles may be silica extracted from husk. Amorphous silica is preferable. Examples of the silicon material particles can include powders of silica particles, elemental silicon (Si), silicon monoxide (SiO), silicon carbide (SiC), silicon oxycarbide, silicate, etc. Among these, preferable silicon material particles are any of silica particles, Si particles, SiO particles, and SiC particles, or silicon material powder selected from composites thereof. Alternatively, the silicon material particles may be silicon particles having silica attached on the surfaces as disclosed in JP 2015-3839 A.

The shape of the silicon material particles may be any of spherical, elliptical, irregular, hollow, and porous shapes. Meanwhile, the insides of the silicon material particles may be a metal or resin. It is also possible to use particles obtained by treating silicone particle surfaces with ozone or oxygen plasma to convert the surfaces into silica compound. When porous silicon material particles are treated with an alkoxysilane-containing ionic polymer, the ionic polymer permeates and is attached to not only the surfaces but also the insides of the silicon material particles in some cases. In this manner, the ionic polymer does not always have to be attached only to the surfaces of the silicon material particles.

The inventive composite of the ion polymer and the particles is a promising material not only for bio-electrode applications but also for negative electrode materials of ion batteries. Particularly, as a result of the combination of the ion polymer with silicon powder, deformation of the ion polymer layer on the surface of the silicon powder makes it possible to suppress the deformation of the silicon powder, which would occur due to intercalation of ions moving in and out when charging and discharging are repeated.

In the inventive bio-electrode composition, the component (A) is blended in an amount of preferably 0.1 to 300 parts by mass, more preferably 1 to 200 parts by mass, relative to 100 parts by mass of the component (B) to be described below. Additionally, one kind of the component (A) may be used alone, or two or more kinds thereof may be used in mixture.

In some cases, not all of alkoxysilyl groups contained in the ionic polymer are consumed in the reaction with the silica. In this case, the alkoxysilyl groups in the ionic polymer condense with each other. In this case also, the performance as a bio-electrode is not lowered, and the irritation to skin is not increased.

[(B) Adhesive Resin]

The adhesive resin (B) to be blended in the inventive bio-electrode composition is a component compatibilized (well mixed) with the composite (salt) (A) of an ionic polymer material and particles to prevent elution of the salt, and this component also functions to hold an electric conductivity improver such as metal powder, carbon powder, silicon powder, and lithium titanate powder, and exhibit adhesion. When the ionic polymer material in the component (A) has adhesion, the adhesive resin (B) is not necessarily essential. Note that the resin as the component (B) may be any resin other than the component (A), and is preferably either or both of a thermosetting resin and a photo-curable resin, particularly preferably one or more selected from the group consisting of silicone-based, acrylic-based, and urethane-based resins.

Examples of the adherent (adhesive) silicone-based resin include an addition reaction-curable (addition-curable) type and a radical crosslinking reaction-curable (radical curable) type. As the addition reaction-curable type, it is possible to use one that contains diorganosiloxane having an alkenyl group(s), an MQ resin having $R_3SiO_{0.5}$ and $SiO_2$ units, organohydrogenpolysiloxane having multiple SiH groups, a platinum catalyst, an addition-reaction inhibitor, and an organic solvent, for example, described in JP 2015-193803A. As the radical crosslinking reaction-curable type, it is possible to use one that contains diorganopolysiloxane with or without an alkenyl group, an MQ resin having $R_3SiO_{0.5}$ and $SiO_2$ units, organic peroxide, and an organic solvent, for example, described in JP 2015-193803A. Here, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols, and improves adhesive strength by addition of it, but does not bind to the polysiloxane in molecular level because it is not crosslinkable. The adhesive strength can be increased by integrating the polysiloxane and the resin as described above.

The silicone-based resin may contain modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the component (A) in the silicone resin. The modified siloxane may be modified at any part such as one terminal, both terminals, or a side chain of the siloxane.

As the adherent acrylic-based resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane-based resin, it is possible to use one having a urethane bond with a polyether bond, a polyester bond, a polycarbonate bond, or a siloxane bond described in JP 2016-065238A, for example.

In the inventive bio-electrode composition, the resin of the component (B) preferably has high compatibility with the component (A) to prevent lowering of the electric conductivity due to separation of the component (A) from the living body contact layer. In the inventive bio-electrode composition, the resin of the component (B) preferably has high adhesion to the electro-conductive base material to prevent peeling of the living body contact layer from the electro-conductive base material. In order to increase the adhesion to the electro-conductive base material and the compatibility with the salt, a use of a resin with high polarity as the resin of the component (B) is effective. Examples of such a resin include resin having one or more moieties selected from an ether bond, an ester bond, an amide bond, an imide bond, a urethane bond, a thiourethane bond, and a thiol group; a polyacrylic resin, a polyamide resin, a polyimide resin, a polyurethane resin, a polythiourethane resin; etc. On the other hand, the living body contact layer is to be contacted with a living body, thereby being susceptible to perspiration. Accordingly, in the inventive bio-electrode composition, the resin of the component (B) preferably has high repellency and is hardly hydrolyzed. To make the resin of the component (B) be highly repellent and hardly hydrolyzed, the use of a silicon-containing resin is effective.

The silicon atom-containing polyacrylic resin includes a polymer that has a silicone main chain and a polymer that has a silicon atom(s) on the side chain, either of which can be suitably used. As the polymer that has a silicone main chain, silsesquioxane, siloxane having a (meth)acrylpropyl group, or the like can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680B, for example. Such polyamide silicone resins can be synthesized by combining, for example, a silicone or non-silicone compound having amino groups at both terminals and a non-silicone or silicone compound having carboxyl groups at both terminals.

It is also possible to use polyamic acid before cyclization thereof, which is obtained by reacting carboxylic anhydride and amine. The carboxyl group of the polyamic acid may be crosslinked by using a crosslinking agent such as an epoxy type and an oxetane type. It is also possible to esterify the carboxyl group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-crosslinked as described in JP 2005-320418A. It is also possible to photo-crosslink a polymer having both of a siloxane bond(s) and a urethane bond(s), with the terminal having a (meth)acrylate group(s). Particularly, a polyurethane main chain having a silicone chain on a side chain as described in JP 2018-123304A and JP 2019-70109A is preferable because of the properties of high strength and high stretchability.

The silicon atom-containing polythiourethane resin can be obtained by reaction of a compound having a thiol group(s) and a compound having an isocyanate group(s), provided that either of them contains a silicon atom(s). It can also be photo-cured if (meth)acrylate groups are contained at the terminals.

The silicone-based resin can be improved in compatibility with the foregoing salt by adding modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R_3SiO_{0.5}$ and $SiO_2$ units, and the organohydrogenpolysiloxane having multiple SiH groups.

The diorganosiloxane having an alkenyl group(s) and the organohydrogenpolysiloxane having multiple SiH groups can be crosslinked through an addition reaction with a platinum catalyst.

Examples of the platinum catalyst include platinum-based catalysts such as chloroplatinic acid, alcohol solution of chloroplatinic acid, reaction product of chloroplatinic acid and alcohol, reaction product of chloroplatinic acid and an olefin compound, reaction product of chloroplatinic acid and vinyl group-containing siloxane, a platinum-olefin complex, and a complex of platinum and vinyl group-containing siloxane; platinum group metal-based catalysts such as a rhodium complex and a ruthenium complex; etc. These catalysts may be used after dissolved or dispersed in alcohol solvent, hydrocarbon solvent, or siloxane solvent.

Note that the platinum catalyst is added in an amount preferably within 5 to 2,000 ppm, particularly preferably 10 to 500 ppm, relative to 100 parts by mass of the resin of the component (B).

In the inventive bio-electrode composition, the component (B) is blended in an amount of preferably 0 to 2000 parts by mass, more preferably 10 to 1000 parts by mass, relative to 100 parts by mass of the composite (A) of an ionic polymer material and particles. Moreover, one kind of each component (B) may be used singly, or two or more kinds thereof may be used in mixture.

When the addition-curable silicone resin is used, an addition-reaction inhibitor may be added. This addition-reaction inhibitor is added as a quencher to prevent the action of the platinum catalyst in the solution and under a low temperature circumstance after forming the coating film and before heat curing. Specific examples of the addition-reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The addition-reaction inhibitor is added in an amount preferably within 0 to 10 parts by mass, particularly preferably 0.05 to 3 parts by mass, relative to 100 parts by mass of the resin of the component (B).

In crosslinking the radical-crosslinkable group in the component (B) in the present invention, it is effective to add a radical generator. Such a radical generator includes a photoradical generator and a thermal radical generator.

Examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dicumyl peroxide, etc.

Note that the radical generator is added in an amount preferably within 0.1 to 50 parts by mass relative to 100 parts by mass of the resin of the component (B).

Above all, the resin of the component (B) more preferably contains diorganosiloxane having an alkenyl group, and organohydrogenpolysiloxane having an SiH group. Particularly preferably, the resin of the component (B) further contains a silicone resin having an $SiO_2$ unit and an $R_xSiO_{(4-x)/2}$ unit, where R represents a substituted or unsubstituted monovalent hydrocarbon group having 1 to 10 carbon atoms, and "X" represents a number in a range of 2.5 to 3.5.

As will be described later, the living body contact layer is a cured product of the bio-electrode composition. The curing improves the adhesion of the living body contact layer to both of skin and the electro-conductive base material. The curing means is not particularly limited, and common means can be used, including crosslinking reaction by either or both of heat and light, or with an acid catalyst or a base catalyst, for example. The crosslinking reaction can be performed, for example, by appropriately selecting methods described in "Kakyou han-nou handbook (handbook of crosslinking reaction)", Chapter 2, pages 51-371, Yasuharu Nakayama, Maruzen Publishing Co., Ltd. (2013).

[(C) Blend Ionic Polymer]

The inventive bio-electrode composition can also contain an ionic polymer (blend ionic polymer) other than the component (A). As repeating units of the blend ionic polymer, it is possible to employ those described for the ionic polymer in the component (A), particularly those shown by the general formula (2). The blend ionic polymer is added in an amount preferably within 0.1 to 100 parts by mass relative to 100 parts by mass of the resin of the component (B).

[(D) Electro-Conductive Powder]
[Metal Powder]

The inventive bio-electrode composition may contain a metal powder as the component (D) in order to improve electron conductivity. The metal powder is a powder of a metal selected from the group consisting of gold, silver, platinum, copper, tin, titanium, nickel, aluminum, tungsten, molybdenum, ruthenium, chromium, and indium. The metal powder is added in an amount preferably within 1 to 50 parts by mass relative to 100 parts by mass of the resin of the component (B).

As the kind of the metal powder, gold, silver, and platinum are preferable from the viewpoint of electric conductivity; and silver, copper, tin, titanium, nickel, aluminum, tungsten, molybdenum, ruthenium, and chromium are preferable from the viewpoint of cost. From the viewpoint of biocompatibility, noble metals are preferable. From comprehensive viewpoint including the above, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of not more than 5 g/cm$^3$, and a specific surface area of not less than 0.5 m$^2$/g.

[Carbon Powder]

A carbon material (carbon powder) can be added as an electric conductivity improver. Examples of the carbon material include carbon black, graphite, carbon nanotube, carbon fiber, etc. The carbon nanotube may be either single layer or multilayer, and the surface may be modified with an organic group(s). The carbon material is added in an amount preferably within 1 to 50 parts by mass relative to 100 parts by mass of the resin of the component (B).

[Silicon Powder]

The inventive bio-electrode composition may contain a silicon powder to enhance ion reception sensitivity. Examples of the silicon powder include powders of silicon, silicon monoxide, or silicon carbide. The particle diameter of the powder is preferably smaller than 100 μm, more preferably 1 μm or less. Since finer particles have a larger surface area, the resulting bio-electrode can receive a larger amount of ions and has higher sensitivity. The silicon powder is added in an amount preferably within 1 to 50 parts by mass relative to 100 parts by mass of the resin of the component (B)

[Lithium Titanate Powder]

The inventive bio-electrode composition may contain a lithium titanate powder to enhance ion reception sensitivity. Examples of the lithium titanate powder include powders containing a compound shown by molecular formulae $Li_2TiO_3$, $LiTiO_2$, or $Li_4Ti_5O_{12}$ with a spinel structure. The lithium titanate powder preferably has a spinel structure. It is also possible to use carbon-incorporated lithium titanate particles. The particle diameter of the powder is preferably smaller than 100 μm, more preferably 1 μm or less. Since finer particles have a larger surface area, the bio-electrode can receive a larger amount of ions, and has higher sensitivity. The aforementioned powders may be composite powders with carbon. The lithium titanate powder is added in an amount preferably within 1 to 50 parts by mass relative to 100 parts by mass of the resin of the component (B).

[(E) Organic Solvent]

Further, the inventive bio-electrode composition may contain the component (E), which is an organic solvent. Specific examples of the organic solvent include: aromatic hydrocarbon solvents, such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvents, such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[$6.2.1.0^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvents, such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvents, such as 3-methoxybutanol, 3-methyl-3-methoxybutanol, 1-methoxy-2-propanol, and 1-ethoxy-2-propanol; ether solvents, such as propylene glycol monomethyl ether, ethylene glycol monomethyl ether, propylene glycol monoethyl ether, ethylene glycol monoethyl ether, propylene glycol dimethyl ether, diethylene glycol monomethyl ether, diethylene glycol monoethyl ether, diethylene glycol monopropyl ether, diethylene glycol monobutyl ether, diethylene glycol monopentyl ether, diethylene glycol monoheptyl ether, diethylene glycol diethyl ether, diethylene glycol dipropyl ether, diethylene glycol dibutyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvents, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvents, such as γ-butyrolactone; water; etc.

Note that the organic solvent is added in an amount preferably within 10 to 50,000 parts by mass relative to 100 parts by mass of the resin of the component (B).

[(F) Other Additives]

The inventive bio-electrode composition can be mixed with a crosslinking agent, a crosslinking catalyst, and an ionic additive, and further with silica particles, polyether silicone, and polyglycerin silicone, besides the platinum catalyst, addition-reaction inhibitor, and radical generators described for the component (B). Silica particles have hydrophilic surfaces and favorable compatibility with the hydrophilic ion polymer, polyether silicone, and polyglycerin silicone, and can improve the dispersibility of the ionic polymer, polyether silicone, and polyglycerin silicone in the hydrophobic silicone adhesive. The silica particles may be either dry type or wet type both of which are preferably usable.

[Crosslinking Agent]

The inventive bio-electrode composition may contain an epoxy-type crosslinking agent. This crosslinking agent is a compound having multiple epoxy groups or oxetane groups in one molecule. The amount of the crosslinking agent added is preferably 1 to 30 parts by mass relative to 100 parts by mass of the resin of the component (B).

[Crosslinking Catalyst]

The inventive bio-electrode composition may also contain a catalyst for crosslinking the epoxy groups or the oxetane groups. As this catalyst, ones described in paragraphs 0027 to 0029 of JP 2019-503406A can be used. The amount of the catalyst added is preferably 0.01 to 10 parts by mass relative to 100 parts by mass of the resin of the component (B).

[Ionic Additive]

The inventive bio-electrode composition may contain an ionic additive to enhance ionic conductivity. In consideration of biocompatibility, examples of the ionic additive include sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, betaine, and salts disclosed in JP 2018-44147A, JP 2018-59050A, JP 2018-59052A, and JP 2018-130534A.

[Silicone Compound Having Polyglycerin Structure]

The inventive bio-electrode composition may contain a silicone compound having a polyglycerin structure to enhance the sensitivity to ions released from skin and the ionic conductivity by enhancing the moisture-holding property of the film. The silicone compound having a polyglycerin structure is blended in an amount of preferably 0.01 to 100 parts by mass, more preferably 0.5 to 60 parts by mass, relative to 100 parts by mass of a total of the components (A) and (B). Additionally, one kind of the silicone compound having a polyglycerin structure may be used alone, or two or more kinds thereof may be used in mixture.

The silicone compound having a polyglycerin structure is preferably shown by any of the following general formulae (4)' and (5)'.

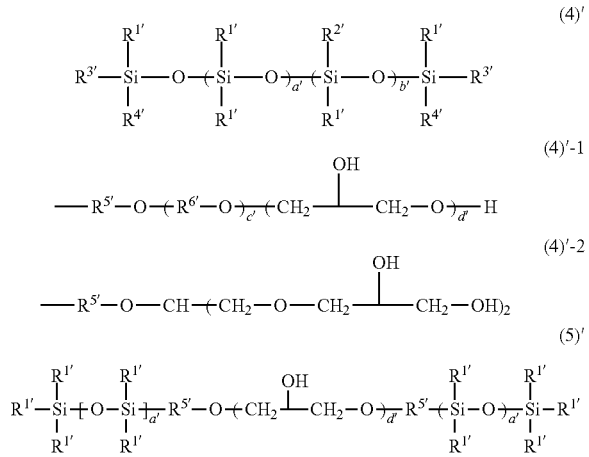

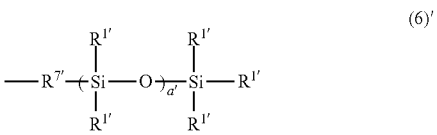

In the formulae (4)' and (5)', each $R^{1\prime}$ is identical to or different from one another, and independently represents a hydrogen atom, a phenyl group, a linear or branched alkyl group having 1 to 50 carbon atoms, or a silicone chain shown by a general formula (6)', and optionally contains an ether group. $R^{2\prime}$ represents a group having a polyglycerin group structure shown by a formula (4)'-1 or (4)'-2. Each $R^{3\prime}$ is identical to or different from the other, and independently represents the $R^{1\prime}$ group or the $R^{2\prime}$ group. Each $R^{4\prime}$ is identical to or different from the other, and independently represents the $R^{1\prime}$ group, the $R^{2\prime}$ group, or an oxygen atom. When $R^{4\prime}$ represents an oxygen atom, the two $R^{4\prime}$ moieties bond to each other and optionally constitute an ether group to form a ring together with silicon atoms. Each a' is identical to or different from one another and represents 0 to 100, b' represents 0 to 100, and a'+b' is 0 to 200. Nevertheless, when b' is 0, at least one $R^{3\prime}$ is the $R^{2\prime}$ group. In the formulae (4)'-1, (4)'-2, and (5)', $R^{5\prime}$ represents an alkylene group having 2 to 10 carbon atoms or an aralkylene group having 7 to 10 carbon atoms. $R^{6\prime}$ and $R^{7\prime}$ each represent an alkylene group having 2 to 6 carbon atoms, but $R^{7\prime}$ may represent an ether bond. c' represents 0 to 20. d' represents 1 to 20.

Examples of such a silicone compound having a polyglycerin structure can include the following.

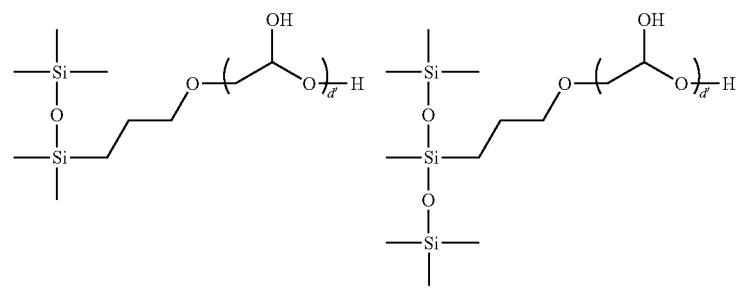

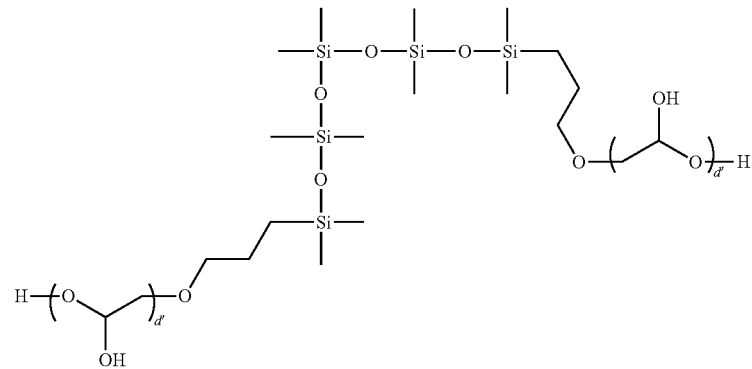

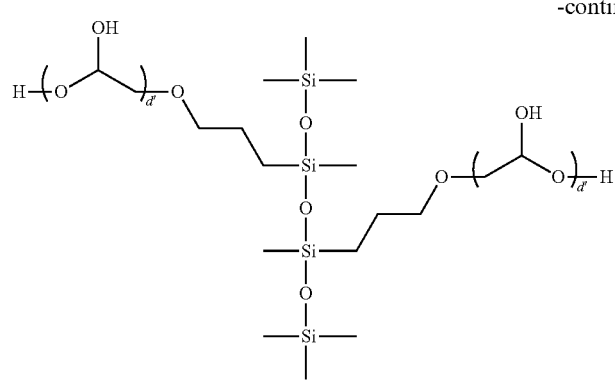
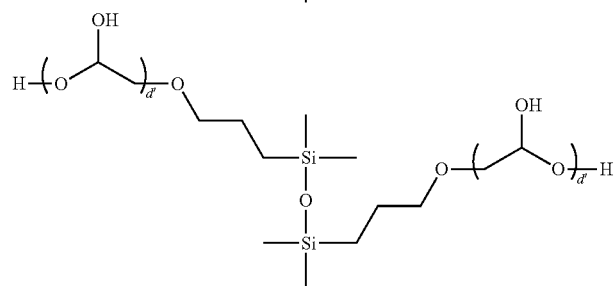
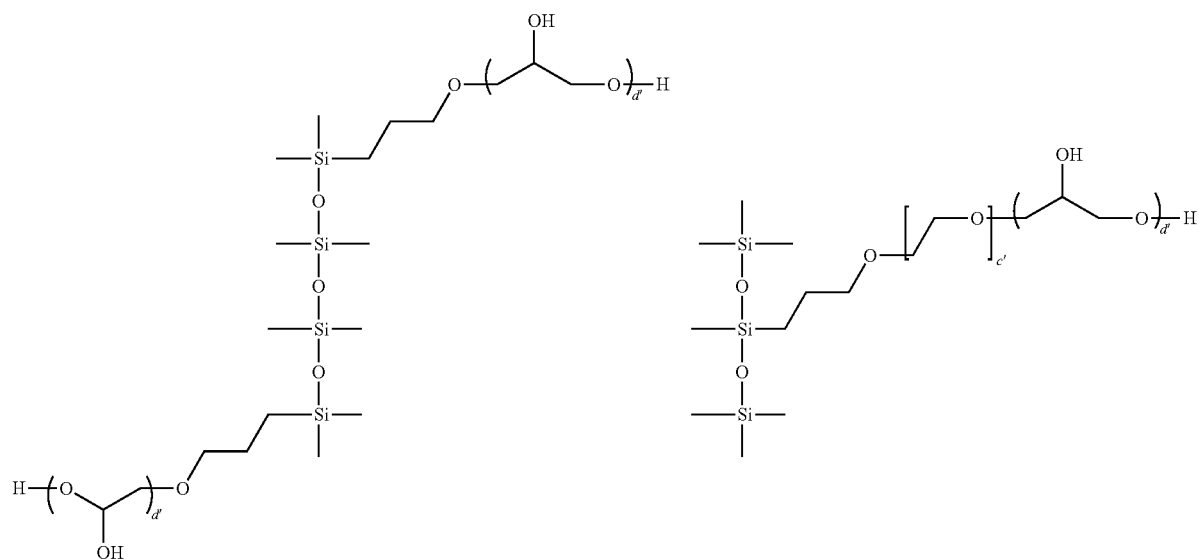
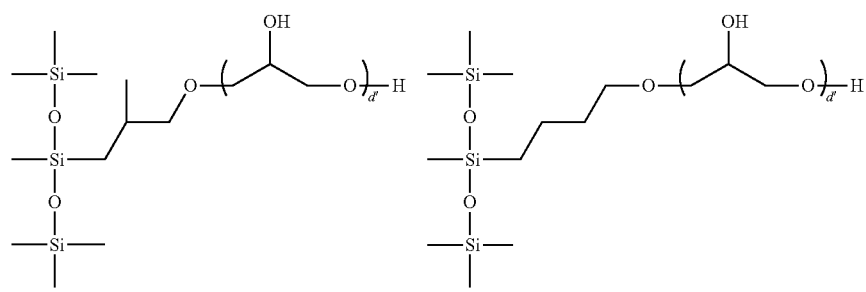

-continued
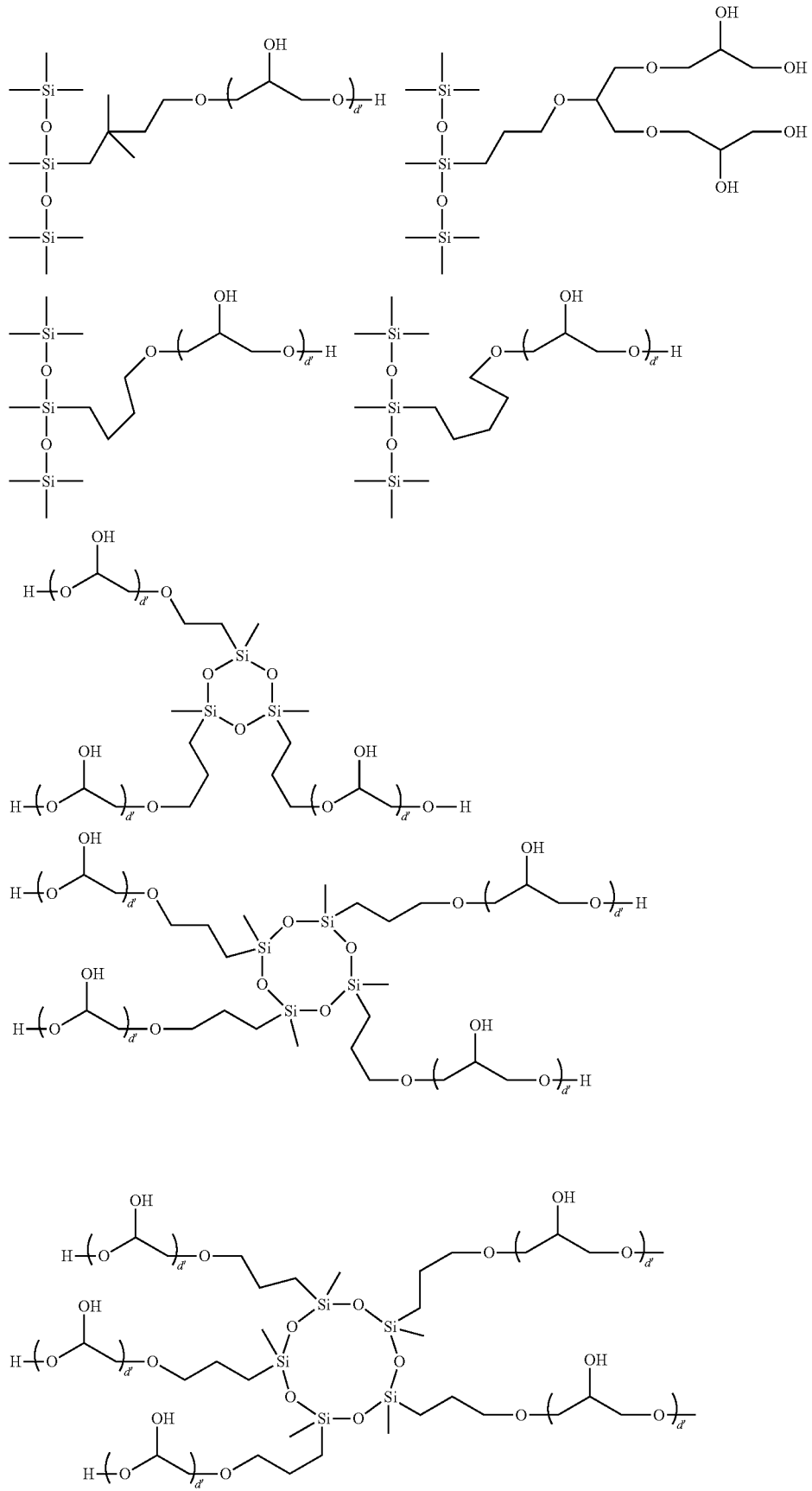

-continued
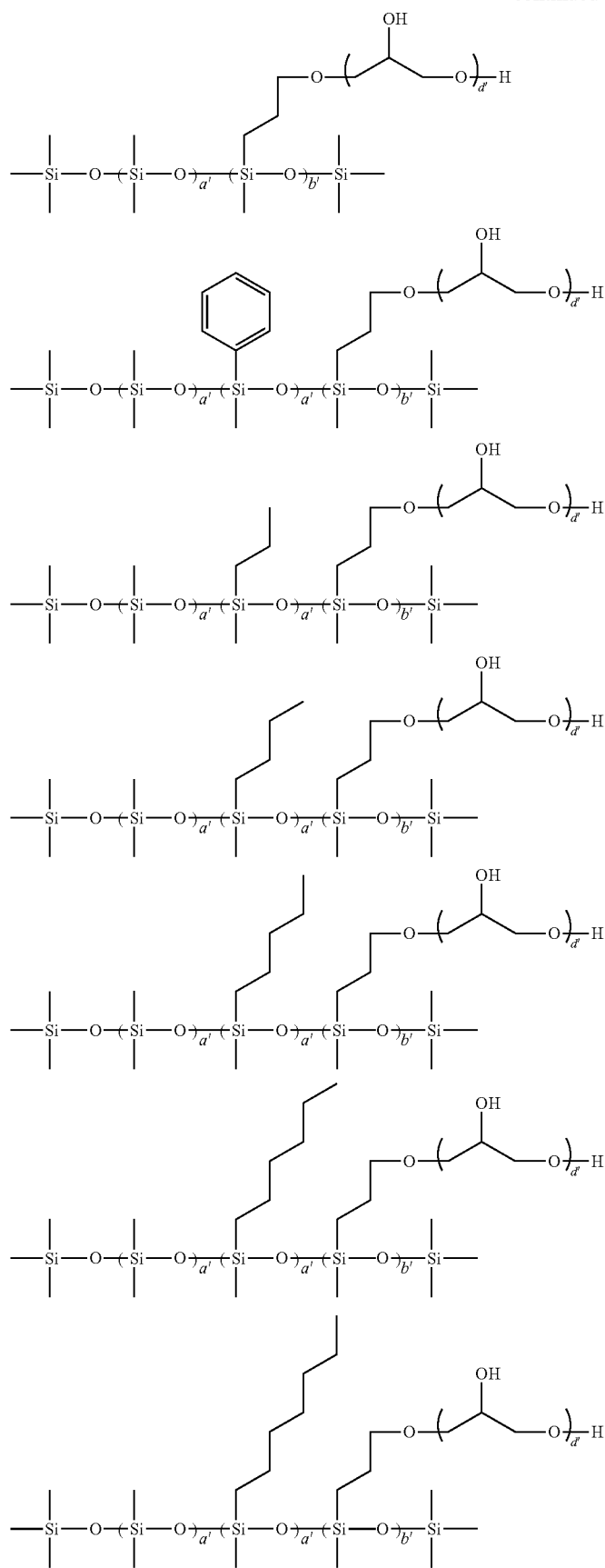

-continued
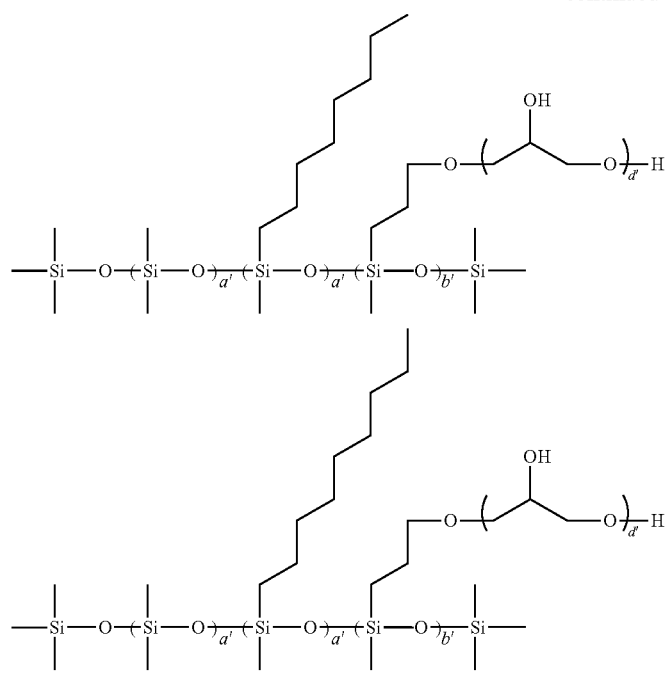
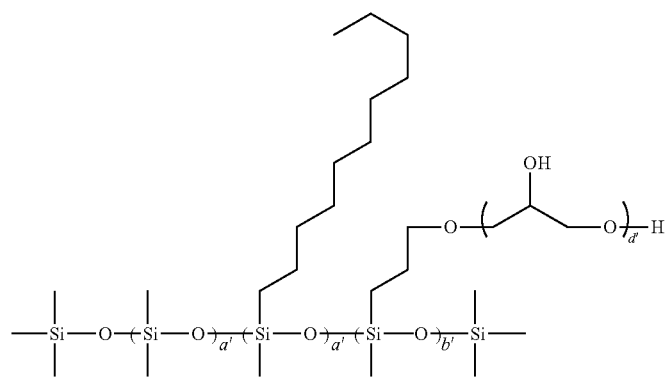
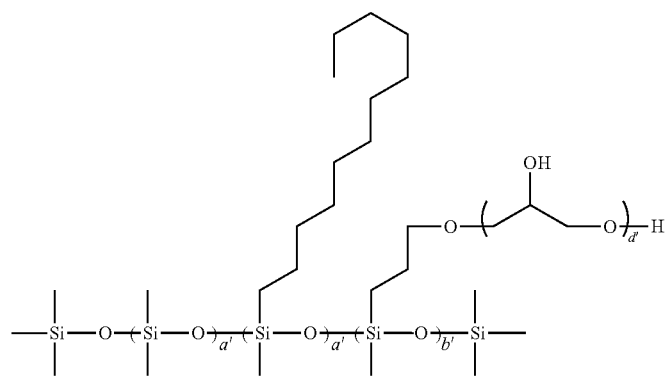

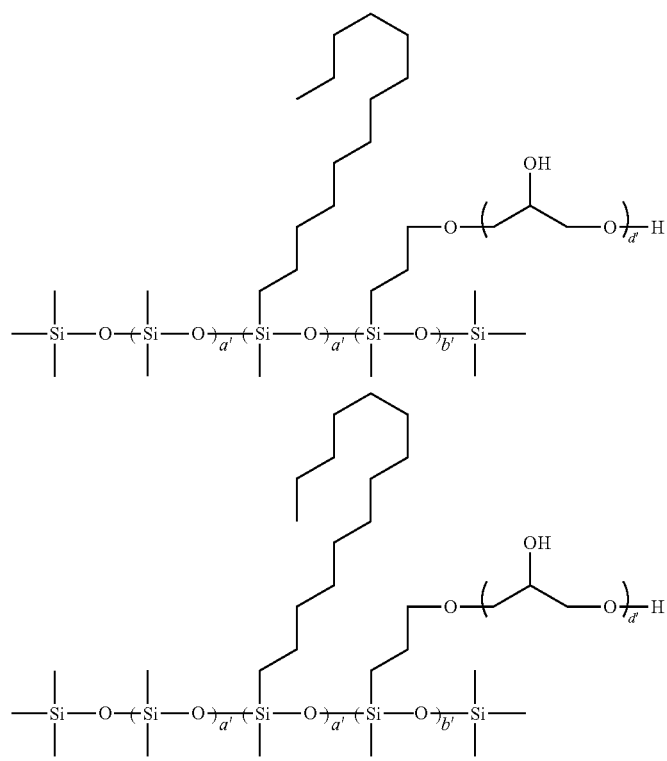
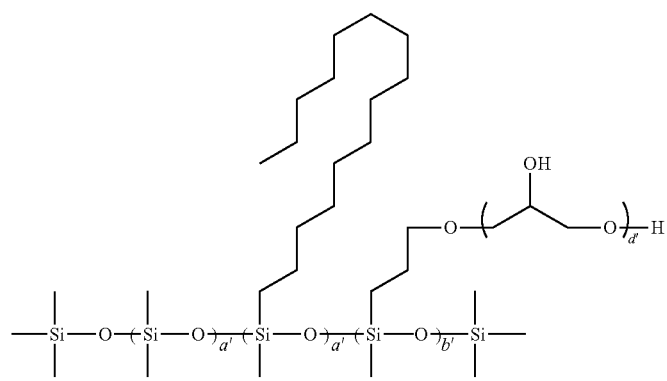
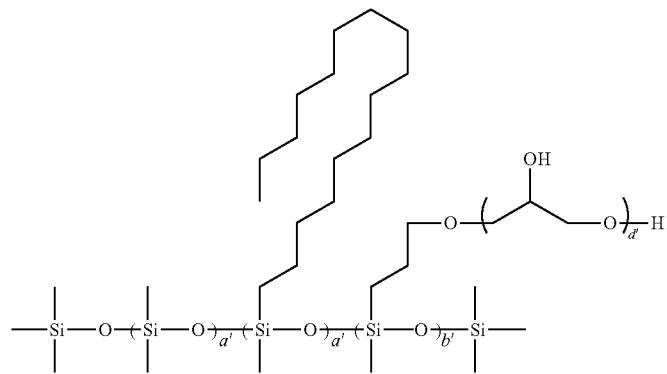

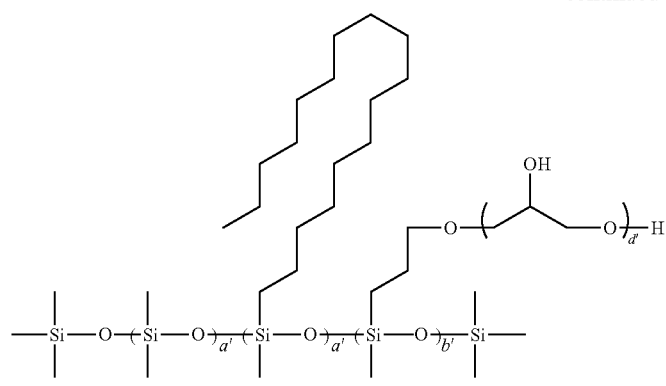
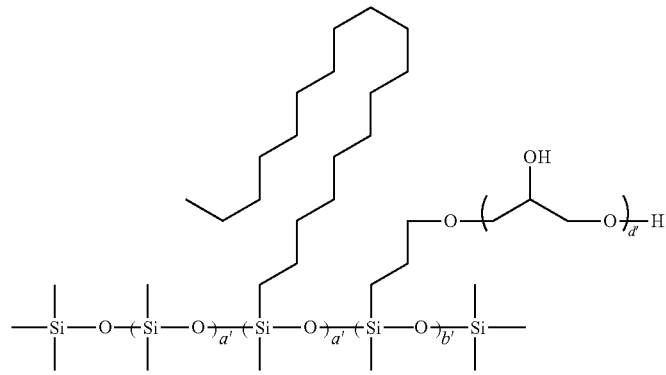
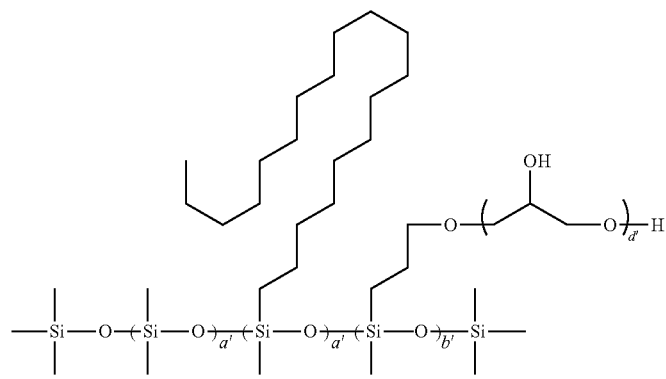
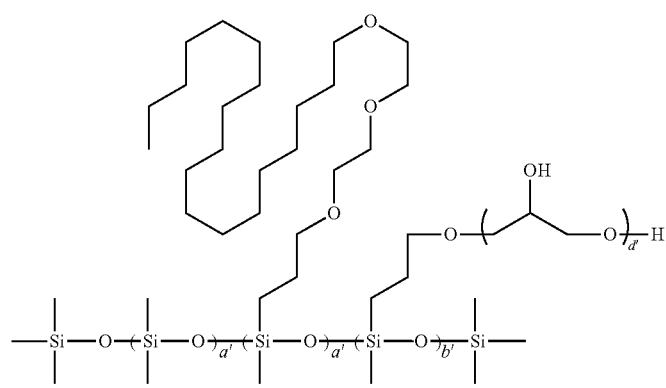

-continued
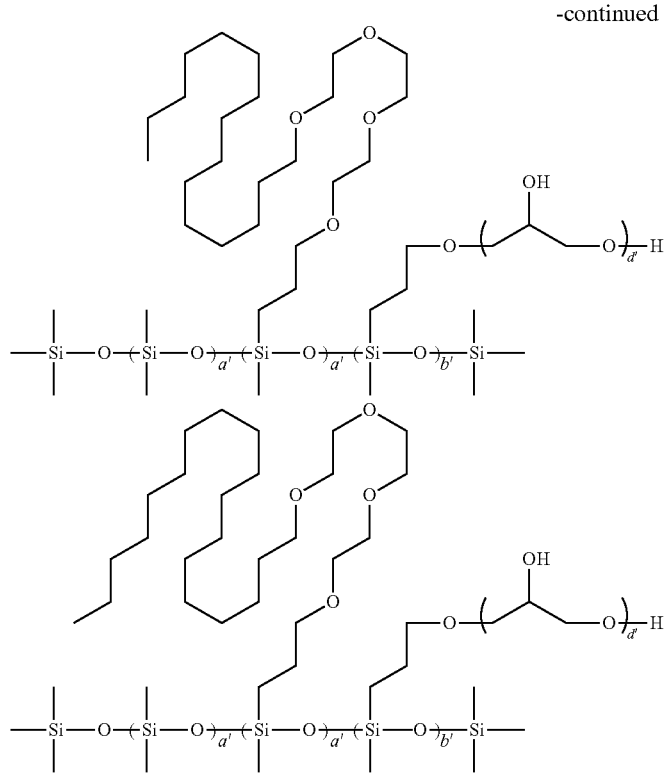
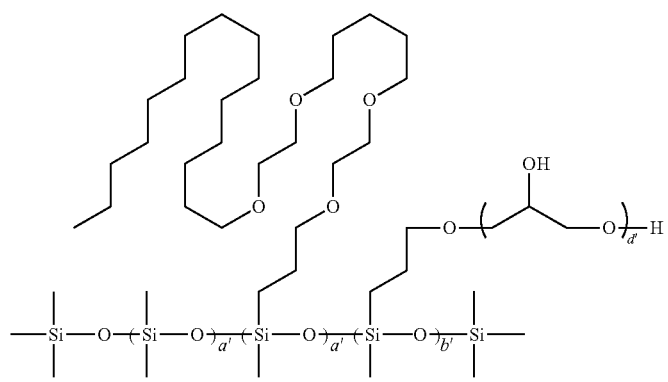
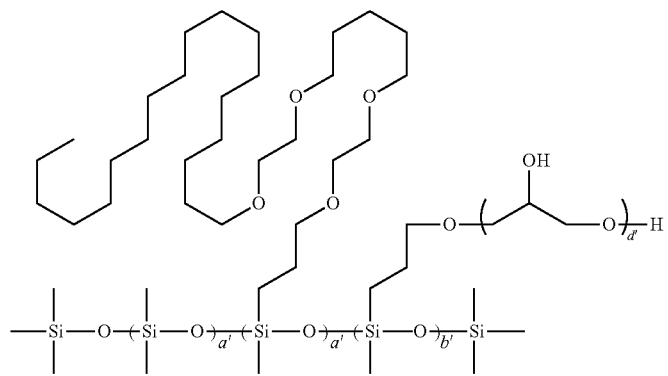

-continued
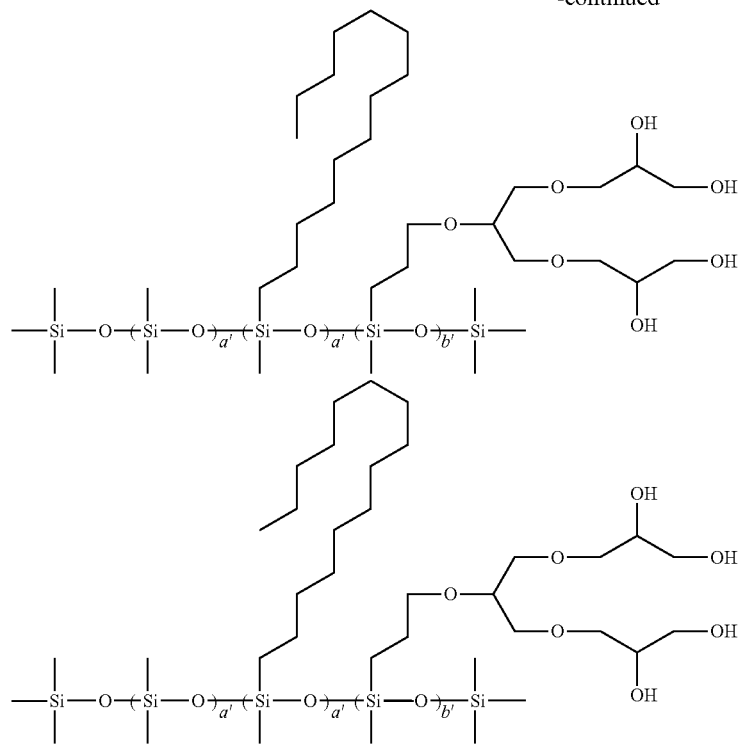
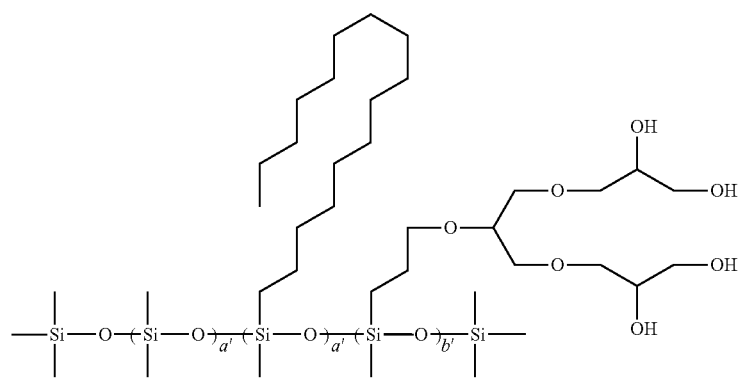
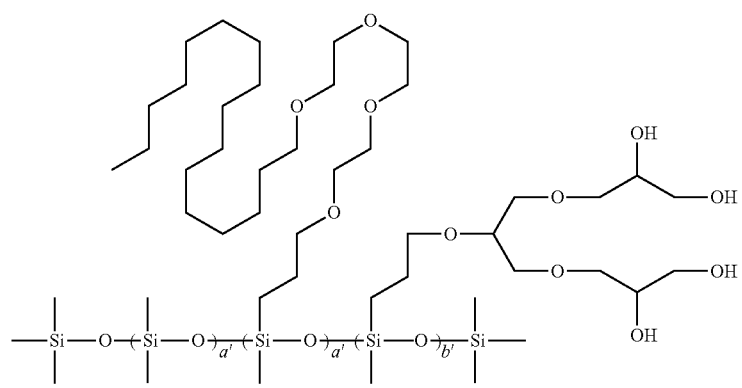

-continued
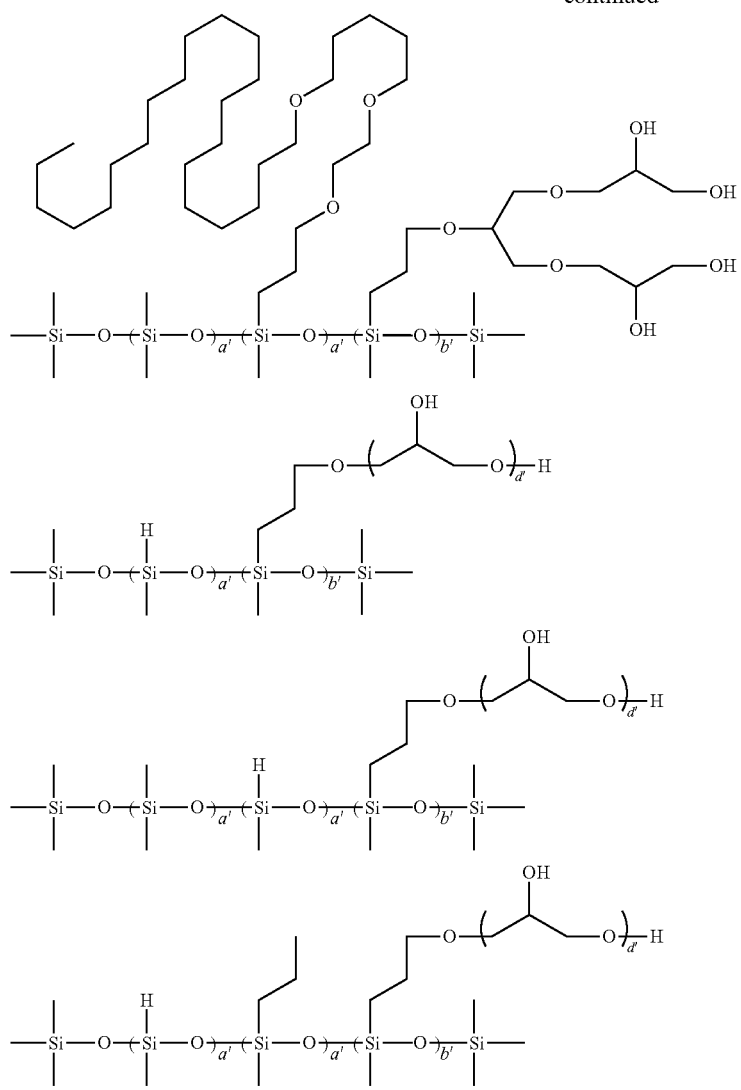
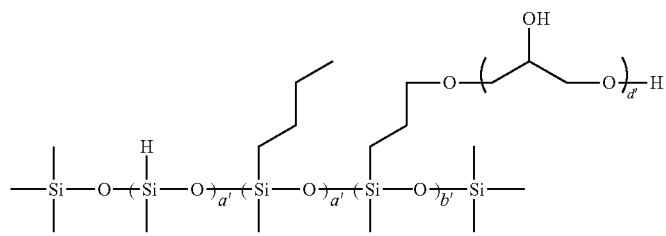
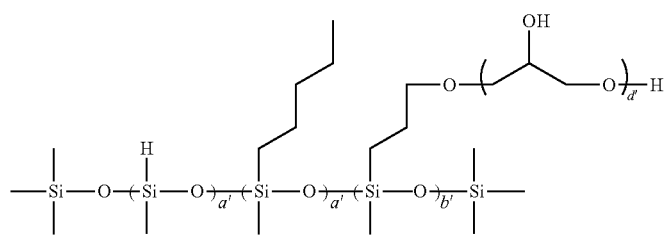

-continued
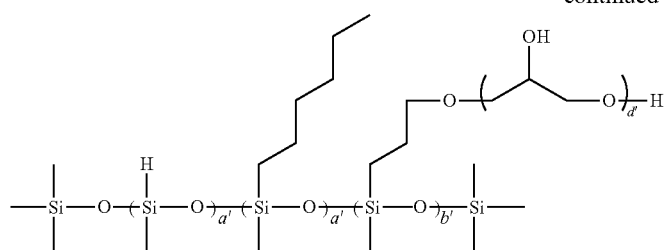
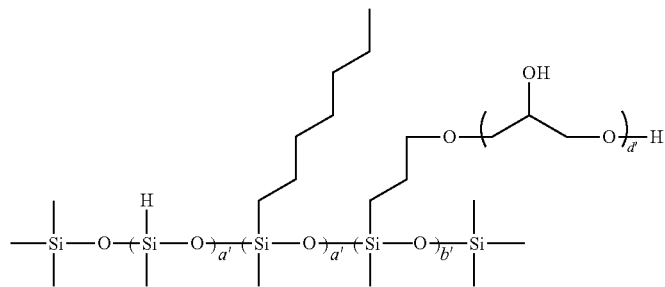
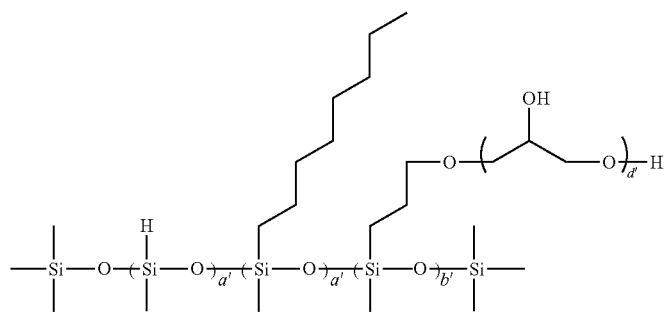
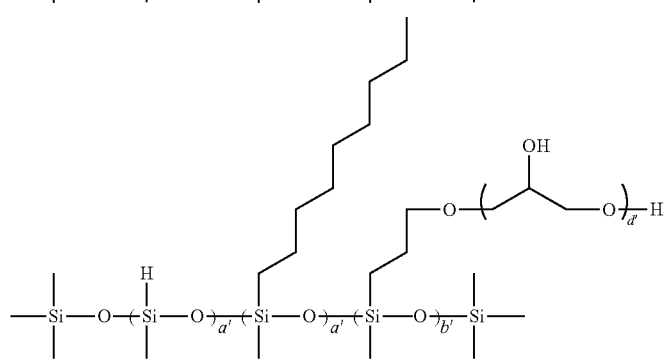
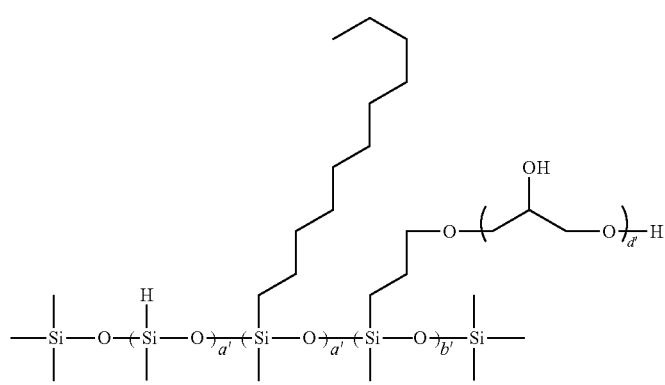

-continued
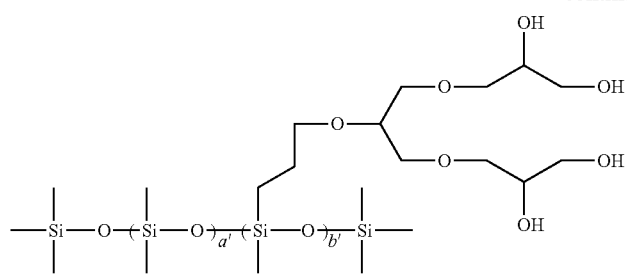
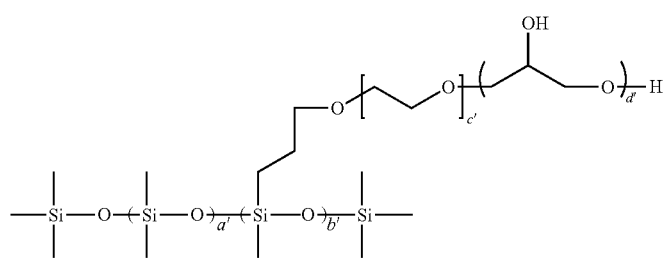
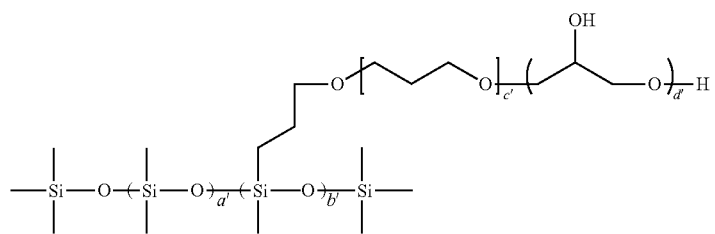
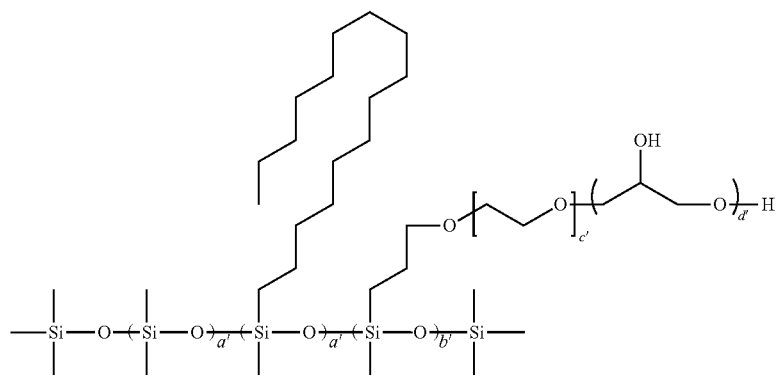
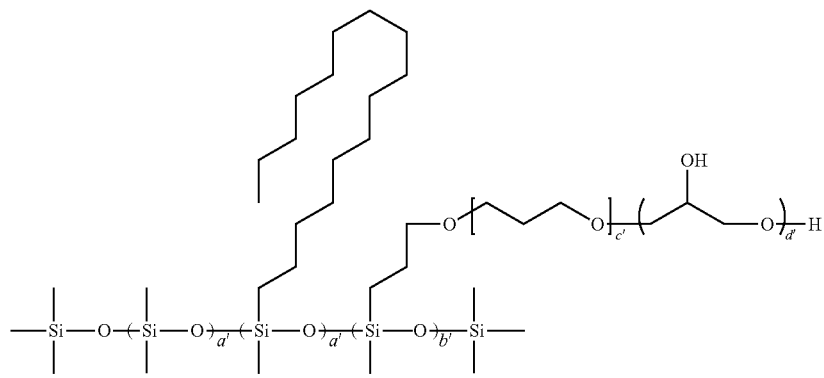

-continued
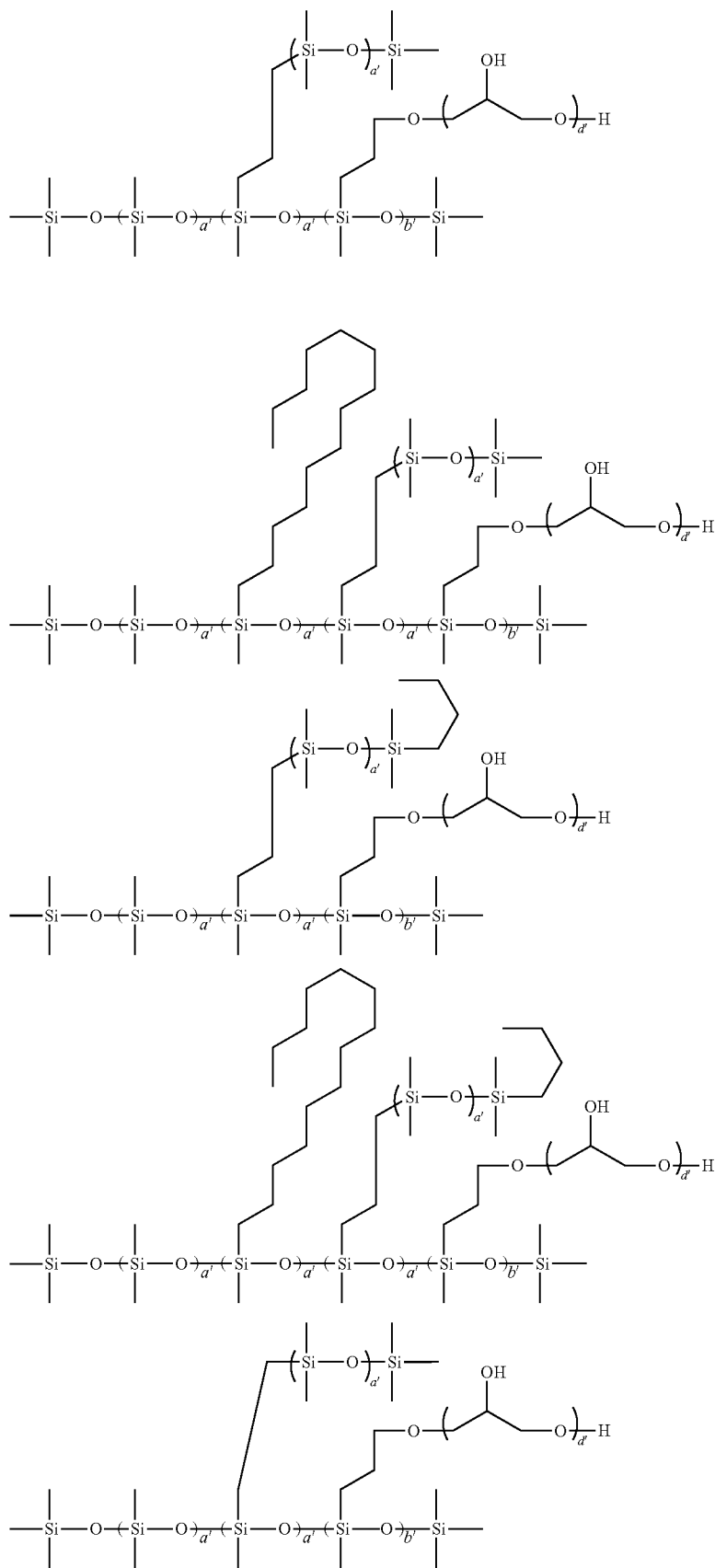

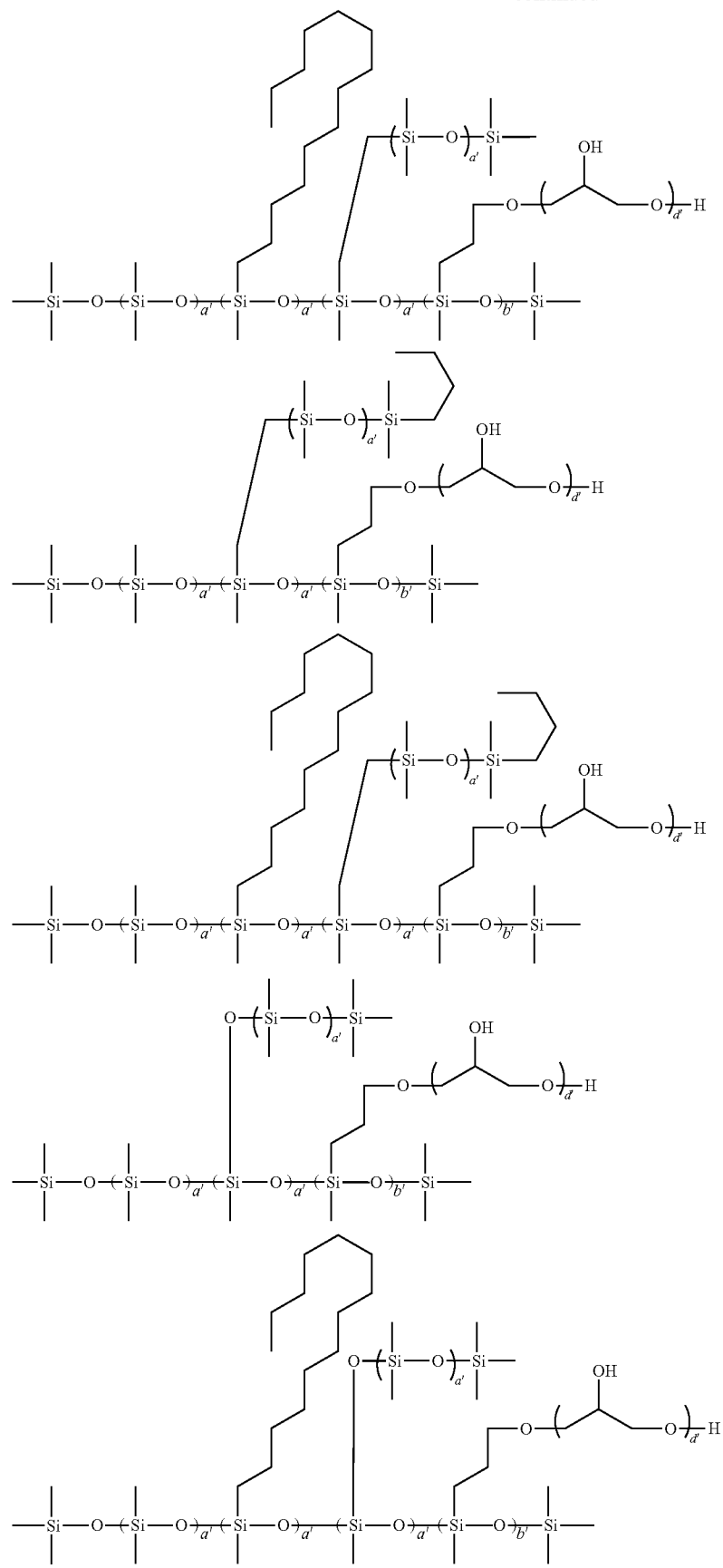

-continued
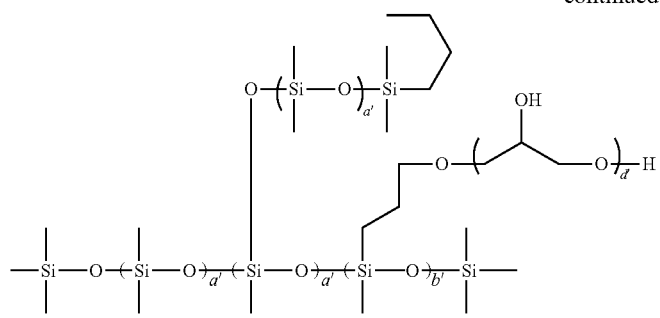
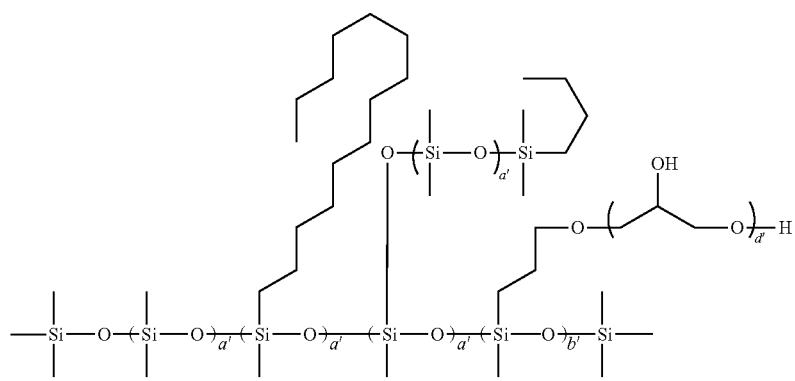
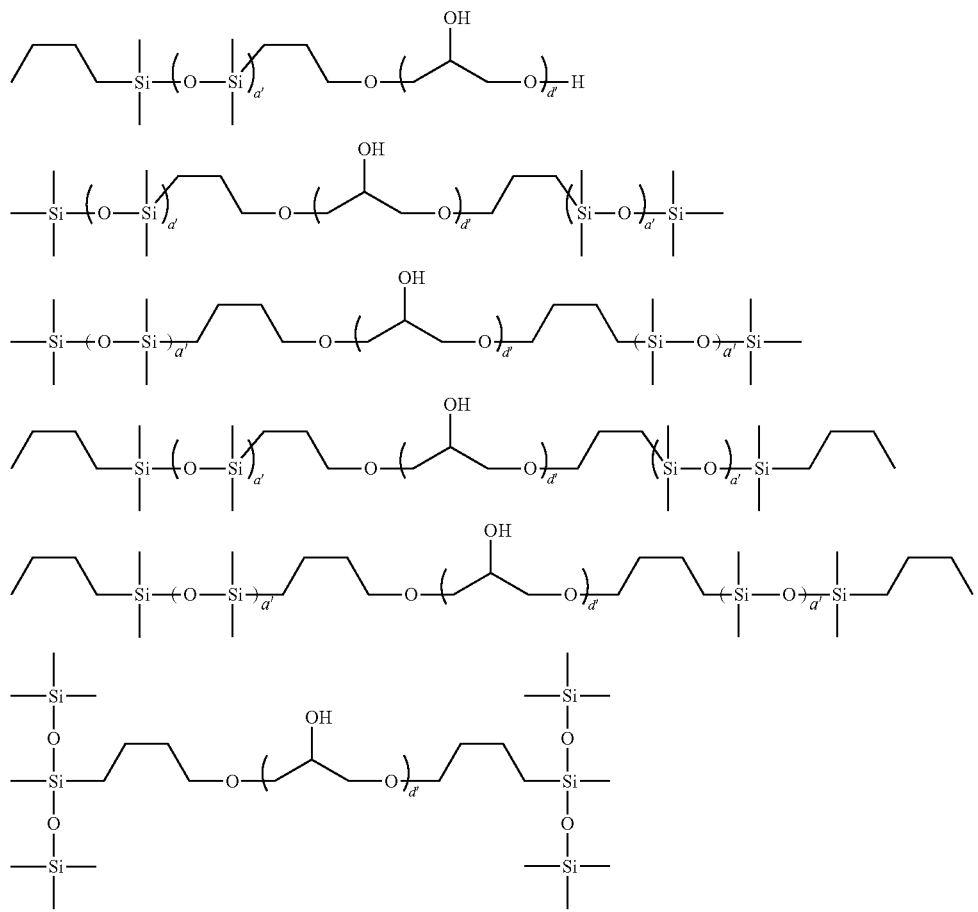

-continued

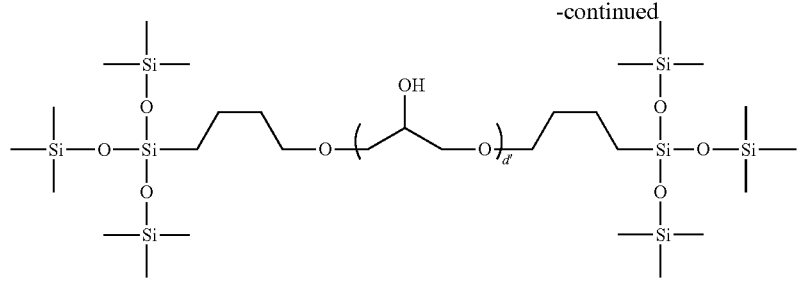

In the formulae, a', b', c', and d' are as defined above.

When such a silicone compound having a polyglycerin structure is incorporated, the resulting bio-electrode composition is capable of forming a living body contact layer that can exhibit more excellent moisture-holding property and consequently exhibit more excellent sensitivity to ions released from skin.

As has been described above, the inventive bio-electrode composition makes it possible to form a living body contact layer for a bio-electrode that is capable of efficiently conducting electric signals from skin to a device (i.e., excellent in electric conductivity), free from a risk of causing allergies even when the bio-electrode is attached to skin for a long period (i.e., excellent in biocompatibility), light-weight, manufacturable at low cost, and free from significant reduction in the electric conductivity even when the bio-electrode is wetted with water or dried. Moreover, it is possible to further enhance the electric conductivity by adding electro-conductive powder (carbon powder, metal powder), and it is possible to manufacture a bio-electrode with particularly high adhesive strength and high stretchability by combining the inventive bio-electrode composition with a resin having adhesion and stretchability. Further, the stretchability and adhesion to skin can be enhanced with an additive and so forth. The stretchability and adhesion can also be controlled by appropriately adjusting the composition of the resin and the thickness of the living body contact layer.

<Bio-Electrode>

The present invention also provides a bio-electrode including an electro-conductive base material and a living body contact layer formed on the electro-conductive base material, the living body contact layer being a cured product of the inventive bio-electrode composition described above.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is formed from a cured product of the inventive bio-electrode composition. The living body contact layer 3 is constituted of an ionic composite 4 that is the above-described composite of an ionic polymer material and particles (e.g., the silicon material particles modified with an ionic polymer). The living body contact layer 3 can further contain an adhesive resin 6 and a blend ionic polymer 5 other than the ionic composite 4. Hereinbelow, with reference to FIGS. 1 and 2, the living body contact layer 3 is described as a layer in which the ionic composite 4 and the blend ionic polymer 5 are dispersed in the adhesive resin 6. Nevertheless, the inventive bio-electrode is not limited to this embodiment.

When the bio-electrode 1 as shown in FIG. 1 is used, the living body contact layer 3 (i.e., the layer in which the ionic composite 4 and the blend ionic polymer 5 are dispersed in the adhesive resin 6) is brought into contact with a living body 7 as shown in FIG. 2. Electric signals are picked from the living body 7 through the ionic composite 4 and the blend ionic polymer 5, and then conducted to a sensor device or the like (not shown) via the electro-conductive base material 2. As described above, the inventive bio-electrode is capable of coping with both electric conductivity and biocompatibility by using the ionic composite 4 described above, and obtaining electric signals from skin stably in high sensitivity because the contact area with the skin is kept constant due to the adhesion thereof.

Hereinafter, each component of the inventive bio-electrode will be described more specifically.

[Electro-Conductive Base Material]

The inventive bio-electrode has an electro-conductive base material. This electro-conductive base material is usually connected electrically with a sensor device etc., and conducts electrical signals picked from a living body through the living body contact layer to the sensor device etc.

The electro-conductive base material is not particularly limited, as long as it has electric conductivity. The electro-conductive base material preferably contains one or more selected from the group consisting of gold, silver, silver chloride, platinum, aluminum, magnesium, tin, tungsten, iron, copper, nickel, stainless steel, chromium, titanium, carbon, and electro-conductive polymer, for example.

The electro-conductive base material may be a hard electro-conductive substrate, an electro-conductive film having flexibility, a cloth with the surface being coated with electro-conductive paste, a cloth into which electro-conductive polymer is kneaded, or the like without being limited to particular substrates. The electro-conductive base material may be flat, uneven, or mesh-form of woven metal wires, which can be appropriately selected in accordance with the use of the bio-electrode, and so forth.

[Living Body Contact Layer]

The inventive bio-electrode has a living body contact layer formed on the electro-conductive base material. This living body contact layer is a part to be actually in contact with a living body when using the bio-electrode. The living body contact layer has electric conductivity and adhesion. The living body contact layer is a cured product of the inventive bio-electrode composition described above; that is, an adherent resin layer formed from a cured composition containing: the component (A); and as necessary the component (B), the component (C), the component (D), the component (E), and the other component(s) (F).

The living body contact layer preferably has an adhesive strength in a range of 0.5 N/25 mm or more and 20 N/25 mm or less. The adhesive strength is commonly measured by the method described in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and the energy is as low as that of Teflon (registered trademark). Human skin is hard to adhere.

The living body contact layer of the bio-electrode has a thickness of preferably 1 µm or more and 5 mm or less, more preferably 2 µm or more and 3 mm or less. As the living body contact layer is thinner, the adhesive strength lowers, but the flexibility is improved, the weight decreases and the compatibility with skin is improved. The thickness of the living body contact layer can be selected based on the balance of adhesion and texture to the skin.

The inventive bio-electrode may be additionally provided with an adherent film on the living body contact layer as in conventional bio-electrodes (e.g., the bio-electrode described in JP 2004-033468A) in order to prevent peeling off of the bio-electrode from a living body during the use. When the adherent film is provided separately, the adherent film may be formed by using a raw material for the adherent film such as an acrylic type, a urethane type, and a silicone type. Particularly, the silicone type is suitable because of: the high oxygen permeability, which enables dermal respiration while the electrode is attached to the skin; the high water repellency, which suppresses lowering of adhesion due to perspiration; and the low irritation to skin. It is to be noted that the inventive bio-electrode does not necessarily require this adherent film that is provided separately, because peeling off from a living body can be prevented by adding a tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to employ ones described in JP 2004-033468A.

As described above, since the inventive bio-electrode includes the living body contact layer formed from the cured product of the aforementioned inventive bio-electrode composition, the inventive bio-electrode is capable of efficiently conducting electric signals from skin to a device (i.e., excellent in electric conductivity), does not cause allergies even after long-period attachment to skin (i.e., excellent in biocompatibility), is light-weight and manufacturable at low cost, and prevents significant reduction in the electric conductivity even when wetted with water or dried. In addition, it is possible to further improve the electric conductivity by adding an electro-conductive powder, and it is possible to manufacture a bio-electrode with particularly high adhesive strength and high stretchability by combining the inventive bio-electrode composition with a resin having adhesion and stretchability. Further, the stretchability and adhesion to skin can be improved with an additive and so forth. The stretchability and adhesion can also be controlled by appropriately adjusting the composition of the resin and the thickness of the living body contact layer. Accordingly, the inventive bio-electrode as described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, the method including:

applying the inventive bio-electrode composition onto the electro-conductive base material; and curing the bio-electrode composition to form the living body contact layer.

Note that the electro-conductive base material etc. used in the inventive method for manufacturing a bio-electrode may be the same as those described above.

The method for applying the bio-electrode composition onto the electro-conductive base material is not particularly limited. Examples of the suitable method include dip coating, spray coating, spin coating, roll coating, flow coating, doctor coating, screen printing, flexographic printing, gravure printing, inkjet printing, etc.

The method for curing the resin is not particularly limited and can be appropriately selected based on the kind of the components (A) and (B) used for the bio-electrode composition. For example, the bio-electrode composition is preferably cured by either or both of heat and light. The foregoing bio-electrode composition can also be cured by adding a catalyst in advance to generate acid or base to the bio-electrode composition, which causes a crosslinking reaction.

The heating temperature is not particularly limited and may be appropriately selected based on the kind of the components (A) and (B) used for the bio-electrode composition, but is preferably about 50 to 250° C., for example.

When the heating and light irradiation are combined, it is possible to perform the heating and the light irradiation simultaneously, to perform the light irradiation and then the heating, or to perform the heating and then the light irradiation. It is also possible to perform air-drying to evaporate the solvent before heating the coating film.

Water droplets may be attached to the surface of the cured film; alternatively, the film surface may be sprayed with water vapor or mist. These treatments improve the compatibility with skin, and enable quick collection of biological signals. Water mixed with alcohol can be used to reduce size of water vapor or mist. The film surface may be wetted by bringing an absorbent cotton or cloth containing water into contact therewith.

The water for making the surface of the cured film wet may contain a salt. The water-soluble salt mixed with the water is selected from the group consisting of sodium salts, potassium salts, calcium salts, magnesium salts, and betaines.

Specifically, the water-soluble salt can be a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines. It should be noted that the components (A) and (C) described above are excluded from the water-soluble salt.

More specific examples of the water-soluble salt include, besides the aforementioned examples, sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl sethionate, sodium lauroyl methylalanine, sodium methyl cocoyl taurate, sodium cocoyl glutamate, sodium cocoyl sarcosinate, sodium lauroyl methyl taurate, lauramidopropyl betaine, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, and calcium methanesulfonate. The term betaines is a general term for inner salts. Specific examples thereof include amino acid compounds in each of which three methyl groups are added to an amino group. More specific examples include trimethylglycine, carnitine, and proline betaines.

The water for wetting the surface of the cured film can further contain a monohydric alcohol or polyhydric alcohol having 1 to 4 carbon atoms. The alcohol is preferably selected from the group consisting of ethanol, isopropyl alcohol, ethylene glycol, diethylene glycol, triethylene glycol, glycerin, polyethylene glycol, polypropylene glycol, polyglycerin, diglycerin, and a silicone compound having a polyglycerin structure. More preferably, the silicone compound having a polyglycerin structure is shown by the general formula (4)' or (5)'.

In the pretreatment methods with the aqueous solution containing the water-soluble salt, the cured bio-electrode film can be wetted by a spraying method, a droplet-dispensing method, etc. The bio-electrode film can also be wetted under a high-temperature, high-humidity condition like sauna. To prevent drying after the wetting, a protective film can be further stacked on the permeated layer to cover the surface. Since the protective film needs to be removed immediately before the bio-electrode is attached to skin, the protective film may be coated with a release agent, or a peelable Teflon(registered trademark) film may be used as the protective film. For long-time storage, the dry electrode covered with the peelable film is preferably sealed in a bag that is covered with aluminum etc. To prevent drying in the bag covered with aluminum, it is preferable to include water therein, too.

Before the inventive bio-electrode is attached to skin, the skin may be moisturized with water, alcohol, etc., or the skin may be wiped with a cloth or absorbent cotton containing water, alcohol, etc. The water and the alcohol may contain the above-described salts.

As has been described above, the inventive method for manufacturing a bio-electrode makes it possible to manufacture the inventive bio-electrode easily and at low cost, with the bio-electrode being excellent in electric conductivity and biocompatibility, light-weight, and capable of preventing significant reduction in the electric conductivity even when wetted with water or dried.

EXAMPLE

Hereinafter, the present invention will be specifically described with reference to Examples and Comparative Examples, but the present invention is not limited thereto. Incidentally, "Me" represents a methyl group, and "Vi" represents a vinyl group.
(Ionic Polymer)

Ionic polymers 1 to 14, which were blended as ionic material (conductive material) to bio-electrode composition solutions, were synthesized as follows. First, 30 mass % solutions of corresponding monomers in cyclopentanone were introduced into a reaction vessel and mixed. The reaction vessel was cooled to −70° C. under a nitrogen atmosphere, and subjected to vacuum degassing and nitrogen blowing, which were repeated three times. After raising the temperature to room temperature, azobisisobutyronitrile (AIBN) was added thereto as a polymerization initiator in an amount of 0.02 moles per 1 mole of the whole monomers. This was warmed to 60° C. and then allowed to react for 15 hours. After drying the solvent, the composition of the resulting polymer was identified by $^1$H-NMR. The molecular weight (Mw) and the dispersity (Mw/Mn) of the obtained polymer were determined by gel permeation chromatography (GPC) using tetrahydrofuran (THF) as a solvent. Thus synthesized Ionic polymers 1 to 14 having alkoxysilyl groups are shown below.

Ionic Polymer 1

Mw=34, 100

Mw/Mn=2.11

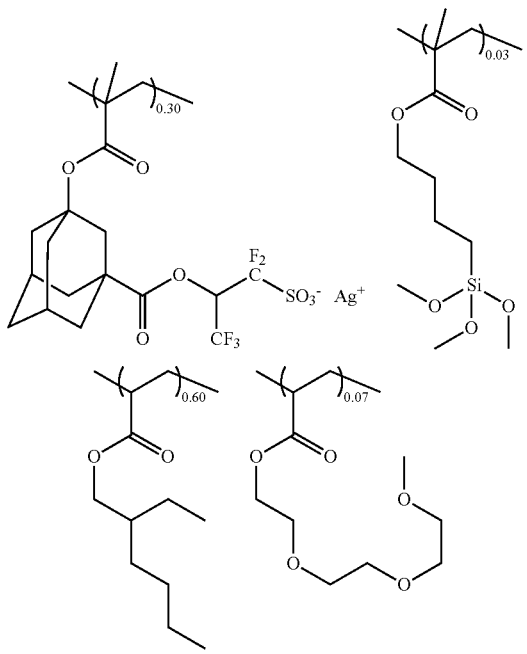

Ionic Polymer 2

Mw=16, 600

Mw/Mn=1.65

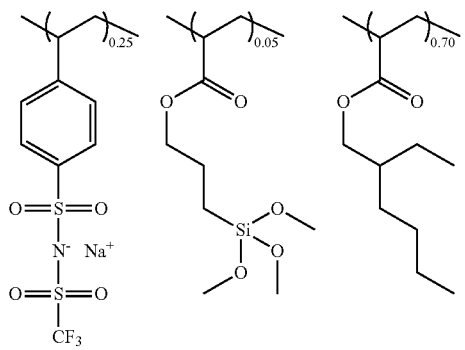

Ionic Polymer 3
Mw=31,900
Mw/Mn=1.89
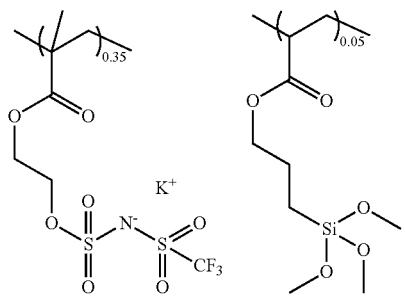
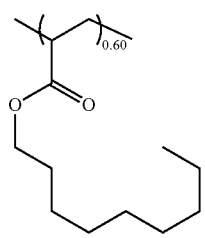
Ionic Polymer 4
Mw=16,500
Mw/Mn=1.79
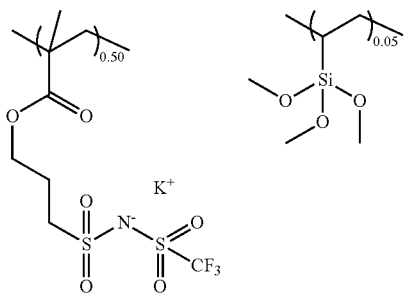
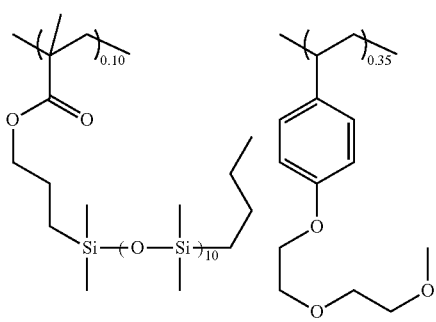
The repeating number in each formula shows the average value.
Ionic Polymer 5
Mw=51,100
Mw/Mn=1.91
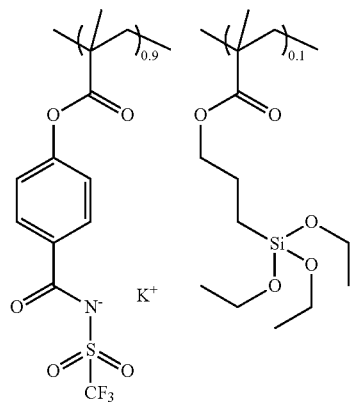
Ionic Polymer 6
Mw=27,400
Mw/Mn=1.91
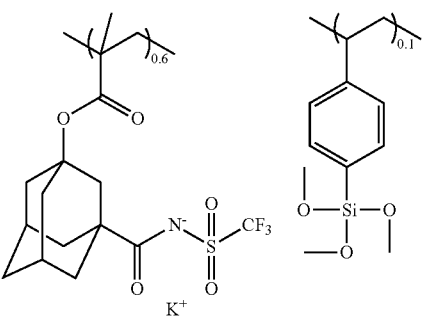
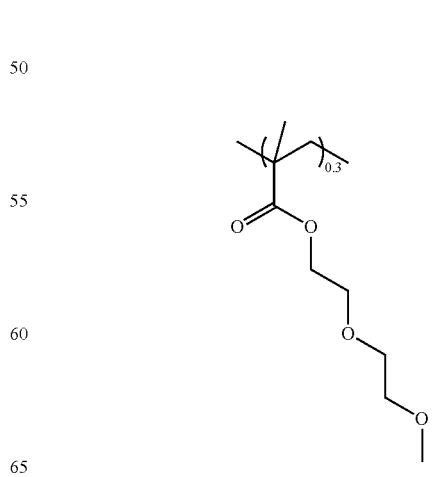

Ionic Polymer 7
  Mw=42, 100
  Mw/Mn=2.11
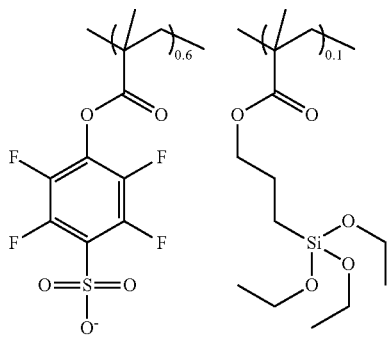
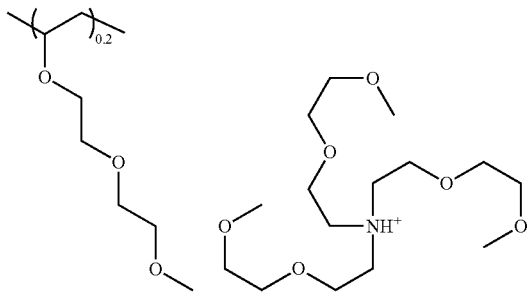
The repeating number in each formula shows the average value.
Ionic Polymer 8
  Mw=19, 800
  Mw/Mn=1.91
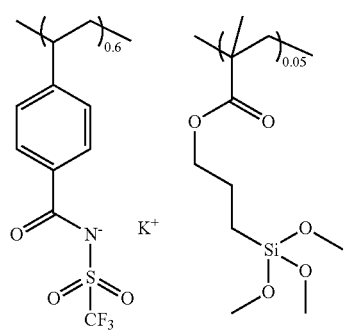
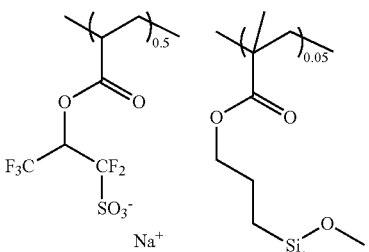
The repeating number in each formula shows the average value.
Ionic Polymer 9
  Mw=21, 300
  Mw/Mn=2.05
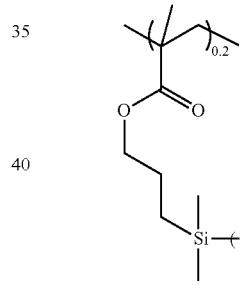
The repeating number in each formula shows the average value.
Ionic polymer 10
  Mw=21, 500
  Mw/Mn=1.70
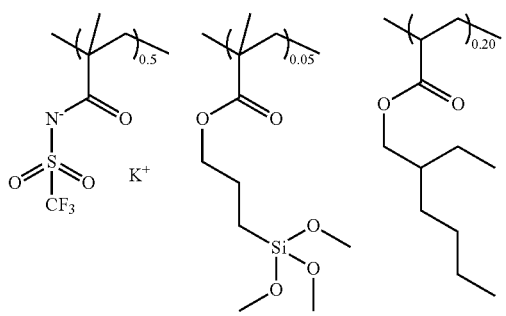

Ionic Polymer 11
 Mw=21,800
 Mw/Mn=1.91
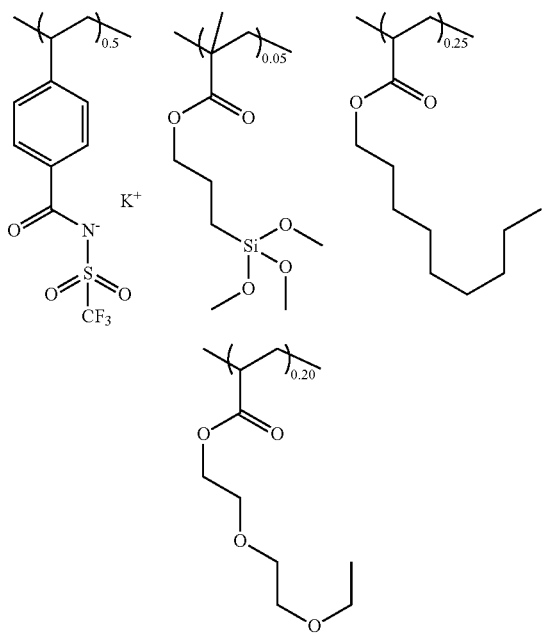
Ionic Polymer 12
 Mw=21,500
 Mw/Mn=1.75
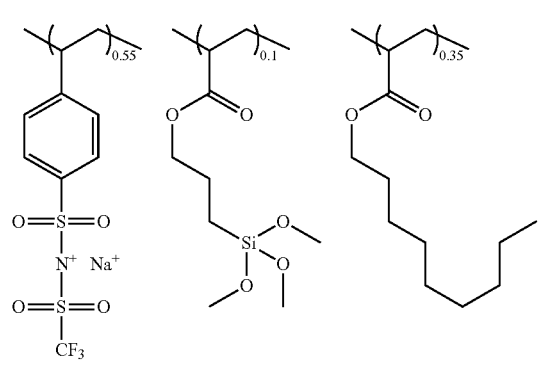
Ionic Polymer 13
 Mw=22,100
 Mw/Mn=1.60
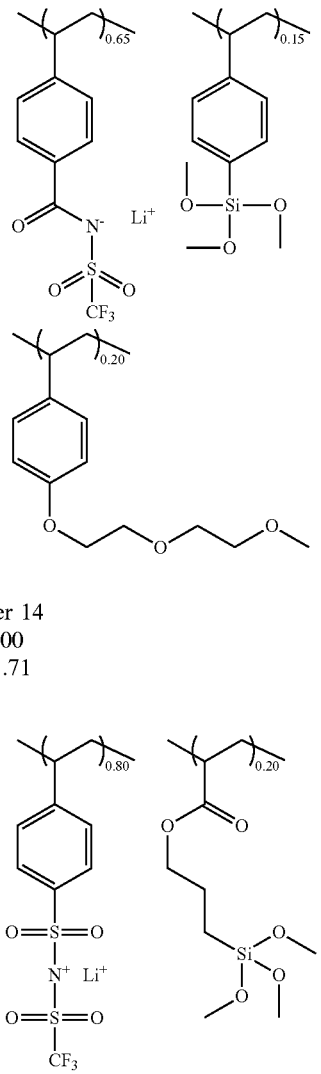
Ionic Polymer 14
 Mw=26,600
 Mw/Mn=1.71
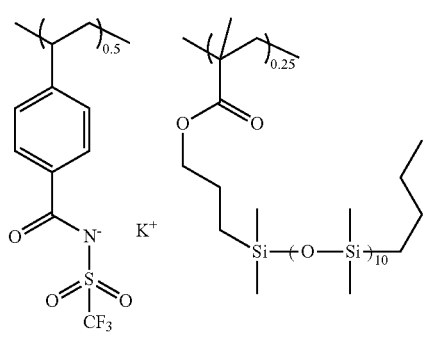
Blend ionic polymer 1 and Comparative ionic polymer 1 for Comparative Example are shown below.
Blend Ionic Polymer 1
 Mw=39,100
 Mw/Mn=1.91

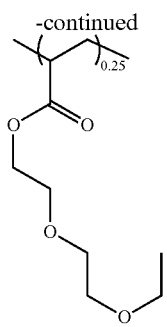

The repeating number in each formula shows the average value.

Comparative Ionic Polymer 1
 Mw=26, 900
 Mw/Mn=1.99

Comparative ionic polymer 1

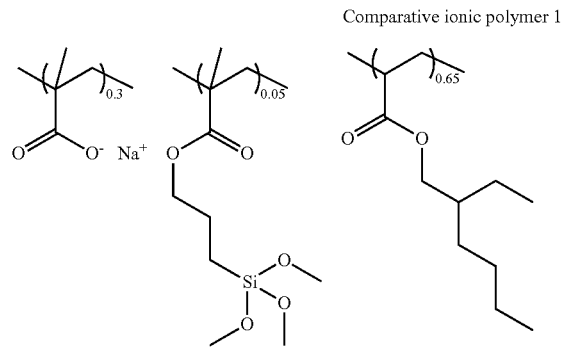

(Composite Silica)

Into 100 g of methyl isobutyl ketone (MIBK) dried with a molecular sieve, 5 g of dry silica (manufactured by SIGMA-Aldrich Co., LLC., size: 5 to 20 nm) was added and stirred for 1 day. Into the resultant, 15 g of a cyclopentanone solution containing Ionic polymer 1 at a concentration of 30 weight % was added dropwise and stirred at room temperature for 20 hours. Then, the solvent was dried. Thus, Ionic polymer 1-composite silica having Ionic polymer 1 in a pendant form was synthesized.

In the same way, Ionic polymer 2-composite silica to Ionic polymer 12-composite silica, and Comparative ionic polymer 1-composite silica were synthesized.

In the same way, Ionic polymer 13-composite silicon powder, Ionic polymer 13-composite silicon carbide powder, and Ionic polymer 13-composite silicon monoxide powder were synthesized, except that silicon powder manufactured by Sigma-Aldrich Co., LLC. with a size of 100 nm or less, silicon carbide powder manufactured by Sigma-Aldrich Co., LLC. with a size of 100 nm or less, and silicon monoxide powder manufactured by Sigma-Aldrich Co., LLC. with a size of 440 nm or less were respectively used instead of the dry silica and respectively reacted with Ionic polymer 13.

In the same way, Ionic polymer 14-composite silicon powder, Ionic polymer 14-composite silicon carbide powder, and Ionic polymer 14-composite silicon monoxide powder were synthesized, except that silicon powder manufactured by Sigma-Aldrich Co., LLC. with a size of 100 nm or less, silicon carbide powder manufactured by Sigma-Aldrich Co., LLC. with a size of 100 nm or less, and silicon monoxide powder manufactured by Sigma-Aldrich Co., LLC. with a size of 440 nm or less were respectively used instead of the dry silica and respectively reacted with Ionic polymer 14.

In the same way, Ionic polymer 5-composite alumina powder, Ionic polymer 5-composite titania powder, Ionic polymer 5-composite zirconia powder, and Ionic polymer 5-composite lithium titanate powder were synthesized, except that aluminum oxide powder manufactured by Sigma-Aldrich Co., LLC. with a size of 50 nm or less, titanium oxide powder manufactured by Sigma-Aldrich Co., LLC. with a size of 100 nm or less, zirconium oxide powder manufactured by Sigma-Aldrich Co., LLC. with a size of 100 nm or less, and lithium titanate powder manufactured by Sigma-Aldrich Co., LLC. with a size of 200 nm or less were respectively used instead of the dry silica and respectively reacted with Ionic polymer 5.

Siloxane compounds 1 to 4, which were blended as silicone-based resin to the bio-electrode composition solutions, are shown below.

(Siloxane Compound 1)

Siloxane compound 1 was vinyl group-containing polydimethylsiloxane having an alkenyl group-content of 0.007 mol/100 g in which the terminals of molecular chain were capped with $SiMe_2Vi$ groups, with the 30% solution in toluene having a viscosity of 27,000 mPa s.

(Siloxane Compound 2)

Siloxane compound 2 was a 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene.

(Siloxane Compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were capped with OH, with the 30% solution in toluene having a viscosity of 42,000 mPa·s; 100 parts by mass of 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene; and 26.7 parts by mass of toluene) with refluxing for 4 hours, followed by cooling.

(Siloxane Compound 4)

As methylhydrogensilicone oil, KF-99 manufactured by Shin-Etsu Chemical Co., Ltd. was used.

Silicone pendant urethane acrylates 1 to 3 and Urethane acrylate 1, which were blended to the bio-electrode composition solutions, are shown below.

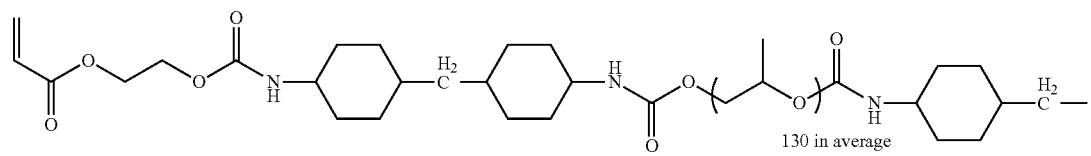

-continued
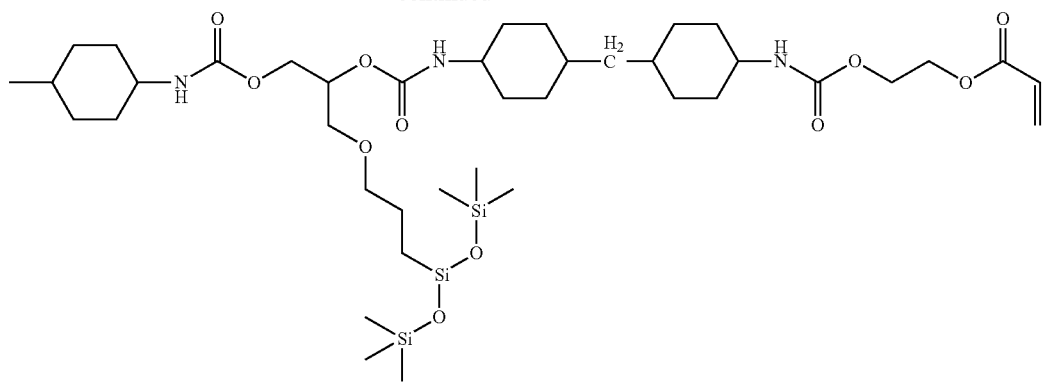
Silicone pendant urethane acrylate 1
Mw 24800 Mw/Mn 2.65
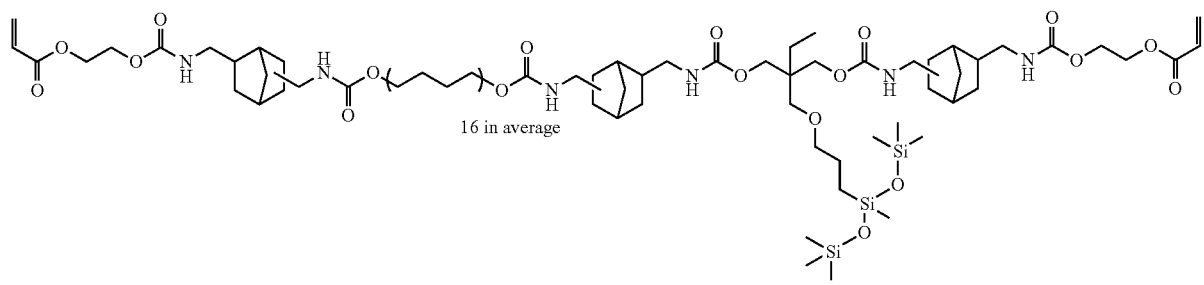
Silicone pendant urethane acrylate 2
Mw 8900 Mw/Mn 2.67
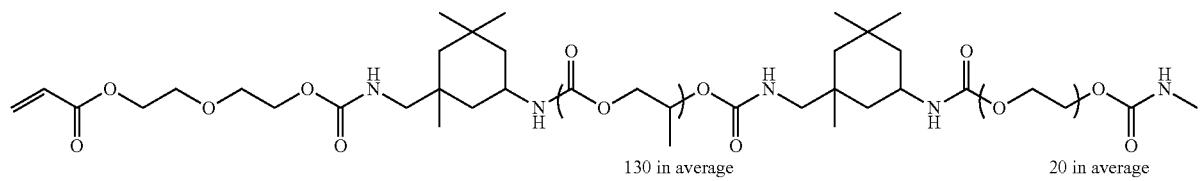
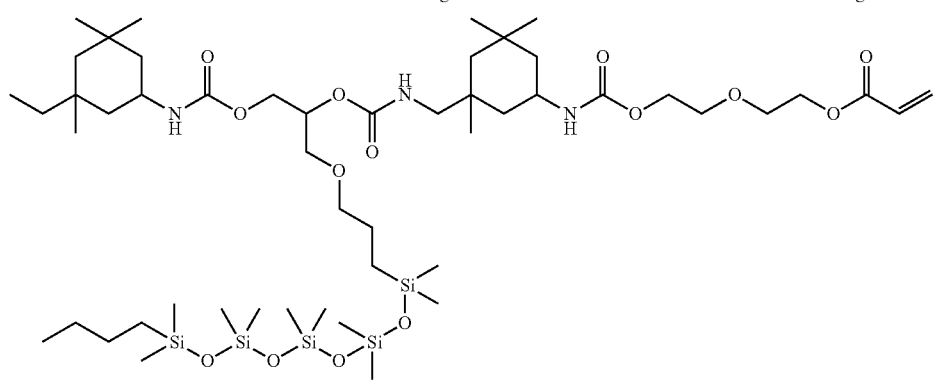
Silicone pendant urethane acrylate 3
Mw 8100 Mw/Mn 2.69
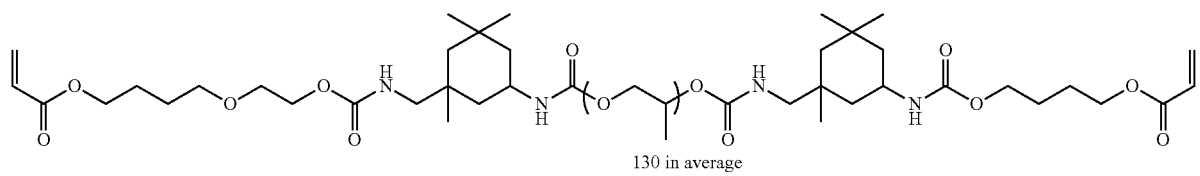
Urethane acrylate 1
Mw 26300 Mw/Mn 2.21

The repeating number in each formula shows the average value.

Acrylic polymer blended as acrylic-based resin to the bio-electrode composition solutions is shown below.

Acrylic Polymer 1
  Mw=127,000
  Mw/Mn=2.28

Acrylic polymer 1

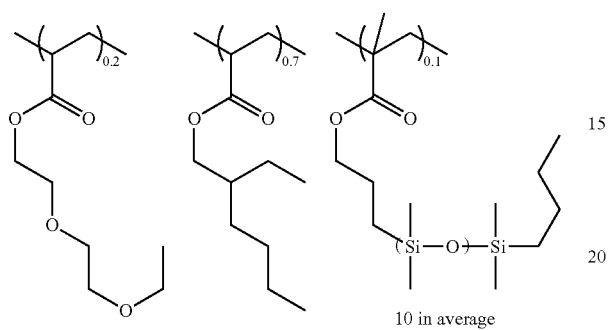

10 in average

The repeating number in each formula shows the average value.

Polyglycerin-silicone compounds 1 to 8 are shown below.

Polyglycerin-silicone compound 1

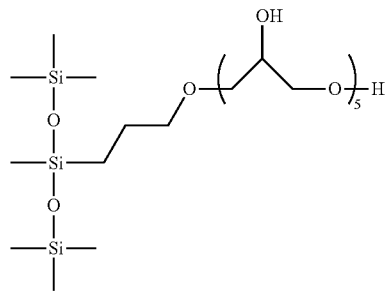

Polyglycerin-silicone compound 2

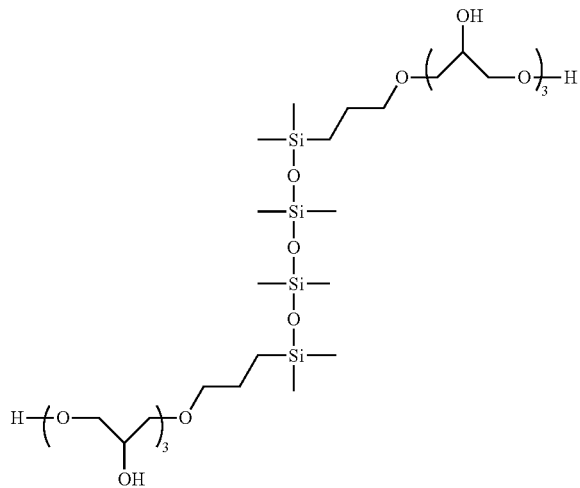

Polyglycerin-silicone compound 3

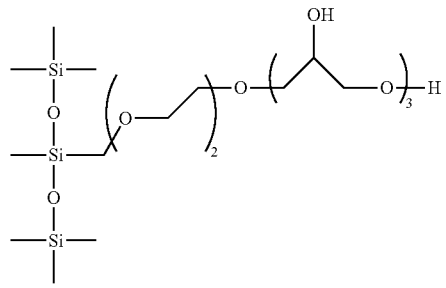

Polyglycerin-silicone compound 4

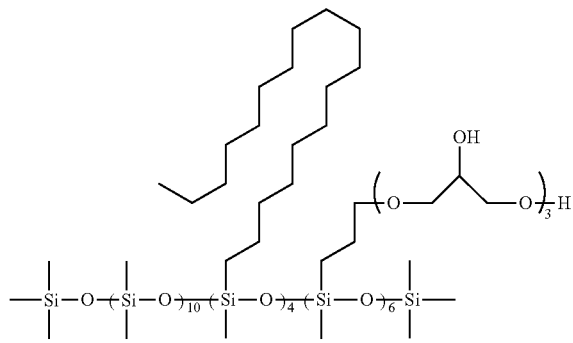

-continued

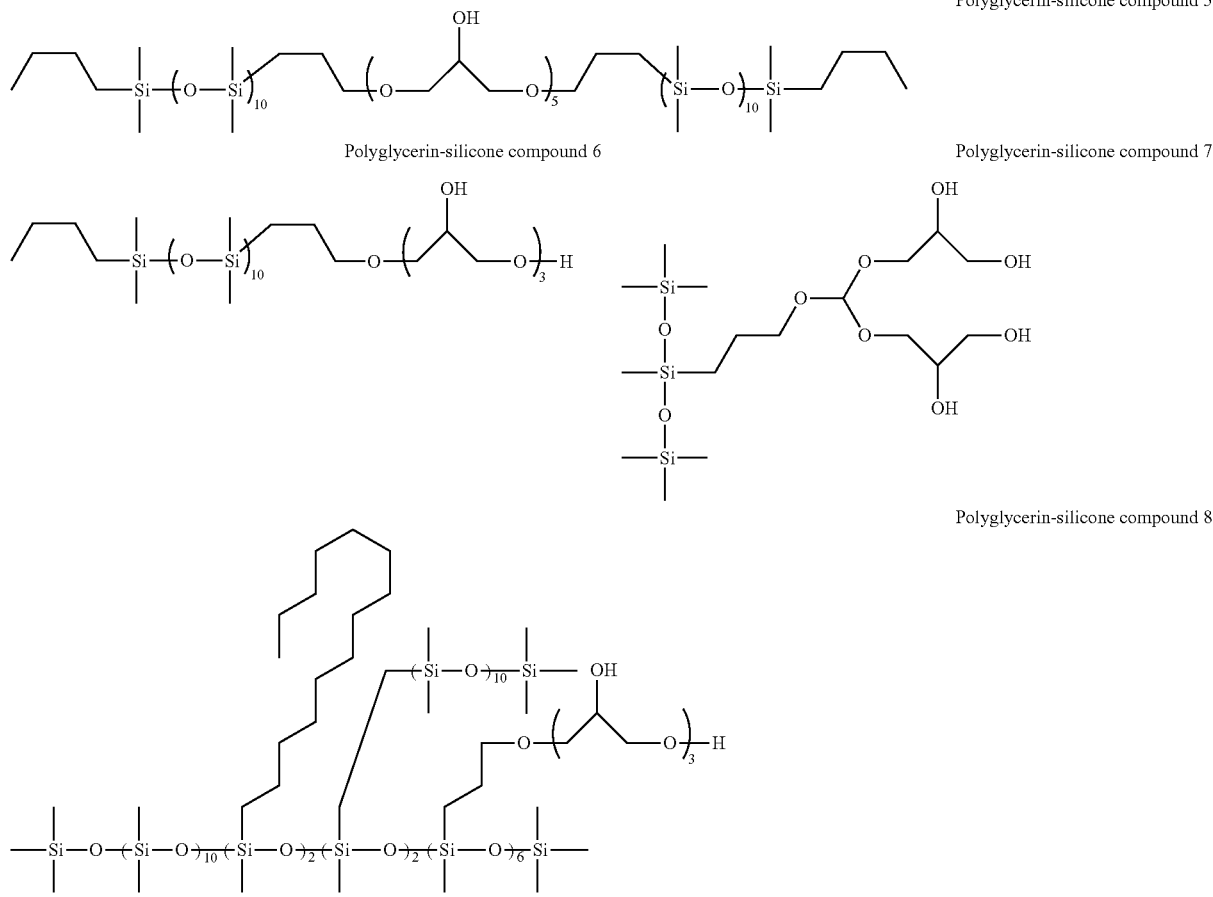

Organic solvents blended to the bio-electrode composition solutions are shown below.
EDE: diethylene glycol diethyl ether
ISOPAR G: isoparaffin base solvent manufactured by Standard Sekiyu CO., LTD.
ISOPAR M: isoparaffin base solvent manufactured by Standard Sekiyu CO., LTD.

Lithium titanate powder, radical generator, platinum catalyst, and electric conductivity improver (carbon black, carbon nanotube, metal powder), which were blended as additives to the bio-electrode composition solutions, are shown below.
Metal powder: silver powder of silver flake with the diameter of 10 μm manufactured by Sigma-Aldrich Co., LLC.
Lithium titanate powder, spinel: with the size of 200 nm or less manufactured by Sigma-Aldrich Co., LLC.
Radical generator: IRGACURE TPO manufactured by BASF SE
Platinum catalyst: CAT-PL-50T manufactured by Shin-Etsu Chemical Co., Ltd.
Carbon black: DENKA BLACK Li-400 manufactured by Denka Co., Ltd.
Multilayer carbon nanotube: with the diameter of 110 to 170 nm and length of 5 to 9 μm manufactured by Sigma-Aldrich Co., LLC.
Dry silica (manufactured by SIGMA-Aldrich Co., LLC., size: 5 to 20 nm) was used as silica in Comparative Example.

Examples 1 to 29, Comparative Examples 1 to 4

According to the compositions shown in Tables 1 to 3, the ionic polymer-composite particles, resins, ionic polymer, organic solvents, and additives (radical generator, platinum catalyst, electric conductivity improver, etc.) were blended to prepare bio-electrode composition solutions (Bio-electrode composition solutions 1 to 29, Comparative bio-electrode composition solutions 1 to 4).

TABLE 1

| Bio-electrode composition solution | Particle material (parts by mass) | Resin (parts by mass) | Blend ionic polymer (parts by mass) | Organic solvent (parts by mass) | Additive (parts by mass) |
|---|---|---|---|---|---|
| Bio-electrode composition solution 1 | Ionic polymer 1-composite silica (20) | Siloxane compound 1 (40) Siloxane compound 2 (100) Siloxane compound 4 (3) | — | ISOPAR G (60) cyclopentanone (70) silver flake (8) | CAT-PL-50T (0.7) lithium titanate powder (12) |

TABLE 1-continued

| Bio-electrode composition solution | Particle material (parts by mass) | Resin (parts by mass) | Blend ionic polymer (parts by mass) | Organic solvent (parts by mass) | Additive (parts by mass) |
|---|---|---|---|---|---|
| Bio-electrode composition solution 2 | Ionic polymer 2-composite silica (25) | Siloxane compound 3 (126) Siloxane compound 4 (3) | — | n-octane (40) n-decane (20) cyclopentanone (70) | CAT-PL-50T (1.5) carbon black (5) |
| Bio-electrode composition solution 3 | Ionic polymer 3-composite silica (30) | Siloxane compound 3 (126) Siloxane compound 4 (3) | — | n-nonane (60) 2-heptanone (14) | CAT-PL-50T (1.5) carbon black (5) |
| Bio-electrode composition solution 4 | Ionic polymer 4-composite silica (25) | Siloxane compound 3 (126) Siloxane compound 4 (3) | — | ISOPAR 5 (60) cyclopentanone (60) | CAT-PL-50T (1.5) carbon black (6) |
| Bio-electrode composition solution 5 | Ionic polymer 5-composite silica (10) | Siloxane compound 3 (126) Siloxane compound 4 (3) | — | n-decane (30) n-octane (30) 2-heptanone (14) | CAT-PL-50T (1.5) |
| Bio-electrode composition solution 6 | Ionic polymer 6-composite silica (10) | Siloxane compound 3 (126) Siloxane compound 4 (3) | Blend ionic polymer 1 (10) | ISOPAR G (60) cyclopentanone (70) | CAT-PL-50T (1.5) multilayer carbon nanotube (3) |
| Bio-electrode composition solution 7 | Ionic polymer 8-composite silica (100) | Siloxane compound 3 (126) Siloxane compound 4 (3) | — | ISOPAR M (60) cyclopentanone (70) | CAT-PL-50T (1.5) carbon black (6) |
| Bio-electrode composition solution 8 | Ionic polymer 5-composite silica (10) | Siloxane compound 3 (126) Siloxane compound 4 (3) | — | n-decane (30) n-octane (30) 2-heptanone (14) | CAT-PL-50T (1.5) Polyglycerin silicone compound 1 (5) |
| Bio-electrode composition solution 9 | Ionic polymer 8-composite silica (10) | Siloxane compound 3 (126) Siloxane compound 4 (3) | Blend ionic polymer 1 (10) | n-decane (30) n-octane (30) 2-heptanone (14) | CAT-PL-50T (1.5) Polyglycerin silicone compound 2 (5) |
| Bio-electrode composition solution 10 | Ionic polymer 8-composite silica (10) | Siloxane compound 3 (126) Siloxane compound 4 (3) | Blend ionic polymer 1 (10) | n-decane (30) n-octane (30) 2-heptanone (14) | CAT-PL-50T (1.5) Polyglycerin silicone compound 3 (5) |
| Bio-electrode composition solution 11 | Ionic polymer 8-composite silica (10) | Siloxane compound 3 (126) Siloxane compound 4 (3) | Blend ionic polymer 1 (10) | n-dcane (30) n-octane (30) 2-heptanone (14) | CAT-PL-50T (1.5) Polyglycerin silicone compound 4 (5) |
| Bio-electrode composition solution 12 | Ionic polymer 8-composite silica (10) | Siloxane compound 3 (126) Siloxane compound 4 (3) | Blend ionic polymer 1 (10) | n-decane (30) n-octane (30) 2-heptanone (14) | CAT-PL-50T (1.5) Polyglycerin silicone compound 5 (5) |
| Bio-electrode composition solution 13 | Ionic polymer 8-composite silica (10) | Siloxane compound 3 (126) Siloxane compound 4 (3) | Blend ionic polymer 1 (10) | n-decane (30) n-octane 2-heptanone (14) | CAT-PL-50T (1.5) Polyglycerin silicone compound 6 (5) |
| Bio-electrode composition solution 14 | Ionic polymer 7-composite silica (20) | Silicone pendant urethane acrylate 1 (80) | — | EDE (60) cyclopentanone (70) | IRGACURE TPO (1) Polyglycerin silicone compound 7 (5) |
| Bic-electrode composition solution 15 | Ionic polymer 9-composite silica (20) | Silicone pendant urethane acrylate 2 (80) | — | EDE (60) cyclopentanone (70) | IRGACURE TPO (1) Polyglycerin silicone compound 7 (5) |
| Bio-electrode composition solution 16 | Ionic polymer 10-composite silica (18) | Silicone pendant urethane acrylate 3 (80) | — | EDE (60) cyclopentanone (70) | IRGACURE TPO (1) Polyglycerin silicone compound 7 (5) |

TABLE 2

| Bio-electrode composition solution | Particle material (parts by mass) | Resin (parts by mass) | Blend ionic polymer (parts by mass) | Organic solvent (parts by mass) | Additive (parts by mass) |
|---|---|---|---|---|---|
| Bio-electrode composition solution 17 | Ionic polymer 11-composite silica (22) | Urethane acrylate 1 (80) | — | EDE (60) cyclopentanone (70) | IRGACURE TPO (1) Polyglycerin silicone compound 7 (5) |
| Bio-electrode composition solution 18 | Ionic polymer 12-composite silica (24) | Silicone pendant urethane acrylate 1 (80) | — | EDE (60) cyclopentanone (70) | IRGACURE TPO (1) Polyglycerin silicone compound 8 (5) |

TABLE 2-continued

| Bio-electrode composition solution | Particle material (parts by mass) | Resin (parts by mass) | Blend ionic polymer (parts by mass) | Organic solvent (parts by mass) | Additive (parts by mass) |
|---|---|---|---|---|---|
| Bio-electrode composition solution 19 | Ionic polymer 12-composite silica (10) | Acrylic polymer 1 (90) | Blend ionic polymer 1 (10) | EDE (60) cyclopentanone (70) | — |
| Bio-electrode composition solution 20 | Ionic polymer 13-composite silicon carbide powder (20) | Siloxane compound 1 (40) Siloxane compound 2 (100) Siloxane compound 4 (3) | — | ISOPAR G (60) cyclopentanone (70) | CAT-PL-50T (1.5) carbon black (5) |
| Bio-electrode composition solution 21 | Ionic polymer 13-composite silicon nonoxide powder (20) | Siloxane compound 3 (126) Siloxane compound 4 (3) | — | n-octane n-decane (20) cyclopentanone (70) | CAT-PL-50T (1.5) carbon black (5) |
| Bio-electrode composition solution 22 | Ionic polymer 13-composite silicon powder (20) | Siloxane compound 3 (126) Siloxane compound 4 (3) | — | n-nonane (60) 2-heptanone (14) | CAT-PL-50T (1.5) carbon black (5) |
| Bio-electrode composition solution 23 | Ionic polymer 14-composite silicon carbide powder (20) | Siloxane compound 1 (40) Siloxane compound 2 (100) Siloxane compound 4 (3) | — | ISOPAR G (60) cyclopentanone (70) | CAT-PL-50T (1.5) carbon black (5) |
| Bio-electrode composition solution 24 | Ionic polymer 14-composite silicon monoxide powder (20) | Siloxane compound 3 (126) Siloxane compound 4 (3) cyclopentanone (70) | — | n-octane (40) n-decane (20) | CAT-PL-50T (1.5) carbon black (5) |
| Bio-electrode composition solution 25 | Ionic polymer 14-composite silicon powder (20) | Siloxane compound 3 (126) Siloxane compound 4 (3) | — | n-nonane (60) 2-heptanone (14) | CAT-PL-50T (1.5) carbon black (5) |
| Bio-electrode composition solution 26 | Ionic polymer 5-composite alumina powder (20) | Siloxane compound 1 (40) Siloxane compound 2 (100) Siloxane compound 4 (3) | — | ISOPAR G (60) cyclopentanone (70) | CAT-PL-50T (1.5) carbon black (5) |
| Bio-electrode composition solution 27 | Ionic polymer 5-composite titania powder (20) | Siloxane compound 3 (126) Siloxane compound 4 (3) | — | n-octane n-decane (20) cyclopentanone (70) | CAT-PL-50T (1.5) carbon black (5) |
| Bio-electrode composition solution 28 | Ionic polymer 5-composite zirconia powder (20) | Siloxane compound 3 (126) Siloxane compound 4 (3) | — | n-nonane (60) 2-heptanone (14) | CAT-PL-50T (1.5) carbon black (5) |
| Bio-electrode composition solution 29 | Ionic polymer 5-composite lithium titanate powder (10) | Siloxane compound 3 (126) Siloxane compound 4 (3) | Blend ionic polymer 1 (10) | n-nonane (60) 2-heptanone (14) | CAT-PL-50T (1.5) carbon black (5) |

TABLE 3

| Bio-electrode composition solution | Particle material (parts by mass) | Resin (parts by mass) | Blend ionic polymer (parts by mass) | Organic solvent (parts by mass) | Additive (parts by mass) |
|---|---|---|---|---|---|
| Comparative bio-electrode composition solution 1 | — | Siloxane compound 1 (40) Siloxane compound 2 (100) Siloxane compound 4 (3) | — | ISOPAR G (60) cyclopentanone (70) | CAT-PL-50T (1.5) carbon black (14) |
| Comparative bio-electrode composition solution 2 | — | Siloxane compound 1 (40) Siloxane compound 2 (100) Siloxane compound 4 (3) | Blend ionic polymer 1 (20) | ISOPAR G (60) cyclopentanone (70) | CAT-PL-50T (1.5) carbon black (14) |
| Comparative bio-electrode composition solution 3 | Silica (20) | Siloxane compound 1 (40) Siloxane compound 2 (100) Siloxane compound 4 (3) | — | ISOPAR G (60) cyclopentanone (70) | CAT-PL-50T (1.5) carbon black (14) |
| Comparative bio-electrode composition solution 4 | Comparative ionic polymer 1-composite silica (20) | Siloxane compound 1 (40) Siloxane compound 2 (100) Siloxane compound 4 (3) | — | ISOPAR G (60) cyclopentanone (70) | CAT-PL-50T (1.5) carbon black (14) |

(Preparation of Bio-Electrodes)

As shown in FIG. 3, a thermoplastic urethane (TPU) film ST-604 (manufactured by Bemis Associates Inc.) designated by 20 was coated with an electro-conductive paste DOTITE FA-333 (manufactured by Fujikura Kasei Co., Ltd.) by screen printing. The coating film was baked in an oven at 120° C. for 10 minutes to print a keyhole-shaped electro-conductive pattern 2 including a circular portion with a diameter of 2 cm. Then, one of the bio-electrode composition solutions shown in Tables 1 to 3 was applied onto the circular portion by screen printing. After air-dried at room temperature for 10 minutes, the coating film was baked using an oven at 125° C. for 10 minutes to evaporate the solvent and form a living body contact layer 3 by curing. In this manner, bio-electrodes 1 were prepared. In Examples 14 to 18, the curing was further continued by irradiation with a xenon lamp at 200 mJ/cm² under a nitrogen atmosphere. Next, as shown in FIG. 4, the thermoplastic urethane film 20 having the bio-electrode 1 printed thereon was cut out and pasted on a double-sided tape 21. In this manner, three bio-electrode samples 10 were prepared for each of the composition solutions.

(Thickness Measurement of Living Body Contact Layer)

The thickness of the living body contact layer of each bio-electrode prepared as described above was measured with a micrometer. Table 4 shows the result.

(Biological Signal Measurement)

The electro-conductive wiring pattern formed from the electro-conductive paste of each bio-electrode sample was connected to a portable electrocardiograph HCG-901 (manufactured by OMRON HEALTHCARE Co., Ltd.) through an electro-conductive wire. A positive electrode of the electrocardiograph was attached to a location LA in FIG. 5 on a human body, a negative electrode was attached to a location LL, and an earth was attached to a location RA. Immediately after the attachments, the electrocardiogram measurement was started to measure the time until an electrocardiogram waveform (ECG signal) including P, Q, R, S, and T waves appeared as shown in FIG. 6. Table 4 shows the result.

TABLE 4

| Example | Living body contact, adhesive solution | Resin thickness (μm) | Time (min.) until ECG signal appeared |
|---|---|---|---|
| Example 1 | Bio-electrode composition solution 1 | 25 | 3 |
| Example 2 | Bio-electrode composition solution 2 | 33 | 2 |
| Example 3 | Bio-electrode composition solution 3 | 34 | 2 |
| Example 4 | Bio-electrode composition solution 4 | 37 | 2 |
| Example 5 | Bio-electrode composition solution 5 | 39 | 1 |
| Example 6 | Bio-electrode composition solution 6 | 41 | 1.8 |
| Example 7 | Bio-electrode composition solution 7 | 31 | 1.6 |
| Example 8 | Bio-electrode composition solution 8 | 37 | 1.8 |
| Example 9 | Bio-electrode composition solution 9 | 31 | 1.2 |
| Example 10 | Bio-electrode composition solution 10 | 33 | 1.6 |
| Example 11 | Bio-electrode composition solution 11 | 38 | 1.3 |
| Example 12 | Bio-electrode composition solution 12 | 38 | 1.5 |
| Example 13 | Bio-electrode composition solution 13 | 39 | 1.4 |
| Example 14 | Bio-electrode composition solution 14 | 36 | 1.6 |
| Example 15 | Bio-electrode composition solution 15 | 35 | 1.8 |
| Example 16 | Bio-electrode composition solution 16 | 23 | 1.5 |
| Example 17 | Bio-electrode composition solution 17 | 32 | 1.5 |
| Example 18 | Bio-electrode composition solution 18 | 28 | 1.4 |
| Example 19 | Bio-electrode composition solution 19 | 30 | 2 |
| Example 20 | Bio-electrode composition solution 20 | 25 | 2 |
| Example 21 | Bio-electrode composition solution 21 | 33 | 2 |
| Example 22 | Bio-electrode composition solution 22 | 34 | 2 |
| Example 23 | Bio-electrode composition solution 23 | 37 | 2.2 |
| Example 24 | Bio-electrode composition solution 24 | 39 | 3.6 |
| Example 25 | Bio-electrode composition solution 25 | 41 | 3.8 |
| Example 26 | Bio-electrode composition solution 26 | 31 | 2.6 |
| Example 27 | Bio-electrode composition solution 27 | 36 | 2 |
| Example 28 | Bio-electrode composition solution 28 | 33 | 2.3 |
| Example 29 | Bio-electrode composition solution 29 | 38 | 3.3 |
| Comparative Example 1 | Comparative bio-electrode composition solution 1 | 32 | N/A |
| Comparative Example 2 | Comparative bio-electrode composition solution 2 | 33 | 30 |
| Comparative Example 3 | Comparative bio-electrode composition solution 3 | 38 | N/A |
| Comparative Example 4 | Comparative bio-electrode composition solution 4 | 39 | N/A |

As shown in Table 4, biological signals were detected within short times after the attachment to the body in Examples 1 to 29, in which the living body contact layers were each formed using the inventive bio-electrode composition including the composite of an ionic polymer and particles. In contrast, no biological signals were detected in Comparative Examples 1, 3, and 4 not containing the ionic component having a particular structure. In Comparative Example 2 containing only an ionic polymer, it took longer time for the biological signal to appear after the attachment to the skin.

From the foregoing, the bio-electrode including the living body contact layer formed from the inventive bio-electrode composition is excellent in electric conductivity, biocompatibility, and adhesion to the electro-conductive base material, and the ionic conductivity is so high that biological signals can be obtained immediately after the attachment to skin.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A bio-electrode composition comprising
   a component (A) which is a composite comprising an ionic polymer material and particles, wherein
   the component (A) comprises the particles bonded to the polymer comprising a repeating unit having a structure selected from the group consisting of salts of ammonium, lithium, sodium, potassium, and silver formed with any of fluorosulfonic acid, fluorosulfonimide, and N-carbonyl-fluorosulfonamide.

2. The bio-electrode composition according to claim 1, wherein the particles have diameters of 2 nm to 50 μm.

3. The bio-electrode composition according to claim 1, wherein the particles are any of silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolium oxide particles, indium oxide particles, molybdenum oxide particles, and scandium oxide particles.

4. The bio-electrode composition according to claim 1, wherein the repeating unit having a structure selected from the group consisting of salts of ammonium, lithium, sodium, potassium, and silver formed with any of fluorosulfonic acid, fluorosulfonimide, and N-carbonyl-fluorosulfonamide comprises a structure shown by any of the following general formulae (1)-1 to (1)-4,

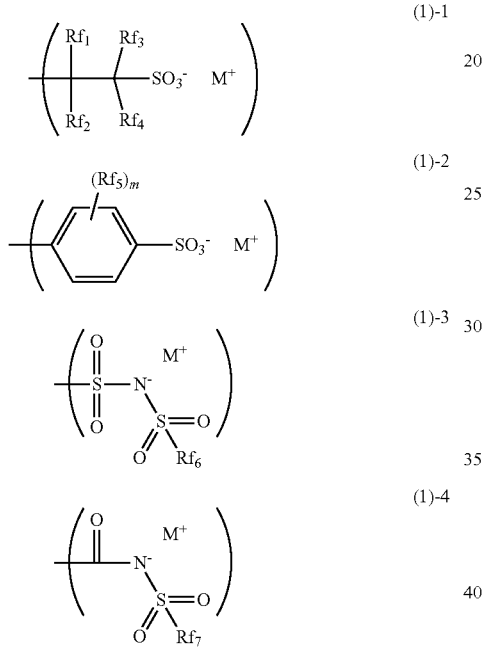

wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, and have at least one fluorine atom; "m" represents an integer of 1 to 4; and $M^+$ represents an ion selected from the group consisting of an ammonium ion, a lithium ion, a sodium ion, a potassium ion, and a silver ion.

5. The bio-electrode composition according to claim 1, wherein the repeating unit having a structure selected from the group consisting of salts of ammonium, lithium, sodium, potassium, and silver formed with any of fluorosulfonic acid, fluorosulfonimide, and N-carbonyl-fluorosulfonamide comprises at least one repeating unit selected from the group consisting of repeating units-a1 to -a7 shown by the following general formula (2),

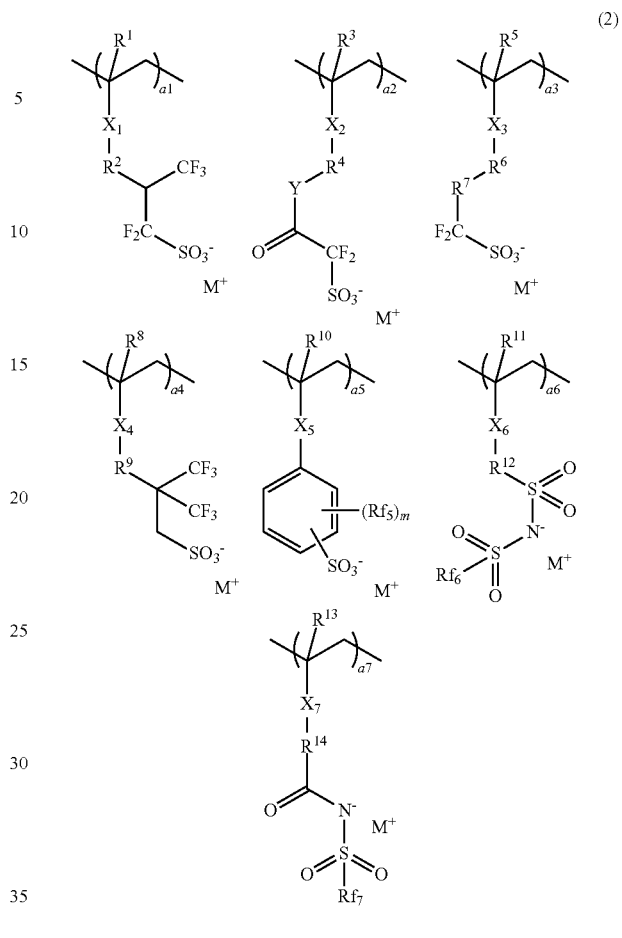

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent any of a single bond, and a linear, branched, or cyclic hydrocarbon group having 1 to 13 carbon atoms optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom, or a linear or branched alkyl group having 1 to 4 carbon atoms and optionally bonded to $R^4$ to form a ring; "m" represents an integer of 1 to 4; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$; $M^+$ represents an ion selected from the group consisting of an ammonium ion, a lithium ion, a sodium ion, a potassium ion, and a silver ion; and $Rf_5$, $Rf_6$, and $Rf_7$ each represent a fluorine atom, or a linear or branched alkyl group having 1 to 4 carbon atoms, and have at least one fluorine atom.

6. The bio-electrode composition according to claim 5, wherein the component (A) is a reaction product between the particles and a polymer having the repeating unit shown by the general formula (2) and an alkoxysilyl group copolymerized with a repeating unit shown by the following general formula (4),

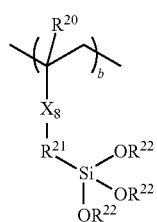

(4)

wherein $R^{20}$ represents a hydrogen atom or a methyl group; $X_8$ represents any of a single bond, a phenylene group, a naphthylene group, an ether group, an ester group, and an amide group; $R^{21}$ represents a single bond, a linear, branched, or cyclic alkylene group having 1 to 10 carbon atoms, or a phenylene group, and optionally contains an oxygen atom or a nitrogen atom; each $R^{22}$ is identical to or different from one another and represents an alkyl group having 1 to 4 carbon atoms; and "b" satisfies $0<b<1.0$.

7. The bio-electrode composition according to claim 6, wherein
   the particles in the component (A) are silicon material particles, and
   the component (A) is a reaction product between 100 parts by mass of the silicon material particles and 5 parts by mass or more of the polymer having an alkoxysilyl group.

8. The bio-electrode composition according to claim 1, wherein the component (A) comprises an ammonium ion shown by the following general formula (3) as an ammonium ion for forming the ammonium salts,

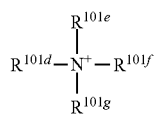

(3)

wherein $R^{101d}$, $R^{101e}$, $R^{101f}$, and $R^{101g}$ each represent a hydrogen atom, a linear, branched, or cyclic alkyl group having 1 to 14 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$ or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

9. The bio-electrode composition according to claim 1, further comprising a component (B) which is an adhesive resin.

10. The bio-electrode composition according to claim 9, wherein the component (B) is one or more selected from the group consisting of a silicone resin, a (meth) acrylate resin, and a urethane resin.

11. The bio-electrode composition according to claim 9, wherein the component (B) comprises diorganosiloxane having an alkenyl group, and organohydrogenpolysiloxane having an SiH group.

12. The bio-electrode composition according to claim 11, wherein
    the component (B) further comprises a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

13. The bio-electrode composition according to claim 1, further comprising a component (C) which is a polymer compound having an ionic repeating unit.

14. The bio-electrode composition according to claim 13, wherein the ionic repeating unit of the component (C) comprises a repeating unit having a structure selected from the group consisting of salts of ammonium, lithium, sodium, potassium, and silver formed with any of fluorosulfonic acid, fluorosulfonimide, and N-carbonyl-fluorosulfonamide shown by the following general formula (2),

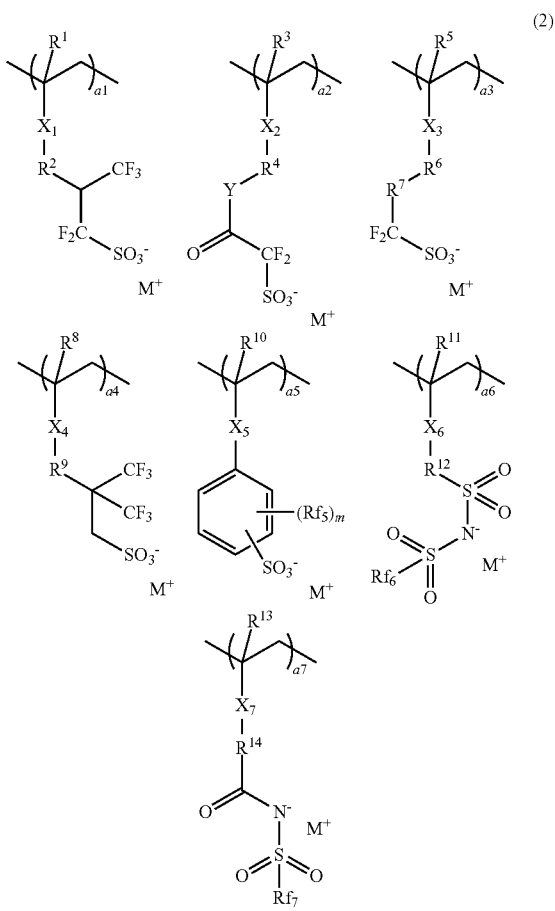

(2)

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent any of a single bond, and a linear, branched, or cyclic hydrocarbon group having 1 to 13 carbon atoms optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom, or a linear or branched alkyl group having 1 to 4 carbon atoms and optionally bonded to $R^4$ to form a ring; "m" represents an integer of 1 to 4; a1, a2, a3, a4, a5, a6, and a7 satisfy $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 \le 1.0$; $M^+$ represents an ion selected from the group consisting of an ammonium ion, a lithium ion, a sodium ion, a potassium ion, and a silver ion; and $Rf_5$, $Rf_6$, and $Rf_7$ each represent a fluorine atom, or a linear or branched alkyl group having 1 to 4 carbon atoms, and have at least one fluorine atom.

15. The bio-electrode composition according to claim 1, further comprising a component (D) which is a carbon powder and/or a metal powder.

16. The bio-electrode composition according to claim 15, wherein the carbon powder is one or both of carbon black and carbon nanotube.

17. The bio-electrode composition according to claim 15, wherein the metal powder is a powder of a metal selected from the group consisting of gold, silver, platinum, copper, tin, titanium, nickel, aluminum, tungsten, molybdenum, ruthenium, chromium, and indium.

18. The bio-electrode composition according to claim 17, wherein the metal powder is a silver powder.

19. The bio-electrode composition according to claim 1, further comprising a component (E) which is an organic solvent.

20. A bio-electrode comprising an electro-conductive base material and a living body contact layer formed on the electro-conductive base material, wherein
the living body contact layer is a cured product of the bio-electrode composition according to claim 1.

21. The bio-electrode according to claim 20, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

22. A method for manufacturing a bio-electrode having an electro-conductive base material and a living body contact layer formed on the electro-conductive base material, comprising:
applying the bio-electrode composition according to claim 1 onto the electro-conductive base material; and
curing the bio-electrode composition to form the living body contact layer.

23. The method for manufacturing a bio-electrode according to claim 22, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

24. A composite comprising an ionic polymer material and particles bonded thereto, wherein
the composite comprises the particles bonded to the polymer comprising a repeating unit having a structure selected from the group consisting of salts of ammonium, lithium, sodium, potassium, and silver formed with any of fluorosulfonic acid, fluorosulfonimide, and N-carbonyl-fluorosulfonamide.

25. The composite according to claim 24, wherein
the composite comprises the particles bonded to the polymer comprising a repeating unit having a structure selected from the group consisting of salts of ammonium, lithium, sodium, potassium, and silver formed with N-carbonyl-fluorosulfonamide.

26. The composite according to claim 24, wherein the particles have diameters of 2 nm to 50 μm.

27. The composite according to claim 24, wherein the particles are any of silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolium oxide particles, indium oxide particles, molybdenum oxide particles, and scandium oxide particles.

* * * * *